United States Patent
Kondou et al.

(10) Patent No.: US 11,827,941 B2
(45) Date of Patent: Nov. 28, 2023

(54) LIVER CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoshi Kondou, Kamakura (JP); Hitoshi Nobumasa, Kamakura (JP); Satoko Kozono, Kamakura (JP); Hiroko Sudo, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 0 days.

(21) Appl. No.: 17/970,824

(22) Filed: Oct. 21, 2022

(65) Prior Publication Data
US 2023/0106565 A1    Apr. 6, 2023

Related U.S. Application Data

(62) Division of application No. 16/785,233, filed on Feb. 7, 2020, now Pat. No. 11,512,355, which is a division of application No. 15/319,585, filed as application No. PCT/JP2015/067552 on Jun. 18, 2015, now Pat. No. 10,590,487.

(30) Foreign Application Priority Data

Jun. 18, 2014   (JP) ................................ 2014-124880

(51) Int. Cl.
| | | |
|---|---|---|
| C12Q 1/68 | (2018.01) | |
| C12P 19/34 | (2006.01) | |
| C12Q 1/6886 | (2018.01) | |
| G01N 33/574 | (2006.01) | |
| G01N 37/00 | (2006.01) | |
| G01N 33/53 | (2006.01) | |
| C12N 15/09 | (2006.01) | |
| C12Q 1/04 | (2006.01) | |
| C12M 1/34 | (2006.01) | |

(52) U.S. Cl.
CPC ............. *C12Q 1/6886* (2013.01); *C12M 1/34* (2013.01); *C12N 15/09* (2013.01); *C12Q 1/04* (2013.01); *G01N 33/53* (2013.01); *G01N 33/574* (2013.01); *G01N 37/00* (2013.01); *C12Q 2600/118* (2013.01); *C12Q 2600/158* (2013.01); *C12Q 2600/178* (2013.01)

(58) Field of Classification Search
CPC ........ C12Q 2600/158; C12Q 2600/178; C12Q 1/6886; C12Q 1/68; C12Q 1/6876
See application file for complete search history.

(56) References Cited

U.S. PATENT DOCUMENTS

| | | |
|---|---|---|
| 2001/0053519 A1 | 12/2001 | Fodor |
| 2011/0003704 A1 | 1/2011 | Skog et al. |
| 2012/0115139 A1 | 5/2012 | Kuroda et al. |
| 2014/0200261 A1 | 7/2014 | Hoge et al. |

FOREIGN PATENT DOCUMENTS

| | | |
|---|---|---|
| CN | 102816861 A | 12/2012 |
| EP | 3 150 707 A1 | 4/2017 |
| EP | 3 156 483 A1 | 4/2017 |
| EP | 3 159 416 A1 | 4/2017 |
| JP | 2013/538583 A | 10/2013 |
| WO | WO 2009/166507 A1 | 12/2009 |
| WO | WO 2010/054386 A9 | 5/2010 |
| WO | WO 2010/055488 A2 | 5/2010 |
| WO | WO 2010/123043 A1 | 10/2010 |
| WO | WO 2011/012074 A1 | 2/2011 |
| WO | WO 2011/076141 A1 | 6/2011 |
| WO | WO 2011/076142 A1 | 6/2011 |
| WO | WO 2012/151212 A1 | 11/2012 |
| WO | WO 2012/151736 A1 | 11/2012 |
| WO | WO 2012/174282 A2 | 12/2012 |
| WO | WO 2014/048441 A1 | 4/2014 |
| WO | WO 2014/114802 A1 | 7/2014 |

OTHER PUBLICATIONS

Yang J,et al. "A meta-analysis of microRNA expression in liver cancer". PLOS One. Dec. 9, 2014;9(12):e114533. (Year: 2014).*
"*Homo sapiens* microRNA hsa-miR-1343-3p," EBI Database Accession No. FR772692, (Jan. 13, 2011), sequence.
American Cancer Society, "Liver Cancer", 2013, total 58 pages, pp. 5-8, 14-15, 17-23,and 27-41.
Anonymous: "Mature sequence hsa-miR-1343-3p," Accession No. MIMAT0019776, miRBase (Jan. 1, 2011), ID hsa-miR-1343-3P, Databse EMBL XP055431878 (Cancer Res. 71:78-86 (2011)).
Anonymous: "miRNA Search Results," miRBase (Jan. 1, 2011), PMID 21199797, XP055431877 (Cancer Res. 71:78-86 (2011)).
Blondal et al., "Assessing sample and miRNA profile quality in serum and plasma or other biofluids," Methods, vol. 59, 2013, pp. 51-56.
Cheung et al., "Natural variation in human gene expression assessed in lymphoblastoid cells," Nature Genetics (Mar. 2003), vol. 33, pp. 422-425.
Cobb et al., "Sepsis gene expression profiling: Murine splenic compared with hepatic responses determined by using complementary DNA microarrays," Crit. Care Med. (2002), vol. 30, pp. 2711-2721.

(Continued)

*Primary Examiner* — Stephen T Kapushoc
(74) *Attorney, Agent, or Firm* — Birch, Stewart, Kolasch & Birch, LLP

(57) ABSTRACT

It is intended to provide a kit or device for the detection of liver cancer and a method for detecting liver cancer. The present invention relates to a kit or device for the detection of liver cancer, comprising a nucleic acid capable of specifically binding to miRNA in a sample of a subject, and a method for detecting liver cancer, comprising measuring the miRNA in vitro.

6 Claims, 4 Drawing Sheets
Specification includes a Sequence Listing.

(56) References Cited

OTHER PUBLICATIONS

Eguchi et al., "Usefulness of microRNA in peripheral blood as tumor marker for liver cancer", Journal of Japan Society of Clinical Oncology, 2011, vol. 46, No. 2, pp. 606. OS66-2.
Estal et al., "MicroRNA signatures in hereditary breast cancer," Breast Cancer Res. Treat. (2013), vol. 142, pp. 19-30.
Eto et al., "Prospect of microRNA toward laboratory medicine Gastrointestinal Cancer and microRNA", Clinical Chemistry, Apr. 2014, vol. 43, No. 2, pp. 99-105.
Extended European Search Report dated Dec. 15, 2017, in European Patent Application No. 15810147.7.
Fu et al., "Circulating microRNA-101 as a potential biomarker for hepatitis B virus-related hepatocellular carcinoma," Oncology Letters (2013), vol. 6, pp. 1811-1815.
GenBank Locus NR_039836, "Homo sapiens microRNA 1343 (MIR13243), microRNA," (Feb. 27, 2014), from www.ncbi.nlm.nih.gov, pp. 1-3 (2014).
GenBank Locus NR_106842.1, "Homo sapiens microRNA mir-6784 (MIR6784), microRNA," Dec. 4, 2013, from https://www.ncbi.nlm.nih.gov/nuccore/NR_106842, 2 pages.
Homo sapiens microRNA 1343 (MIR1343), NCBI[online] (2014), URL, https://ncbi.nlm.nih.gov/nuccore/337756711?sat=18&satkey=18652513.
Hoshikawa et al., "Hypoxia induces different genes in the lungs of rats compared with mice," Physiol. Genomics (2003), vol. 12, pp. 209-219.
Hu et al., "Fluorescence in situ hybridization (FISH): an increasingly demanded tool for biomarker research and personalized medicine," Biomarker Research (2014), vol. 2, No. 3, pp. 1-13.
International Search Report, issued in PCT/JP2015/067552, dated Sep. 8, 2015.
Li et al., "Expression of serum miR-221 in human hepatocellular carcinoma and its prognostic significance", Biochemical and Biophysical Research Communications, 2011, vol. 406, No. 1, pp. 70-73.
Li et al., "MicroRNA-561 Promotes Acetaminophen-Induced Hepatoxicity in HepG2 Cells and Primary Human Hepatocytes through Downregulation of the Nuclear Receptor Corepressor Dosage-Sensitive Sex-Reversal Adrenal Hypoplasia Congenital Critical Region on the X Chromosome, Gene 1 (DAX-1)," Drug Metab. Dispos. (Jan. 2014), vol. 42, pp. 44-61.
MiScriptTM miRNA PCT Array (384-well, 384HC), Human miRBase Profiler HC Plate 4, Qiagen, printed pp. 1-10 from https://b2b.qiagen.com/-/media/genetable/mi/hs/34/mihs-3404z (2012).
NCCN Guidelines, "Hepatobiliary Cancers, the 2nd edition", 2014, MS-4.
Office Action dated Apr. 8, 2018, in Chinese Patent Application No. 201580032544.9.
Office Action dated Jun. 10, 2022, in Canadian Patent Application No. 2,951,624.
Office Action dated May 14, 2019, in Japanese Patent Application No. 2016-529424.
Office Action dated May 22, 2019, in Chinese Patent Application No. 201580032544.9.
Office Action dated Nov. 20, 2016, in Chinese Patent Application No. 201580032544.9.
Office Action dated Sep. 24, 2021, in Korean Patent Application No. 10-2017-7000870.
Partial European Search Report dated Jul. 6, 2021, in European Patent Application No. 20183289.6.
Persson et al., "Identification of New MicroRNAs in Paired Normal and Tumor Breast Tissue Suggests a Dual Role for the ERBB2/Her2 Gene," Cancer Res. (2011), vol. 71, No. 1, pp. 78-86.
Shen et al., "Exploration of Genome-Wide Circulating MicroRNA in Hepatocellular Carcinoma: MiR-483-5p as a Potential Biomarker," Cancer Epidemiol. Biomarkers Prev. (2013), vol. 22, No. 12, pp. 2364-2373.
Sobin et al., "TNM Classification of Malignant Tumours, the 7th edition", 2010, pp. 104-107.
Sun et al., "MicroRNA Expression Profiles of Circulating Microvesicles in Hepatocellular Carcinoma." Acta Gastroenterol. Belg. (2013), vol. 76, pp. 386-392.
Takashi et al., "Case of clear-cell hepatocellular carcinoma that developed in the normal liver of a middle-aged woman", World Journal of Gastroenterology, 2008, vol. 14 (1), pp. 129-131.
Takizawa et al., "miRNA Profiling in Serum Samples Using DNA Chip 3D-Gene®", BIO Clinica, Jun. 10, 2014, vol. 29, No. 6, pp. 588-589.
Turato et al., "MicroRNAs and SerpinB3 in hepatocellular carcinoma", Life Sciences, Mar. 2014, vol. 100, No. 1, pp. 9-17.
Written Opinion of the International Searching Authority, issued in PCT/JP2015/067552, dated Sep. 8, 2015.
Zhang et al., "Combined . fetoprotein testing and ultrasonography as a screening test for primary liver cancer", Journal of Medical Screening, 1999, vol. 6 (2), pp. 108-110.
Zhu, Kai (2012). Study on Role and Mechanisms of Angiogenesis-Related microRNAs in Infestation and Metastasis of Hepatocellular Carcinoma (Doctoral Dissertation). Shanghai Medical College, Fudan University, China.
Arata et al., "Rapid and Sensitive MicroRNA Detection with Laminar Flow-Assisted Dendritic Amplification on Power-Free Microfluidic Chip," PLOS One, vol. 7, Issue 11, Nov. 2012, e48329 (6 pages total).
Canadian Office Action and Search Report for corresponding Canadian Application No. 2951624, dated Jul. 31, 2023.
Liu et al., "Amplification-free detection of miRNA via an ECL chips system," Optics in Health Care and Biomedical Optics V., Proc. of SPIE, vol. 8553, 2012, pp. 855336-1 to 855336-6.
Riken, "New portable device enables RNA detection from ultra-small sample in only 20 minutes," ScienceDaily, Nov. 7, 2012, pp. 1-2.

* cited by examiner

LIVER CANCER DETECTION KIT OR DEVICE, AND DETECTION METHOD

CROSS-REFERENCE TO RELATED APPLICATIONS

This application is a Divisional of co-pending application Ser. No. 16/785,233, filed on Feb. 7, 2020, which is a Divisional of application Ser. No. 15/319,585, filed on Dec. 16, 2016, now U.S. Pat. No. 10,590,487, which is the National Phase under 35 U.S.C. § 371 of International Application No. PCT/JP2015/067552, filed on Jun. 18, 2015, which claims the benefit under 35 U.S.C. § 119(a) to Patent Application No. 2014-124880, filed in Japan on Jun. 18, 2014, all of which are hereby expressly incorporated by reference into the present application.

REFERENCE TO ELECTRONIC SEQUENCE LISTING

This application contains a Sequence Listing which has been submitted electronically in .XML format and is hereby incorporated by reference in its entirety. Said .XML copy, created on Oct. 18, 2022, is named "PH-6238-PCT-US-DIV1-DIV1.xml" and is 688,621 bytes in size. The sequence listing contained in this .XML file is part of the specification and is hereby incorporated by reference herein in its entirety.

TECHNICAL FIELD

The present invention relates to a kit or a device for the detection of liver cancer, comprising a nucleic acid capable of specifically binding to a particular miRNA, which is used for examining the presence or absence of liver cancer in a subject, and a method for detecting liver cancer, comprising measuring an expression level of the miRNA using the nucleic acid.

BACKGROUND ART

The liver is the largest organ in the body and is positioned in the upper right portion of the abdomen. Its main roles are the metabolism of nutrients and the detoxication and elimination of harmful substances. According to the 2011 statistics of cancer types in Japan disclosed by the Center for Cancer Control and Information Services, National Cancer Center, the number of individuals affected by liver cancer is 47,271 people. Namely, it is estimated that one out of every 35 Japanese individuals experience liver cancer. The number of individuals affected by liver cancer among other cancer types takes the 6th in place. Also, men are nearly twice as likely as women to develop liver cancer. The number of liver cancer deaths in men and women together climbed to 30,690 people and takes the 4th in place. An estimate of the number of American individuals affected by liver cancer in 2014 climbs to 33,190 people, among which approximately 23,000 people will die (Non-Patent Literature 1).

In general, primary liver cancer often refers to hepatocellular carcinoma which accounts for approximately 80% of primary liver cancer cases. However, there are other sub-types of primary liver cancer such as intrahepatic bile duct carcinoma which accounts for 10 to 20% of all primary liver cancer cases, and biliary cystadenocarcinoma which is a rarer cancer type.

The stages of liver cancer progression are specified separately for hepatocellular carcinoma and intrahepatic bile duct carcinoma in Non-Patent Literature 2. Herein, particularly, the hepatocellular carcinoma is classified into stage I (T1/N0/M0), stage II (T2/N0/M0), stage IIIA (T3a/N0/M0), stage IIIB (T3b/N0/M0), stage IIIC (T4/N0/M0), stage IVA (N1/M0), and stage IVB (M1) according to the degrees of tumor spread (T0 to T4), lymph node metastasis (N0 and N1), and distant metastasis (M0 and M1).

The 5-year relative survival rate of liver cancer differs depending on the stages of progression. According to Non-Patent Literature 1, the 5-year relative survival rate of liver cancer is reportedly 28% for tumors localized within liver (stage 1, stage 2 and some cases of stage 3), 7% for tumors found to have metastasized to a surrounding area of liver (stage IIIC and stage IVA), and 2% for tumors found to have metastasized distantly (stage IVB). Thus, the detection and treatment of liver cancer at an early stage before metastasis makes a significant contribution to improvement in the survival rate.

The treatment of liver cancer is performed mainly by 3 procedures: surgical therapy mainly involving resection and/or liver transplantation; local therapy which involves injecting a drug through centesis or performing cauterization to kill cancer; and hepatic arterial embolization. These procedures are used in combination with drug therapy or radiotherapy. Particularly, early liver cancer which is found not to metastasize to a blood vessel or an adjacent site is often cured by the partial resection of the liver (Non-Patent Literature 1). On the other hand, even if cancer is localized, liver transplantation is desirable for the cases where such resection is impossible on the ground that the tumors have a large size or are placed in proximity to a blood vessel, for example. If metastasis is found, systemic drug therapy or radiotherapy is performed (Non-Patent Literature 1).

As described in Non-Patent Literature 1, primary tests of liver cancer are inspection and palpation as well as imaging tests such as ultrasonography, CT scan, MRI scan, and angiography. For example, AFP (alpha fetoprotein) and PIVKA-II are known as tumor markers for the detection of liver cancer. The tests using these tumor markers are often performed in combination with ultrasonography. When there are findings that suspect liver cancer by these primary tests, pathological examination which involves inserting a needle into a lesion and collecting cells or tissues, which are then examined under a microscope is carried out as a secondary test.

Meanwhile, it is known that the most important leading cause of liver cancer is prolonged infection with hepatitis B or C virus. Therefore, subjects suspected of having liver cancer may be subjected to a hepatitis virus test in addition to the primary tests described above.

As shown in Patent Literatures 1 to 5, there are reports, albeit at a research stage, on methods for detecting liver cancer using the expression levels of microRNAs (miRNAs) in biological samples including blood and hepatic tissues.

Patent Literature 1 discloses a method for detecting leukemia, breast cancer, and liver cancer using miRNAs: hsa-miR-92a-3p, hsa-miR-92b-3p, hsa-miR-92a-2-5p, and hsa-miR-92b-5p in tissues as markers.

Patent Literature 2 has reported a method for diagnosing various cancers using, as markers, miRNAs such as hsa-miR-23a-3p, hsa-miR-23b-3p, hsa-miR-24-3p, hsa-miR-557, hsa-miR-564, hsa-miR-614, hsa-miR-150-3p, and hsa-miR-486-3p contained in vesicles circulating in body fluids.

Patent Literature 3 discloses a method for detecting various diseases including liver cancer using miRNAs such as hsa-miR-23b-3p, hsa-miR-30c-1-3p, hsa-miR-125a-3p, and hsa-miR-486-3p in tissues or body fluids as markers.

Patent Literature 4 discloses a method for detecting various pathological conditions including liver cancer using, as markers, miRNAs such as hsa-miR-16-5p, hsa-miR-92a-3p, hsa-miR-663a, hsa-miR-1913, and hsa-miR-625-3p, or proteins contained in vesicles circulating in body fluids.

Patent Literature 5 discloses that hsa-miR-187-5p, hsa-miR-92a-3p, hsa-miR-16-5p, and hsa-miR-30c-1-3p in plasma are markers for colorectal cancer, liver cancer, and lung cancer.

CITATION LIST

Patent Literature

Patent Literature 1: International Publication No. WO 2010/123043
Patent Literature 2: U.S. Patent Application Publication No. 2011/003704
Patent Literature 3: International Publication No. WO 2010/054386
Patent Literature 4: International Publication No. WO 2012/174282
Patent Literature 5: International Publication No. WO 2011/076142

Non-Patent Literature

Non-Patent Literature 1: American Cancer Society, "Liver Cancer", 2013, p. 5 to 8, 14 to 15, 17 to 23, and 27 to 41
Non-Patent Literature 2: Sobin, L. et al., "TNM Classification of Malignant Tumours, the 7th edition", 2010, p. 104-107
Non-Patent Literature 3: NCCN Guidelines, "Hepatobiliary Cancers, the 2nd edition", 2014, MS-4
Non-Patent Literature 4: Zhang, B and Yang, B., 1999, Journal of Medical Screening, Vol. 6 (2), p. 108-110
Non-Patent Literature 5: Takahashi, A. et al., 2008, World Journal of Gastroenterology, Vol. 14 (1), p. 129-31

SUMMARY OF INVENTION

Problem to be Solved by Invention

An object of the present invention is to find a novel tumor marker for liver cancer and to provide a method that can effectively detect liver cancer using a nucleic acid capable of specifically binding to the marker.

Liver cancer progresses without particular symptoms and is therefore difficult to detect early. Since the most part of the liver is housed in the right rib, liver cancer is difficult to detect by palpation. An effective method for liver cancer screening has not yet been established for ordinary people lacking a risk of liver cancer such as hepatitis virus infection or liver cirrhosis (Non-Patent Literature 1). Ultrasonography is a widely prevalent method for liver cancer screening because this method places less burden on patients and is convenient. Nonetheless, liver cancer may be difficult to detect depending on its site of occurrence by ultrasonography. In addition, examination results of ultrasonography largely depend on the skill of technicians. Therefore, it is considered to be desirable that ultrasonography should be used in combination with a tumor marker (Non-Patent Literature 3). Although AFP is known as a tumor marker for the detection of liver cancer, liver cancer found to have an elevated level of AFP is already at an advanced stage and is impossible to resect or has metastasized to an area outside the liver in many cases (Non-Patent Literature 1). It has been reported that some liver cancers do not produce AFP. Meanwhile, AFP is known to also elevate in cancers other than liver cancer, for example, testicular cancer or ovary cancer, and further to elevate in non-cancer liver diseases, for example, sustained hepatitis virus infection, and is therefore regarded as a low specific marker (Non-Patent Literature 1). For example, false diagnosis of other cancers as liver cancer wastes appropriate therapeutic opportunity or places unnecessary economical and physical burdens on patients due to the application of wrong medicine. According to results of large-scale screening research targeting hepatitis B-infected people and prolonged hepatitis patients (Non-Patent Literature 4), the AFP test has liver cancer detection sensitivity as low as 69% and thus has insufficient examination performance for use as a liver cancer screening test. Furthermore, CT scan or MRI scan can detect liver cancer with high performance, but is not suitable as a widely prevalent primary test because these tests require a specific apparatus and high examination cost.

As described below, there are reports, albeit at a research stage, on the determination of liver cancer using the expression levels of microRNAs (miRNAs) in biological samples including blood, none of which, however, have yet been brought into practical use.

Patent Literature 1 discloses a method for detecting leukemia, breast cancer, and liver cancer using miRNAs hsa-miR-92a-3p, hsa-miR-92b-3p, hsa-miR-92a-2-5p, and hsa-miR-92b-5p in blood cells or tissues as markers. This detection method, however, inevitably requires tissue resection by surgical operation for obtaining samples, and this step places a heavy physical burden on patients. Therefore, this method is not favorable as an examination method. In addition, Patent Literature 1 does not describe specific detection performance such as accuracy, sensitivity, or specificity for determining liver cancer as to this detection method, which is thus industrially less practical.

Patent Literature 2 has reported a method for diagnosing various cancers using, as markers, miRNAs such as hsa-miR-23a-3p, hsa-miR-23b-3p, hsa-miR-24-3p, hsa-miR-557, hsa-miR-564, hsa-miR-614, hsa-miR-150-3p, and hsa-miR-486-3p contained in vesicles circulating in body fluids. Patent Literature 2, however, neither describes a specific method for diagnosing liver cancer by use of this detection method nor describes detection performance such as accuracy, sensitivity, or specificity for determining liver cancer. Therefore, this detection method is industrially less practical.

Patent Literature 3 discloses a method for detecting various diseases including liver cancer using miRNAs such as hsa-miR-23b-3p, hsa-miR-30c-1-3p, hsa-miR-125a-3p, and hsa-miR-486-3p in tissues or body fluids as markers. This detection method, however, is based on results of experiments using mouse models, and the detection of liver cancer in humans is unknown about the method. In addition, Patent Literature 3 does not describe detection performance such as accuracy, sensitivity, or specificity for determining liver cancer. Therefore, this detection method is industrially less practical.

Patent Literature 4 discloses a method for detecting various pathological conditions including liver cancer using, as markers, miRNAs such as hsa-miR-16-5p, hsa-miR-92a-3p, hsa-miR-663a, hsa-miR-1913, and hsa-miR-625-3p, or proteins contained in vesicles circulating in body fluids. Patent Literature 4, however, neither describes a specific method for diagnosing liver cancer by use of this detection method nor validated these miRNA markers in an independent sample group. Therefore, this detection method is less reliable.

Patent Literature 5 discloses that hsa-miR-187-5p, hsa-miR-92a-3p, hsa-miR-16-5p, and hsa-miR-30c-1-3p in plasma are markers for colorectal cancer, liver cancer, and lung cancer. These markers, however, are markers for discriminating a group of colorectal cancers from a group of liver cancers, lung cancers, and healthy subjects and is not a marker for detecting liver cancer.

As mentioned above, the existing tumor markers exhibit low performance in the detection of liver cancer, and neither performance nor detection methods are specifically shown as to the markers at a research stage. Therefore, use of these markers might lead to carrying out needless extra examination due to the false detection of healthy subjects as being liver cancer patients, or might waste therapeutic opportunity because of overlooking liver cancer patients. In addition, the measurement of several dozens to several hundreds of miRNAs increases examination cost and is therefore difficult to use in large-scale screening such as medical checkup. Furthermore, the collection of liver tissues for measuring the tumor markers is highly invasive to patients and is not favorable. Hence, there is a demand for a highly accurate liver cancer marker that is detectable from blood, which can be collected with limited invasiveness, and is capable of correctly determining a liver cancer patient as a liver cancer patient and a healthy subject as a healthy subject. Particularly, the early detection and treatment of liver cancer can improve the survival rates. In addition, such liver cancer is often cured by the partial resection of the liver. Therefore, a highly sensitive liver cancer marker capable of detecting liver cancer even at an early stage of progression is desired.

Means for Solution of Problem

The present inventors have conducted diligent studies to attain the object and consequently completed the present invention by finding multiple genes usable as markers for the detection of liver cancer from blood, which can be collected with limited invasiveness, and finding that liver cancer can be significantly detected by using nucleic acid(s) capable of specifically binding to any of these markers.

SUMMARY OF INVENTION

Specifically, the present invention has the following features:
(1) A kit for the detection of liver cancer, comprising nucleic acid(s) capable of specifically binding to at least one or more polynucleotide(s) selected from the group consisting of liver cancer markers: miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p.

(2) The kit according to (1), wherein miR-1343-3p is hsa-miR-1343-3p, miR-6726-5p is hsa-miR-6726-5p, miR-6515-3p is hsa-miR-6515-3p, miR-4651 is hsa-miR-4651, miR-4257 is hsa-miR-4257, miR-3188 is hsa-miR-3188, miR-6131 is hsa-miR-6131, miR-6766-3p is hsa-miR-6766-3p, miR-7641 is hsa-miR-7641, miR-1249 is hsa-miR-1249, miR-3679-3p is hsa-miR-3679-3p, miR-6787-5p is hsa-miR-6787-5p, miR-4454 is hsa-miR-4454, miR-3135b is hsa-miR-3135b, miR-6765-3p is hsa-miR-6765-3p, miR-7975 is hsa-miR-7975, miR-204-3p is hsa-miR-204-3p, miR-7977 is hsa-miR-7977, miR-7110-5p is hsa-miR-7110-5p, miR-6717-5p is hsa-miR-6717-5p, miR-6870-5p is hsa-miR-6870-5p, miR-663b is hsa-miR-663b, miR-6875-5p is hsa-miR-6875-5p, miR-8072 is hsa-miR-8072, miR-6816-5p is hsa-miR-6816-5p, miR-4281 is hsa-miR-4281, miR-6729-5p is hsa-miR-6729-5p, miR-8069 is hsa-miR-8069, miR-4706 is hsa-miR-4706, miR-7108-5p is hsa-miR-7108-5p, miR-4433b-3p is hsa-miR-4433b-3p, miR-6893-5p is hsa-miR-6893-5p, miR-6857-5p is hsa-miR-6857-5p, miR-1227-5p is hsa-miR-1227-5p, miR-6741-5p is hsa-miR-6741-5p, miR-451a is hsa-miR-451a, miR-8063 is hsa-miR-8063, miR-3622a-5p is hsa-miR-3622a-5p, miR-615-5p is hsa-miR-615-5p, miR-128-1-5p is hsa-miR-128-1-5p, miR-6825-5p is hsa-miR-6825-5p, miR-1260b is hsa-miR-1260b, miR-4433-3p is hsa-miR-4433-3p, miR-4665-5p is hsa-miR-4665-5p, miR-7845-5p is hsa-miR-7845-5p, miR-1908-5p is hsa-miR-1908-5p, miR-6840-3p is hsa-miR-6840-3p, miR-6765-5p is hsa-miR-6765-5p, miR-296-5p is hsa-miR-296-5p, miR-3675-3p is hsa-miR-3675-3p, miR-6781-5p is hsa-miR-6781-5p, miR-423-5p is hsa-miR-423-5p, miR-3663-3p is hsa-miR-3663-3p, miR-6784-5p is hsa-miR-6784-5p, miR-6749-5p is hsa-miR-6749-5p, miR-1231 is hsa-miR-1231, miR-4746-3p is hsa-miR-4746-3p, miR-6780b-5p is hsa-miR-6780b-5p, miR-4758-5p is hsa-miR-4758-5p, miR-3679-5p is hsa-miR-3679-5p, miR-3184-5p is hsa-miR-3184-5p, miR-6125 is hsa-miR-6125, miR-6721-5p is hsa-miR-6721-5p, miR-6791-5p is hsa-miR-6791-5p, miR-3185 is hsa-miR-3185, miR-1260a is hsa-miR-1260a, miR-3197 is hsa-miR-3197, miR-6845-5p is hsa-miR-6845-5p, miR-6887-5p is hsa-miR-6887-5p, miR-6738-5p is hsa-miR-6738-5p, miR-6872-3p is hsa-miR-6872-3p, miR-4497 is hsa-miR-4497, miR-1229-5p is hsa-miR-1229-5p, miR-6820-5p is hsa-miR-6820-5p, miR-6777-5p is hsa-miR-6777-5p, miR-3917 is hsa-miR-3917, miR-5787 is hsa-miR-5787, miR-4286 is hsa-miR-4286, miR-6877-5p is hsa-miR-6877-5p, miR-1225-3p is hsa-miR-1225-3p, miR-6088 is hsa-miR-6088, miR-6800-5p is hsa-miR-6800-5p, miR-1246 is hsa-miR-1246, miR-4467 is hsa-miR-4467, miR-4419b is hsa-miR-4419b, miR-1914-3p is hsa-miR-1914-3p, miR-4632-5p is hsa-miR-4632-5p, miR-1915-5p is hsa-miR-1915-5p, miR-3940-5p is hsa-miR-3940-5p, miR-1185-2-3p is hsa-miR-1185-2-3p, miR-6746-5p is hsa-miR-6746-5p, miR-5001-5p is hsa-miR-5001-5p, miR-1228-5p is hsa-miR-1228-5p, miR-5572 is hsa-miR-5572, miR-4327 is hsa-miR-4327, miR-4638-5p is hsa-miR-4638-5p, miR-6799-5p is hsa-miR-6799-5p, miR-6861-5p is hsa-miR-6861-5p, miR-6727-5p is hsa-miR-6727-5p, miR-4513 is hsa-miR-4513, miR-6805-3p is hsa-miR-6805-3p, miR-6808-5p is hsa-miR-6808-5p, miR-4449 is hsa-miR-4449, miR-1199-5p is hsa-miR-1199-5p, miR-1275 is hsa-miR-1275, miR-4792 is hsa-miR-4792, miR-4443 is hsa-miR-4443, miR-6891-5p is hsa-miR-6891-5p, miR-6826-5p is hsa-miR-6826-5p, miR-6807-5p is hsa-miR-6807-5p, miR-7150 is hsa-miR-7150, miR-4534 is hsa-miR-4534, miR-4476 is hsa-miR-4476, miR-4649-5p is hsa-miR-4649-5p, miR-4525 is hsa-miR-4525, miR-1915-3p is hsa-miR-1915-3p, miR-4516 is hsa-miR-4516, miR-4417 is hsa-miR-4417, miR-642b-3p is hsa-miR-642b-3p, miR-3141 is hsa-miR-3141, miR-5100 is hsa-miR-5100, miR-6848-5p is hsa-miR-6848-5p, miR-4739 is hsa-miR-4739, miR-4459 is hsa-miR-4459, miR-1237-5p is hsa-miR-1237-5p, miR-296-3p is hsa-miR-296-3p, miR-4665-3p is hsa-miR-4665-3p, miR-6786-5p is hsa-miR-6786-5p, miR-4258 is hsa-miR-4258, miR-6510-5p is hsa-miR-6510-5p, miR-1343-5p is hsa-miR-1343-5p, miR-1247-3p is hsa-miR-1247-3p, miR-6805-5p is hsa-miR-6805-5p, miR-4492 is hsa-miR-4492, miR-1469 is hsa-miR-1469, miR-1268b is hsa-miR-1268b, miR-6858-5p is hsa-miR-6858-5p, miR-3937 is hsa-miR-3937, miR-939-5p is hsa-miR-939-5p, miR-3656 is hsa-miR-3656, miR-744-5p is hsa-miR-744-5p, miR-4687-3p is hsa-miR-4687-3p, miR-4763-3p is hsa-miR-4763-3p, miR-3620-5p is hsa-miR-3620-5p, miR-3195 is hsa-miR-3195, miR-6842-5p is hsa-miR-6842-5p, miR-4707-5p is hsa-miR-4707-5p, miR-642a-3p is hsa-miR-642a-3p, miR-7113-3p is hsa-miR-7113-3p, miR-4728-5p is hsa-miR-4728-5p, miR-5195-3p is hsa-miR-5195-3p, miR-1185-1-3p is hsa-miR-1185-1-3p, miR-6774-5p is hsa-miR-6774-5p, miR-8059 is hsa-miR-8059, miR-3131 is hsa-miR-3131, miR-7847-3p is hsa-miR-7847-3p, miR-4463 is hsa-miR-4463, miR-128-2-5p is hsa-miR-128-2-5p, miR-4508 is hsa-miR-4508, miR-6806-5p is hsa-miR-6806-5p, miR-7111-5p is hsa-miR-7111-5p, miR-6782-5p is hsa-miR-6782-5p, miR-4734 is hsa-miR-4734, miR-3162-5p is hsa-miR-3162-5p, miR-887-3p is hsa-miR-887-3p, miR-6752-5p is hsa-miR-6752-5p, miR-6724-5p is hsa-miR-6724-5p, miR-6757-5p is hsa-miR-6757-5p, miR-4448 is hsa-miR-4448, miR-671-5p is hsa-miR-671-5p, miR-3178 is hsa-miR-3178, miR-4725-3p is hsa-miR-4725-3p, miR-940 is hsa-miR-940, miR-6789-5p is hsa-miR-6789-5p, miR-4484 is hsa-miR-4484, miR-4634 is hsa-miR-4634, miR-4745-5p is hsa-miR-4745-5p, miR-4730 is hsa-miR-4730, miR-6803-5p is hsa-miR-6803-5p, miR-6798-5p is hsa-miR-6798-5p, miR-3648 is hsa-miR-3648, miR-4783-3p is hsa-miR-4783-3p, and miR-6836-3p is hsa-miR-6836-3p.

(3) The kit according to (1) or (2), wherein the nucleic acid is a polynucleotide selected from the group consisting of the following polynucleotides (a) to (e):
(a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 167 and 714 to 729,
(c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and (e) a polynucleotide hybridizing under stringent conditions to any of the polynucleotides (a) to (d).
(4) The kit according to any of (1) to (3), wherein the kit further comprises nucleic acid(s) capable of specifically binding to at least one or more polynucleotide(s) selected from the group consisting of other liver cancer markers: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a.
(5) The kit according to (4), wherein miR-23b-3p is hsa-miR-23b-3p, miR-23a-3p is hsa-miR-23a-3p, miR-625-3p is hsa-miR-625-3p, miR-1228-3p is hsa-miR-1228-3p, miR-614 is hsa-miR-614, miR-1913 is hsa-miR-1913, miR-92a-2-5p is hsa-miR-92a-2-5p, miR-187-5p is hsa-miR-187-5p, miR-16-5p is hsa-miR-16-5p, miR-92b-3p is hsa-miR-92b-3p, miR-150-3p is hsa-miR-150-3p, miR-564 is hsa-miR-564, miR-125a-3p is hsa-miR-125a-3p, miR-92b-5p is hsa-miR-92b-5p, miR-92a-3p is hsa-miR-92a-3p, and miR-663a is hsa-miR-663a.
(6) The kit according to (4) or (5), wherein the nucleic acid is a polynucleotide selected from the group consisting of the following polynucleotides (f) to (j):
(f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 168 to 183, (h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 168 to 183 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises nucleic acid(s) capable of specifically binding to at least one or more polynucleotide(s) selected from the group consisting of other liver cancer markers: miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090.

(8) The kit according to (7), wherein miR-4688 is hsa-miR-4688, miR-4648 is hsa-miR-4648, miR-6085 is hsa-miR-6085, miR-6126 is hsa-miR-6126, miR-6880-5p is hsa-miR-6880-5p, miR-328-5p is hsa-miR-328-5p, miR-6768-5p is hsa-miR-6768-5p, miR-3180 is hsa-miR-3180, miR-6087 is hsa-miR-6087, miR-1273g-3p is hsa-miR-1273g-3p, miR-1225-5p is hsa-miR-1225-5p, miR-3196 is hsa-miR-3196, miR-4695-5p is hsa-miR-4695-5p, miR-6732-5p is hsa-miR-6732-5p, miR-638 is hsa-miR-638, miR-6813-5p is hsa-miR-6813-5p, miR-665 is hsa-miR-665, miR-486-3p is hsa-miR-486-3p, miR-4466 is hsa-miR-4466, miR-30c-1-3p is hsa-miR-30c-1-3p, miR-3621 is hsa-miR-3621, miR-6743-5p is hsa-miR-6743-5p, miR-4298 is hsa-miR-4298, miR-4741 is hsa-miR-4741, miR-3619-3p is hsa-miR-3619-3p, miR-6824-5p is hsa-miR-6824-5p, miR-5698 is hsa-miR-5698, miR-371a-5p is hsa-miR-371a-5p, miR-4488 is hsa-miR-4488, miR-1233-5p is hsa-miR-1233-5p, miR-4723-5p is hsa-miR-4723-5p, miR-24-3p is hsa-miR-24-3p, miR-1238-5p is hsa-miR-1238-5p, miR-4442 is hsa-miR-4442, miR-3928-3p is hsa-miR-3928-3p, miR-6716-5p is hsa-miR-6716-5p, miR-6089 is hsa-miR-6089, miR-6124 is hsa-miR-6124, miR-6778-5p is hsa-miR-6778-5p, miR-557 is hsa-miR-557, and miR-6090 is hsa-miR-6090.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 184 to 224, (m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 184 to 224 or a nucleotide sequence derived from the nucleotide sequence by the replacement of u with t, and (o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from all of the liver cancer markers according to (1) or (2).

(11) A device for the detection of liver cancer, comprising nucleic acid(s) capable of specifically binding to at least one or more polynucleotide(s) selected from the group consisting of liver cancer markers: miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR- 4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p.

(12) The device according to (11), wherein miR-1343-3p is hsa-miR-1343-3p, miR-6726-5p is hsa-miR-6726-5p, miR-6515-3p is hsa-miR-6515-3p, miR-4651 is hsa-miR-4651, miR-4257 is hsa-miR-4257, miR-3188 is hsa-miR-3188, miR-6131 is hsa-miR-6131, miR-6766-3p is hsa-miR-6766-3p, miR-7641 is hsa-miR-7641, miR-1249 is hsa-miR-1249, miR-3679-3p is hsa-miR-3679-3p, miR-6787-5p is hsa-miR-6787-5p, miR-4454 is hsa-miR-4454, miR-3135b is hsa-miR-3135b, miR-6765-3p is hsa-miR-6765-3p, miR-7975 is hsa-miR-7975, miR-204-3p is hsa-miR-204-3p, miR-7977 is hsa-miR-7977, miR-7110-5p is hsa-miR-7110-5p, miR-6717-5p is hsa-miR-6717-5p, miR-6870-5p is hsa-miR-6870-5p, miR-663b is hsa-miR-663b, miR-6875-5p is hsa-miR-6875-5p, miR-8072 is hsa-miR-8072, miR-6816-5p is hsa-miR-6816-5p, miR-4281 is hsa-miR-4281, miR-6729-5p is hsa-miR-6729-5p, miR-8069 is hsa-miR-8069, miR-4706 is hsa-miR-4706, miR-7108-5p is hsa-miR-7108-5p, miR-4433b-3p is hsa-miR-4433b-3p, miR-6893-5p is hsa-miR-6893-5p, miR-6857-5p is hsa-miR-6857-5p, miR-1227-5p is hsa-miR-1227-5p, miR-6741-5p is hsa-miR-6741-5p, miR-451a is hsa-miR-451a, miR-8063 is hsa-miR-8063, miR-3622a-5p is hsa-miR-3622a-5p, miR-615-5p is hsa-miR-615-5p, miR-128-1-5p is hsa-miR-128-1-5p, miR-6825-5p is hsa-miR-6825-5p, miR-1260b is hsa-miR-1260b, miR-4433-3p is hsa-miR-4433-3p, miR-4665-5p is hsa-miR-4665-5p, miR-7845-5p is hsa-miR-7845-5p, miR-1908-5p is hsa-miR-1908-5p, miR-6840-3p is hsa-miR-6840-3p, miR-6765-5p is hsa-miR-6765-5p, miR-296-5p is hsa-miR-296-5p, miR-3675-3p is hsa-miR-3675-3p, miR-6781-5p is hsa-miR-6781-5p, miR-423-5p is hsa-miR-423-5p, miR-3663-3p is hsa-miR-3663-3p, miR-6784-5p is hsa-miR-6784-5p, miR-6749-5p is hsa-miR-6749-5p, miR-1231 is hsa-miR-1231, miR-4746-3p is hsa-miR-4746-3p, miR-6780b-5p is hsa-miR-6780b-5p, miR-4758-5p is hsa-miR-4758-5p, miR-3679-5p is hsa-miR-3679-5p, miR-3184-5p is hsa-miR-3184-5p, miR-6125 is hsa-miR-6125, miR-6721-5p is hsa-miR-6721-5p, miR-6791-5p is hsa-miR-6791-5p, miR-3185 is hsa-miR-3185, miR-1260a is hsa-miR-1260a, miR-3197 is hsa-miR-3197, miR-6845-5p is hsa-miR-6845-5p, miR-6887-5p is hsa-miR-6887-5p, miR-6738-5p is hsa-miR-6738-5p, miR-6872-3p is hsa-miR-6872-3p, miR-4497 is hsa-miR-4497, miR-1229-5p is hsa-miR-1229-5p, miR-6820-5p is hsa-miR-6820-5p, miR-6777-5p is hsa-miR-6777-5p, miR-3917 is hsa-miR-3917, miR-5787 is hsa-miR-5787, miR-4286 is hsa-miR-4286, miR-6877-5p is hsa-miR-6877-5p, miR-1225-3p is hsa-miR-1225-3p, miR-6088 is hsa-miR-6088, miR-6800-5p is hsa-miR-6800-5p, miR-1246 is hsa-miR-1246, miR-4467 is hsa-miR-4467, miR-4419b is hsa-miR-4419b, miR-1914-3p is hsa-miR-1914-3p, miR-4632-5p is hsa-miR-4632-5p, miR-1915-5p is hsa-miR-1915-5p, miR-3940-5p is hsa-miR-3940-5p, miR-1185-2-3p is hsa-miR-1185-2-3p, miR-6746-5p is hsa-miR-6746-5p, miR-5001-5p is hsa-miR-5001-5p, miR-1228-5p is hsa-miR-1228-5p, miR-5572 is hsa-miR-5572, miR-4327 is hsa-miR-4327, miR-4638-5p is hsa-miR-4638-5p, miR-6799-5p is hsa-miR-6799-5p, miR-6861-5p is hsa-miR-6861-5p, miR-6727-5p is hsa-miR-6727-5p, miR-4513 is hsa-miR-4513, miR-6805-3p is hsa-miR-6805-3p, miR-6808-5p is hsa-miR-6808-5p, miR-4449 is hsa-miR-4449, miR-1199-5p is hsa-miR-1199-5p, miR-1275 is hsa-miR-1275, miR-4792 is hsa-miR-4792, miR-4443 is hsa-miR-4443, miR-6891-5p is hsa-miR-6891-5p, miR-6826-5p is hsa-miR-6826-5p, miR-6807-5p is hsa-miR-6807-5p, miR-7150 is hsa-miR-7150, miR-4534 is hsa-miR-4534, miR-4476 is hsa-miR-4476, miR-4649-5p is hsa-miR-4649-5p, miR-4525 is hsa-miR-4525, miR-1915-3p is hsa-miR-1915-3p, miR-4516 is hsa-miR-4516, miR-4417 is hsa-miR-4417, miR-642b-3p is hsa-miR-642b-3p, miR-3141 is hsa-miR-3141, miR-5100 is hsa-miR-5100, miR-6848-5p is hsa-miR-6848-5p, miR-4739 is hsa-miR-4739, miR-4459 is hsa-miR-4459, miR-1237-5p is hsa-miR-1237-5p, miR-296-3p is hsa-miR-296-3p, miR-4665-3p is hsa-miR-4665-3p, miR-6786-5p is hsa-miR-6786-5p, miR-4258 is hsa-miR-4258, miR-6510-5p is hsa-miR-6510-5p, miR-1343-5p is hsa-miR-1343-5p, miR-1247-3p is hsa-miR-1247-3p, miR-6805-5p is hsa-miR-6805-5p, miR-4492 is hsa-miR-4492, miR-1469 is hsa-miR-1469, miR-1268b is hsa-miR-1268b, miR-6858-5p is hsa-miR-6858-5p, miR-3937 is hsa-miR-3937, miR-939-5p is hsa-miR-939-5p, miR-3656 is hsa-miR-3656, miR-744-5p is hsa-miR-744-5p, miR-4687-3p is hsa-miR-4687-3p, miR-4763-3p is hsa-miR-4763-3p, miR-3620-5p is hsa-miR-3620-5p, miR-3195 is hsa-miR-3195, miR-6842-5p is hsa-miR-6842-5p, miR-4707-5p is hsa-miR-4707-5p, miR-642a-3p is hsa-miR-642a-3p, miR-7113-3p is hsa-miR-7113-3p, miR-4728-5p is hsa-miR-4728-5p, miR-5195-3p is hsa-miR-5195-3p, miR-1185-1-3p is hsa-miR-1185-1-3p, miR-6774-5p is hsa-miR-6774-5p, miR-8059 is hsa-miR-8059, miR-3131 is hsa-miR-3131, miR-7847-3p is hsa-miR-7847-3p, miR-4463 is hsa-miR-4463, miR-128-2-5p is hsa-miR-128-2-5p, miR-4508 is hsa-miR-4508, miR-6806-5p is hsa-miR-6806-5p, miR-7111-5p is hsa-miR-7111-5p, miR-6782-5p is hsa-miR-6782-5p, miR-4734 is hsa-miR-4734, miR-3162-5p is hsa-miR-3162-5p, miR-887-3p is hsa-miR-887-3p, miR-6752-5p is hsa-miR-6752-5p, miR-6724-5p is hsa-miR-6724-5p, miR-6757-5p is hsa-miR-6757-5p, miR-4448 is hsa-miR-4448, miR-671-5p is hsa-miR-671-5p, miR-3178 is hsa-miR-3178, miR-4725-3p is hsa-miR-4725-3p, miR-940 is hsa-miR-940, miR-6789-5p is hsa-miR-6789-5p, miR-4484 is hsa-miR-4484, miR-4634 is hsa-miR-4634, miR-4745-5p is hsa-miR-4745-5p, miR-4730 is hsa-miR-4730, miR-6803-5p is hsa-miR-6803-5p, miR-6798-5p is hsa-miR-6798-5p, miR-3648 is hsa-miR-3648, miR-4783-3p is hsa-miR-4783-3p, and miR-6836-3p is hsa-miR-6836-3p.

(13) The device according to (11) or (12), wherein the nucleic acid is a polynucleotide selected from the group consisting of the following polynucleotides (a) to (e):

(a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 167 and 714 to 729, (c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and (e) a polynucleotide hybridizing under stringent conditions to any of the polynucleotides (a) to (d).

(14) The device according to any of (11) to (13), wherein the device further comprises nucleic acid(s) capable of specifically binding to at least one or more polynucleotide(s) selected from the group consisting of other liver cancer markers: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a.

(15) The device according to (14), wherein miR-23b-3p is hsa-miR-23b-3p, miR-23a-3p is hsa-miR-23a-3p, miR-625-3p is hsa-miR-625-3p, miR-1228-3p is hsa-miR-1228-3p, miR-614 is hsa-miR-614, miR-1913 is hsa-miR-1913, miR-92a-2-5p is hsa-miR-92a-2-5p, miR-187-5p is hsa-miR-187-5p, miR-16-5p is hsa-miR-16-5p, miR-92b-3p is hsa-miR-92b-3p, miR-150-3p is hsa-miR-150-3p, miR-564 is hsa-miR-564, miR-125a-3p is hsa-miR-125a-3p, miR-92b-5p is hsa-miR-92b-5p, miR-92a-3p is hsa-miR-92a-3p, and miR-663a is hsa-miR-663a.

(16) The device according to (14) or (15), wherein the nucleic acid is a polynucleotide selected from the group consisting of the following polynucleotides (f) to (j):

(f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 168 to 183, (h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 168 to 183 or a nucleotide sequence derived from the nucleotide sequence by the replacement of u with t, and (j) a polynucleotide hybridizing under stringent conditions to any of the polynucleotides (f) to (i).

(17) The device according to any of (11) to (16), wherein the device further comprises nucleic acid(s) capable of specifically binding to at least one or more polynucleotide(s) selected from the group consisting of other liver cancer markers: miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090.

(18) The device according to (17), wherein miR-4688 is hsa-miR-4688, miR-4648 is hsa-miR-4648, miR-6085 is hsa-miR-6085, miR-6126 is hsa-miR-6126, miR-6880-5p is hsa-miR-6880-5p, miR-328-5p is hsa-miR-328-5p, miR-6768-5p is hsa-miR-6768-5p, miR-3180 is hsa-miR-3180, miR-6087 is hsa-miR-6087, miR-1273g-3p is hsa-miR-1273g-3p, miR-1225-5p is hsa-miR-1225-5p, miR-3196 is hsa-miR-3196, miR-4695-5p is hsa-miR-4695-5p, miR-6732-5p is hsa-miR-6732-5p, miR-638 is hsa-miR-638, miR-6813-5p is hsa-miR-6813-5p, miR-665 is hsa-miR-665, miR-486-3p is hsa-miR-486-3p, miR-4466 is hsa-miR-4466, miR-30c-1-3p is hsa-miR-30c-1-3p, miR-3621 is hsa-miR-3621, miR-6743-5p is hsa-miR-6743-5p, miR-4298 is hsa-miR-4298, miR-4741 is hsa-miR-4741, miR-3619-3p is hsa-miR-3619-3p, miR-6824-5p is hsa-miR-6824-5p, miR-5698 is hsa-miR-5698, miR-371a-5p is hsa-miR-371a-5p, miR-4488 is hsa-miR-4488, miR-1233-5p is hsa-miR-1233-5p, miR-4723-5p is hsa-miR-4723-5p, miR-24-3p is hsa-miR-24-3p, miR-1238-5p is hsa-miR-1238-5p, miR-4442 is hsa-miR-4442, miR-3928-3p is hsa-miR-3928-3p, miR-6716-5p is hsa-miR-6716-5p, miR-6089 is hsa-miR-6089, miR-6124 is hsa-miR-6124, miR-6778-5p is hsa-miR-6778-5p, miR-557 is hsa-miR-557, and miR-6090 is hsa-miR-6090.

(19) The device according to (17) or (18), wherein the nucleic acid is a polynucleotide selected from the group consisting of the following polynucleotides (k) to (o):

(k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 184 to 224, (m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 184 to 224 or a nucleotide sequence derived from the nucleotide sequence by the replacement of u with t, and (o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the liver cancer markers according to (11) or (12).

(23) A method for detecting liver cancer, comprising measuring an expression level of a target nucleic acid in a sample of a subject using the kit according to any one of (1) to (10) or the device according to any one of (11) to (22); and evaluating in vitro whether or not the subject has liver cancer using the measured expression level and a control expression level for a healthy subject measured in the same way.

(24) The method according to (23), wherein the subject is a human.

(25) The method according to (23) or (24), wherein the sample is blood, serum, or plasma.

Definition of Term

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid, including any of RNA, DNA, and RNA/DNA (chimera). The DNA includes any of cDNA, genomic DNA, and synthetic DNA. The RNA includes all of total RNA, mRNA, rRNA, miRNA, siRNA, snoRNA, snRNA, non-coding RNA and synthetic RNA. The "synthetic DNA" and the "synthetic RNA" used herein refer to DNA and RNA artificially prepared using, for example, an automated nucleic acid synthesizer, on the basis of predetermined nucleotide sequences (which may be any of natural and non-natural sequences). The "non-natural sequence" used herein is intended to be used in a broad sense and includes, for example, a sequence containing substitution, deletion, insertion, and/or addition of one or more nucleotide(s) (i.e., a variant sequence) and a sequence containing one or more modified nucleotide(s) (i.e., a modified sequence), which are different from the natural sequence. As used herein, the term "polynucleotide" is used interchangeably with the term "nucleic acid."

The term "fragment" used herein is a polynucleotide having a nucleotide sequence having a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus strand (or a sense strand) or a complementary strand (or an antisense strand) constituting the duplex. The gene is not particularly limited by its length.

Thus, the "gene" used herein includes all of double-stranded DNA including human genomic DNA, single-stranded DNA (plus strand), single-stranded DNA having a sequence complementary to the plus strand (complementary strand) including cDNA, microRNA (miRNA), and their fragments, and transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 765 or a nucleotide sequence derived from the nucleotide sequence by the replacement of u with t. The "gene" is not particularly limited by its functional region and can contain, for example, an expression regulatory region, a coding region, an exon, or an intron. The "gene" may be contained in a cell or may exist alone after being released into the outside of a cell. Alternatively, the "gene" may be in a state enclosed in a vesicle called exosome.

The term "exosome" used herein is a vesicle that is delimited by a lipid bilayer and secreted from a cell. The exosome is derived from a multivesicular endosome and may incorporate biomaterials such as "gene(s)" (e.g., RNA or DNA) or protein(s) when released into an extracellular environment. The exosome is known to be contained in a body fluid such as blood, serum, plasma, serum, or lymph.

The term "transcript" used herein refers to RNA synthesized from the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including an expression regulatory region, a coding region, an exon, or an intron.

The term "microRNA (miRNA)" used herein is intended to mean a 15- to 25-nucleotide non-coding RNA that is transcribed as an RNA precursor having a hairpin-like structure, cleaved by a dsRNA-cleaving enzyme which has RNase III cleavage activity, and integrated into a protein complex called RISC, and involved in the suppression of translation of mRNA, unless otherwise specified. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 765. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship of A:T (U) and G:C base pairs with the full-length sequence of a polynucleotide consisting of a nucleotide sequence defined by any of SEQ ID NOs: 1 to 765 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" is mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 765 or a nucleotide sequence derived from the nucleotide sequence by the replacement of u with t, or a partial sequence thereof, a variant that exhibits percent (%) identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

As used herein, the "nucleic acid" capable of specifically binding to a polynucleotide selected from the group of the miRNAs described above which are the liver cancer markers is a synthesized or prepared nucleic acid and specifically includes a "nucleic acid probe" or a "primer". The "nucleic acid" is utilized directly or indirectly for detecting the presence or absence of liver cancer in a subject, for diagnosing the presence or absence of liver cancer, the severity of liver cancer, the presence or absence of amelioration or the degree of amelioration of liver cancer, or the therapeutic sensitivity of liver cancer, or for screening for a candidate substance useful in the prevention, amelioration, or treatment of liver cancer. The "nucleic acid" includes a nucleotide, an oligonucleotide, and a polynucleotide capable of specifically recognizing and binding to a transcript represented by any of SEQ ID NOs: 1 to 765 or a synthetic cDNA nucleic acid thereof in vivo, particularly, in a sample such as a body fluid (e.g., blood or urine), in relation to the development of liver cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection" or "decision support". The term "evaluation" used herein is meant to include diagnosis or evaluation support on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "liver cancer" used herein means "primary liver cancer", which develops primarily in the liver. The liver cancer includes, for example, "hepatocellular carcinoma" and "combined hepatocellular and cholangiocellular carcinoma" caused by the malignant transformation of cells of the liver.

The term "P" or "P value" used herein refers to a probability at which a more extreme statistic than that actually calculated from data under null hypothesis is observed in a statistical test. Thus, smaller "P" or "P value" is regarded as being more significant difference between subjects to be compared.

The term "sensitivity" used herein means a value of (the number of true positives)/(the number of true positives+the number of false negatives). High sensitivity allows liver cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being liver cancer patients, leading to reduction in burden on patients and reduction in medical expense.

The term "accuracy" used herein means a value of (the number of true positives+the number of true negatives)/(the total number of cases). The accuracy indicates the ratio of samples that are correctly identified in the discriminant results to all samples, and serves as a primary index for evaluating detection performance.

As used herein, the "sample" that is subjected to determination, detection, or diagnosis refers to a tissue and a biological material in which the expression of the gene of the present invention varies as liver cancer develops, as liver cancer progresses, or as therapeutic effects on liver cancer are exerted. Specifically, the "sample" refers to a hepatic tissue, a perihepatic vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-1343-3p gene" or "hsa-miR-1343-3p" used herein includes the hsa-miR-1343-3p gene (miRBase Accession No. MIMAT0019776) described in SEQ ID NO: 1, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 225) having a hairpin-like structure is known as a precursor of "hsa-miR-1343-3p".

The term "hsa-miR-6726-5p gene" or "hsa-miR-6726-5p" used herein includes the hsa-miR-6726-5p gene (miRBase Accession No. MIMAT0027353) described in SEQ ID NO: 2, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 226) having a hairpin-like structure is known as a precursor of "hsa-miR-6726-5p".

The term "hsa-miR-6515-3p gene" or "hsa-miR-6515-3p" used herein includes the hsa-miR-6515-3p gene (miRBase Accession No. MIMAT0025487) described in SEQ ID NO: 3, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 227) having a hairpin-like structure is known as a precursor of "hsa-miR-6515-3p".

The term "hsa-miR-4651 gene" or "hsa-miR-4651" used herein includes the hsa-miR-4651 gene (miRBase Accession No. MIMAT0019715) described in SEQ ID NO: 4, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 228) having a hairpin-like structure is known as a precursor of "hsa-miR-4651".

The term "hsa-miR-4257 gene" or "hsa-miR-4257" used herein includes the hsa-miR-4257 gene (miRBase Accession No. MIMAT0016878) described in SEQ ID NO: 5, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 229) having a hairpin-like structure is known as a precursor of "hsa-miR-4257".

The term "hsa-miR-3188 gene" or "hsa-miR-3188" used herein includes the hsa-miR-3188 gene (miRBase Accession No. MIMAT0015070) described in SEQ ID NO: 6, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 230) having a hairpin-like structure is known as a precursor of "hsa-miR-3188".

The term "hsa-miR-6131 gene" or "hsa-miR-6131" used herein includes the hsa-miR-6131 gene (miRBase Accession No. MIMAT0024615) described in SEQ ID NO: 7, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 231) having a hairpin-like structure is known as a precursor of "hsa-miR-6131".

The term "hsa-miR-6766-3p gene" or "hsa-miR-6766-3p" used herein includes the hsa-miR-6766-3p gene (miRBase Accession No. MIMAT0027433) described in SEQ ID NO: 8, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 232) having a hairpin-like structure is known as a precursor of "hsa-miR-6766-3p".

The term "hsa-miR-7641 gene" or "hsa-miR-7641" used herein includes the hsa-miR-7641 gene (miRBase Accession No. MIMAT0029782) described in SEQ ID NO: 9, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1" and "hsa-mir-7641-2" (miRBase Accession Nos. MI0024975 and MI0024976, SEQ ID NOs: 233 and 234) having a hairpin-like structure are known as precursors of "hsa-miR-7641".

The term "hsa-miR-1249 gene" or "hsa-miR-1249" used herein includes the hsa-miR-1249 gene (miRBase Accession No. MIMAT0005901) described in SEQ ID NO: 10, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 235) having a hairpin-like structure is known as a precursor of "hsa-miR-1249".

The term "hsa-miR-3679-3p gene" or "hsa-miR-3679-3p" used herein includes the hsa-miR-3679-3p gene (miRBase Accession No. MIMAT0018105) described in SEQ ID NO: 11, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 236) having a hairpin-like structure is known as a precursor of "hsa-miR-3679-3p".

The term "hsa-miR-6787-5p gene" or "hsa-miR-6787-5p" used herein includes the hsa-miR-6787-5p gene (miRBase Accession No. MIMAT0027474) described in SEQ ID NO: 12, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 237) having a hairpin-like structure is known as a precursor of "hsa-miR-6787-5p".

The term "hsa-miR-4454 gene" or "hsa-miR-4454" used herein includes the hsa-miR-4454 gene (miRBase Accession No. MIMAT0018976) described in SEQ ID NO: 13, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 238) having a hairpin-like structure is known as a precursor of "hsa-miR-4454".

The term "hsa-miR-3135b gene" or "hsa-miR-3135b" used herein includes the hsa-miR-3135b gene (miRBase Accession No. MIMAT0018985) described in SEQ ID NO: 14, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 239) having a hairpin-like structure is known as a precursor of "hsa-miR-3135b".

The term "hsa-miR-6765-3p gene" or "hsa-miR-6765-3p" used herein includes the hsa-miR-6765-3p gene (miRBase Accession No. MIMAT0027431) described in SEQ ID NO: 15, a homolog or an ortholog of a different organism species, and the like. The hsa-miR-6765-3p p. 1634-1645. Also, "hsa-mir-6765" (miRBase Accession No. MI0022610, SEQ ID NO: 240) having a hairpin-like structure is known as a precursor of "hsa-miR-6765-3p".

The term "hsa-miR-7975 gene" or "hsa-miR-7975" used herein includes the hsa-miR-7975 gene (miRBase Accession No. MIMAT0031178) described in SEQ ID NO: 16, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 241) having a hairpin-like structure is known as a precursor of "hsa-miR-7975".

The term "hsa-miR-204-3p gene" or "hsa-miR-204-3p" used herein includes the hsa-miR-204-3p gene (miRBase Accession No. MIMAT0022693) described in SEQ ID NO: 17, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 242) having a hairpin-like structure is known as a precursor of "hsa-miR-204-3p".

The term "hsa-miR-7977 gene" or "hsa-miR-7977" used herein includes the hsa-miR-7977 gene (miRBase Accession No. MIMAT0031180) described in SEQ ID NO: 18, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 243) having a hairpin-like structure is known as a precursor of "hsa-miR-7977".

The term "hsa-miR-7110-5p gene" or "hsa-miR-7110-5p" used herein includes the hsa-miR-7110-5p gene (miRBase Accession No. MIMAT0028117) described in SEQ ID NO: 19, a homolog or an ortholog of a different organism species, and the like. The hsa-miR-7110-5p p. 1634-1645. Also, "hsa-mir-7110" (miRBase Accession No. MI0022961, SEQ ID NO: 244) having a hairpin-like structure is known as a precursor of "hsa-miR-7110-5p".

The term "hsa-miR-6717-5p gene" or "hsa-miR-6717-5p" used herein includes the hsa-miR-6717-5p gene (miRBase Accession No. MIMAT0025846) described in SEQ ID NO: 20, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 245) having a hairpin-like structure is known as a precursor of "hsa-miR-6717-5p".

The term "hsa-miR-6870-5p gene" or "hsa-miR-6870-5p" used herein includes the hsa-miR-6870-5p gene (miRBase Accession No. MIMAT0027640) described in SEQ ID NO: 21, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 246) having a hairpin-like structure is known as a precursor of "hsa-miR-6870-5p".

The term "hsa-miR-663b gene" or "hsa-miR-663b" used herein includes the hsa-miR-663b gene (miRBase Accession No. MIMAT0005867) described in SEQ ID NO: 22, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 247) having a hairpin-like structure is known as a precursor of "hsa-miR-663b".

The term "hsa-miR-6875-5p gene" or "hsa-miR-6875-5p" used herein includes the hsa-miR-6875-5p gene (miRBase Accession No. MIMAT0027650) described in SEQ ID NO: 23, a homolog or an ortholog of a different organism species, and the like. The hsa-miR-6875-5p p. 1634-1645. Also, "hsa-mir-6875" (miRBase Accession No. MI0022722, SEQ ID NO: 248) having a hairpin-like structure is known as a precursor of "hsa-miR-6875-5p".

The term "hsa-miR-8072 gene" or "hsa-miR-8072" used herein includes the hsa-miR-8072 gene (miRBase Accession No. MIMAT0030999) described in SEQ ID NO: 24, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 249) having a hairpin-like structure is known as a precursor of "hsa-miR-8072".

The term "hsa-miR-6816-5p gene" or "hsa-miR-6816-5p" used herein includes the hsa-miR-6816-5p gene (miRBase Accession No. MIMAT0027532) described in SEQ ID NO: 25, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 250) having a hairpin-like structure is known as a precursor of "hsa-miR-6816-5p".

The term "hsa-miR-4281 gene" or "hsa-miR-4281" used herein includes the hsa-miR-4281 gene (miRBase Accession No. MIMAT0016907) described in SEQ ID NO: 26, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 251) having a hairpin-like structure is known as a precursor of "hsa-miR-4281".

The term "hsa-miR-6729-5p gene" or "hsa-miR-6729-5p" used herein includes the hsa-miR-6729-5p gene (miRBase Accession No. MIMAT0027359) described in SEQ ID NO: 27, a homolog or an ortholog of a different organism species, and the like. The hsa-miR-6729-5p p. 1634-1645. Also, "hsa-mir-6729" (miRBase Accession No. MI0022574, SEQ ID NO: 252) having a hairpin-like structure is known as a precursor of "hsa-miR-6729-5p".

The term "hsa-miR-8069 gene" or "hsa-miR-8069" used herein includes the hsa-miR-8069 gene (miRBase Accession No. MIMAT0030996) described in SEQ ID NO: 28, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 253) having a hairpin-like structure is known as a precursor of "hsa-miR-8069".

The term "hsa-miR-4706 gene" or "hsa-miR-4706" used herein includes the hsa-miR-4706 gene (miRBase Accession No. MIMAT0019806) described in SEQ ID NO: 29, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 254) having a hairpin-like structure is known as a precursor of "hsa-miR-4706".

The term "hsa-miR-7108-5p gene" or "hsa-miR-7108-5p" used herein includes the hsa-miR-7108-5p gene (miRBase Accession No. MIMAT0028113) described in SEQ ID NO: 30, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 255) having a hairpin-like structure is known as a precursor of "hsa-miR-7108-5p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 31, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 256) having a hairpin-like structure is known as a precursor of "hsa-miR-4433b-3p".

The term "hsa-miR-6893-5p gene" or "hsa-miR-6893-5p" used herein includes the hsa-miR-6893-5p gene (miRBase Accession No. MIMAT0027686) described in SEQ ID NO: 32, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 257) having a hairpin-like structure is known as a precursor of "hsa-miR-6893-5p".

The term "hsa-miR-6857-5p gene" or "hsa-miR-6857-5p" used herein includes the hsa-miR-6857-5p gene (miRBase Accession No. MIMAT0027614) described in SEQ ID NO: 33, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 258) having a hairpin-like structure is known as a precursor of "hsa-miR-6857-5p".

The term "hsa-miR-1227-5p gene" or "hsa-miR-1227-5p" used herein includes the hsa-miR-1227-5p gene (miRBase Accession No. MIMAT0022941) described in SEQ ID NO: 34, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 259) having a hairpin-like structure is known as a precursor of "hsa-miR-1227-5p".

The term "hsa-miR-6741-5p gene" or "hsa-miR-6741-5p" used herein includes the hsa-miR-6741-5p gene (miRBase Accession No. MIMAT0027383) described in SEQ ID NO: 35, a homolog or an ortholog of a different organism species, and the like. The hsa-miR-6741-5p p. 1634-1645. Also, "hsa-mir-6741" (miRBase Accession No. MI0022586, SEQ ID NO: 260) having a hairpin-like structure is known as a precursor of "hsa-miR-6741-5p".

The term "hsa-miR-451a gene" or "hsa-miR-451a" used herein includes the hsa-miR-451a gene (miRBase Accession No. MIMAT0001631) described in SEQ ID NO: 36, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 261) having a hairpin-like structure is known as a precursor of "hsa-miR-451a".

The term "hsa-miR-8063 gene" or "hsa-miR-8063" used herein includes the hsa-miR-8063 gene (miRBase Accession No. MIMAT0030990) described in SEQ ID NO: 37, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 262) having a hairpin-like structure is known as a precursor of "hsa-miR-8063".

The term "hsa-miR-3622a-5p gene" or "hsa-miR-3622a-5p" used herein includes the hsa-miR-3622a-5p gene (miRBase Accession No. MIMAT0018003) described in SEQ ID NO: 38, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 263) having a hairpin-like structure is known as a precursor of "hsa-miR-3622a-5p".

The term "hsa-miR-615-5p gene" or "hsa-miR-615-5p" used herein includes the hsa-miR-615-5p gene (miRBase Accession No. MIMAT0004804) described in SEQ ID NO: 39, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 264) having a hairpin-like structure is known as a precursor of "hsa-miR-615-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 40, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 265) having a hairpin-like structure is known as a precursor of "hsa-miR-128-1-5p".

The term "hsa-miR-6825-5p gene" or "hsa-miR-6825-5p" used herein includes the hsa-miR-6825-5p gene (miRBase Accession No. MIMAT0027550) described in SEQ ID NO: 41, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 266) having a hairpin-like structure is known as a precursor of "hsa-miR-6825-5p".

The term "hsa-miR-1260b gene" or "hsa-miR-1260b" used herein includes the hsa-miR-1260b gene (miRBase Accession No. MIMAT0015041) described in SEQ ID NO: 42, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No.

MI0014197, SEQ ID NO: 267) having a hairpin-like structure is known as a precursor of "hsa-miR-1260b".

The term "hsa-miR-4433-3p gene" or "hsa-miR-4433-3p" used herein includes the hsa-miR-4433-3p gene (miRBase Accession No. MIMAT0018949) described in SEQ ID NO: 43, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 268) having a hairpin-like structure is known as a precursor of "hsa-miR-4433-3p".

The term "hsa-miR-4665-5p gene" or "hsa-miR-4665-5p" used herein includes the hsa-miR-4665-5p gene (miRBase Accession No. MIMAT0019739) described in SEQ ID NO: 44, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 269) having a hairpin-like structure is known as a precursor of "hsa-miR-4665-5p".

The term "hsa-miR-7845-5p gene" or "hsa-miR-7845-5p" used herein includes the hsa-miR-7845-5p gene (miRBase Accession No. MIMAT0030420) described in SEQ ID NO: 45, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 270) having a hairpin-like structure is known as a precursor of "hsa-miR-7845-5p".

The term "hsa-miR-1908-5p gene" or "hsa-miR-1908-5p" used herein includes the hsa-miR-1908-5p gene (miRBase Accession No. MIMAT0007881) described in SEQ ID NO: 46, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 271) having a hairpin-like structure is known as a precursor of "hsa-miR-1908-5p".

The term "hsa-miR-6840-3p gene" or "hsa-miR-6840-3p" used herein includes the hsa-miR-6840-3p gene (miRBase Accession No. MIMAT0027583) described in SEQ ID NO: 47, a homolog or an ortholog of a different organism species, and the like. The hsa-miR-6840-3p p. 1634-1645. Also, "hsa-mir-6840" (miRBase Accession No. MI0022686, SEQ ID NO: 272) having a hairpin-like structure is known as a precursor of "hsa-miR-6840-3p".

The term "hsa-miR-6765-5p gene" or "hsa-miR-6765-5p" used herein includes the hsa-miR-6765-5p gene (miRBase Accession No. MIMAT0027430) described in SEQ ID NO: 48, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 240) having a hairpin-like structure is known as a precursor of "hsa-miR-6765-5p".

The term "hsa-miR-296-5p gene" or "hsa-miR-296-5p" used herein includes the hsa-miR-296-5p gene (miRBase Accession No. MIMAT0000690) described in SEQ ID NO: 49, a homolog or an ortholog of a different organism species, and the like. The hsa-miR-296-5p gene can be obtained by a method described in Houbaviy H B et al., 2003, Dev Cell, Vol. 5, p. 351-358. Also, "hsa-mir-296" (miRBase Accession No. MI0000747, SEQ ID NO: 273) having a hairpin-like structure is known as a precursor of "hsa-miR-296-5p".

The term "hsa-miR-3675-3p gene" or "hsa-miR-3675-3p" used herein includes the hsa-miR-3675-3p gene (miRBase Accession No. MIMAT0018099) described in SEQ ID NO: 50, a homolog or an ortholog of a different organism species, and the like. The hsa-miR-3675-3p gene can be obtained by a method described in Vaz C et al., 2010, BMC Genomics, Vol. 11, p. 288. Also, "hsa-mir-3675" (miRBase Accession No. MI0016076, SEQ ID NO: 274) having a hairpin-like structure is known as a precursor of "hsa-miR-3675-3p".

The term "hsa-miR-6781-5p gene" or "hsa-miR-6781-5p" used herein includes the hsa-miR-6781-5p gene (miRBase Accession No. MIMAT0027462) described in SEQ ID NO: 51, a homolog or an ortholog of a different organism species, and the like. The hsa-miR-6781-5p p. 1634-1645. Also, "hsa-mir-6781" (miRBase Accession No. MI0022626, SEQ ID NO: 275) having a hairpin-like structure is known as a precursor of "hsa-miR-6781-5p".

The term "hsa-miR-423-5p gene" or "hsa-miR-423-5p" used herein includes the hsa-miR-423-5p gene (miRBase Accession No. MIMAT0004748) described in SEQ ID NO: 52, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 276) having a hairpin-like structure is known as a precursor of "hsa-miR-423-5p".

The term "hsa-miR-3663-3p gene" or "hsa-miR-3663-3p" used herein includes the hsa-miR-3663-3p gene (miRBase Accession No. MIMAT0018085) described in SEQ ID NO: 53, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 277) having a hairpin-like structure is known as a precursor of "hsa-miR-3663-3p".

The term "hsa-miR-6784-5p gene" or "hsa-miR-6784-5p" used herein includes the hsa-miR-6784-5p gene (miRBase Accession No. MIMAT0027468) described in SEQ ID NO: 54, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 278) having a hairpin-like structure is known as a precursor of "hsa-miR-6784-5p".

The term "hsa-miR-6749-5p gene" or "hsa-miR-6749-5p" used herein includes the hsa-miR-6749-5p gene (miRBase Accession No. MIMAT0027398) described in SEQ ID NO: 55, a homolog or an ortholog of a different organism species, and the like. The hsa-miR-6749-5p p. 1634-1645. Also, "hsa-mir-6749" (miRBase Accession No. MI0022594, SEQ ID NO: 279) having a hairpin-like structure is known as a precursor of "hsa-miR-6749-5p".

The term "hsa-miR-1231 gene" or "hsa-miR-1231" used herein includes the hsa-miR-1231 gene (miRBase Accession No. MIMAT0005586) described in SEQ ID NO: 56, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 280) having a hairpin-like structure is known as a precursor of "hsa-miR-1231".

The term "hsa-miR-4746-3p gene" or "hsa-miR-4746-3p" used herein includes the hsa-miR-4746-3p gene (miRBase Accession No. MIMAT0019881) described in SEQ ID NO: 57, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 281) having a hairpin-like structure is known as a precursor of "hsa-miR-4746-3p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 58, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 282) having a hairpin-like structure is known as a precursor of "hsa-miR-6780b-5p".

The term "hsa-miR-4758-5p gene" or "hsa-miR-4758-5p" used herein includes the hsa-miR-4758-5p gene (miRBase Accession No. MIMAT0019903) described in SEQ ID NO: 59, a homolog or an ortholog of a different organism species, and the like. The hsa-miR-4758-5p 78-86. Also, "hsa-mir-4758" (miRBase Accession No. MI0017399, SEQ ID NO: 283) having a hairpin-like structure is known as a precursor of "hsa-miR-4758-5p".

The term "hsa-miR-3679-5p gene" or "hsa-miR-3679-5p" used herein includes the hsa-miR-3679-5p gene (miRBase Accession No. MIMAT0018104) described in SEQ ID NO: 60, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 236) having a hairpin-like structure is known as a precursor of "hsa-miR-3679-5p".

The term "hsa-miR-3184-5p gene" or "hsa-miR-3184-5p" used herein includes the hsa-miR-3184-5p gene (miRBase Accession No. MIMAT0015064) described in SEQ ID NO: 61, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 284) having a hairpin-like structure is known as a precursor of "hsa-miR-3184-5p".

The term "hsa-miR-6125 gene" or "hsa-miR-6125" used herein includes the hsa-miR-6125 gene (miRBase Accession No. MIMAT0024598) described in SEQ ID NO: 62, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 285) having a hairpin-like structure is known as a precursor of "hsa-miR-6125".

The term "hsa-miR-6721-5p gene" or "hsa-miR-6721-5p" used herein includes the hsa-miR-6721-5p gene (miRBase Accession No. MIMAT0025852) described in SEQ ID NO: 63, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 286) having a hairpin-like structure is known as a precursor of "hsa-miR-6721-5p".

The term "hsa-miR-6791-5p gene" or "hsa-miR-6791-5p" used herein includes the hsa-miR-6791-5p gene (miRBase Accession No. MIMAT0027482) described in SEQ ID NO: 64, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 287) having a hairpin-like structure is known as a precursor of "hsa-miR-6791-5p".

The term "hsa-miR-3185 gene" or "hsa-miR-3185" used herein includes the hsa-miR-3185 gene (miRBase Accession No. MIMAT0015065) described in SEQ ID NO: 65, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 288) having a hairpin-like structure is known as a precursor of "hsa-miR-3185".

The term "hsa-miR-1260a gene" or "hsa-miR-1260a" used herein includes the hsa-miR-1260a gene (miRBase Accession No. MIMAT0005911) described in SEQ ID NO: 66, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 289) having a hairpin-like structure is known as a precursor of "hsa-miR-1260a".

The term "hsa-miR-3197 gene" or "hsa-miR-3197" used herein includes the hsa-miR-3197 gene (miRBase Accession No. MIMAT0015082) described in SEQ ID NO: 67, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 290) having a hairpin-like structure is known as a precursor of "hsa-miR-3197".

The term "hsa-miR-6845-5p gene" or "hsa-miR-6845-5p" used herein includes the hsa-miR-6845-5p gene (miRBase Accession No. MIMAT0027590) described in SEQ ID NO: 68, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 291) having a hairpin-like structure is known as a precursor of "hsa-miR-6845-5p".

The term "hsa-miR-6887-5p gene" or "hsa-miR-6887-5p" used herein includes the hsa-miR-6887-5p gene (miRBase Accession No. MIMAT0027674) described in SEQ ID NO: 69, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 292) having a hairpin-like structure is known as a precursor of "hsa-miR-6887-5p".

The term "hsa-miR-6738-5p gene" or "hsa-miR-6738-5p" used herein includes the hsa-miR-6738-5p gene (miRBase Accession No. MIMAT0027377) described in SEQ ID NO: 70, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 293) having a hairpin-like structure is known as a precursor of "hsa-miR-6738-5p".

The term "hsa-miR-6872-3p gene" or "hsa-miR-6872-3p" used herein includes the hsa-miR-6872-3p gene (miRBase Accession No. MIMAT0027645) described in SEQ ID NO: 71, a homolog or an ortholog of a different organism species, and the like. The hsa-miR-6872-3p p. 1634-1645. Also, "hsa-mir-6872" (miRBase Accession No. MI0022719, SEQ ID NO: 294) having a hairpin-like structure is known as a precursor of "hsa-miR-6872-3p".

The term "hsa-miR-4497 gene" or "hsa-miR-4497" used herein includes the hsa-miR-4497 gene (miRBase Accession No. MIMAT0019032) described in SEQ ID NO: 72, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 295) having a hairpin-like structure is known as a precursor of "hsa-miR-4497".

The term "hsa-miR-1229-5p gene" or "hsa-miR-1229-5p" used herein includes the hsa-miR-1229-5p gene (miRBase Accession No. MIMAT0022942) described in SEQ ID NO: 73, a homolog or an ortholog of a different organism species, and the like. The hsa-miR-1229-5p gene can be obtained by a method described in Berezikov E et al., 2007, Mol Cell, Vol. 28, p. 328-336. Also, "hsa-mir-1229" (miRBase Accession No. MI0006319, SEQ ID NO: 296) having a hairpin-like structure is known as a precursor of "hsa-miR-1229-5p".

The term "hsa-miR-6820-5p gene" or "hsa-miR-6820-5p" used herein includes the hsa-miR-6820-5p gene (miRBase Accession No. MIMAT0027540) described in SEQ ID NO: 74, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 297) having a hairpin-like structure is known as a precursor of "hsa-miR-6820-5p".

The term "hsa-miR-6777-5p gene" or "hsa-miR-6777-5p" used herein includes the hsa-miR-6777-5p gene (miRBase Accession No. MIMAT0027454) described in SEQ ID NO: 75, a homolog or an ortholog of a different organism species, and the like. The hsa-miR-6777-5p p. 1634-1645. Also, "hsa-mir-6777" (miRBase Accession No. MI0022622, SEQ ID NO: 298) having a hairpin-like structure is known as a precursor of "hsa-miR-6777-5p".

The term "hsa-miR-3917 gene" or "hsa-miR-3917" used herein includes the hsa-miR-3917 gene (miRBase Accession No. MIMAT0018191) described in SEQ ID NO: 76, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 299) having a hairpin-like structure is known as a precursor of "hsa-miR-3917".

The term "hsa-miR-5787 gene" or "hsa-miR-5787" used herein includes the hsa-miR-5787 gene (miRBase Accession No. MIMAT0023252) described in SEQ ID NO: 77, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 300) having a hairpin-like structure is known as a precursor of "hsa-miR-5787".

The term "hsa-miR-4286 gene" or "hsa-miR-4286" used herein includes the hsa-miR-4286 gene (miRBase Accession No. MIMAT0016916) described in SEQ ID NO: 78, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 301) having a hairpin-like structure is known as a precursor of "hsa-miR-4286".

The term "hsa-miR-6877-5p gene" or "hsa-miR-6877-5p" used herein includes the hsa-miR-6877-5p gene (miRBase Accession No. MIMAT0027654) described in SEQ ID NO: 79, a homolog or an ortholog of a different organism species, and the like. The hsa-miR-6877-5p p. 1634-1645. Also, "hsa-mir-6877" (miRBase Accession No. MI0022724, SEQ ID NO: 302) having a hairpin-like structure is known as a precursor of "hsa-miR-6877-5p".

The term "hsa-miR-1225-3p gene" or "hsa-miR-1225-3p" used herein includes the hsa-miR-1225-3p gene (miRBase Accession No. MIMAT0005573) described in SEQ ID NO: 80, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 303) having a hairpin-like structure is known as a precursor of "hsa-miR-1225-3p".

The term "hsa-miR-6088 gene" or "hsa-miR-6088" used herein includes the hsa-miR-6088 gene (miRBase Accession No. MIMAT0023713) described in SEQ ID NO: 81, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 304) having a hairpin-like structure is known as a precursor of "hsa-miR-6088".

The term "hsa-miR-6800-5p gene" or "hsa-miR-6800-5p" used herein includes the hsa-miR-6800-5p gene (miRBase Accession No. MIMAT0027500) described in SEQ ID NO: 82, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 305) having a hairpin-like structure is known as a precursor of "hsa-miR-6800-5p".

The term "hsa-miR-1246 gene" or "hsa-miR-1246" used herein includes the hsa-miR-1246 gene (miRBase Accession No. MIMAT0005898) described in SEQ ID NO: 83, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 306) having a hairpin-like structure is known as a precursor of "hsa-miR-1246".

The term "hsa-miR-4467 gene" or "hsa-miR-4467" used herein includes the hsa-miR-4467 gene (miRBase Accession No. MIMAT0018994) described in SEQ ID NO: 84, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 307) having a hairpin-like structure is known as a precursor of "hsa-miR-4467".

The term "hsa-miR-4419b gene" or "hsa-miR-4419b" used herein includes the hsa-miR-4419b gene (miRBase Accession No. MIMAT0019034) described in SEQ ID NO: 85, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 308) having a hairpin-like structure is known as a precursor of "hsa-miR-4419b".

The term "hsa-miR-1914-3p gene" or "hsa-miR-1914-3p" used herein includes the hsa-miR-1914-3p gene (miRBase Accession No. MIMAT0007890) described in SEQ ID NO: 86, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 309) having a hairpin-like structure is known as a precursor of "hsa-miR-1914-3p".

The term "hsa-miR-4632-5p gene" or "hsa-miR-4632-5p" used herein includes the hsa-miR-4632-5p gene (miRBase Accession No. MIMAT0022977) described in SEQ ID NO: 87, a homolog or an ortholog of a different organism species, and the like. The hsa-miR-4632-5p 78-86. Also, "hsa-mir-4632" (miRBase Accession No. MI0017259, SEQ ID NO: 310) having a hairpin-like structure is known as a precursor of "hsa-miR-4632-5p".

The term "hsa-miR-1915-5p gene" or "hsa-miR-1915-5p" used herein includes the hsa-miR-1915-5p gene (miRBase Accession No. MIMAT0007891) described in SEQ ID NO: 88, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 311) having a hairpin-like structure is known as a precursor of "hsa-miR-1915-5p".

The term "hsa-miR-3940-5p gene" or "hsa-miR-3940-5p" used herein includes the hsa-miR-3940-5p gene (miRBase Accession No. MIMAT0019229) described in SEQ ID NO: 89, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 312) having a hairpin-like structure is known as a precursor of "hsa-miR-3940-5p".

The term "hsa-miR-1185-2-3p gene" or "hsa-miR-1185-2-3p" used herein includes the hsa-miR-1185-2-3p gene (miRBase Accession No. MIMAT0022713) described in SEQ ID NO: 90, a homolog or an ortholog of a different organism species, and the like. The hsa-miR-1185-2-3p gene can be obtained by a method described in Berezikov E et al., 2006, Genome Res, Vol. 16, p. 1289-1298. Also, "hsa-mir-1185-2" (miRBase Accession No. MI0003821, SEQ ID NO: 313) having a hairpin-like structure is known as a precursor of "hsa-miR-1185-2-3p".

The term "hsa-miR-6746-5p gene" or "hsa-miR-6746-5p" used herein includes the hsa-miR-6746-5p gene (miRBase Accession No. MIMAT0027392) described in SEQ ID NO: 91, a homolog or an ortholog of a different organism species, and the like. The hsa-miR-6746-5p p. 1634-1645. Also, "hsa-mir-6746" (miRBase Accession No. MI0022591, SEQ ID NO: 314) having a hairpin-like structure is known as a precursor of "hsa-miR-6746-5p".

The term "hsa-miR-5001-5p gene" or "hsa-miR-5001-5p" used herein includes the hsa-miR-5001-5p gene (miRBase Accession No. MIMAT0021021) described in SEQ ID NO: 92, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 315) having a hairpin-like structure is known as a precursor of "hsa-miR-5001-5p".

The term "hsa-miR-1228-5p gene" or "hsa-miR-1228-5p" used herein includes the hsa-miR-1228-5p gene (miRBase Accession No. MIMAT0005582) described in SEQ ID NO: 93, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 316) having a hairpin-like structure is known as a precursor of "hsa-miR-1228-5p".

The term "hsa-miR-5572 gene" or "hsa-miR-5572" used herein includes the hsa-miR-5572 gene (miRBase Accession No. MIMAT0022260) described in SEQ ID NO: 94, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 317) having a hairpin-like structure is known as a precursor of "hsa-miR-5572".

The term "hsa-miR-4327 gene" or "hsa-miR-4327" used herein includes the hsa-miR-4327 gene (miRBase Accession No. MIMAT0016889) described in SEQ ID NO: 95, a homolog or an ortholog of a different organism species, and the like. The hsa-miR-4327 gene can be obtained by a method described in Goff L A et al., 2009, PLoS One, Vol. 4, e7192. Also, "hsa-mir-4327" (miRBase Accession No. MI0015867, SEQ ID NO: 318) having a hairpin-like structure is known as a precursor of "hsa-miR-4327".

The term "hsa-miR-4638-5p gene" or "hsa-miR-4638-5p" used herein includes the hsa-miR-4638-5p gene (miRBase Accession No. MIMAT0019695) described in SEQ ID NO: 96, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 319) having a hairpin-like structure is known as a precursor of "hsa-miR-4638-5p".

The term "hsa-miR-6799-5p gene" or "hsa-miR-6799-5p" used herein includes the hsa-miR-6799-5p gene (miRBase Accession No. MIMAT0027498) described in SEQ ID NO: 97, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 320) having a hairpin-like structure is known as a precursor of "hsa-miR-6799-5p".

The term "hsa-miR-6861-5p gene" or "hsa-miR-6861-5p" used herein includes the hsa-miR-6861-5p gene (miRBase Accession No. MIMAT0027623) described in SEQ ID NO: 98, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 321) having a hairpin-like structure is known as a precursor of "hsa-miR-6861-5p".

The term "hsa-miR-6727-5p gene" or "hsa-miR-6727-5p" used herein includes the hsa-miR-6727-5p gene (miRBase Accession No. MIMAT0027355) described in SEQ ID NO: 99, a homolog or an ortholog of a different organism species, and the like. The hsa-miR-6727-5p p. 1634-1645. Also, "hsa-mir-6727" (miRBase Accession No. MI0022572, SEQ ID NO: 322) having a hairpin-like structure is known as a precursor of "hsa-miR-6727-5p".

The term "hsa-miR-4513 gene" or "hsa-miR-4513" used herein includes the hsa-miR-4513 gene (miRBase Accession No. MIMAT0019050) described in SEQ ID NO: 100, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 323) having a hairpin-like structure is known as a precursor of "hsa-miR-4513".

The term "hsa-miR-6805-3p gene" or "hsa-miR-6805-3p" used herein includes the hsa-miR-6805-3p gene (miRBase Accession No. MIMAT0027511) described in SEQ ID NO: 101, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 324) having a hairpin-like structure is known as a precursor of "hsa-miR-6805-3p".

The term "hsa-miR-6808-5p gene" or "hsa-miR-6808-5p" used herein includes the hsa-miR-6808-5p gene (miRBase Accession No. MIMAT0027516) described in SEQ ID NO: 102, a homolog or an ortholog of a different organism species, and the like. The hsa-miR-6808-5p gene can be obtained by a method described in Ladewig E et al., 2012, Genome Res, Vol. 22, p. 1634-1645. Also, "hsa-mir-6808" (miRBase Accession No. MI0022653, SEQ ID NO: 325) having a hairpin-like structure is known as a precursor of "hsa-miR-6808-5p".

The term "hsa-miR-4449 gene" or "hsa-miR-4449" used herein includes the hsa-miR-4449 gene (miRBase Accession No. MIMAT0018968) described in SEQ ID NO: 103, a homolog or an ortholog of a different organism species, and the like. The hsa-miR-4449 gene can be obtained by a method described in Jima D D et al., 2010, Blood, Vol. 116, e118-e127.

Also, "hsa-mir-4449" (miRBase Accession No. MI0016792, SEQ ID NO: 326) having a hairpin-like structure is known as a precursor of "hsa-miR-4449".

The term "hsa-miR-1199-5p gene" or "hsa-miR-1199-5p" used herein includes the hsa-miR-1199-5p gene (miRBase Accession No. MIMAT0031119) described in SEQ ID NO: 104, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 327) having a hairpin-like structure is known as a precursor of "hsa-miR-1199-5p".

The term "hsa-miR-1275 gene" or "hsa-miR-1275" used herein includes the hsa-miR-1275 gene (miRBase Accession No. MIMAT0005929) described in SEQ ID NO: 105, a homolog or an ortholog of a different organism species, and the like. The hsa-miR-1275 gene can be obtained by a method described in Morin R D et al., 2008, Genome Res, Vol. 18, p. 610-621. Also, "hsa-mir-1275" (miRBase Accession No. MI0006415, SEQ ID NO: 328) having a hairpin-like structure is known as a precursor of "hsa-miR-1275".

The term "hsa-miR-4792 gene" or "hsa-miR-4792" used herein includes the hsa-miR-4792 gene (miRBase Accession No. MIMAT0019964) described in SEQ ID NO: 106, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 329) having a hairpin-like structure is known as a precursor of "hsa-miR-4792".

The term "hsa-miR-4443 gene" or "hsa-miR-4443" used herein includes the hsa-miR-4443 gene (miRBase Accession No. MIMAT0018961) described in SEQ ID NO: 107, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 330) having a hairpin-like structure is known as a precursor of "hsa-miR-4443".

The term "hsa-miR-6891-5p gene" or "hsa-miR-6891-5p" used herein includes the hsa-miR-6891-5p gene (miRBase Accession No. MIMAT0027682) described in SEQ ID NO: 108, a homolog or an ortholog of a different organism species, and the like. The hsa-miR-6891-5p gene can be obtained by a method described in Ladewig E et al., 2012, Genome Res, Vol. 22, p. 1634-1645. Also, "hsa-mir-6891" (miRBase Accession No. MI0022738, SEQ ID NO: 331) having a hairpin-like structure is known as a precursor of "hsa-miR-6891-5p".

The term "hsa-miR-6826-5p gene" or "hsa-miR-6826-5p" used herein includes the hsa-miR-6826-5p gene (miRBase Accession No. MIMAT0027552) described in SEQ ID NO: 109, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 332) having a hairpin-like structure is known as a precursor of "hsa-miR-6826-5p".

The term "hsa-miR-6807-5p gene" or "hsa-miR-6807-5p" used herein includes the hsa-miR-6807-5p gene (miRBase Accession No. MIMAT0027514) described in SEQ ID NO: 110, a homolog or an ortholog of a different organism species, and the like. The hsa-miR-6807-5p gene can be obtained by a method described in Ladewig E et al., 2012, Genome Res, Vol. 22, p. 1634-1645. Also, "hsa-mir-6807" (miRBase Accession No. MI0022652, SEQ ID NO: 333) having a hairpin-like structure is known as a precursor of "hsa-miR-6807-5p".

The term "hsa-miR-7150 gene" or "hsa-miR-7150" used herein includes the hsa-miR-7150 gene (miRBase Accession No. MIMAT0028211) described in SEQ ID NO: 111, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 334) having a hairpin-like structure is known as a precursor of "hsa-miR-7150".

The term "hsa-miR-4534 gene" or "hsa-miR-4534" used herein includes the hsa-miR-4534 gene (miRBase Accession No. MIMAT0019073) described in SEQ ID NO: 112, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 335) having a hairpin-like structure is known as a precursor of "hsa-miR-4534".

The term "hsa-miR-4476 gene" or "hsa-miR-4476" used herein includes the hsa-miR-4476 gene (miRBase Accession No. MIMAT0019003) described in SEQ ID NO: 113, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 336) having a hairpin-like structure is known as a precursor of "hsa-miR-4476".

The term "hsa-miR-4649-5p gene" or "hsa-miR-4649-5p" used herein includes the hsa-miR-4649-5p gene (miRBase Accession No. MIMAT0019711) described in SEQ ID NO: 114, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 337) having a hairpin-like structure is known as a precursor of "hsa-miR-4649-5p".

The term "hsa-miR-4525 gene" or "hsa-miR-4525" used herein includes the hsa-miR-4525 gene (miRBase Accession No. MIMAT0019064) described in SEQ ID NO: 115, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 338) having a hairpin-like structure is known as a precursor of "hsa-miR-4525".

The term "hsa-miR-1915-3p gene" or "hsa-miR-1915-3p" used herein includes the hsa-miR-1915-3p gene (miRBase Accession No. MIMAT0007892) described in SEQ ID NO: 116, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 311) having a hairpin-like structure is known as a precursor of "hsa-miR-1915-3p".

The term "hsa-miR-4516 gene" or "hsa-miR-4516" used herein includes the hsa-miR-4516 gene (miRBase Accession No. MIMAT0019053) described in SEQ ID NO: 117, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 339) having a hairpin-like structure is known as a precursor of "hsa-miR-4516".

The term "hsa-miR-4417 gene" or "hsa-miR-4417" used herein includes the hsa-miR-4417 gene (miRBase Accession No. MIMAT0018929) described in SEQ ID NO: 118, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 340) having a hairpin-like structure is known as a precursor of "hsa-miR-4417".

The term "hsa-miR-642b-3p gene" or "hsa-miR-642b-3p" used herein includes the hsa-miR-642b-3p gene (miRBase Accession No. MIMAT0018444) described in SEQ ID NO: 119, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 341) having a hairpin-like structure is known as a precursor of "hsa-miR-642b-3p".

The term "hsa-miR-3141 gene" or "hsa-miR-3141" used herein includes the hsa-miR-3141 gene (miRBase Accession No. MIMAT0015010) described in SEQ ID NO: 120, a homolog or an ortholog of a different organism species, and the like. The hsa-miR-3141 gene can be obtained by a method described in Stark M S et al., 2010, PLoS One, Vol. 5, e9685. Also, "hsa-mir-3141" (miRBase Accession No. MI0014165, SEQ ID NO: 342) having a hairpin-like structure is known as a precursor of "hsa-miR-3141".

The term "hsa-miR-5100 gene" or "hsa-miR-5100" used herein includes the hsa-miR-5100 gene (miRBase Accession No. MIMAT0022259) described in SEQ ID NO: 121, a homolog or an ortholog of a different organism species, and the like. The hsa-miR-5100 gene can be obtained by a method described in Tandon M et al., 2012, Oral Dis, Vol. 18, p. 127-131. Also, "hsa-mir-5100" (miRBase Accession No. MI0019116, SEQ ID NO: 343) having a hairpin-like structure is known as a precursor of "hsa-miR-5100".

The term "hsa-miR-6848-5p gene" or "hsa-miR-6848-5p" used herein includes the hsa-miR-6848-5p gene (miRBase Accession No. MIMAT0027596) described in SEQ ID NO: 122, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 344) having a hairpin-like structure is known as a precursor of "hsa-miR-6848-5p".

The term "hsa-miR-4739 gene" or "hsa-miR-4739" used herein includes the hsa-miR-4739 gene (miRBase Accession No. MIMAT0019868) described in SEQ ID NO: 123, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 345) having a hairpin-like structure is known as a precursor of "hsa-miR-4739".

The term "hsa-miR-4459 gene" or "hsa-miR-4459" used herein includes the hsa-miR-4459 gene (miRBase Accession No. MIMAT0018981) described in SEQ ID NO: 124, a homolog or an ortholog of a different organism species, and the like. The hsa-miR-4459 gene can be obtained by a method described in Jima D D et al., 2010, Blood, Vol. 116, e118-e127. Also, "hsa-mir-4459" (miRBase Accession No. MI0016805, SEQ ID NO: 346) having a hairpin-like structure is known as a precursor of "hsa-miR-4459".

The term "hsa-miR-1237-5p gene" or "hsa-miR-1237-5p" used herein includes the hsa-miR-1237-5p gene (miRBase Accession No. MIMAT0022946) described in SEQ ID NO: 125, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 347) having a hairpin-like structure is known as a precursor of "hsa-miR-1237-5p".

The term "hsa-miR-296-3p gene" or "hsa-miR-296-3p" used herein includes the hsa-miR-296-3p gene (miRBase Accession No. MIMAT0004679) described in SEQ ID NO: 126, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 273) having a hairpin-like structure is known as a precursor of "hsa-miR-296-3p".

The term "hsa-miR-4665-3p gene" or "hsa-miR-4665-3p" used herein includes the hsa-miR-4665-3p gene (miRBase Accession No. MIMAT0019740) described in SEQ ID NO: 127, a homolog or an ortholog of a different organism species, and the like. The hsa-miR-4665-3p 78-86. Also, "hsa-mir-4665" (miRBase Accession No. MI0017295, SEQ ID NO: 269) having a hairpin-like structure is known as a precursor of "hsa-miR-4665-3p".

The term "hsa-miR-6786-5p gene" or "hsa-miR-6786-5p" used herein includes the hsa-miR-6786-5p gene (miRBase Accession No. MIMAT0027472) described in SEQ ID NO: 128, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786"

(miRBase Accession No. MI0022631, SEQ ID NO: 348) having a hairpin-like structure is known as a precursor of "hsa-miR-6786-5p".

The term "hsa-miR-4258 gene" or "hsa-miR-4258" used herein includes the hsa-miR-4258 gene (miRBase Accession No. MIMAT0016879) described in SEQ ID NO: 129, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 349) having a hairpin-like structure is known as a precursor of "hsa-miR-4258".

The term "hsa-miR-6510-5p gene" or "hsa-miR-6510-5p" used herein includes the hsa-miR-6510-5p gene (miRBase Accession No. MIMAT0025476) described in SEQ ID NO: 130, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 350) having a hairpin-like structure is known as a precursor of "hsa-miR-6510-5p".

The term "hsa-miR-1343-5p gene" or "hsa-miR-1343-5p" used herein includes the hsa-miR-1343-5p gene (miRBase Accession No. MIMAT0027038) described in SEQ ID NO: 131, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 225) having a hairpin-like structure is known as a precursor of "hsa-miR-1343-5p".

The term "hsa-miR-1247-3p gene" or "hsa-miR-1247-3p" used herein includes the hsa-miR-1247-3p gene (miRBase Accession No. MIMAT0022721) described in SEQ ID NO: 132, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 351) having a hairpin-like structure is known as a precursor of "hsa-miR-1247-3p".

The term "hsa-miR-6805-5p gene" or "hsa-miR-6805-5p" used herein includes the hsa-miR-6805-5p gene (miRBase Accession No. MIMAT0027510) described in SEQ ID NO: 133, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 324) having a hairpin-like structure is known as a precursor of "hsa-miR-6805-5p".

The term "hsa-miR-4492 gene" or "hsa-miR-4492" used herein includes the hsa-miR-4492 gene (miRBase Accession No. MIMAT0019027) described in SEQ ID NO: 134, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 352) having a hairpin-like structure is known as a precursor of "hsa-miR-4492".

The term "hsa-miR-1469 gene" or "hsa-miR-1469" used herein includes the hsa-miR-1469 gene (miRBase Accession No. MIMAT0007347) described in SEQ ID NO: 135, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 353) having a hairpin-like structure is known as a precursor of "hsa-miR-1469".

The term "hsa-miR-1268b gene" or "hsa-miR-1268b" used herein includes the hsa-miR-1268b gene (miRBase Accession No. MIMAT0018925) described in SEQ ID NO: 136, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 354) having a hairpin-like structure is known as a precursor of "hsa-miR-1268b".

The term "hsa-miR-6858-5p gene" or "hsa-miR-6858-5p" used herein includes the hsa-miR-6858-5p gene (miRBase Accession No. MIMAT0027616) described in SEQ ID NO: 137, a homolog or an ortholog of a different organism species, and the like. The hsa-miR-6858-5p gene can be obtained by a method described in Ladewig E et al., 2012, Genome Res, Vol. 22, p. 1634-1645. Also, "hsa-mir-6858" (miRBase Accession No. MI0022704, SEQ ID NO: 355) having a hairpin-like structure is known as a precursor of "hsa-miR-6858-5p".

The term "hsa-miR-3937 gene" or "hsa-miR-3937" used herein includes the hsa-miR-3937 gene (miRBase Accession No. MIMAT0018352) described in SEQ ID NO: 138, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 356) having a hairpin-like structure is known as a precursor of "hsa-miR-3937".

The term "hsa-miR-939-5p gene" or "hsa-miR-939-5p" used herein includes the hsa-miR-939-5p gene (miRBase Accession No. MIMAT0004982) described in SEQ ID NO: 139, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 357) having a hairpin-like structure is known as a precursor of "hsa-miR-939-5p".

The term "hsa-miR-3656 gene" or "hsa-miR-3656" used herein includes the hsa-miR-3656 gene (miRBase Accession No. MIMAT0018076) described in SEQ ID NO: 140, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 358) having a hairpin-like structure is known as a precursor of "hsa-miR-3656".

The term "hsa-miR-744-5p gene" or "hsa-miR-744-5p" used herein includes the hsa-miR-744-5p gene (miRBase Accession No. MIMAT0004945) described in SEQ ID NO: 141, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 359) having a hairpin-like structure is known as a precursor of "hsa-miR-744-5p".

The term "hsa-miR-4687-3p gene" or "hsa-miR-4687-3p" used herein includes the hsa-miR-4687-3p gene (miRBase Accession No. MIMAT0019775) described in SEQ ID NO: 142, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 360) having a hairpin-like structure is known as a precursor of "hsa-miR-4687-3p".

The term "hsa-miR-4763-3p gene" or "hsa-miR-4763-3p" used herein includes the hsa-miR-4763-3p gene (miRBase Accession No. MIMAT0019913) described in SEQ ID NO: 143, a homolog or an ortholog of a different organism species, and the like. The hsa-miR-4763-3p 78-86. Also, "hsa-mir-4763" (miRBase Accession No. MI0017404, SEQ ID NO: 361) having a hairpin-like structure is known as a precursor of "hsa-miR-4763-3p".

The term "hsa-miR-3620-5p gene" or "hsa-miR-3620-5p" used herein includes the hsa-miR-3620-5p gene (miRBase Accession No. MIMAT0022967) described in SEQ ID NO: 144, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 362) having a hairpin-like structure is known as a precursor of "hsa-miR-3620-5p".

The term "hsa-miR-3195 gene" or "hsa-miR-3195" used herein includes the hsa-miR-3195 gene (miRBase Accession No. MIMAT0015079) described in SEQ ID NO: 145, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 363) having a hairpin-like structure is known as a precursor of "hsa-miR-3195".

The term "hsa-miR-6842-5p gene" or "hsa-miR-6842-5p" used herein includes the hsa-miR-6842-5p gene (miRBase Accession No. MIMAT0027586) described in SEQ ID NO: 146, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 364) having a hairpin-like structure is known as a precursor of "hsa-miR-6842-5p".

The term "hsa-miR-4707-5p gene" or "hsa-miR-4707-5p" used herein includes the hsa-miR-4707-5p gene (miRBase Accession No. MIMAT0019807) described in SEQ ID NO: 147, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 365) having a hairpin-like structure is known as a precursor of "hsa-miR-4707-5p".

The term "hsa-miR-642a-3p gene" or "hsa-miR-642a-3p" used herein includes the hsa-miR-642a-3p gene (miRBase Accession No. MIMAT0020924) described in SEQ ID NO: 148, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 366) having a hairpin-like structure is known as a precursor of "hsa-miR-642a-3p".

The term "hsa-miR-7113-3p gene" or "hsa-miR-7113-3p" used herein includes the hsa-miR-7113-3p gene (miRBase Accession No. MIMAT0028124) described in SEQ ID NO: 149, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 367) having a hairpin-like structure is known as a precursor of "hsa-miR-7113-3p".

The term "hsa-miR-4728-5p gene" or "hsa-miR-4728-5p" used herein includes the hsa-miR-4728-5p gene (miRBase Accession No. MIMAT0019849) described in SEQ ID NO: 150, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 368) having a hairpin-like structure is known as a precursor of "hsa-miR-4728-5p".

The term "hsa-miR-5195-3p gene" or "hsa-miR-5195-3p" used herein includes the hsa-miR-5195-3p gene (miRBase Accession No. MIMAT0021127) described in SEQ ID NO: 151, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 369) having a hairpin-like structure is known as a precursor of "hsa-miR-5195-3p".

The term "hsa-miR-1185-1-3p gene" or "hsa-miR-1185-1-3p" used herein includes the hsa-miR-1185-1-3p gene (miRBase Accession No. MIMAT0022838) described in SEQ ID NO: 152, a homolog or an ortholog of a different organism species, and the like. The hsa-miR-1185-1-3p gene can be obtained by a method described in Berezikov E et al., 2006, Genome Res, Vol. 16, p. 1289-1298. Also, "hsa-mir-1185-1" (miRBase Accession No. MI0003844, SEQ ID NO: 370) having a hairpin-like structure is known as a precursor of "hsa-miR-1185-1-3p".

The term "hsa-miR-6774-5p gene" or "hsa-miR-6774-5p" used herein includes the hsa-miR-6774-5p gene (miRBase Accession No. MIMAT0027448) described in SEQ ID NO: 153, a homolog or an ortholog of a different organism species, and the like. The hsa-miR-6774-5p gene can be obtained by a method described in Ladewig E et al., 2012, Genome Res, Vol. 22, p. 1634-1645. Also, "hsa-mir-6774" (miRBase Accession No. MI0022619, SEQ ID NO: 371) having a hairpin-like structure is known as a precursor of "hsa-miR-6774-5p".

The term "hsa-miR-8059 gene" or "hsa-miR-8059" used herein includes the hsa-miR-8059 gene (miRBase Accession No. MIMAT0030986) described in SEQ ID NO: 154, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 372) having a hairpin-like structure is known as a precursor of "hsa-miR-8059".

The term "hsa-miR-3131 gene" or "hsa-miR-3131" used herein includes the hsa-miR-3131 gene (miRBase Accession No. MIMAT0014996) described in SEQ ID NO: 155, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 373) having a hairpin-like structure is known as a precursor of "hsa-miR-3131".

The term "hsa-miR-7847-3p gene" or "hsa-miR-7847-3p" used herein includes the hsa-miR-7847-3p gene (miRBase Accession No. MIMAT0030422) described in SEQ ID NO: 156, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 374) having a hairpin-like structure is known as a precursor of "hsa-miR-7847-3p".

The term "hsa-miR-4463 gene" or "hsa-miR-4463" used herein includes the hsa-miR-4463 gene (miRBase Accession No. MIMAT0018987) described in SEQ ID NO: 157, a homolog or an ortholog of a different organism species, and the like. The hsa-miR-4463 gene can be obtained by a method described in Jima D D et al., 2010, Blood, Vol. 116, e118-e127. Also, "hsa-mir-4463" (miRBase Accession No. MI0016811, SEQ ID NO: 375) having a hairpin-like structure is known as a precursor of "hsa-miR-4463".

The term "hsa-miR-128-2-5p gene" or "hsa-miR-128-2-5p" used herein includes the hsa-miR-128-2-5p gene (miRBase Accession No. MIMAT0031095) described in SEQ ID NO: 158, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 376) having a hairpin-like structure is known as a precursor of "hsa-miR-128-2-5p".

The term "hsa-miR-4508 gene" or "hsa-miR-4508" used herein includes the hsa-miR-4508 gene (miRBase Accession No. MIMAT0019045) described in SEQ ID NO: 159, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 377) having a hairpin-like structure is known as a precursor of "hsa-miR-4508".

The term "hsa-miR-6806-5p gene" or "hsa-miR-6806-5p" used herein includes the hsa-miR-6806-5p gene (miRBase Accession No. MIMAT0027512) described in SEQ ID NO: 160, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 378) having a hairpin-like structure is known as a precursor of "hsa-miR-6806-5p".

The term "hsa-miR-7111-5p gene" or "hsa-miR-7111-5p" used herein includes the hsa-miR-7111-5p gene (miRBase Accession No. MIMAT0028119) described in SEQ ID NO: 161, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 379) having a hairpin-like structure is known as a precursor of "hsa-miR-7111-5p".

The term "hsa-miR-6782-5p gene" or "hsa-miR-6782-5p" used herein includes the hsa-miR-6782-5p gene (miRBase Accession No. MIMAT0027464) described in SEQ ID NO: 162, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 380) having a hairpin-like structure is known as a precursor of "hsa-miR-6782-5p".

The term "hsa-miR-4734 gene" or "hsa-miR-4734" used herein includes the hsa-miR-4734 gene (miRBase Accession No. MIMAT0019859) described in SEQ ID NO: 163, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 381) having a hairpin-like structure is known as a precursor of "hsa-miR-4734".

The term "hsa-miR-3162-5p gene" or "hsa-miR-3162-5p" used herein includes the hsa-miR-3162-5p gene (miRBase Accession No. MIMAT0015036) described in SEQ ID NO: 164, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 382) having a hairpin-like structure is known as a precursor of "hsa-miR-3162-5p".

The term "hsa-miR-887-3p gene" or "hsa-miR-887-3p" used herein includes the hsa-miR-887-3p gene (miRBase Accession No. MIMAT0004951) described in SEQ ID NO: 165, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 383) having a hairpin-like structure is known as a precursor of "hsa-miR-887-3p".

The term "hsa-miR-6752-5p gene" or "hsa-miR-6752-5p" used herein includes the hsa-miR-6752-5p gene (miRBase Accession No. MIMAT0027404) described in SEQ ID NO: 166, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 384) having a hairpin-like structure is known as a precursor of "hsa-miR-6752-5p".

The term "hsa-miR-6724-5p gene" or "hsa-miR-6724-5p" used herein includes the hsa-miR-6724-5p gene (miRBase Accession No. MIMAT0025856) described in SEQ ID NO: 167, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 385) having a hairpin-like structure is known as a precursor of "hsa-miR-6724-5p".

The term "hsa-miR-23b-3p gene" or "hsa-miR-23b-3p" used herein includes the hsa-miR-23b-3p gene (miRBase Accession No. MIMAT0000418) described in SEQ ID NO: 168, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 386) having a hairpin-like structure is known as a precursor of "hsa-miR-23b-3p".

The term "hsa-miR-23a-3p gene" or "hsa-miR-23a-3p" used herein includes the hsa-miR-23a-3p gene (miRBase Accession No. MIMAT0000078) described in SEQ ID NO: 169, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 387) having a hairpin-like structure is known as a precursor of "hsa-miR-23a-3p".

The term "hsa-miR-625-3p gene" or "hsa-miR-625-3p" used herein includes the hsa-miR-625-3p gene (miRBase Accession No. MIMAT0004808) described in SEQ ID NO: 170, a homolog or an ortholog of a different organism species, and the like. The hsa-miR-625-3p gene can be obtained by a method described in Cummins J M et al., 2006, Proc Natl Acad Sci U.S.A., Vol. 103, p. 3687-3692. Also, "hsa-mir-625" (miRBase Accession No. MI0003639, SEQ ID NO: 388) having a hairpin-like structure is known as a precursor of "hsa-miR-625-3p".

The term "hsa-miR-1228-3p gene" or "hsa-miR-1228-3p" used herein includes the hsa-miR-1228-3p gene (miRBase Accession No. MIMAT0005583) described in SEQ ID NO: 171, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 316) having a hairpin-like structure is known as a precursor of "hsa-miR-1228-3p".

The term "hsa-miR-614 gene" or "hsa-miR-614" used herein includes the hsa-miR-614 gene (miRBase Accession No. MIMAT0003282) described in SEQ ID NO: 172, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 389) having a hairpin-like structure is known as a precursor of "hsa-miR-614".

The term "hsa-miR-1913 gene" or "hsa-miR-1913" used herein includes the hsa-miR-1913 gene (miRBase Accession No. MIMAT0007888) described in SEQ ID NO: 173, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 390) having a hairpin-like structure is known as a precursor of "hsa-miR-1913".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 174, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 391) having a hairpin-like structure is known as a precursor of "hsa-miR-92a-2-5p".

The term "hsa-miR-187-5p gene" or "hsa-miR-187-5p" used herein includes the hsa-miR-187-5p gene (miRBase Accession No. MIMAT0004561) described in SEQ ID NO: 175, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 392) having a hairpin-like structure is known as a precursor of "hsa-miR-187-5p".

The term "hsa-miR-16-5p gene" or "hsa-miR-16-5p" used herein includes the hsa-miR-16-5p gene (miRBase Accession No. MIMAT0000069) described in SEQ ID NO: 176, a homolog or an ortholog of a different organism species, and the like. The hsa-miR-16-5p gene can be obtained by a method described in Lagos-Quintana M et al., 2001, Science, Vol. 294, p. 853-858. Also, "hsa-mir-16-1" and "hsa-mir-16-2" (miRBase Accession Nos. MI0000070 and MI0000115, SEQ ID NOs: 393 and 394) having a hairpin-like structure are known as precursors of "hsa-miR-16-5p".

The term "hsa-miR-92b-3p gene" or "hsa-miR-92b-3p" used herein includes the hsa-miR-92b-3p gene (miRBase Accession No. MIMAT0003218) described in SEQ ID NO: 177, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 395) having a hairpin-like structure is known as a precursor of "hsa-miR-92b-3p".

The term "hsa-miR-150-3p gene" or "hsa-miR-150-3p" used herein includes the hsa-miR-150-3p gene (miRBase Accession No. MIMAT0004610) described in SEQ ID NO: 178, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 396) having a hairpin-like structure is known as a precursor of "hsa-miR-150-3p".

The term "hsa-miR-564 gene" or "hsa-miR-564" used herein includes the hsa-miR-564 gene (miRBase Accession No. MIMAT0003228) described in SEQ ID NO: 179, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 397) having a hairpin-like structure is known as a precursor of "hsa-miR-564".

The term "hsa-miR-125a-3p gene" or "hsa-miR-125a-3p" used herein includes the hsa-miR-125a-3p gene (miRBase Accession No. MIMAT0004602) described in SEQ ID NO: 180, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 398) having a hairpin-like structure is known as a precursor of "hsa-miR-125a-3p".

The term "hsa-miR-92b-5p gene" or "hsa-miR-92b-5p" used herein includes the hsa-miR-92b-5p gene (miRBase Accession No. MIMAT0004792) described in SEQ ID NO: 181, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 395) having a hairpin-like structure is known as a precursor of "hsa-miR-92b-5p".

The term "hsa-miR-92a-3p gene" or "hsa-miR-92a-3p" used herein includes the hsa-miR-92a-3p gene (miRBase Accession No. MIMAT0000092) described in SEQ ID NO: 182, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1" and "hsa-mir-92a-2" (miRBase Accession Nos. MI0000093 and MI0000094, SEQ ID NOs: 399 and 391) having a hairpin-like structure are known as precursors of "hsa-miR-92a-3p".

The term "hsa-miR-663a gene" or "hsa-miR-663a" used herein includes the hsa-miR-663a gene (miRBase Accession No. MIMAT0003326) described in SEQ ID NO: 183, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 400) having a hairpin-like structure is known as a precursor of "hsa-miR-663a".

The term "hsa-miR-4688 gene" or "hsa-miR-4688" used herein includes the hsa-miR-4688 gene (miRBase Accession No. MIMAT0019777) described in SEQ ID NO: 184, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 401) having a hairpin-like structure is known as a precursor of "hsa-miR-4688".

The term "hsa-miR-4648 gene" or "hsa-miR-4648" used herein includes the hsa-miR-4648 gene (miRBase Accession No. MIMAT0019710) described in SEQ ID NO: 185, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 402) having a hairpin-like structure is known as a precursor of "hsa-miR-4648".

The term "hsa-miR-6085 gene" or "hsa-miR-6085" used herein includes the hsa-miR-6085 gene (miRBase Accession No. MIMAT0023710) described in SEQ ID NO: 186, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 403) having a hairpin-like structure is known as a precursor of "hsa-miR-6085".

The term "hsa-miR-6126 gene" or "hsa-miR-6126" used herein includes the hsa-miR-6126 gene (miRBase Accession No. MIMAT0024599) described in SEQ ID NO: 187, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 404) having a hairpin-like structure is known as a precursor of "hsa-miR-6126".

The term "hsa-miR-6880-5p gene" or "hsa-miR-6880-5p" used herein includes the hsa-miR-6880-5p gene (miRBase Accession No. MIMAT0027660) described in SEQ ID NO: 188, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 405) having a hairpin-like structure is known as a precursor of "hsa-miR-6880-5p".

The term "hsa-miR-328-5p gene" or "hsa-miR-328-5p" used herein includes the hsa-miR-328-5p gene (miRBase Accession No. MIMAT0026486) described in SEQ ID NO: 189, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. MI0000804, SEQ ID NO: 406) having a hairpin-like structure is known as a precursor of "hsa-miR-328-5p".

The term "hsa-miR-6768-5p gene" or "hsa-miR-6768-5p" used herein includes the hsa-miR-6768-5p gene (miRBase Accession No. MIMAT0027436) described in SEQ ID NO: 190, a homolog or an ortholog of a different organism species, and the like. The hsa-miR-6768-5p gene can be obtained by a method described in Ladewig E et al., 2012, Genome Res, Vol. 22, p. 1634-1645. Also, "hsa-mir-6768" (miRBase Accession No. MI0022613, SEQ ID NO: 407) having a hairpin-like structure is known as a precursor of "hsa-miR-6768-5p".

The term "hsa-miR-3180 gene" or "hsa-miR-3180" used herein includes the hsa-miR-3180 gene (miRBase Accession No. MIMAT0018178) described in SEQ ID NO: 191, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4" and "hsa-mir-3180-5" (miRBase Accession Nos. MI0016408 and MI0016409, SEQ ID NOs: 408 and 409) having a hairpin-like structure are known as precursors of "hsa-miR-3180".

The term "hsa-miR-6087 gene" or "hsa-miR-6087" used herein includes the hsa-miR-6087 gene (miRBase Accession No. MIMAT0023712) described in SEQ ID NO: 192, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 410) having a hairpin-like structure is known as a precursor of "hsa-miR-6087".

The term "hsa-miR-1273g-3p gene" or "hsa-miR-1273g-3p" used herein includes the hsa-miR-1273g-3p gene (miRBase Accession No. MIMAT0022742) described in SEQ ID NO: 193, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 411) having a hairpin-like structure is known as a precursor of "hsa-miR-1273g-3p".

The term "hsa-miR-1225-5p gene" or "hsa-miR-1225-5p" used herein includes the hsa-miR-1225-5p gene (miRBase Accession No. MIMAT0005572) described in SEQ ID NO: 194, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 303) having a hairpin-like structure is known as a precursor of "hsa-miR-1225-5p".

The term "hsa-miR-3196 gene" or "hsa-miR-3196" used herein includes the hsa-miR-3196 gene (miRBase Accession No. MIMAT0015080) described in SEQ ID NO: 195, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 412) having a hairpin-like structure is known as a precursor of "hsa-miR-3196".

The term "hsa-miR-4695-5p gene" or "hsa-miR-4695-5p" used herein includes the hsa-miR-4695-5p gene (miRBase Accession No. MIMAT0019788) described in SEQ ID NO: 196, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 413) having a hairpin-like structure is known as a precursor of "hsa-miR-4695-5p".

The term "hsa-miR-6732-5p gene" or "hsa-miR-6732-5p" used herein includes the hsa-miR-6732-5p gene (miRBase Accession No. MIMAT0027365) described in SEQ ID NO:

197, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 414) having a hairpin-like structure is known as a precursor of "hsa-miR-6732-5p".

The term "hsa-miR-638 gene" or "hsa-miR-638" used herein includes the hsa-miR-638 gene (miRBase Accession No. MIMAT0003308) described in SEQ ID NO: 198, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 415) having a hairpin-like structure is known as a precursor of "hsa-miR-638".

The term "hsa-miR-6813-5p gene" or "hsa-miR-6813-5p" used herein includes the hsa-miR-6813-5p gene (miRBase Accession No. MIMAT0027526) described in SEQ ID NO: 199, a homolog or an ortholog of a different organism species, and the like. The hsa-miR-6813-5p p. 1634-1645. Also, "hsa-mir-6813" (miRBase Accession No. MI0022658, SEQ ID NO: 416) having a hairpin-like structure is known as a precursor of "hsa-miR-6813-5p".

The term "hsa-miR-665 gene" or "hsa-miR-665" used herein includes the hsa-miR-665 gene (miRBase Accession No. MIMAT0004952) described in SEQ ID NO: 200, a homolog or an ortholog of a different organism species, and the like. The hsa-miR-665 gene can be obtained by a method described in Berezikov E et al., 2006, Genome Res, Vol. 16, p. 1289-1298. Also, "hsa-mir-665" (miRBase Accession No. MI0005563, SEQ ID NO: 417) having a hairpin-like structure is known as a precursor of "hsa-miR-665".

The term "hsa-miR-486-3p gene" or "hsa-miR-486-3p" used herein includes the hsa-miR-486-3p gene (miRBase Accession No. MIMAT0004762) described in SEQ ID NO: 201, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486" and "hsa-mir-486-2" (miRBase Accession Nos. MI0002470 and MI0023622, SEQ ID NOs: 418 and 419) having a hairpin-like structure are known as precursors of "hsa-miR-486-3p".

The term "hsa-miR-4466 gene" or "hsa-miR-4466" used herein includes the hsa-miR-4466 gene (miRBase Accession No. MIMAT0018993) described in SEQ ID NO: 202, a homolog or an ortholog of a different organism species, and the like. The hsa-miR-4466 gene can be obtained by a method described in Jima D D et al., 2010, Blood, Vol. 116, e118-e127. Also, "hsa-mir-4466" (miRBase Accession No. MI0016817, SEQ ID NO: 420) having a hairpin-like structure is known as a precursor of "hsa-miR-4466".

The term "hsa-miR-30c-1-3p gene" or "hsa-miR-30c-1-3p" used herein includes the hsa-miR-30c-1-3p gene (miRBase Accession No. MIMAT0004674) described in SEQ ID NO: 203, a homolog or an ortholog of a different organism species, and the like. The hsa-miR-30c-1-3p gene can be obtained by a method described in Lagos-Quintana M et al., 2002, Curr Biol, Vol. 12, p. 735-739. Also, "hsa-mir-30c-1" (miRBase Accession No. MI0000736, SEQ ID NO: 421) having a hairpin-like structure is known as a precursor of "hsa-miR-30c-1-3p".

The term "hsa-miR-3621 gene" or "hsa-miR-3621" used herein includes the hsa-miR-3621 gene (miRBase Accession No. MIMAT0018002) described in SEQ ID NO: 204, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 422) having a hairpin-like structure is known as a precursor of "hsa-miR-3621".

The term "hsa-miR-6743-5p gene" or "hsa-miR-6743-5p" used herein includes the hsa-miR-6743-5p gene (miRBase Accession No. MIMAT0027387) described in SEQ ID NO: 205, a homolog or an ortholog of a different organism species, and the like. The hsa-miR-6743-5p gene can be obtained by a method described in Ladewig E et al., 2012, Genome Res, Vol. 22, p. 1634-1645. Also, "hsa-mir-6743" (miRBase Accession No. MI0022588, SEQ ID NO: 423) having a hairpin-like structure is known as a precursor of "hsa-miR-6743-5p".

The term "hsa-miR-4298 gene" or "hsa-miR-4298" used herein includes the hsa-miR-4298 gene (miRBase Accession No. MIMAT0016852) described in SEQ ID NO: 206, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 424) having a hairpin-like structure is known as a precursor of "hsa-miR-4298".

The term "hsa-miR-4741 gene" or "hsa-miR-4741" used herein includes the hsa-miR-4741 gene (miRBase Accession No. MIMAT0019871) described in SEQ ID NO: 207, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 425) having a hairpin-like structure is known as a precursor of "hsa-miR-4741".

The term "hsa-miR-3619-3p gene" or "hsa-miR-3619-3p" used herein includes the hsa-miR-3619-3p gene (miRBase Accession No. MIMAT0019219) described in SEQ ID NO: 208, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 426) having a hairpin-like structure is known as a precursor of "hsa-miR-3619-3p".

The term "hsa-miR-6824-5p gene" or "hsa-miR-6824-5p" used herein includes the hsa-miR-6824-5p gene (miRBase Accession No. MIMAT0027548) described in SEQ ID NO: 209, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 427) having a hairpin-like structure is known as a precursor of "hsa-miR-6824-5p".

The term "hsa-miR-5698 gene" or "hsa-miR-5698" used herein includes the hsa-miR-5698 gene (miRBase Accession No. MIMAT0022491) described in SEQ ID NO: 210, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 428) having a hairpin-like structure is known as a precursor of "hsa-miR-5698".

The term "hsa-miR-371a-5p gene" or "hsa-miR-371a-5p" used herein includes the hsa-miR-371a-5p gene (miRBase Accession No. MIMAT0004687) described in SEQ ID NO: 211, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 429) having a hairpin-like structure is known as a precursor of "hsa-miR-371a-5p".

The term "hsa-miR-4488 gene" or "hsa-miR-4488" used herein includes the hsa-miR-4488 gene (miRBase Accession No. MIMAT0019022) described in SEQ ID NO: 212, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 430) having a hairpin-like structure is known as a precursor of "hsa-miR-4488".

The term "hsa-miR-1233-5p gene" or "hsa-miR-1233-5p" used herein includes the hsa-miR-1233-5p gene (miRBase Accession No. MIMAT0022943) described in SEQ ID NO: 213, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1" and "hsa-mir-1233-2" (miRBase Accession Nos. MI0006323 and MI0015973, SEQ ID NOs: 431 and 432) having a hairpin-like structure are known as precursors of "hsa-miR-1233-5p".

The term "hsa-miR-4723-5p gene" or "hsa-miR-4723-5p" used herein includes the hsa-miR-4723-5p gene (miRBase Accession No. MIMAT0019838) described in SEQ ID NO: 214, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 433) having a hairpin-like structure is known as a precursor of "hsa-miR-4723-5p".

The term "hsa-miR-24-3p gene" or "hsa-miR-24-3p" used herein includes the hsa-miR-24-3p gene (miRBase Accession No. MIMAT0000080) described in SEQ ID NO: 215, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1" and "hsa-mir-24-2" (miRBase Accession Nos. MI0000080 and MI0000081, SEQ ID NOs: 434 and 435) having a hairpin-like structure are known as precursors of "hsa-miR-24-3p".

The term "hsa-miR-1238-5p gene" or "hsa-miR-1238-5p" used herein includes the hsa-miR-1238-5p gene (miRBase Accession No. MIMAT0022947) described in SEQ ID NO: 216, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 436) having a hairpin-like structure is known as a precursor of "hsa-miR-1238-5p".

The term "hsa-miR-4442 gene" or "hsa-miR-4442" used herein includes the hsa-miR-4442 gene (miRBase Accession No. MIMAT0018960) described in SEQ ID NO: 217, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 437) having a hairpin-like structure is known as a precursor of "hsa-miR-4442".

The term "hsa-miR-3928-3p gene" or "hsa-miR-3928-3p" used herein includes the hsa-miR-3928-3p gene (miRBase Accession No. MIMAT0018205) described in SEQ ID NO: 218, a homolog or an ortholog of a different organism species, and the like. The hsa-miR-3928-3p gene can be obtained by a method described in Creighton C J et al., 2010, PLoS One, Vol. 5, e9637. Also, "hsa-mir-3928" (miRBase Accession No. MI0016438, SEQ ID NO: 438) having a hairpin-like structure is known as a precursor of "hsa-miR-3928-3p".

The term "hsa-miR-6716-5p gene" or "hsa-miR-6716-5p" used herein includes the hsa-miR-6716-5p gene (miRBase Accession No. MIMAT0025844) described in SEQ ID NO: 219, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 439) having a hairpin-like structure is known as a precursor of "hsa-miR-6716-5p".

The term "hsa-miR-6089 gene" or "hsa-miR-6089" used herein includes the hsa-miR-6089 gene (miRBase Accession No. MIMAT0023714) described in SEQ ID NO: 220, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1" and "hsa-mir-6089-2" (miRBase Accession Nos. MI0020366 and MI0023563, SEQ ID NOs: 440 and 441) having a hairpin-like structure are known as precursors of "hsa-miR-6089".

The term "hsa-miR-6124 gene" or "hsa-miR-6124" used herein includes the hsa-miR-6124 gene (miRBase Accession No. MIMAT0024597) described in SEQ ID NO: 221, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 442) having a hairpin-like structure is known as a precursor of "hsa-miR-6124".

The term "hsa-miR-6778-5p gene" or "hsa-miR-6778-5p" used herein includes the hsa-miR-6778-5p gene (miRBase Accession No. MIMAT0027456) described in SEQ ID NO: 222, a homolog or an ortholog of a different organism species, and the like. The hsa-miR-6778-5p gene can be obtained by a method described in Ladewig E et al., 2012, Genome Res, Vol. 22, p. 1634-1645. Also, "hsa-mir-6778" (miRBase Accession No. MI0022623, SEQ ID NO: 443) having a hairpin-like structure is known as a precursor of "hsa-miR-6778-5p".

The term "hsa-miR-557 gene" or "hsa-miR-557" used herein includes the hsa-miR-557 gene (miRBase Accession No. MIMAT0003221) described in SEQ ID NO: 223, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 444) having a hairpin-like structure is known as a precursor of "hsa-miR-557".

The term "hsa-miR-6090 gene" or "hsa-miR-6090" used herein includes the hsa-miR-6090 gene (miRBase Accession No. MIMAT0023715) described in SEQ ID NO: 224, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 445) having a hairpin-like structure is known as a precursor of "hsa-miR-6090".

The term "hsa-miR-6757-5p gene" or "hsa-miR-6757-5p" used herein includes the hsa-miR-6757-5p gene (miRBase Accession No. MIMAT0027414) described in SEQ ID NO: 714, a homolog or an ortholog of a different organism species, and the like. The hsa-miR-6757-5p gene can be obtained by a method described in Ladewig E et al., 2012, Genome Res., Vol. 22, p. 1634-1645. Also, "hsa-mir-6757" (miRBase Accession No. MI0022602, SEQ ID NO: 730) having a hairpin-like structure is known as a precursor of "hsa-miR-6757-5p".

The term "hsa-miR-4448 gene" or "hsa-miR-4448" used herein includes the hsa-miR-4448 gene (miRBase Accession No. MIMAT0018967) described in SEQ ID NO: 715, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 731) having a hairpin-like structure is known as a precursor of "hsa-miR-4448".

The term "hsa-miR-671-5p gene" or "hsa-miR-671-5p" used herein includes the hsa-miR-671-5p gene (miRBase Accession No. MIMAT0003880) described in SEQ ID NO: 716, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 732) having a hairpin-like structure is known as a precursor of "hsa-miR-671-5p".

The term "hsa-miR-3178 gene" or "hsa-miR-3178" used herein includes the hsa-miR-3178 gene (miRBase Accession No. MIMAT0015055) described in SEQ ID NO: 717, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 733) having a hairpin-like structure is known as a precursor of "hsa-miR-3178".

The term "hsa-miR-4725-3p gene" or "hsa-miR-4725-3p" used herein includes the hsa-miR-4725-3p gene (miRBase Accession No. MIMAT0019844) described in SEQ ID NO: 718, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 734) having a hairpin-like structure is known as a precursor of "hsa-miR-4725-3p".

The term "hsa-miR-940 gene" or "hsa-miR-940" used herein includes the hsa-miR-940 gene (miRBase Accession No. MIMAT0004983) described in SEQ ID NO: 719, a homolog or an ortholog of a different organism species, and the like. The hsa-miR-940 gene can be obtained by a method described in Lui W O et al., 2007, A Cancer Res., Vol. 67, p. 6031-6043. Also, "hsa-mir-940" (miRBase Accession No. MI0005762, SEQ ID NO: 735) having a hairpin-like structure is known as a precursor of "hsa-miR-940".

The term "hsa-miR-6789-5p gene" or "hsa-miR-6789-5p" used herein includes the hsa-miR-6789-5p gene (miRBase Accession No. MIMAT0027478) described in SEQ ID NO: 720, a homolog or an ortholog of a different organism species, and the like. The hsa-miR-6789-5p gene can be obtained by a method described in Ladewig E et al., 2012, Genome Res., Vol. 22, p. 1634-1645. Also, "hsa-mir-6789" (miRBase Accession No. MI0022634, SEQ ID NO: 736) having a hairpin-like structure is known as a precursor of "hsa-miR-6789-5p".

The term "hsa-miR-4484 gene" or "hsa-miR-4484" used herein includes the hsa-miR-4484 gene (miRBase Accession No. MIMAT0019018) described in SEQ ID NO: 721, a homolog or an ortholog of a different organism species, and the like. The hsa-miR-4484 gene can be obtained by a method described in Jima D D et al., 2010, Blood., Vol. 116, e118-e127. Also, "hsa-mir-4484" (miRBase Accession No. MI0016845, SEQ ID NO: 737) having a hairpin-like structure is known as a precursor of "hsa-miR-4484".

The term "hsa-miR-4634 gene" or "hsa-miR-4634" used herein includes the hsa-miR-4634 gene (miRBase Accession No. MIMAT0019691) described in SEQ ID NO: 722, a homolog or an ortholog of a different organism species, and the like. The hsa-miR-4634 gene can be obtained by a method described in Persson H et al., 2011, Cancer Res., Vol. 71, p. 78-86. Also, "hsa-mir-4634" (miRBase Accession No. MI0017261, SEQ ID NO: 738) having a hairpin-like structure is known as a precursor of "hsa-miR-4634".

The term "hsa-miR-4745-5p gene" or "hsa-miR-4745-5p" used herein includes the hsa-miR-4745-5p gene (miRBase Accession No. MIMAT0019878) described in SEQ ID NO: 723, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 739) having a hairpin-like structure is known as a precursor of "hsa-miR-4745-5p".

The term "hsa-miR-4730 gene" or "hsa-miR-4730" used herein includes the hsa-miR-4730 gene (miRBase Accession No. MIMAT0019852) described in SEQ ID NO: 724, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 740) having a hairpin-like structure is known as a precursor of "hsa-miR-4730".

The term "hsa-miR-6803-5p gene" or "hsa-miR-6803-5p" used herein includes the hsa-miR-6803-5p gene (miRBase Accession No. MIMAT0027506) described in SEQ ID NO: 725, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 741) having a hairpin-like structure is known as a precursor of "hsa-miR-6803-5p".

The term "hsa-miR-6798-5p gene" or "hsa-miR-6798-5p" used herein includes the hsa-miR-6798-5p gene (miRBase Accession No. MIMAT0027496) described in SEQ ID NO: 726, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 742) having a hairpin-like structure is known as a precursor of "hsa-miR-6798-5p".

The term "hsa-miR-3648 gene" or "hsa-miR-3648" used herein includes the hsa-miR-3648 gene (miRBase Accession No. MIMAT0018068) described in SEQ ID NO: 727, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 743) having a hairpin-like structure is known as a precursor of "hsa-miR-3648".

The term "hsa-miR-4783-3p gene" or "hsa-miR-4783-3p" used herein includes the hsa-miR-4783-3p gene (miRBase Accession No. MIMAT0019947) described in SEQ ID NO: 728, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 744) having a hairpin-like structure is known as a precursor of "hsa-miR-4783-3p".

The term "hsa-miR-6836-3p gene" or "hsa-miR-6836-3p" used herein includes the hsa-miR-6836-3p gene (miRBase Accession No. MIMAT0027575) described in SEQ ID NO: 729, a homolog or an ortholog of a different organism species, and the like. The hsa-miR-6836-3p gene can be obtained by a method described in Ladewig E et al., 2012, Genome Res., Vol. 22, p. 1634-1645. Also, "hsa-mir-6836" (miRBase Accession No. MI0022682, SEQ ID NO: 745) having a hairpin-like structure is known as a precursor of "hsa-miR-6836-3p".

A mature miRNA may become a variant due to the sequence cleaved shorter or longer by one to several flanking nucleotides, or nucleotide substitution, when cleaved as the mature miRNA from its RNA precursor having a hairpin-like structure. This variant is called isomiR (Morin R D. et al., 2008, Genome Res., Vol. 18, p. 610-621). miRBase Release 20 shows the nucleotide sequences represented by SEQ ID NOs: 1 to 224 and 714 to 729 as well as a large number of the nucleotide sequence variants and fragments represented by SEQ ID NOs: 446 to 713 and 746 to 765, called isomiRs. These variants can also be obtained as miRNAs having a nucleotide sequence represented by any of SEQ ID NOs: 1 to 224 and 714 to 729.

Specifically, among the variants of polynucleotides consisting of a nucleotide sequence represented by any of SEQ ID NOs: 1, 3, 4, 6, 7, 10, 11, 13, 14, 16, 17, 20, 22, 26, 29, 36, 38, 39, 40, 42, 43, 44, 46, 49, 52, 59, 60, 62, 63, 65, 66, 67, 72, 76, 77, 78, 81, 83, 84, 85, 86, 87, 88, 89, 90, 92, 93, 94, 96, 100, 103, 105, 106, 107, 113, 114, 115, 116, 117, 118, 119, 120, 121, 123, 124, 125, 126, 130, 132, 134, 136, 139, 140, 141, 142, 143, 144, 145, 147, 148, 150, 151, 152, 155, 157, 158, 159, 163, 164, 165, 167, 168, 169, 170, 171, 172, 173, 174, 175, 176, 177, 178, 179, 180, 181, 182, 183, 184, 185, 187, 189, 191, 192, 193, 195, 196, 198, 200, 201, 202, 203, 206, 207, 210, 211, 212, 213, 214, 215, 217, 218, 219, 220, 221, 715, 716, 717, 718, 719, 721, 723, 724, 727 and 728 or a nucleotide sequence derived from the nucleotide sequence by the replacement of u with t according to the present invention, examples of the longest variants registered in miRBase Release 20 include polynucleotides represented by SEQ ID NOs: 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 746, 748, 750, 752, 754, 756, 758, 760, 762 and 764, respectively.

Also, among the variants of polynucleotides consisting of a nucleotide sequence represented by any of SEQ ID NOs: 1, 3, 4, 6, 7, 10, 11, 13, 14, 16, 17, 20, 22, 26, 29, 36, 38, 39, 40, 42, 43, 44, 46, 49, 52, 59, 60, 62, 63, 65, 66, 67, 72, 76, 77, 78, 81, 83, 84, 85, 86, 87, 88, 89, 90, 92, 93, 94, 96, 100, 103, 105, 106, 107, 113, 114, 115, 116, 117, 118, 119, 120, 121, 123, 124, 125, 126, 130, 132, 134, 136, 139, 140, 141, 142, 143, 144, 145, 147, 148, 150, 151, 152, 155, 157, 158, 159, 163, 164, 165, 167, 168, 169, 170, 171, 172, 173, 174, 175, 176, 177, 178, 179, 180, 181, 182, 183, 184, 185, 187, 189, 191, 192, 193, 195, 196, 198, 200, 201, 202, 203, 206, 207, 210, 211, 212, 213, 214, 215, 217, 218, 219, 220, 221, 715, 716, 717, 718, 719, 721, 723, 724, 727 and 728 or a nucleotide sequence derived from the nucleotide sequence by the replacement of u with t according to the present invention, examples of the shortest variants registered in miRBase Release 20 include polynucleotides having sequences represented by SEQ ID NOs: 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 747, 749, 751, 753, 755, 757, 759, 761, 763 and 765, respectively.

In addition to these variants and fragments, examples thereof include a large number of isomiR polynucleotides of SEQ ID NOs: 1 to 224 and 714 to 729 registered in miRBase. Examples of the polynucleotide comprising a nucleotide sequence represented by any of SEQ ID NOs: 1 to 224 and 714 to 729 include a polynucleotide represented by any of SEQ ID NOs: 225 to 445 and 730 to 745, which are their respective precursors.

The names and miRBase Accession Nos. (registration numbers) of the genes represented by SEQ ID NOs: 1 to 765 are shown in Table 1.

As used herein, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-1343-3p | MIMAT0019776 |
| 2 | hsa-miR-6726-5p | MIMAT0027353 |
| 3 | hsa-miR-6515-3p | MIMAT0025487 |
| 4 | hsa-miR-4651 | MIMAT0019715 |
| 5 | hsa-miR-4257 | MIMAT0016878 |
| 6 | hsa-miR-3188 | MIMAT0015070 |
| 7 | hsa-miR-6131 | MIMAT0024615 |
| 8 | hsa-miR-6766-3p | MIMAT0027433 |
| 9 | hsa-miR-7641 | MIMAT0029782 |
| 10 | hsa-miR-1249 | MIMAT0005901 |
| 11 | hsa-miR-3679-3p | MIMAT0018105 |
| 12 | hsa-miR-6787-5p | MIMAT0027474 |
| 13 | hsa-miR-4454 | MIMAT0018976 |
| 14 | hsa-miR-3135b | MIMAT0018985 |
| 15 | hsa-miR-6765-3p | MIMAT0027431 |
| 16 | hsa-miR-7975 | MIMAT0031178 |
| 17 | hsa-miR-204-3p | MIMAT0022693 |
| 18 | hsa-miR-7977 | MIMAT0031180 |
| 19 | hsa-miR-7110-5p | MIMAT0028117 |
| 20 | hsa-miR-6717-5p | MIMAT0025846 |
| 21 | hsa-miR-6870-5p | MIMAT0027640 |
| 22 | hsa-miR-663b | MIMAT0005867 |
| 23 | hsa-miR-6875-5p | MIMAT0027650 |

TABLE 1-continued

| SEQ ID NO: | Gene name | miRBase registration No. |
|---|---|---|
| 24 | hsa-miR-8072 | MIMAT0030999 |
| 25 | hsa-miR-6816-5p | MIMAT0027532 |
| 26 | hsa-miR-4281 | MIMAT0016907 |
| 27 | hsa-miR-6729-5p | MIMAT0027359 |
| 28 | hsa-miR-8069 | MIMAT0030996 |
| 29 | hsa-miR-4706 | MIMAT0019806 |
| 30 | hsa-miR-7108-5p | MIMAT0028113 |
| 31 | hsa-miR-4433b-3p | MIMAT0030414 |
| 32 | hsa-miR-6893-5p | MIMAT0027686 |
| 33 | hsa-miR-6857-5p | MIMAT0027614 |
| 34 | hsa-miR-1227-5p | MIMAT0022941 |
| 35 | hsa-miR-6741-5p | MIMAT0027383 |
| 36 | hsa-miR-451a | MIMAT0001631 |
| 37 | hsa-miR-8063 | MIMAT0030990 |
| 38 | hsa-miR-3622a-5p | MIMAT0018003 |
| 39 | hsa-miR-615-5p | MIMAT0004804 |
| 40 | hsa-miR-128-1-5p | MIMAT0026477 |
| 41 | hsa-miR-6825-5p | MIMAT0027550 |
| 42 | hsa-miR-1260b | MIMAT0015041 |
| 43 | hsa-miR-4433-3p | MIMAT0018949 |
| 44 | hsa-miR-4665-5p | MIMAT0019739 |
| 45 | hsa-miR-7845-5p | MIMAT0030420 |
| 46 | hsa-miR-1908-5p | MIMAT0007881 |
| 47 | hsa-miR-6840-3p | MIMAT0027583 |
| 48 | hsa-miR-6765-5p | MIMAT0027430 |
| 49 | hsa-miR-296-5p | MIMAT0000690 |
| 50 | hsa-miR-3675-3p | MIMAT0018099 |
| 51 | hsa-miR-6781-5p | MIMAT0027462 |
| 52 | hsa-miR-423-5p | MIMAT0004748 |
| 53 | hsa-miR-3663-3p | MIMAT0018085 |
| 54 | hsa-miR-6784-5p | MIMAT0027468 |
| 55 | hsa-miR-6749-5p | MIMAT0027398 |
| 56 | hsa-miR-1231 | MIMAT0005586 |
| 57 | hsa-miR-4746-3p | MIMAT0019881 |
| 58 | hsa-miR-6780b-5p | MIMAT0027572 |
| 59 | hsa-miR-4758-5p | MIMAT0019903 |
| 60 | hsa-miR-3679-5p | MIMAT0018104 |
| 61 | hsa-miR-3184-5p | MIMAT0015064 |
| 62 | hsa-miR-6125 | MIMAT0024598 |
| 63 | hsa-miR-6721-5p | MIMAT0025852 |
| 64 | hsa-miR-6791-5p | MIMAT0027482 |
| 65 | hsa-miR-3185 | MIMAT0015065 |
| 66 | hsa-miR-1260a | MIMAT0005911 |
| 67 | hsa-miR-3197 | MIMAT0015082 |
| 68 | hsa-miR-6845-5p | MIMAT0027590 |
| 69 | hsa-miR-6887-5p | MIMAT0027674 |
| 70 | hsa-miR-6738-5p | MIMAT0027377 |
| 71 | hsa-miR-6872-3p | MIMAT0027645 |
| 72 | hsa-miR-4497 | MIMAT0019032 |
| 73 | hsa-miR-1229-5p | MIMAT0022942 |
| 74 | hsa-miR-6820-5p | MIMAT0027540 |
| 75 | hsa-miR-6777-5p | MIMAT0027454 |
| 76 | hsa-miR-3917 | MIMAT0018191 |
| 77 | hsa-miR-5787 | MIMAT0023252 |
| 78 | hsa-miR-4286 | MIMAT0016916 |
| 79 | hsa-miR-6877-5p | MIMAT0027654 |
| 80 | hsa-miR-1225-3p | MIMAT0005573 |
| 81 | hsa-miR-6088 | MIMAT0023713 |
| 82 | hsa-miR-6800-5p | MIMAT0027500 |
| 83 | hsa-miR-1246 | MIMAT0005898 |
| 84 | hsa-miR-4467 | MIMAT0018994 |
| 85 | hsa-miR-4419b | MIMAT0019034 |
| 86 | hsa-miR-1914-3p | MIMAT0007890 |
| 87 | hsa-miR-4632-5p | MIMAT0022977 |
| 88 | hsa-miR-1915-5p | MIMAT0007891 |
| 89 | hsa-miR-3940-5p | MIMAT0019229 |
| 90 | hsa-miR-1185-2-3p | MIMAT0022713 |
| 91 | hsa-miR-6746-5p | MIMAT0027392 |
| 92 | hsa-miR-5001-5p | MIMAT0021021 |
| 93 | hsa-miR-1228-5p | MIMAT0005582 |
| 94 | hsa-miR-5572 | MIMAT0022260 |
| 95 | hsa-miR-4327 | MIMAT0016889 |
| 96 | hsa-miR-4638-5p | MIMAT0019695 |
| 97 | hsa-miR-6799-5p | MIMAT0027498 |
| 98 | hsa-miR-6861-5p | MIMAT0027623 |
| 99 | hsa-miR-6727-5p | MIMAT0027355 |
| 100 | hsa-miR-4513 | MIMAT0019050 |
| 101 | hsa-miR-6805-3p | MIMAT0027511 |
| 102 | hsa-miR-6808-5p | MIMAT0027516 |
| 103 | hsa-miR-4449 | MIMAT0018968 |
| 104 | hsa-miR-1199-5p | MIMAT0031119 |
| 105 | hsa-miR-1275 | MIMAT0005929 |
| 106 | hsa-miR-4792 | MIMAT0019964 |
| 107 | hsa-miR-4443 | MIMAT0018961 |
| 108 | hsa-miR-6891-5p | MIMAT0027682 |
| 109 | hsa-miR-6826-5p | MIMAT0027552 |
| 110 | hsa-miR-6807-5p | MIMAT0027514 |
| 111 | hsa-miR-7150 | MIMAT0028211 |
| 112 | hsa-miR-4534 | MIMAT0019073 |
| 113 | hsa-miR-4476 | MIMAT0019003 |
| 114 | hsa-miR-4649-5p | MIMAT0019711 |
| 115 | hsa-miR-4525 | MIMAT0019064 |
| 116 | hsa-miR-1915-3p | MIMAT0007892 |
| 117 | hsa-miR-4516 | MIMAT0019053 |
| 118 | hsa-miR-4417 | MIMAT0018929 |
| 119 | hsa-miR-642b-3p | MIMAT0018444 |
| 120 | hsa-miR-3141 | MIMAT0015010 |
| 121 | hsa-miR-5100 | MIMAT0022259 |
| 122 | hsa-miR-6848-5p | MIMAT0027596 |
| 123 | hsa-miR-4739 | MIMAT0019868 |
| 124 | hsa-miR-4459 | MIMAT0018981 |
| 125 | hsa-miR-1237-5p | MIMAT0022946 |
| 126 | hsa-miR-296-3p | MIMAT0004679 |
| 127 | hsa-miR-4665-3p | MIMAT0019740 |
| 128 | hsa-miR-6786-5p | MIMAT0027472 |
| 129 | hsa-miR-4258 | MIMAT0016879 |
| 130 | hsa-miR-6510-5p | MIMAT0025476 |
| 131 | hsa-miR-1343-5p | MIMAT0027038 |
| 132 | hsa-miR-1247-3p | MIMAT0022721 |
| 133 | hsa-miR-6805-5p | MIMAT0027510 |
| 134 | hsa-miR-4492 | MIMAT0019027 |
| 135 | hsa-miR-1469 | MIMAT0007347 |
| 136 | hsa-miR-1268b | MIMAT0018925 |
| 137 | hsa-miR-6858-5p | MIMAT0027616 |
| 138 | hsa-miR-3937 | MIMAT0018352 |
| 139 | hsa-miR-939-5p | MIMAT0004982 |
| 140 | hsa-miR-3656 | MIMAT0018076 |
| 141 | hsa-miR-744-5p | MIMAT0004945 |
| 142 | hsa-miR-4687-3p | MIMAT0019775 |
| 143 | hsa-miR-4763-3p | MIMAT0019913 |
| 144 | hsa-miR-3620-5p | MIMAT0022967 |
| 145 | hsa-miR-3195 | MIMAT0015079 |
| 146 | hsa-miR-6842-5p | MIMAT0027586 |
| 147 | hsa-miR-4707-5p | MIMAT0019807 |
| 148 | hsa-miR-642a-3p | MIMAT0020924 |
| 149 | hsa-miR-7113-3p | MIMAT0028124 |
| 150 | hsa-miR-4728-5p | MIMAT0019849 |
| 151 | hsa-miR-5195-3p | MIMAT0021127 |
| 152 | hsa-miR-1185-1-3p | MIMAT0022838 |
| 153 | hsa-miR-6774-5p | MIMAT0027448 |
| 154 | hsa-miR-8059 | MIMAT0030986 |
| 155 | hsa-miR-3131 | MIMAT0014996 |
| 156 | hsa-miR-7847-3p | MIMAT0030422 |
| 157 | hsa-miR-4463 | MIMAT0018987 |
| 158 | hsa-miR-128-2-5p | MIMAT0031095 |
| 159 | hsa-miR-4508 | MIMAT0019045 |
| 160 | hsa-miR-6806-5p | MIMAT0027512 |
| 161 | hsa-miR-7111-5p | MIMAT0028119 |
| 162 | hsa-miR-6782-5p | MIMAT0027464 |
| 163 | hsa-miR-4734 | MIMAT0019859 |
| 164 | hsa-miR-3162-5p | MIMAT0015036 |
| 165 | hsa-miR-887-3p | MIMAT0004951 |
| 166 | hsa-miR-6752-5p | MIMAT0027404 |
| 167 | hsa-miR-6724-5p | MIMAT0025856 |
| 168 | hsa-miR-23b-3p | MIMAT0000418 |
| 169 | hsa-miR-23a-3p | MIMAT0000078 |
| 170 | hsa-miR-625-3p | MIMAT0004808 |
| 171 | hsa-miR-1228-3p | MIMAT0005583 |
| 172 | hsa-miR-614 | MIMAT0003282 |
| 173 | hsa-miR-1913 | MIMAT0007888 |
| 174 | hsa-miR-92a-2-5p | MIMAT0004508 |
| 175 | hsa-miR-187-5p | MIMAT0004561 |

TABLE 1-continued

| SEQ ID NO: | Gene name | miRBase registration No. |
|---|---|---|
| 176 | hsa-miR-16-5p | MIMAT0000069 |
| 177 | hsa-miR-92b-3p | MIMAT0003218 |
| 178 | hsa-miR-150-3p | MIMAT0004610 |
| 179 | hsa-miR-564 | MIMAT0003228 |
| 180 | hsa-miR-125a-3p | MIMAT0004602 |
| 181 | hsa-miR-92b-5p | MIMAT0004792 |
| 182 | hsa-miR-92a-3p | MIMAT0000092 |
| 183 | hsa-miR-663a | MIMAT0003326 |
| 184 | hsa-miR-4688 | MIMAT0019777 |
| 185 | hsa-miR-4648 | MIMAT0019710 |
| 186 | hsa-miR-6085 | MIMAT0023710 |
| 187 | hsa-miR-6126 | MIMAT0024599 |
| 188 | hsa-miR-6880-5p | MIMAT0027660 |
| 189 | hsa-miR-328-5p | MIMAT0026486 |
| 190 | hsa-miR-6768-5p | MIMAT0027436 |
| 191 | hsa-miR-3180 | MIMAT0018178 |
| 192 | hsa-miR-6087 | MIMAT0023712 |
| 193 | hsa-miR-1273g-3p | MIMAT0022742 |
| 194 | hsa-miR-1225-5p | MIMAT0005572 |
| 195 | hsa-miR-3196 | MIMAT0015080 |
| 196 | hsa-miR-4695-5p | MIMAT0019788 |
| 197 | hsa-miR-6732-5p | MIMAT0027365 |
| 198 | hsa-miR-638 | MIMAT0003308 |
| 199 | hsa-miR-6813-5p | MIMAT0027526 |
| 200 | hsa-miR-665 | MIMAT0004952 |
| 201 | hsa-miR-486-3p | MIMAT0004762 |
| 202 | hsa-miR-4466 | MIMAT0018993 |
| 203 | hsa-miR-30c-1-3p | MIMAT0004674 |
| 204 | hsa-miR-3621 | MIMAT0018002 |
| 205 | hsa-miR-6743-5p | MIMAT0027387 |
| 206 | hsa-miR-4298 | MIMAT0016852 |
| 207 | hsa-miR-4741 | MIMAT0019871 |
| 208 | hsa-miR-3619-3p | MIMAT0019219 |
| 209 | hsa-miR-6824-5p | MIMAT0027548 |
| 210 | hsa-miR-5698 | MIMAT0022491 |
| 211 | hsa-miR-371a-5p | MIMAT0004687 |
| 212 | hsa-miR-4488 | MIMAT0019022 |
| 213 | hsa-miR-1233-5p | MIMAT0022943 |
| 214 | hsa-miR-4723-5p | MIMAT0019838 |
| 215 | hsa-miR-24-3p | MIMAT0000080 |
| 216 | hsa-miR-1238-5p | MIMAT0022947 |
| 217 | hsa-miR-4442 | MIMAT0018960 |
| 218 | hsa-miR-3928-3p | MIMAT0018205 |
| 219 | hsa-miR-6716-5p | MIMAT0025844 |
| 220 | hsa-miR-6089 | MIMAT0023714 |
| 221 | hsa-miR-6124 | MIMAT0024597 |
| 222 | hsa-miR-6778-5p | MIMAT0027456 |
| 223 | hsa-miR-557 | MIMAT0003221 |
| 224 | hsa-miR-6090 | MIMAT0023715 |
| 225 | hsa-mir-1343 | MI0017320 |
| 226 | hsa-mir-6726 | MI0022571 |
| 227 | hsa-mir-6515 | MI0022227 |
| 228 | hsa-mir-4651 | MI0017279 |
| 229 | hsa-mir-4257 | MI0015856 |
| 230 | hsa-mir-3188 | MI0014232 |
| 231 | hsa-mir-6131 | MI0021276 |
| 232 | hsa-mir-6766 | MI0022611 |
| 233 | hsa-mir-7641-1 | MI0024975 |
| 234 | hsa-mir-7641-2 | MI0024976 |
| 235 | hsa-mir-1249 | MI0006384 |
| 236 | hsa-mir-3679 | MI0016080 |
| 237 | hsa-mir-6787 | MI0022632 |
| 238 | hsa-mir-4454 | MI0016800 |
| 239 | hsa-mir-3135b | MI0016809 |
| 240 | hsa-mir-6765 | MI0022610 |
| 241 | hsa-mir-7975 | MI0025751 |
| 242 | hsa-mir-204 | MI0000284 |
| 243 | hsa-mir-7977 | MI0025753 |
| 244 | hsa-mir-7110 | MI0022961 |
| 245 | hsa-mir-6717 | MI0022551 |
| 246 | hsa-mir-6870 | MI0022717 |
| 247 | hsa-mir-663b | MI0006336 |
| 248 | hsa-mir-6875 | MI0022722 |
| 249 | hsa-mir-8072 | MI0025908 |
| 250 | hsa-mir-6816 | MI0022661 |
| 251 | hsa-mir-4281 | MI0015885 |
| 252 | hsa-mir-6729 | MI0022574 |
| 253 | hsa-mir-8069 | MI0025905 |
| 254 | hsa-mir-4706 | MI0017339 |
| 255 | hsa-mir-7108 | MI0022959 |
| 256 | hsa-mir-4433b | MI0025511 |
| 257 | hsa-mir-6893 | MI0022740 |
| 258 | hsa-mir-6857 | MI0022703 |
| 259 | hsa-mir-1227 | MI0006316 |
| 260 | hsa-mir-6741 | MI0022586 |
| 261 | hsa-mir-451a | MI0001729 |
| 262 | hsa-mir-8063 | MI0025899 |
| 263 | hsa-mir-3622a | MI0016013 |
| 264 | hsa-mir-615 | MI0003628 |
| 265 | hsa-mir-128-1 | MI0000447 |
| 266 | hsa-mir-6825 | MI0022670 |
| 267 | hsa-mir-1260b | MI0014197 |
| 268 | hsa-mir-4433 | MI0016773 |
| 269 | hsa-mir-4665 | MI0017295 |
| 270 | hsa-mir-7845 | MI0025515 |
| 271 | hsa-mir-1908 | MI0008329 |
| 272 | hsa-mir-6840 | MI0022686 |
| 240 | hsa-mir-6765 | MI0022610 |
| 273 | hsa-mir-296 | MI0000747 |
| 274 | hsa-mir-3675 | MI0016076 |
| 275 | hsa-mir-6781 | MI0022626 |
| 276 | hsa-mir-423 | MI0001445 |
| 277 | hsa-mir-3663 | MI0016064 |
| 278 | hsa-mir-6784 | MI0022629 |
| 279 | hsa-mir-6749 | MI0022594 |
| 280 | hsa-mir-1231 | MI0006321 |
| 281 | hsa-mir-4746 | MI0017385 |
| 282 | hsa-mir-6780b | MI0022681 |
| 283 | hsa-mir-4758 | MI0017399 |
| 236 | hsa-mir-3679 | MI0016080 |
| 284 | hsa-mir-3184 | MI0014226 |
| 285 | hsa-mir-6125 | MI0021259 |
| 286 | hsa-mir-6721 | MI0022556 |
| 287 | hsa-mir-6791 | MI0022636 |
| 288 | hsa-mir-3185 | MI0014227 |
| 289 | hsa-mir-1260a | MI0006394 |
| 290 | hsa-mir-3197 | MI0014245 |
| 291 | hsa-mir-6845 | MI0022691 |
| 292 | hsa-mir-6887 | MI0022734 |
| 293 | hsa-mir-6738 | MI0022583 |
| 294 | hsa-mir-6872 | MI0022719 |
| 295 | hsa-mir-4497 | MI0016859 |
| 296 | hsa-mir-1229 | MI0006319 |
| 297 | hsa-mir-6820 | MI0022665 |
| 298 | hsa-mir-6777 | MI0022622 |
| 299 | hsa-mir-3917 | MI0016423 |
| 300 | hsa-mir-5787 | MI0019797 |
| 301 | hsa-mir-4286 | MI0015894 |
| 302 | hsa-mir-6877 | MI0022724 |
| 303 | hsa-mir-1225 | MI0006311 |
| 304 | hsa-mir-6088 | MI0020365 |
| 305 | hsa-mir-6800 | MI0022645 |
| 306 | hsa-mir-1246 | MI0006381 |
| 307 | hsa-mir-4467 | MI0016818 |
| 308 | hsa-mir-4419b | MI0016861 |
| 309 | hsa-mir-1914 | MI0008335 |
| 310 | hsa-mir-4632 | MI0017259 |
| 311 | hsa-mir-1915 | MI0008336 |
| 312 | hsa-mir-3940 | MI0016597 |
| 313 | hsa-mir-1185-2 | MI0003821 |
| 314 | hsa-mir-6746 | MI0022591 |
| 315 | hsa-mir-5001 | MI0017867 |
| 316 | hsa-mir-1228 | MI0006318 |
| 317 | hsa-mir-5572 | MI0019117 |
| 318 | hsa-mir-4327 | MI0015867 |
| 319 | hsa-mir-4638 | MI0017265 |
| 320 | hsa-mir-6799 | MI0022644 |
| 321 | hsa-mir-6861 | MI0022708 |
| 322 | hsa-mir-6727 | MI0022572 |
| 323 | hsa-mir-4513 | MI0016879 |
| 324 | hsa-mir-6805 | MI0022650 |
| 325 | hsa-mir-6808 | MI0022653 |

TABLE 1-continued

| SEQ ID NO: | Gene name | miRBase registration No. |
|---|---|---|
| 326 | hsa-mir-4449 | MI0016792 |
| 327 | hsa-mir-1199 | MI0020340 |
| 328 | hsa-mir-1275 | MI0006415 |
| 329 | hsa-mir-4792 | MI0017439 |
| 330 | hsa-mir-4443 | MI0016786 |
| 331 | hsa-mir-6891 | MI0022738 |
| 332 | hsa-mir-6826 | MI0022671 |
| 333 | hsa-mir-6807 | MI0022652 |
| 334 | hsa-mir-7150 | MI0023610 |
| 335 | hsa-mir-4534 | MI0016901 |
| 336 | hsa-mir-4476 | MI0016828 |
| 337 | hsa-mir-4649 | MI0017276 |
| 338 | hsa-mir-4525 | MI0016892 |
| 311 | hsa-mir-1915 | MI0008336 |
| 339 | hsa-mir-4516 | MI0016882 |
| 340 | hsa-mir-4417 | MI0016753 |
| 341 | hsa-mir-642b | MI0016685 |
| 342 | hsa-mir-3141 | MI0014165 |
| 343 | hsa-mir-5100 | MI0019116 |
| 344 | hsa-mir-6848 | MI0022694 |
| 345 | hsa-mir-4739 | MI0017377 |
| 346 | hsa-mir-4459 | MI0016805 |
| 347 | hsa-mir-1237 | MI0006327 |
| 273 | hsa-mir-296 | MI0000747 |
| 269 | hsa-mir-4665 | MI0017295 |
| 348 | hsa-mir-6786 | MI0022631 |
| 349 | hsa-mir-4258 | MI0015857 |
| 350 | hsa-mir-6510 | MI0022222 |
| 225 | hsa-mir-1343 | MI0017320 |
| 351 | hsa-mir-1247 | MI0006382 |
| 324 | hsa-mir-6805 | MI0022650 |
| 352 | hsa-mir-4492 | MI0016854 |
| 353 | hsa-mir-1469 | MI0007074 |
| 354 | hsa-mir-1268b | MI0016748 |
| 355 | hsa-mir-6858 | MI0022704 |
| 356 | hsa-mir-3937 | MI0016593 |
| 357 | hsa-mir-939 | MI0005761 |
| 358 | hsa-mir-3656 | MI0016056 |
| 359 | hsa-mir-744 | MI0005559 |
| 360 | hsa-mir-4687 | MI0017319 |
| 361 | hsa-mir-4763 | MI0017404 |
| 362 | hsa-mir-3620 | MI0016011 |
| 363 | hsa-mir-3195 | MI0014240 |
| 364 | hsa-mir-6842 | MI0022688 |
| 365 | hsa-mir-4707 | MI0017340 |
| 366 | hsa-mir-642a | MI0003657 |
| 367 | hsa-mir-7113 | MI0022964 |
| 368 | hsa-mir-4728 | MI0017365 |
| 369 | hsa-mir-5195 | MI0018174 |
| 370 | hsa-mir-1185-1 | MI0003844 |
| 371 | hsa-mir-6774 | MI0022619 |
| 372 | hsa-mir-8059 | MI0025895 |
| 373 | hsa-mir-3131 | MI0014151 |
| 374 | hsa-mir-7847 | MI0025517 |
| 375 | hsa-mir-4463 | MI0016811 |
| 376 | hsa-mir-128-2 | MI0000727 |
| 377 | hsa-mir-4508 | MI0016872 |
| 378 | hsa-mir-6806 | MI0022651 |
| 379 | hsa-mir-7111 | MI0022962 |
| 380 | hsa-mir-6782 | MI0022627 |
| 381 | hsa-mir-4734 | MI0017371 |
| 382 | hsa-mir-3162 | MI0014192 |
| 383 | hsa-mir-887 | MI0005562 |
| 384 | hsa-mir-6752 | MI0022597 |
| 385 | hsa-mir-6724 | MI0022559 |
| 386 | hsa-mir-23b | MI0000439 |
| 387 | hsa-mir-23a | MI0000079 |
| 388 | hsa-mir-625 | MI0003639 |
| 316 | hsa-mir-1228 | MI0006318 |
| 389 | hsa-mir-614 | MI0003627 |
| 390 | hsa-mir-1913 | MI0008334 |
| 391 | hsa-mir-92a-2 | MI0000094 |
| 392 | hsa-mir-187 | MI0000274 |
| 393 | hsa-mir-16-1 | MI0000070 |
| 394 | hsa-mir-16-2 | MI0000115 |
| 395 | hsa-mir-92b | MI0003560 |
| 396 | hsa-mir-150 | MI0000479 |
| 397 | hsa-mir-564 | MI0003570 |
| 398 | hsa-mir-125a | MI0000469 |
| 395 | hsa-mir-92b | MI0003560 |
| 399 | hsa-mir-92a-1 | MI0000093 |
| 391 | hsa-mir-92a-2 | MI0000094 |
| 400 | hsa-mir-663a | MI0003672 |
| 401 | hsa-mir-4688 | MI0017321 |
| 402 | hsa-mir-4648 | MI0017275 |
| 403 | hsa-mir-6085 | MI0020362 |
| 404 | hsa-mir-6126 | MI0021260 |
| 405 | hsa-mir-6880 | MI0022727 |
| 406 | hsa-mir-328 | MI0000804 |
| 407 | hsa-mir-6768 | MI0022613 |
| 408 | hsa-mir-3180-4 | MI0016408 |
| 409 | hsa-mir-3180-5 | MI0016409 |
| 410 | hsa-mir-6087 | MI0020364 |
| 411 | hsa-mir-1273g | MI0018003 |
| 303 | hsa-mir-1225 | MI0006311 |
| 412 | hsa-mir-3196 | MI0014241 |
| 413 | hsa-mir-4695 | MI0017328 |
| 414 | hsa-mir-6732 | MI0022577 |
| 415 | hsa-mir-638 | MI0003653 |
| 416 | hsa-mir-6813 | MI0022658 |
| 417 | hsa-mir-665 | MI0005563 |
| 418 | hsa-mir-486 | MI0002470 |
| 419 | hsa-mir-486-2 | MI0023622 |
| 420 | hsa-mir-4466 | MI0016817 |
| 421 | hsa-mir-30c-1 | MI0000736 |
| 422 | hsa-mir-3621 | MI0016012 |
| 423 | hsa-mir-6743 | MI0022588 |
| 424 | hsa-mir-4298 | MI0015830 |
| 425 | hsa-mir-4741 | MI0017379 |
| 426 | hsa-mir-3619 | MI0016009 |
| 427 | hsa-mir-6824 | MI0022669 |
| 428 | hsa-mir-5698 | MI0019305 |
| 429 | hsa-mir-371a | MI0000779 |
| 430 | hsa-mir-4488 | MI0016849 |
| 431 | hsa-mir-1233-1 | MI0006323 |
| 432 | hsa-mir-1233-2 | MI0015973 |
| 433 | hsa-mir-4723 | MI0017359 |
| 434 | hsa-mir-24-1 | MI0000080 |
| 435 | hsa-mir-24-2 | MI0000081 |
| 436 | hsa-mir-1238 | MI0006328 |
| 437 | hsa-mir-4442 | MI0016785 |
| 438 | hsa-mir-3928 | MI0016438 |
| 439 | hsa-mir-6716 | MI0022550 |
| 440 | hsa-mir-6089-1 | MI0020366 |
| 441 | hsa-mir-6089-2 | MI0023563 |
| 442 | hsa-mir-6124 | MI0021258 |
| 443 | hsa-mir-6778 | MI0022623 |
| 444 | hsa-mir-557 | MI0003563 |
| 445 | hsa-mir-6090 | MI0020367 |
| 446 | isomiR example 1 of SEQ ID NO: 1 | — |
| 447 | isomiR example 2 of SEQ ID NO: 1 | — |
| 448 | isomiR example 1 of SEQ ID NO: 3 | — |
| 449 | isomiR example 2 of SEQ ID NO: 3 | — |
| 450 | isomiR example 1 of SEQ ID NO: 4 | — |
| 451 | isomiR example 2 of SEQ ID NO: 4 | — |
| 452 | isomiR example 1 of SEQ ID NO: 6 | — |
| 453 | isomiR example 2 of SEQ ID NO: 6 | — |
| 454 | isomiR example 1 of SEQ ID NO: 7 | — |
| 455 | isomiR example 2 of SEQ ID NO: 7 | — |
| 456 | isomiR example 1 of SEQ ID NO: 10 | — |
| 457 | isomiR example 2 of SEQ ID NO: 10 | — |
| 458 | isomiR example 1 of SEQ ID NO: 11 | — |
| 459 | isomiR example 2 of SEQ ID NO: 11 | — |
| 460 | isomiR example 1 of SEQ ID NO: 13 | — |
| 461 | isomiR example 2 of SEQ ID NO: 13 | — |
| 462 | isomiR example 1 of SEQ ID NO: 14 | — |
| 463 | isomiR example 2 of SEQ ID NO: 14 | — |
| 464 | isomiR example 1 of SEQ ID NO: 16 | — |
| 465 | isomiR example 2 of SEQ ID NO: 16 | — |
| 466 | isomiR example 1 of SEQ ID NO: 17 | — |
| 467 | isomiR example 2 of SEQ ID NO: 17 | — |
| 468 | isomiR example 1 of SEQ ID NO: 20 | — |

TABLE 1-continued

| SEQ ID NO: | Gene name | miRBase registration No. |
|---|---|---|
| 469 | isomiR example 2 of SEQ ID NO: 20 | — |
| 470 | isomiR example 1 of SEQ ID NO: 22 | — |
| 471 | isomiR example 2 of SEQ ID NO: 22 | — |
| 472 | isomiR example 1 of SEQ ID NO: 26 | — |
| 473 | isomiR example 2 of SEQ ID NO: 26 | — |
| 474 | isomiR example 1 of SEQ ID NO: 29 | — |
| 475 | isomiR example 2 of SEQ ID NO: 29 | — |
| 476 | isomiR example 1 of SEQ ID NO: 36 | — |
| 477 | isomiR example 2 of SEQ ID NO: 36 | — |
| 478 | isomiR example 1 of SEQ ID NO: 38 | — |
| 479 | isomiR example 2 of SEQ ID NO: 38 | — |
| 480 | isomiR example 1 of SEQ ID NO: 39 | — |
| 481 | isomiR example 2 of SEQ ID NO: 39 | — |
| 482 | isomiR example 1 of SEQ ID NO: 40 | — |
| 483 | isomiR example 2 of SEQ ID NO: 40 | — |
| 484 | isomiR example 1 of SEQ ID NO: 42 | — |
| 485 | isomiR example 2 of SEQ ID NO: 42 | — |
| 486 | isomiR example 1 of SEQ ID NO: 43 | — |
| 487 | isomiR example 2 of SEQ ID NO: 43 | — |
| 488 | isomiR example 1 of SEQ ID NO: 44 | — |
| 489 | isomiR example 2 of SEQ ID NO: 44 | — |
| 490 | isomiR example 1 of SEQ ID NO: 46 | — |
| 491 | isomiR example 2 of SEQ ID NO: 46 | — |
| 492 | isomiR example 1 of SEQ ID NO: 49 | — |
| 493 | isomiR example 2 of SEQ ID NO: 49 | — |
| 494 | isomiR example 1 of SEQ ID NO: 52 | — |
| 495 | isomiR example 2 of SEQ ID NO: 52 | — |
| 496 | isomiR example 1 of SEQ ID NO: 59 | — |
| 497 | isomiR example 2 of SEQ ID NO: 59 | — |
| 498 | isomiR example 1 of SEQ ID NO: 60 | — |
| 499 | isomiR example 2 of SEQ ID NO: 60 | — |
| 500 | isomiR example 1 of SEQ ID NO: 62 | — |
| 501 | isomiR example 2 of SEQ ID NO: 62 | — |
| 502 | isomiR example 1 of SEQ ID NO: 63 | — |
| 503 | isomiR example 2 of SEQ ID NO: 63 | — |
| 504 | isomiR example 1 of SEQ ID NO: 65 | — |
| 505 | isomiR example 2 of SEQ ID NO: 65 | — |
| 506 | isomiR example 1 of SEQ ID NO: 66 | — |
| 507 | isomiR example 2 of SEQ ID NO: 66 | — |
| 508 | isomiR example 1 of SEQ ID NO: 67 | — |
| 509 | isomiR example 2 of SEQ ID NO: 67 | — |
| 510 | isomiR example 1 of SEQ ID NO: 72 | — |
| 511 | isomiR example 2 of SEQ ID NO: 72 | — |
| 512 | isomiR example 1 of SEQ ID NO: 76 | — |
| 513 | isomiR example 2 of SEQ ID NO: 76 | — |
| 514 | isomiR example 1 of SEQ ID NO: 77 | — |
| 515 | isomiR example 2 of SEQ ID NO: 77 | — |
| 516 | isomiR example 1 of SEQ ID NO: 78 | — |
| 517 | isomiR example 2 of SEQ ID NO: 78 | — |
| 518 | isomiR example 1 of SEQ ID NO: 81 | — |
| 519 | isomiR example 2 of SEQ ID NO: 81 | — |
| 520 | isomiR example 1 of SEQ ID NO: 83 | — |
| 521 | isomiR example 2 of SEQ ID NO: 83 | — |
| 522 | isomiR example 1 of SEQ ID NO: 84 | — |
| 523 | isomiR example 2 of SEQ ID NO: 84 | — |
| 524 | isomiR example 1 of SEQ ID NO: 85 | — |
| 525 | isomiR example 2 of SEQ ID NO: 85 | — |
| 526 | isomiR example 1 of SEQ ID NO: 86 | — |
| 527 | isomiR example 2 of SEQ ID NO: 86 | — |
| 528 | isomiR example 1 of SEQ ID NO: 87 | — |
| 529 | isomiR example 2 of SEQ ID NO: 87 | — |
| 530 | isomiR example 1 of SEQ ID NO: 88 | — |
| 531 | isomiR example 2 of SEQ ID NO: 88 | — |
| 532 | isomiR example 1 of SEQ ID NO: 89 | — |
| 533 | isomiR example 2 of SEQ ID NO: 89 | — |
| 534 | isomiR example 1 of SEQ ID NO: 90 | — |
| 535 | isomiR example 2 of SEQ ID NO: 90 | — |
| 536 | isomiR example 1 of SEQ ID NO: 92 | — |
| 537 | isomiR example 2 of SEQ ID NO: 92 | — |
| 538 | isomiR example 1 of SEQ ID NO: 93 | — |
| 539 | isomiR example 2 of SEQ ID NO: 93 | — |
| 540 | isomiR example 1 of SEQ ID NO: 94 | — |
| 541 | isomiR example 2 of SEQ ID NO: 94 | — |
| 542 | isomiR example 1 of SEQ ID NO: 96 | — |
| 543 | isomiR example 2 of SEQ ID NO: 96 | — |
| 544 | isomiR example 1 of SEQ ID NO: 100 | — |
| 545 | isomiR example 2 of SEQ ID NO: 100 | — |
| 546 | isomiR example 1 of SEQ ID NO: 103 | — |
| 547 | isomiR example 2 of SEQ ID NO: 103 | — |
| 548 | isomiR example 1 of SEQ ID NO: 105 | — |
| 549 | isomiR example 2 of SEQ ID NO: 105 | — |
| 550 | isomiR example 1 of SEQ ID NO: 106 | — |
| 551 | isomiR example 2 of SEQ ID NO: 106 | — |
| 552 | isomiR example 1 of SEQ ID NO: 107 | — |
| 553 | isomiR example 2 of SEQ ID NO: 107 | — |
| 554 | isomiR example 1 of SEQ ID NO: 113 | — |
| 555 | isomiR example 2 of SEQ ID NO: 113 | — |
| 556 | isomiR example 1 of SEQ ID NO: 114 | — |
| 557 | isomiR example 2 of SEQ ID NO: 114 | — |
| 558 | isomiR example 1 of SEQ ID NO: 115 | — |
| 559 | isomiR example 2 of SEQ ID NO: 115 | — |
| 560 | isomiR example 1 of SEQ ID NO: 116 | — |
| 561 | isomiR example 2 of SEQ ID NO: 116 | — |
| 562 | isomiR example 1 of SEQ ID NO: 117 | — |
| 563 | isomiR example 2 of SEQ ID NO: 117 | — |
| 564 | isomiR example 1 of SEQ ID NO: 118 | — |
| 565 | isomiR example 2 of SEQ ID NO: 118 | — |
| 566 | isomiR example 1 of SEQ ID NO: 119 | — |
| 567 | isomiR example 2 of SEQ ID NO: 119 | — |
| 568 | isomiR example 1 of SEQ ID NO: 120 | — |
| 569 | isomiR example 2 of SEQ ID NO: 120 | — |
| 570 | isomiR example 1 of SEQ ID NO: 121 | — |
| 571 | isomiR example 2 of SEQ ID NO: 121 | — |
| 572 | isomiR example 1 of SEQ ID NO: 123 | — |
| 573 | isomiR example 2 of SEQ ID NO: 123 | — |
| 574 | isomiR example 1 of SEQ ID NO: 124 | — |
| 575 | isomiR example 2 of SEQ ID NO: 124 | — |
| 576 | isomiR example 1 of SEQ ID NO: 125 | — |
| 577 | isomiR example 2 of SEQ ID NO: 125 | — |
| 578 | isomiR example 1 of SEQ ID NO: 126 | — |
| 579 | isomiR example 2 of SEQ ID NO: 126 | — |
| 580 | isomiR example 1 of SEQ ID NO: 130 | — |
| 581 | isomiR example 2 of SEQ ID NO: 130 | — |
| 582 | isomiR example 1 of SEQ ID NO: 132 | — |
| 583 | isomiR example 2 of SEQ ID NO: 132 | — |
| 584 | isomiR example 1 of SEQ ID NO: 134 | — |
| 585 | isomiR example 2 of SEQ ID NO: 134 | — |
| 586 | isomiR example 1 of SEQ ID NO: 136 | — |
| 587 | isomiR example 2 of SEQ ID NO: 136 | — |
| 588 | isomiR example 1 of SEQ ID NO: 139 | — |
| 589 | isomiR example 2 of SEQ ID NO: 139 | — |
| 590 | isomiR example 1 of SEQ ID NO: 140 | — |
| 591 | isomiR example 2 of SEQ ID NO: 140 | — |
| 592 | isomiR example 1 of SEQ ID NO: 141 | — |
| 593 | isomiR example 2 of SEQ ID NO: 141 | — |
| 594 | isomiR example 1 of SEQ ID NO: 142 | — |
| 595 | isomiR example 2 of SEQ ID NO: 142 | — |
| 596 | isomiR example 1 of SEQ ID NO: 143 | — |
| 597 | isomiR example 2 of SEQ ID NO: 143 | — |
| 598 | isomiR example 1 of SEQ ID NO: 144 | — |
| 599 | isomiR example 2 of SEQ ID NO: 144 | — |
| 600 | isomiR example 1 of SEQ ID NO: 145 | — |
| 601 | isomiR example 2 of SEQ ID NO: 145 | — |
| 602 | isomiR example 1 of SEQ ID NO: 147 | — |
| 603 | isomiR example 2 of SEQ ID NO: 147 | — |
| 604 | isomiR example 1 of SEQ ID NO: 148 | — |
| 605 | isomiR example 2 of SEQ ID NO: 148 | — |
| 606 | isomiR example 1 of SEQ ID NO: 150 | — |
| 607 | isomiR example 2 of SEQ ID NO: 150 | — |
| 608 | isomiR example 1 of SEQ ID NO: 151 | — |
| 609 | isomiR example 2 of SEQ ID NO: 151 | — |
| 610 | isomiR example 1 of SEQ ID NO: 152 | — |
| 611 | isomiR example 2 of SEQ ID NO: 152 | — |
| 612 | isomiR example 1 of SEQ ID NO: 155 | — |
| 613 | isomiR example 2 of SEQ ID NO: 155 | — |
| 614 | isomiR example 1 of SEQ ID NO: 157 | — |
| 615 | isomiR example 2 of SEQ ID NO: 157 | — |
| 616 | isomiR example 1 of SEQ ID NO: 158 | — |
| 617 | isomiR example 2 of SEQ ID NO: 158 | — |
| 618 | isomiR example 1 of SEQ ID NO: 159 | — |
| 619 | isomiR example 2 of SEQ ID NO: 159 | — |
| 620 | isomiR example 1 of SEQ ID NO: 163 | — |

TABLE 1-continued

| SEQ ID NO: | Gene name | miRBase registration No. |
|---|---|---|
| 621 | isomiR example 2 of SEQ ID NO: 163 | — |
| 622 | isomiR example 1 of SEQ ID NO: 164 | — |
| 623 | isomiR example 2 of SEQ ID NO: 164 | — |
| 624 | isomiR example 1 of SEQ ID NO: 165 | — |
| 625 | isomiR example 2 of SEQ ID NO: 165 | — |
| 626 | isomiR example 1 of SEQ ID NO: 167 | — |
| 627 | isomiR example 2 of SEQ ID NO: 167 | — |
| 628 | isomiR example 1 of SEQ ID NO: 168 | — |
| 629 | isomiR example 2 of SEQ ID NO: 168 | — |
| 630 | isomiR example 1 of SEQ ID NO: 169 | — |
| 631 | isomiR example 2 of SEQ ID NO: 169 | — |
| 632 | isomiR example 1 of SEQ ID NO: 170 | — |
| 633 | isomiR example 2 of SEQ ID NO: 170 | — |
| 634 | isomiR example 1 of SEQ ID NO: 171 | — |
| 635 | isomiR example 2 of SEQ ID NO: 171 | — |
| 636 | isomiR example 1 of SEQ ID NO: 172 | — |
| 637 | isomiR example 2 of SEQ ID NO: 172 | — |
| 638 | isomiR example 1 of SEQ ID NO: 173 | — |
| 639 | isomiR example 2 of SEQ ID NO: 173 | — |
| 640 | isomiR example 1 of SEQ ID NO: 174 | — |
| 641 | isomiR example 2 of SEQ ID NO: 174 | — |
| 642 | isomiR example 1 of SEQ ID NO: 175 | — |
| 643 | isomiR example 2 of SEQ ID NO: 175 | — |
| 644 | isomiR example 1 of SEQ ID NO: 176 | — |
| 645 | isomiR example 2 of SEQ ID NO: 176 | — |
| 646 | isomiR example 1 of SEQ ID NO: 177 | — |
| 647 | isomiR example 2 of SEQ ID NO: 177 | — |
| 648 | isomiR example 1 of SEQ ID NO: 178 | — |
| 649 | isomiR example 2 of SEQ ID NO: 178 | — |
| 650 | isomiR example 1 of SEQ ID NO: 179 | — |
| 651 | isomiR example 2 of SEQ ID NO: 179 | — |
| 652 | isomiR example 1 of SEQ ID NO: 180 | — |
| 653 | isomiR example 2 of SEQ ID NO: 180 | — |
| 654 | isomiR example 1 of SEQ ID NO: 181 | — |
| 655 | isomiR example 2 of SEQ ID NO: 181 | — |
| 656 | isomiR example 1 of SEQ ID NO: 182 | — |
| 657 | isomiR example 2 of SEQ ID NO: 182 | — |
| 658 | isomiR example 1 of SEQ ID NO: 183 | — |
| 659 | isomiR example 2 of SEQ ID NO: 183 | — |
| 660 | isomiR example 1 of SEQ ID NO: 184 | — |
| 661 | isomiR example 2 of SEQ ID NO: 184 | — |
| 662 | isomiR example 1 of SEQ ID NO: 185 | — |
| 663 | isomiR example 2 of SEQ ID NO: 185 | — |
| 664 | isomiR example 1 of SEQ ID NO: 187 | — |
| 665 | isomiR example 2 of SEQ ID NO: 187 | — |
| 666 | isomiR example 1 of SEQ ID NO: 189 | — |
| 667 | isomiR example 2 of SEQ ID NO: 189 | — |
| 668 | isomiR example 1 of SEQ ID NO: 191 | — |
| 669 | isomiR example 2 of SEQ ID NO: 191 | — |
| 670 | isomiR example 1 of SEQ ID NO: 192 | — |
| 671 | isomiR example 2 of SEQ ID NO: 192 | — |
| 672 | isomiR example 1 of SEQ ID NO: 193 | — |
| 673 | isomiR example 2 of SEQ ID NO: 193 | — |
| 674 | isomiR example 1 of SEQ ID NO: 195 | — |
| 675 | isomiR example 2 of SEQ ID NO: 195 | — |
| 676 | isomiR example 1 of SEQ ID NO: 196 | — |
| 677 | isomiR example 2 of SEQ ID NO: 196 | — |
| 678 | isomiR example 1 of SEQ ID NO: 198 | — |
| 679 | isomiR example 2 of SEQ ID NO: 198 | — |
| 680 | isomiR example 1 of SEQ ID NO: 200 | — |
| 681 | isomiR example 2 of SEQ ID NO: 200 | — |
| 682 | isomiR example 1 of SEQ ID NO: 201 | — |
| 683 | isomiR example 2 of SEQ ID NO: 201 | — |
| 684 | isomiR example 1 of SEQ ID NO: 202 | — |
| 685 | isomiR example 2 of SEQ ID NO: 202 | — |
| 686 | isomiR example 1 of SEQ ID NO: 203 | — |
| 687 | isomiR example 2 of SEQ ID NO: 203 | — |
| 688 | isomiR example 1 of SEQ ID NO: 206 | — |
| 689 | isomiR example 2 of SEQ ID NO: 206 | — |
| 690 | isomiR example 1 of SEQ ID NO: 207 | — |
| 691 | isomiR example 2 of SEQ ID NO: 207 | — |
| 692 | isomiR example 1 of SEQ ID NO: 210 | — |
| 693 | isomiR example 2 of SEQ ID NO: 210 | — |
| 694 | isomiR example 1 of SEQ ID NO: 211 | — |
| 695 | isomiR example 2 of SEQ ID NO: 211 | — |
| 696 | isomiR example 1 of SEQ ID NO: 212 | — |
| 697 | isomiR example 2 of SEQ ID NO: 212 | — |
| 698 | isomiR example 1 of SEQ ID NO: 213 | — |
| 699 | isomiR example 2 of SEQ ID NO: 213 | — |
| 700 | isomiR example 1 of SEQ ID NO: 214 | — |
| 701 | isomiR example 2 of SEQ ID NO: 214 | — |
| 702 | isomiR example 1 of SEQ ID NO: 215 | — |
| 703 | isomiR example 2 of SEQ ID NO: 215 | — |
| 704 | isomiR example 1 of SEQ ID NO: 217 | — |
| 705 | isomiR example 2 of SEQ ID NO: 217 | — |
| 706 | isomiR example 1 of SEQ ID NO: 218 | — |
| 707 | isomiR example 2 of SEQ ID NO: 218 | — |
| 708 | isomiR example 1 of SEQ ID NO: 219 | — |
| 709 | isomiR example 2 of SEQ ID NO: 219 | — |
| 710 | isomiR example 1 of SEQ ID NO: 220 | — |
| 711 | isomiR example 2 of SEQ ID NO: 220 | — |
| 712 | isomiR example 1 of SEQ ID NO: 221 | — |
| 713 | isomiR example 2 of SEQ ID NO: 221 | — |
| 714 | hsa-miR-6757-5p | MIMAT0027414 |
| 715 | hsa-miR-4448 | MIMAT0018967 |
| 716 | hsa-miR-671-5p | MIMAT0003880 |
| 717 | hsa-miR-3178 | MIMAT0015055 |
| 718 | hsa-miR-4725-3p | MIMAT0019844 |
| 719 | hsa-miR-940 | MIMAT0004983 |
| 720 | hsa-miR-6789-5p | MIMAT0027478 |
| 721 | hsa-miR-4484 | MIMAT0019018 |
| 722 | hsa-miR-4634 | MIMAT0019691 |
| 723 | hsa-miR-4745-5p | MIMAT0019878 |
| 724 | hsa-miR-4730 | MIMAT0019852 |
| 725 | hsa-miR-6803-5p | MIMAT0027506 |
| 726 | hsa-miR-6798-5p | MIMAT0027496 |
| 727 | hsa-miR-3648 | MIMAT0018068 |
| 728 | hsa-miR-4783-3p | MIMAT0019947 |
| 729 | hsa-miR-6836-3p | MIMAT0027575 |
| 730 | hsa-mir-6757 | MI0022602 |
| 731 | hsa-mir-4448 | MI0016791 |
| 732 | hsa-mir-671 | MI0003760 |
| 733 | hsa-mir-3178 | MI0014212 |
| 734 | hsa-mir-4725 | MI0017362 |
| 735 | hsa-mir-940 | MI0005762 |
| 736 | hsa-mir-6789 | MI0022634 |
| 737 | hsa-mir-4484 | MI0016845 |
| 738 | hsa-mir-4634 | MI0017261 |
| 739 | hsa-mir-4745 | MI0017384 |
| 740 | hsa-mir-4730 | MI0017367 |
| 741 | hsa-mir-6803 | MI0022648 |
| 742 | hsa-mir-6798 | MI0022643 |
| 743 | hsa-mir-3648 | MI0016048 |
| 744 | hsa-mir-4783 | MI0017428 |
| 745 | hsa-mir-6836 | MI0022682 |
| 746 | isomiR example 1 of SEQ ID NO: 715 | — |
| 747 | isomiR example 2 of SEQ ID NO: 715 | — |
| 748 | isomiR example 1 of SEQ ID NO: 716 | — |
| 749 | isomiR example 2 of SEQ ID NO: 716 | — |
| 750 | isomiR example 1 of SEQ ID NO: 717 | — |
| 751 | isomiR example 2 of SEQ ID NO: 717 | — |
| 752 | isomiR example 1 of SEQ ID NO: 718 | — |
| 753 | isomiR example 2 of SEQ ID NO: 718 | — |
| 754 | isomiR example 1 of SEQ ID NO: 719 | — |
| 755 | isomiR example 2 of SEQ ID NO: 719 | — |
| 756 | isomiR example 1 of SEQ ID NO: 721 | — |
| 757 | isomiR example 2 of SEQ ID NO: 721 | — |
| 758 | isomiR example 1 of SEQ ID NO: 723 | — |
| 759 | isomiR example 2 of SEQ ID NO: 723 | — |
| 760 | isomiR example 1 of SEQ ID NO: 724 | — |
| 761 | isomiR example 2 of SEQ ID NO: 724 | — |
| 762 | isomiR example 1 of SEQ ID NO: 727 | — |
| 763 | isomiR example 2 of SEQ ID NO: 727 | — |
| 764 | isomiR example 1 of SEQ ID NO: 728 | — |
| 765 | isomiR example 2 of SEQ ID NO: 728 | — |

The present specification encompasses the contents described in the specifications and drawings of Japanese Patent Application Nos. 2014-124880 on which the priority of the present application is based.

Advantageous Effects of Invention

According to the present invention, liver cancer can be detected easily and highly accurately. For example, the presence or absence of liver cancer in a patient can be easily detected by using, as an indicator, the measurement values of several miRNAs in blood, serum, and/or plasma of the patient, which can be collected with limited invasiveness.

DESCRIPTION OF EMBODIMENTS

Figure 1:
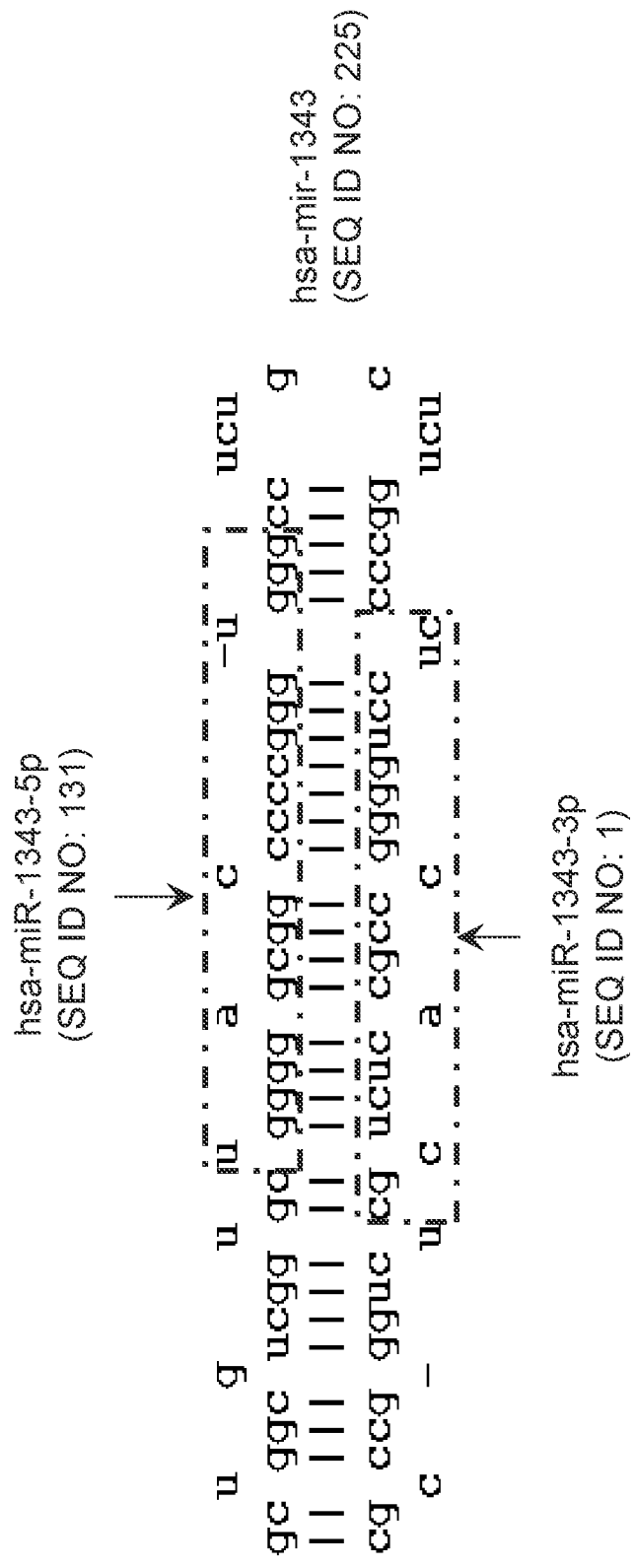
FIG. 1 This figure shows the relationship between the nucleotide sequences of hsa-miR-1343-5p represented by SEQ ID NO: 131 and hsa-miR-1343-3p represented by SEQ ID NO: 1, which are produced from a precursor hsa-mir-1343 represented by SEQ ID NO: 225.

Hereinafter, the present invention will be further described specifically.

1. Target Nucleic Acid for Liver Cancer

As a primary target nucleic acid as a liver cancer marker for detecting the presence and/or absence of liver cancer or liver cancer cells using the nucleic acid probe or the primer for the detection of liver cancer defined above according to the present invention, at least one or more miRNA(s) selected from the group consisting of hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-5p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsamiR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR-671-5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p and hsa-miR-6836-3p can be used. Furthermore, at least one or more miRNA(s) selected from the group consisting of other liver cancer markers that can be combined with these miRNAs, i.e., hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p and hsa-miR-663a can also be preferably used as a target nucleic acid. Moreover, at least one or more miRNA(s) selected from the group consisting of other liver cancer markers that can be combined with these miRNAs, i.e., hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090 can also be preferably used as a target nucleic acid.

These miRNAs include, for example, a human gene comprising a nucleotide sequence represented by any of SEQ ID NOs: 1 to 224 and 714 to 729 (i.e., hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR 5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p, hsa-miR-6836-3p, hsa-miR-23b-3p, hsa-miR-23a-3p, hsa-miR 3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, hsa-miR-663a, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090, respectively), a congener thereof, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 765 or a transcript thereof, more preferably the transcript, i.e., a miRNA or its precursor RNA (pri-miRNA or pre-miRNA).

The first target gene is the hsa-miR-1343-3p gene, a congener thereof, a transcript thereof, or a variant or a derivative thereof. None of the previously known reports show that change in the expression of the gene or the transcript thereof can serve as a marker for liver cancer.

The second target gene is the hsa-miR-6726-5p gene, a congener thereof, a transcript thereof, or a variant or a derivative thereof. None of the previously known reports show that change in the expression of the gene or the transcript thereof can serve as a marker for liver cancer.

The third target gene is the hsa-miR-6515-3p gene, a congener thereof, a transcript thereof, or a variant or a derivative thereof. None of the previously known reports show that change in the expression of the gene or the transcript thereof can serve as a marker for liver cancer.

The fourth target gene is the hsa-miR-4651 gene, a congener thereof, a transcript thereof, or a variant or a derivative thereof. None of the previously known reports show that change in the expression of the gene or the transcript thereof can serve as a marker for liver cancer.

The fifth target gene is the hsa-miR-4257 gene, a congener thereof, a transcript thereof, or a variant or a derivative thereof. None of the previously known reports show that change in the expression of the gene or the transcript thereof can serve as a marker for liver cancer.

The sixth target gene is the hsa-miR-3188 gene, a congener thereof, a transcript thereof, or a variant or a derivative thereof. None of the previously known reports show that change in the expression of the gene or the transcript thereof can serve as a marker for liver cancer.

The seventh target gene is the hsa-miR-6131 gene, a congener thereof, a transcript thereof, or a variant or a derivative thereof. None of the previously known reports show that change in the expression of the gene or the transcript thereof can serve as a marker for liver cancer.

The eighth target gene is the hsa-miR-6766-3p gene, a congener thereof, a transcript thereof, or a variant or a derivative thereof. None of the previously known reports show that change in the expression of the gene or the transcript thereof can serve as a marker for liver cancer.

The ninth target gene is the hsa-miR-7641 gene, a congener thereof, a transcript thereof, or a variant or a derivative thereof. None of the previously known reports show that change in the expression of the gene or the transcript thereof can serve as a marker for liver cancer.

The 10th target gene is the hsa-miR-1249 gene, a congener thereof, a transcript thereof, or a variant or a derivative thereof. None of the previously known reports show that change in the expression of the gene or the transcript thereof can serve as a marker for liver cancer.

The 11th target gene is the hsa-miR-3679-3p gene, a congener thereof, a transcript thereof, or a variant or a derivative thereof. None of the previously known reports show that change in the expression of the gene or the transcript thereof can serve as a marker for liver cancer.

The 12th target gene is the hsa-miR-6787-5p gene, a congener thereof, a transcript thereof, or a variant or a derivative thereof. None of the previously known reports show that change in the expression of the gene or the transcript thereof can serve as a marker for liver cancer.

The 13th target gene is the hsa-miR-4454 gene, a congener thereof, a transcript thereof, or a variant or a derivative thereof. None of the previously known reports show that change in the expression of the gene or the transcript thereof can serve as a marker for liver cancer.

The 14th target gene is the hsa-miR-3135b gene, a congener thereof, a transcript thereof, or a variant or a derivative thereof. None of the previously known reports show that change in the expression of the gene or the transcript thereof can serve as a marker for liver cancer.

The 15th target gene is the hsa-miR-6765-3p gene, a congener thereof, a transcript thereof, or a variant or a derivative thereof. None of the previously known reports show that change in the expression of the gene or the transcript thereof can serve as a marker for liver cancer.

The 16th target gene is the hsa-miR-7975 gene, a congener thereof, a transcript thereof, or a variant or a derivative thereof. None of the previously known reports show that change in the expression of the gene or the transcript thereof can serve as a marker for liver cancer.

The 17th target gene is the hsa-miR-204-3p gene, a congener thereof, a transcript thereof, or a variant or a derivative thereof. None of the previously known reports show that change in the expression of the gene or the transcript thereof can serve as a marker for liver cancer.

The 18th target gene is the hsa-miR-7977 gene, a congener thereof, a transcript thereof, or a variant or a derivative thereof. None of the previously known reports show that change in the expression of the gene or the transcript thereof can serve as a marker for liver cancer.

The 19th target gene is the hsa-miR-7110-5p gene, a congener thereof, a transcript thereof, or a variant or a derivative thereof. None of the previously known reports show that change in the expression of the gene or the transcript thereof can serve as a marker for liver cancer.

The 20th target gene is the hsa-miR-6717-5p gene, a congener thereof, a transcript thereof, or a variant or a derivative thereof. None of the previously known reports show that change in the expression of the gene or the transcript thereof can serve as a marker for liver cancer.

The 21st target gene is the hsa-miR-6870-5p gene, a congener thereof, a transcript thereof, or a variant or a derivative thereof. None of the previously known reports show that change in the expression of the gene or the transcript thereof can serve as a marker for liver cancer.

The 22nd target gene is the hsa-miR-663b gene, a congener thereof, a transcript thereof, or a variant or a derivative thereof. None of the previously known reports show that change in the expression of the gene or the transcript thereof can serve as a marker for liver cancer.

The 23rd target gene is the hsa-miR-6875-5p gene, a congener thereof, a transcript thereof, or a variant or a derivative thereof. None of the previously known reports show that change in the expression of the gene or the transcript thereof can serve as a marker for liver cancer.

The 24th target gene is the hsa-miR-8072 gene, a congener thereof, a transcript thereof, or a variant or a derivative thereof. None of the previously known reports show that change in the expression of the gene or the transcript thereof can serve as a marker for liver cancer.

The 25th target gene is the hsa-miR-6816-5p gene, a congener thereof, a transcript thereof, or a variant or a derivative thereof. None of the previously known reports show that change in the expression of the gene or the transcript thereof can serve as a marker for liver cancer.

The 26th target gene is the hsa-miR-4281 gene, a congener thereof, a transcript thereof, or a variant or a derivative thereof. None of the previously known reports show that change in the expression of the gene or the transcript thereof can serve as a marker for liver cancer.

The 27th target gene is the hsa-miR-6729-5p gene, a congener thereof, a transcript thereof, or a variant or a derivative thereof. None of the previously known reports show that change in the expression of the gene or the transcript thereof can serve as a marker for liver cancer.

The 28th target gene is the hsa-miR-8069 gene, a congener thereof, a transcript thereof, or a variant or a derivative thereof. None of the previously known reports show that change in the expression of the gene or the transcript thereof can serve as a marker for liver cancer.

The 29th target gene is the hsa-miR-4706 gene, a congener thereof, a transcript thereof, or a variant or a derivative thereof. None of the previously known reports show that change in the expression of the gene or the transcript thereof can serve as a marker for liver cancer.

The 30th target gene is the hsa-miR-7108-5p gene, a congener thereof, a transcript thereof, or a variant or a derivative thereof. None of the previously known reports show that change in the expression of the gene or the transcript thereof can serve as a marker for liver cancer.

The 31st target gene is the hsa-miR-4433b-3p gene, a congener thereof, a transcript thereof, or a variant or a derivative thereof. None of the previously known reports show that change in the expression of the gene or the transcript thereof can serve as a marker for liver cancer.

The 32nd target gene is the hsa-miR-6893-5p gene, a congener thereof, a transcript thereof, or a variant or a derivative thereof. None of the previously known reports show that change in the expression of the gene or the transcript thereof can serve as a marker for liver cancer.

The 33rd target gene is the hsa-miR-6857-5p gene, a congener thereof, a transcript thereof, or a variant or a derivative thereof. None of the previously known reports show that change in the expression of the gene or the transcript thereof can serve as a marker for liver cancer.

The 34th target gene is the hsa-miR-1227-5p gene, a congener thereof, a transcript thereof, or a variant or a derivative thereof. None of the previously known reports show that change in the expression of the gene or the transcript thereof can serve as a marker for liver cancer.

The 35th target gene is the hsa-miR-6741-5p gene, a congener thereof, a transcript thereof, or a variant or a derivative thereof. None of the previously known reports show that change in the expression of the gene or the transcript thereof can serve as a marker for liver cancer.

The 36th target gene is the hsa-miR-451a gene, a congener thereof, a transcript thereof, or a variant or a derivative thereof. None of the previously known reports show that change in the expression of the gene or the transcript thereof can serve as a marker for liver cancer.

The 37th target gene is the hsa-miR-8063 gene, a congener thereof, a transcript thereof, or a variant or a derivative thereof. None of the previously known reports show that change in the expression of the gene or the transcript thereof can serve as a marker for liver cancer.

The 38th target gene is the hsa-miR-3622a-5p gene, a congener thereof, a transcript thereof, or a variant or a derivative thereof. None of the previously known reports show that change in the expression of the gene or the transcript thereof can serve as a marker for liver cancer.

The 39th target gene is the hsa-miR-615-5p gene, a congener thereof, a transcript thereof, or a variant or a derivative thereof. None of the previously known reports show that change in the expression of the gene or the transcript thereof can serve as a marker for liver cancer.

The 40th target gene is the hsa-miR-128-1-5p gene, a congener thereof, a transcript thereof, or a variant or a derivative thereof. None of the previously known reports show that change in the expression of the gene or the transcript thereof can serve as a marker for liver cancer.

The 41st target gene is the hsa-miR-6825-5p gene, a congener thereof, a transcript thereof, or a variant or a derivative thereof. None of the previously known reports show that change in the expression of the gene or the transcript thereof can serve as a marker for liver cancer.

The 42nd target gene is the hsa-miR-1260b gene, a congener thereof, a transcript thereof, or a variant or a derivative thereof. None of the previously known reports show that change in the expression of the gene or the transcript thereof can serve as a marker for liver cancer.

The 43rd target gene is the hsa-miR-4433-3p gene, a congener thereof, a transcript thereof, or a variant or a derivative thereof. None of the previously known reports show that change in the expression of the gene or the transcript thereof can serve as a marker for liver cancer.

The 44th target gene is the hsa-miR-4665-5p gene, a congener thereof, a transcript thereof, or a variant or a derivative thereof. None of the previously known reports show that change in the expression of the gene or the transcript thereof can serve as a marker for liver cancer.

The 45th target gene is the hsa-miR-7845-5p gene, a congener thereof, a transcript thereof, or a variant or a derivative thereof. None of the previously known reports show that change in the expression of the gene or the transcript thereof can serve as a marker for liver cancer.

The 46th target gene is the hsa-miR-1908-5p gene, a congener thereof, a transcript thereof, or a variant or a derivative thereof. None of the previously known reports show that change in the expression of the gene or the transcript thereof can serve as a marker for liver cancer.

The 47th target gene is the hsa-miR-6840-3p gene, a congener thereof, a transcript thereof, or a variant or a derivative thereof. None of the previously known reports show that change in the expression of the gene or the transcript thereof can serve as a marker for liver cancer.

The 48th target gene is the hsa-miR-6765-5p gene, a congener thereof, a transcript thereof, or a variant or a derivative thereof. None of the previously known reports show that change in the expression of the gene or the transcript thereof can serve as a marker for liver cancer.

The 49th target gene is the hsa-miR-296-5p gene, a congener thereof, a transcript thereof, or a variant or a derivative thereof. None of the previously known reports show that change in the expression of the gene or the transcript thereof can serve as a marker for liver cancer.

The 50th target gene is the hsa-miR-3675-3p gene, a congener thereof, a transcript thereof, or a variant or a derivative thereof. None of the previously known reports show that change in the expression of the gene or the transcript thereof can serve as a marker for liver cancer.

The 51st target gene is the hsa-miR-6781-5p gene, a congener thereof, a transcript thereof, or a variant or a derivative thereof. None of the previously known reports show that change in the expression of the gene or the transcript thereof can serve as a marker for liver cancer.

The 52nd target gene is the hsa-miR-423-5p gene, a congener thereof, a transcript thereof, or a variant or a derivative thereof. None of the previously known reports show that change in the expression of the gene or the transcript thereof can serve as a marker for liver cancer.

The 53rd target gene is the hsa-miR-3663-3p gene, a congener thereof, a transcript thereof, or a variant or a derivative thereof. None of the previously known reports show that change in the expression of the gene or the transcript thereof can serve as a marker for liver cancer.

The 54th target gene is the hsa-miR-6784-5p gene, a congener thereof, a transcript thereof, or a variant or a derivative thereof. None of the previously known reports show that change in the expression of the gene or the transcript thereof can serve as a marker for liver cancer.

The 55th target gene is the hsa-miR-6749-5p gene, a congener thereof, a transcript thereof, or a variant or a derivative thereof. None of the previously known reports show that change in the expression of the gene or the transcript thereof can serve as a marker for liver cancer.

The 56th target gene is the hsa-miR-1231 gene, a congener thereof, a transcript thereof, or a variant or a derivative thereof. None of the previously known reports show that change in the expression of the gene or the transcript thereof can serve as a marker for liver cancer.

The 57th target gene is the hsa-miR-4746-3p gene, a congener thereof, a transcript thereof, or a variant or a derivative thereof. None of the previously known reports show that change in the expression of the gene or the transcript thereof can serve as a marker for liver cancer.

The 58th target gene is the hsa-miR-6780b-5p gene, a congener thereof, a transcript thereof, or a variant or a derivative thereof. None of the previously known reports show that change in the expression of the gene or the transcript thereof can serve as a marker for liver cancer.

The 59th target gene is the hsa-miR-4758-5p gene, a congener thereof, a transcript thereof, or a variant or a derivative thereof. None of the previously known reports show that change in the expression of the gene or the transcript thereof can serve as a marker for liver cancer.

The 60th target gene is the hsa-miR-3679-5p gene, a congener thereof, a transcript thereof, or a variant or a derivative thereof. None of the previously known reports show that change in the expression of the gene or the transcript thereof can serve as a marker for liver cancer.

The 61st target gene is the hsa-miR-3184-5p gene, a congener thereof, a transcript thereof, or a variant or a derivative thereof. None of the previously known reports show that change in the expression of the gene or the transcript thereof can serve as a marker for liver cancer.

The 62nd target gene is the hsa-miR-6125 gene, a congener thereof, a transcript thereof, or a variant or a derivative thereof. None of the previously known reports show that change in the expression of the gene or the transcript thereof can serve as a marker for liver cancer.

The 63rd target gene is the hsa-miR-6721-5p gene, a congener thereof, a transcript thereof, or a variant or a derivative thereof. None of the previously known reports show that change in the expression of the gene or the transcript thereof can serve as a marker for liver cancer.

The 64th target gene is the hsa-miR-6791-5p gene, a congener thereof, a transcript thereof, or a variant or a derivative thereof. None of the previously known reports show that change in the expression of the gene or the transcript thereof can serve as a marker for liver cancer.

The 65th target gene is the hsa-miR-3185 gene, a congener thereof, a transcript thereof, or a variant or a derivative thereof. None of the previously known reports show that change in the expression of the gene or the transcript thereof can serve as a marker for liver cancer.

The 66th target gene is the hsa-miR-1260a gene, a congener thereof, a transcript thereof, or a variant or a derivative thereof. None of the previously known reports show that change in the expression of the gene or the transcript thereof can serve as a marker for liver cancer.

The 67th target gene is the hsa-miR-3197 gene, a congener thereof, a transcript thereof, or a variant or a derivative thereof. None of the previously known reports show that change in the expression of the gene or the transcript thereof can serve as a marker for liver cancer.

The 68th target gene is the hsa-miR-6845-5p gene, a congener thereof, a transcript thereof, or a variant or a derivative thereof. None of the previously known reports show that change in the expression of the gene or the transcript thereof can serve as a marker for liver cancer.

The 69th target gene is the hsa-miR-6887-5p gene, a congener thereof, a transcript thereof, or a variant or a derivative thereof. None of the previously known reports show that change in the expression of the gene or the transcript thereof can serve as a marker for liver cancer.

The 70th target gene is the hsa-miR-6738-5p gene, a congener thereof, a transcript thereof, or a variant or a derivative thereof. None of the previously known reports show that change in the expression of the gene or the transcript thereof can serve as a marker for liver cancer.

The 71st target gene is the hsa-miR-6872-3p gene, a congener thereof, a transcript thereof, or a variant or a derivative thereof. None of the previously known reports show that change in the expression of the gene or the transcript thereof can serve as a marker for liver cancer.

The 72nd target gene is the hsa-miR-4497 gene, a congener thereof, a transcript thereof, or a variant or a derivative thereof. None of the previously known reports show that change in the expression of the gene or the transcript thereof can serve as a marker for liver cancer.

The 73rd target gene is the hsa-miR-1229-5p gene, a congener thereof, a transcript thereof, or a variant or a derivative thereof. None of the previously known reports show that change in the expression of the gene or the transcript thereof can serve as a marker for liver cancer.

The 74th target gene is the hsa-miR-6820-5p gene, a congener thereof, a transcript thereof, or a variant or a derivative thereof. None of the previously known reports show that change in the expression of the gene or the transcript thereof can serve as a marker for liver cancer.

The 75th target gene is the hsa-miR-6777-5p gene, a congener thereof, a transcript thereof, or a variant or a derivative thereof. None of the previously known reports show that change in the expression of the gene or the transcript thereof can serve as a marker for liver cancer.

The 76th target gene is the hsa-miR-3917 gene, a congener thereof, a transcript thereof, or a variant or a derivative thereof. None of the previously known reports show that change in the expression of the gene or the transcript thereof can serve as a marker for liver cancer.

The 77th target gene is the hsa-miR-5787 gene, a congener thereof, a transcript thereof, or a variant or a derivative thereof. None of the previously known reports show that change in the expression of the gene or the transcript thereof can serve as a marker for liver cancer.

The 78th target gene is the hsa-miR-4286 gene, a congener thereof, a transcript thereof, or a variant or a derivative thereof. None of the previously known reports show that change in the expression of the gene or the transcript thereof can serve as a marker for liver cancer.

The 79th target gene is the hsa-miR-6877-5p gene, a congener thereof, a transcript thereof, or a variant or a derivative thereof. None of the previously known reports show that change in the expression of the gene or the transcript thereof can serve as a marker for liver cancer.

The 80th target gene is the hsa-miR-1225-3p gene, a congener thereof, a transcript thereof, or a variant or a derivative thereof. None of the previously known reports show that change in the expression of the gene or the transcript thereof can serve as a marker for liver cancer.

The 81st target gene is the hsa-miR-6088 gene, a congener thereof, a transcript thereof, or a variant or a derivative thereof. None of the previously known reports show that change in the expression of the gene or the transcript thereof can serve as a marker for liver cancer.

The 82nd target gene is the hsa-miR-6800-5p gene, a congener thereof, a transcript thereof, or a variant or a derivative thereof. None of the previously known reports show that change in the expression of the gene or the transcript thereof can serve as a marker for liver cancer.

The 83rd target gene is the hsa-miR-1246 gene, a congener thereof, a transcript thereof, or a variant or a derivative thereof. None of the previously known reports show that change in the expression of the gene or the transcript thereof can serve as a marker for liver cancer.

The 84th target gene is the hsa-miR-4467 gene, a congener thereof, a transcript thereof, or a variant or a derivative thereof. None of the previously known reports show that change in the expression of the gene or the transcript thereof can serve as a marker for liver cancer.

The 85th target gene is the hsa-miR-4419b gene, a congener thereof, a transcript thereof, or a variant or a derivative thereof. None of the previously known reports show that change in the expression of the gene or the transcript thereof can serve as a marker for liver cancer.

The 86th target gene is the hsa-miR-1914-3p gene, a congener thereof, a transcript thereof, or a variant or a derivative thereof. None of the previously known reports show that change in the expression of the gene or the transcript thereof can serve as a marker for liver cancer.

The 87th target gene is the hsa-miR-4632-5p gene, a congener thereof, a transcript thereof, or a variant or a derivative thereof. None of the previously known reports show that change in the expression of the gene or the transcript thereof can serve as a marker for liver cancer.

The 88th target gene is the hsa-miR-1915-5p gene, a congener thereof, a transcript thereof, or a variant or a derivative thereof. None of the previously known reports show that change in the expression of the gene or the transcript thereof can serve as a marker for liver cancer.

The 89th target gene is the hsa-miR-3940-5p gene, a congener thereof, a transcript thereof, or a variant or a derivative thereof. None of the previously known reports show that change in the expression of the gene or the transcript thereof can serve as a marker for liver cancer.

The 90th target gene is the hsa-miR-1185-2-3p gene, a congener thereof, a transcript thereof, or a variant or a derivative thereof. None of the previously known reports show that change in the expression of the gene or the transcript thereof can serve as a marker for liver cancer.

The 91st target gene is the hsa-miR-6746-5p gene, a congener thereof, a transcript thereof, or a variant or a derivative thereof. None of the previously known reports show that change in the expression of the gene or the transcript thereof can serve as a marker for liver cancer.

The 92nd target gene is the hsa-miR-5001-5p gene, a congener thereof, a transcript thereof, or a variant or a derivative thereof. None of the previously known reports show that change in the expression of the gene or the transcript thereof can serve as a marker for liver cancer.

The 93rd target gene is the hsa-miR-1228-5p gene, a congener thereof, a transcript thereof, or a variant or a derivative thereof. None of the previously known reports show that change in the expression of the gene or the transcript thereof can serve as a marker for liver cancer.

The 94th target gene is the hsa-miR-5572 gene, a congener thereof, a transcript thereof, or a variant or a derivative thereof. None of the previously known reports show that change in the expression of the gene or the transcript thereof can serve as a marker for liver cancer.

The 95th target gene is the hsa-miR-4327 gene, a congener thereof, a transcript thereof, or a variant or a derivative thereof. None of the previously known reports show that change in the expression of the gene or the transcript thereof can serve as a marker for liver cancer.

The 96th target gene is the hsa-miR-4638-5p gene, a congener thereof, a transcript thereof, or a variant or a derivative thereof. None of the previously known reports show that change in the expression of the gene or the transcript thereof can serve as a marker for liver cancer.

The 97th target gene is the hsa-miR-6799-5p gene, a congener thereof, a transcript thereof, or a variant or a derivative thereof. None of the previously known reports show that change in the expression of the gene or the transcript thereof can serve as a marker for liver cancer.

The 98th target gene is the hsa-miR-6861-5p gene, a congener thereof, a transcript thereof, or a variant or a derivative thereof. None of the previously known reports show that change in the expression of the gene or the transcript thereof can serve as a marker for liver cancer.

The 99th target gene is the hsa-miR-6727-5p gene, a congener thereof, a transcript thereof, or a variant or a derivative thereof. None of the previously known reports show that change in the expression of the gene or the transcript thereof can serve as a marker for liver cancer.

The 100th target gene is the hsa-miR-4513 gene, a congener thereof, a transcript thereof, or a variant or a derivative thereof. None of the previously known reports show that change in the expression of the gene or the transcript thereof can serve as a marker for liver cancer.

The 101st target gene is the hsa-miR-6805-3p gene, a congener thereof, a transcript thereof, or a variant or a derivative thereof. None of the previously known reports show that change in the expression of the gene or the transcript thereof can serve as a marker for liver cancer.

The 102nd target gene is the hsa-miR-6808-5p gene, a congener thereof, a transcript thereof, or a variant or a derivative thereof. None of the previously known reports show that change in the expression of the gene or the transcript thereof can serve as a marker for liver cancer.

The 103rd target gene is the hsa-miR-4449 gene, a congener thereof, a transcript thereof, or a variant or a derivative thereof. None of the previously known reports show that change in the expression of the gene or the transcript thereof can serve as a marker for liver cancer.

The 104th target gene is the hsa-miR-1199-5p gene, a congener thereof, a transcript thereof, or a variant or a derivative thereof. None of the previously known reports show that change in the expression of the gene or the transcript thereof can serve as a marker for liver cancer.

The 105th target gene is the hsa-miR-1275 gene, a congener thereof, a transcript thereof, or a variant or a derivative thereof. None of the previously known reports show that change in the expression of the gene or the transcript thereof can serve as a marker for liver cancer.

The 106th target gene is the hsa-miR-4792 gene, a congener thereof, a transcript thereof, or a variant or a derivative thereof. None of the previously known reports show that change in the expression of the gene or the transcript thereof can serve as a marker for liver cancer.

The 107th target gene is the hsa-miR-4443 gene, a congener thereof, a transcript thereof, or a variant or a derivative thereof. None of the previously known reports show that change in the expression of the gene or the transcript thereof can serve as a marker for liver cancer.

The 108th target gene is the hsa-miR-6891-5p gene, a congener thereof, a transcript thereof, or a variant or a derivative thereof. None of the previously known reports show that change in the expression of the gene or the transcript thereof can serve as a marker for liver cancer.

The 109th target gene is the hsa-miR-6826-5p gene, a congener thereof, a transcript thereof, or a variant or a derivative thereof. None of the previously known reports show that change in the expression of the gene or the transcript thereof can serve as a marker for liver cancer.

The 110th target gene is the hsa-miR-6807-5p gene, a congener thereof, a transcript thereof, or a variant or a The 111th target gene is the hsa-miR-7150 gene, a congener thereof, a transcript thereof, or a variant or a derivative thereof. None of the previously known reports show that change in the expression of the gene or the transcript thereof can serve as a marker for liver cancer.

The 112th target gene is the hsa-miR-4534 gene, a congener thereof, a transcript thereof, or a variant or a derivative thereof. None of the previously known reports show that change in the expression of the gene or the transcript thereof can serve as a marker for liver cancer.

The 113th target gene is the hsa-miR-4476 gene, a congener thereof, a transcript thereof, or a variant or a derivative thereof. None of the previously known reports show that change in the expression of the gene or the transcript thereof can serve as a marker for liver cancer.

The 114th target gene is the hsa-miR-4649-5p gene, a congener thereof, a transcript thereof, or a variant or a derivative thereof. None of the previously known reports show that change in the expression of the gene or the transcript thereof can serve as a marker for liver cancer.

The 115th target gene is the hsa-miR-4525 gene, a congener thereof, a transcript thereof, or a variant or a derivative thereof. None of the previously known reports show that change in the expression of the gene or the transcript thereof can serve as a marker for liver cancer.

The 116th target gene is the hsa-miR-1915-3p gene, a congener thereof, a transcript thereof, or a variant or a derivative thereof. None of the previously known reports show that change in the expression of the gene or the transcript thereof can serve as a marker for liver cancer.

The 117th target gene is the hsa-miR-4516 gene, a congener thereof, a transcript thereof, or a variant or a derivative thereof. None of the previously known reports show that change in the expression of the gene or the transcript thereof can serve as a marker for liver cancer.

The 118th target gene is the hsa-miR-4417 gene, a congener thereof, a transcript thereof, or a variant or a derivative thereof. None of the previously known reports show that change in the expression of the gene or the transcript thereof can serve as a marker for liver cancer.

The 119th target gene is the hsa-miR-642b-3p gene, a congener thereof, a transcript thereof, or a variant or a derivative thereof. None of the previously known reports show that change in the expression of the gene or the transcript thereof can serve as a marker for liver cancer.

The 120th target gene is the hsa-miR-3141 gene, a congener thereof, a transcript thereof, or a variant or a derivative thereof. None of the previously known reports show that change in the expression of the gene or the transcript thereof can serve as a marker for liver cancer.

The 121st target gene is the hsa-miR-5100 gene, a congener thereof, a transcript thereof, or a variant or a derivative thereof. None of the previously known reports show that change in the expression of the gene or the transcript thereof can serve as a marker for liver cancer.

The 122nd target gene is the hsa-miR-6848-5p gene, a congener thereof, a transcript thereof, or a variant or a derivative thereof. None of the previously known reports show that change in the expression of the gene or the transcript thereof can serve as a marker for liver cancer.

The 123rd target gene is the hsa-miR-4739 gene, a congener thereof, a transcript thereof, or a variant or a derivative thereof. None of the previously known reports show that change in the expression of the gene or the transcript thereof can serve as a marker for liver cancer.

The 124th target gene is the hsa-miR-4459 gene, a congener thereof, a transcript thereof, or a variant or a derivative thereof. None of the previously known reports show that change in the expression of the gene or the transcript thereof can serve as a marker for liver cancer.

The 125th target gene is the hsa-miR-1237-5p gene, a congener thereof, a transcript thereof, or a variant or a derivative thereof. None of the previously known reports show that change in the expression of the gene or the transcript thereof can serve as a marker for liver cancer.

The 126th target gene is the hsa-miR-296-3p gene, a congener thereof, a transcript thereof, or a variant or a derivative thereof. None of the previously known reports show that change in the expression of the gene or the transcript thereof can serve as a marker for liver cancer.

The 127th target gene is the hsa-miR-4665-3p gene, a congener thereof, a transcript thereof, or a variant or a derivative thereof. None of the previously known reports show that change in the expression of the gene or the transcript thereof can serve as a marker for liver cancer.

The 128th target gene is the hsa-miR-6786-5p gene, a congener thereof, a transcript thereof, or a variant or a derivative thereof. None of the previously known reports show that change in the expression of the gene or the transcript thereof can serve as a marker for liver cancer.

The 129th target gene is the hsa-miR-4258 gene, a congener thereof, a transcript thereof, or a variant or a derivative thereof. None of the previously known reports show that change in the expression of the gene or the transcript thereof can serve as a marker for liver cancer.

The 130th target gene is the hsa-miR-6510-5p gene, a congener thereof, a transcript thereof, or a variant or a derivative thereof. None of the previously known reports show that change in the expression of the gene or the transcript thereof can serve as a marker for liver cancer.

The 131st target gene is the hsa-miR-1343-5p gene, a congener thereof, a transcript thereof, or a variant or a derivative thereof. None of the previously known reports show that change in the expression of the gene or the transcript thereof can serve as a marker for liver cancer.

The 132nd target gene is the hsa-miR-1247-3p gene, a congener thereof, a transcript thereof, or a variant or a derivative thereof. None of the previously known reports show that change in the expression of the gene or the transcript thereof can serve as a marker for liver cancer.

The 133rd target gene is the hsa-miR-6805-5p gene, a congener thereof, a transcript thereof, or a variant or a derivative thereof. None of the previously known reports show that change in the expression of the gene or the transcript thereof can serve as a marker for liver cancer.

The 134th target gene is the hsa-miR-4492 gene, a congener thereof, a transcript thereof, or a variant or a derivative thereof. None of the previously known reports show that change in the expression of the gene or the transcript thereof can serve as a marker for liver cancer.

The 135th target gene is the hsa-miR-1469 gene, a congener thereof, a transcript thereof, or a variant or a derivative thereof. None of the previously known reports show that change in the expression of the gene or the transcript thereof can serve as a marker for liver cancer.

The 136th target gene is the hsa-miR-1268b gene, a congener thereof, a transcript thereof, or a variant or a derivative thereof. None of the previously known reports show that change in the expression of the gene or the transcript thereof can serve as a marker for liver cancer.

The 137th target gene is the hsa-miR-6858-5p gene, a congener thereof, a transcript thereof, or a variant or a derivative thereof. None of the previously known reports show that change in the expression of the gene or the transcript thereof can serve as a marker for liver cancer.

The 138th target gene is the hsa-miR-3937 gene, a congener thereof, a transcript thereof, or a variant or a derivative thereof. None of the previously known reports show that change in the expression of the gene or the transcript thereof can serve as a marker for liver cancer.

The 139th target gene is the hsa-miR-939-5p gene, a congener thereof, a transcript thereof, or a variant or a derivative thereof. None of the previously known reports show that change in the expression of the gene or the transcript thereof can serve as a marker for liver cancer.

The 140th target gene is the hsa-miR-3656 gene, a congener thereof, a transcript thereof, or a variant or a derivative thereof. None of the previously known reports show that change in the expression of the gene or the transcript thereof can serve as a marker for liver cancer.

The 141st target gene is the hsa-miR-744-5p gene, a congener thereof, a transcript thereof, or a variant or a derivative thereof. None of the previously known reports show that change in the expression of the gene or the transcript thereof can serve as a marker for liver cancer.

The 142nd target gene is the hsa-miR-4687-3p gene, a congener thereof, a transcript thereof, or a variant or a derivative thereof. None of the previously known reports show that change in the expression of the gene or the transcript thereof can serve as a marker for liver cancer.

The 143rd target gene is the hsa-miR-4763-3p gene, a congener thereof, a transcript thereof, or a variant or a derivative thereof. None of the previously known reports show that change in the expression of the gene or the transcript thereof can serve as a marker for liver cancer.

The 144th target gene is the hsa-miR-3620-5p gene, a congener thereof, a transcript thereof, or a variant or a derivative thereof. None of the previously known reports show that change in the expression of the gene or the transcript thereof can serve as a marker for liver cancer.

The 145th target gene is the hsa-miR-3195 gene, a congener thereof, a transcript thereof, or a variant or a derivative thereof. None of the previously known reports show that change in the expression of the gene or the transcript thereof can serve as a marker for liver cancer.

The 146th target gene is the hsa-miR-6842-5p gene, a congener thereof, a transcript thereof, or a variant or a derivative thereof. None of the previously known reports show that change in the expression of the gene or the transcript thereof can serve as a marker for liver cancer.

The 147th target gene is the hsa-miR-4707-5p gene, a congener thereof, a transcript thereof, or a variant or a derivative thereof. None of the previously known reports show that change in the expression of the gene or the transcript thereof can serve as a marker for liver cancer.

The 148th target gene is the hsa-miR-642a-3p gene, a congener thereof, a transcript thereof, or a variant or a derivative thereof. None of the previously known reports show that change in the expression of the gene or the transcript thereof can serve as a marker for liver cancer.

The 149th target gene is the hsa-miR-7113-3p gene, a congener thereof, a transcript thereof, or a variant or a derivative thereof. None of the previously known reports show that change in the expression of the gene or the transcript thereof can serve as a marker for liver cancer.

The 150th target gene is the hsa-miR-4728-5p gene, a congener thereof, a transcript thereof, or a variant or a derivative thereof. None of the previously known reports show that change in the expression of the gene or the transcript thereof can serve as a marker for liver cancer.

The 151st target gene is the hsa-miR-5195-3p gene, a congener thereof, a transcript thereof, or a variant or a derivative thereof. None of the previously known reports show that change in the expression of the gene or the transcript thereof can serve as a marker for liver cancer.

The 152nd target gene is the hsa-miR-1185-1-3p gene, a congener thereof, a transcript thereof, or a variant or a derivative thereof. None of the previously known reports show that change in the expression of the gene or the transcript thereof can serve as a marker for liver cancer.

The 153rd target gene is the hsa-miR-6774-5p gene, a congener thereof, a transcript thereof, or a variant or a derivative thereof. None of the previously known reports show that change in the expression of the gene or the transcript thereof can serve as a marker for liver cancer.

The 154th target gene is the hsa-miR-8059 gene, a congener thereof, a transcript thereof, or a variant or a derivative thereof. None of the previously known reports show that change in the expression of the gene or the transcript thereof can serve as a marker for liver cancer.

The 155th target gene is the hsa-miR-3131 gene, a congener thereof, a transcript thereof, or a variant or a derivative thereof. None of the previously known reports show that change in the expression of the gene or the transcript thereof can serve as a marker for liver cancer.

The 156th target gene is the hsa-miR-7847-3p gene, a congener thereof, a transcript thereof, or a variant or a derivative thereof. None of the previously known reports show that change in the expression of the gene or the transcript thereof can serve as a marker for liver cancer.

The 157th target gene is the hsa-miR-4463 gene, a congener thereof, a transcript thereof, or a variant or a derivative thereof. None of the previously known reports show that change in the expression of the gene or the transcript thereof can serve as a marker for liver cancer.

The 158th target gene is the hsa-miR-128-2-5p gene, a congener thereof, a transcript thereof, or a variant or a derivative thereof. None of the previously known reports show that change in the expression of the gene or the transcript thereof can serve as a marker for liver cancer.

The 159th target gene is the hsa-miR-4508 gene, a congener thereof, a transcript thereof, or a variant or a derivative thereof. None of the previously known reports show that change in the expression of the gene or the transcript thereof can serve as a marker for liver cancer.

The 160th target gene is the hsa-miR-6806-5p gene, a congener thereof, a transcript thereof, or a variant or a derivative thereof. None of the previously known reports show that change in the expression of the gene or the transcript thereof can serve as a marker for liver cancer.

The 161st target gene is the hsa-miR-7111-5p gene, a congener thereof, a transcript thereof, or a variant or a derivative thereof. None of the previously known reports show that change in the expression of the gene or the transcript thereof can serve as a marker for liver cancer.

The 162nd target gene is the hsa-miR-6782-5p gene, a congener thereof, a transcript thereof, or a variant or a derivative thereof. None of the previously known reports show that change in the expression of the gene or the transcript thereof can serve as a marker for liver cancer.

The 163rd target gene is the hsa-miR-4734 gene, a congener thereof, a transcript thereof, or a variant or a derivative thereof. None of the previously known reports show that change in the expression of the gene or the transcript thereof can serve as a marker for liver cancer.

The 164th target gene is the hsa-miR-3162-5p gene, a congener thereof, a transcript thereof, or a variant or a derivative thereof. None of the previously known reports show that change in the expression of the gene or the transcript thereof can serve as a marker for liver cancer.

The 165th target gene is the hsa-miR-887-3p gene, a congener thereof, a transcript thereof, or a variant or a derivative thereof. None of the previously known reports show that change in the expression of the gene or the transcript thereof can serve as a marker for liver cancer.

The 166th target gene is the hsa-miR-6752-5p gene, a congener thereof, a transcript thereof, or a variant or a derivative thereof. None of the previously known reports show that change in the expression of the gene or the transcript thereof can serve as a marker for liver cancer.

The 167th target gene is the hsa-miR-6724-5p gene, a congener thereof, a transcript thereof, or a variant or a derivative thereof. None of the previously known reports show that change in the expression of the gene or the transcript thereof can serve as a marker for liver cancer.

The 168th target gene is the hsa-miR-23b-3p gene, a congener thereof, a transcript thereof, or a variant or a derivative thereof. The previously known reports show that change in the expression of the gene or the transcript thereof can serve as a marker for liver cancer (Patent Literatures 2 and 3).

The 169th target gene is the hsa-miR-23a-3p gene, a congener thereof, a transcript thereof, or a variant or a derivative thereof. The previously known report shows that change in the expression of the gene or the transcript thereof can serve as a marker for liver cancer (Patent Literature 2).

The 170th target gene is the hsa-miR-625-3p gene, a congener thereof, a transcript thereof, or a variant or a derivative thereof. The previously known report shows that change in the expression of the gene or the transcript thereof can serve as a marker for liver cancer (Patent Literature 4).

The 171st target gene is the hsa-miR-1228-3p gene, a congener thereof, a transcript thereof, or a variant or a derivative thereof. None of the previously known reports show that change in the expression of the gene or the transcript thereof can serve as a marker for liver cancer.

The 172nd target gene is the hsa-miR-614 gene, a congener thereof, a transcript thereof, or a variant or a derivative thereof. The previously known report shows that change in the expression of the gene or the transcript thereof can serve as a marker for liver cancer (Patent Literature 2).

The 173rd target gene is the hsa-miR-1913 gene, a congener thereof, a transcript thereof, or a variant or a derivative thereof. The previously known report shows that change in the expression of the gene or the transcript thereof can serve as a marker for liver cancer (Patent Literature 4).

The 174th target gene is the hsa-miR-92a-2-5p gene, a congener thereof, a transcript thereof, or a variant or a derivative thereof. The previously known report shows that change in the expression of the gene or the transcript thereof can serve as a marker for liver cancer (Patent Literature 1).

The 175th target gene is the hsa-miR-187-5p gene, a congener thereof, a transcript thereof, or a variant or a derivative thereof. The previously known report shows that change in the expression of the gene or the transcript thereof can serve as a marker for liver cancer (Patent Literature 5).

The 176th target gene is the hsa-miR-16-5p gene, a congener thereof, a transcript thereof, or a variant or a derivative thereof. The previously known report shows that change in the expression of the gene or the transcript thereof can serve as a marker for liver cancer (Patent Literatures 4 and 5).

The 177th target gene is the hsa-miR-92b-3p gene, a congener thereof, a transcript thereof, or a variant or a derivative thereof. The previously known report shows that change in the expression of the gene or the transcript thereof can serve as a marker for liver cancer (Patent Literature 1).

The 178th target gene is the hsa-miR-150-3p gene, a congener thereof, a transcript thereof, or a variant or a derivative thereof. The previously known report shows that change in the expression of the gene or the transcript thereof can serve as a marker for liver cancer (Patent Literature 2).

The 179th target gene is the hsa-miR-564 gene, a congener thereof, a transcript thereof, or a variant or a derivative thereof. The previously known report shows that change in the expression of the gene or the transcript thereof can serve as a marker for liver cancer (Patent Literature 2).

The 180th target gene is the hsa-miR-125a-3p gene, a congener thereof, a transcript thereof, or a variant or a derivative thereof. The previously known report shows that change in the expression of the gene or the transcript thereof can serve as a marker for liver cancer (Patent Literature 3).

The 181st target gene is the hsa-miR-92b-5p gene, a congener thereof, a transcript thereof, or a variant or a derivative thereof. The previously known report shows that change in the expression of the gene or the transcript thereof can serve as a marker for liver cancer (Patent Literature 1).

The 182nd target gene is the hsa-miR-92a-3p gene, a congener thereof, a transcript thereof, or a variant or a derivative thereof. The previously known report shows that change in the expression of the gene or the transcript thereof can serve as a marker for liver cancer (Patent Literatures 1, 4, and 5).

The 183rd target gene is the hsa-miR-663a gene, a congener thereof, a transcript thereof, or a variant or a derivative thereof. The previously known report shows that change in the expression of the gene or the transcript thereof can serve as a marker for liver cancer (Patent Literature 4).

The 184th target gene is the hsa-miR-4688 gene, a congener thereof, a transcript thereof, or a variant or a derivative thereof. None of the previously known reports show that change in the expression of the gene or the transcript thereof can serve as a marker for liver cancer.

The 185th target gene is the hsa-miR-4648 gene, a congener thereof, a transcript thereof, or a variant or a derivative thereof. None of the previously known reports show that change in the expression of the gene or the transcript thereof can serve as a marker for liver cancer.

The 186th target gene is the hsa-miR-6085 gene, a congener thereof, a transcript thereof, or a variant or a derivative thereof. None of the previously known reports show that change in the expression of the gene or the transcript thereof can serve as a marker for liver cancer.

The 187th target gene is the hsa-miR-6126 gene, a congener thereof, a transcript thereof, or a variant or a derivative thereof. None of the previously known reports show that change in the expression of the gene or the transcript thereof can serve as a marker for liver cancer.

The 188th target gene is the hsa-miR-6880-5p gene, a congener thereof, a transcript thereof, or a variant or a derivative thereof. None of the previously known reports show that change in the expression of the gene or the transcript thereof can serve as a marker for liver cancer.

The 189th target gene is the hsa-miR-328-5p gene, a congener thereof, a transcript thereof, or a variant or a derivative thereof. None of the previously known reports show that change in the expression of the gene or the transcript thereof can serve as a marker for liver cancer.

The 190th target gene is the hsa-miR-6768-5p gene, a congener thereof, a transcript thereof, or a variant or a derivative thereof. None of the previously known reports show that change in the expression of the gene or the transcript thereof can serve as a marker for liver cancer.

The 191st target gene is the hsa-miR-3180 gene, a congener thereof, a transcript thereof, or a variant or a derivative thereof. None of the previously known reports show that change in the expression of the gene or the transcript thereof can serve as a marker for liver cancer.

The 192nd target gene is the hsa-miR-6087 gene, a congener thereof, a transcript thereof, or a variant or a derivative thereof. None of the previously known reports show that change in the expression of the gene or the transcript thereof can serve as a marker for liver cancer.

The 193rd target gene is the hsa-miR-1273g-3p gene, a congener thereof, a transcript thereof, or a variant or a derivative thereof. None of the previously known reports show that change in the expression of the gene or the transcript thereof can serve as a marker for liver cancer.

The 194th target gene is the hsa-miR-1225-5p gene, a congener thereof, a transcript thereof, or a variant or a derivative thereof. None of the previously known reports show that change in the expression of the gene or the transcript thereof can serve as a marker for liver cancer.

The 195th target gene is the hsa-miR-3196 gene, a congener thereof, a transcript thereof, or a variant or a derivative thereof. None of the previously known reports show that change in the expression of the gene or the transcript thereof can serve as a marker for liver cancer.

The 196th target gene is the hsa-miR-4695-5p gene, a congener thereof, a transcript thereof, or a variant or a derivative thereof. None of the previously known reports show that change in the expression of the gene or the transcript thereof can serve as a marker for liver cancer.

The 197th target gene is the hsa-miR-6732-5p gene, a congener thereof, a transcript thereof, or a variant or a derivative thereof. None of the previously known reports show that change in the expression of the gene or the transcript thereof can serve as a marker for liver cancer.

The 198th target gene is the hsa-miR-638 gene, a congener thereof, a transcript thereof, or a variant or a derivative thereof. None of the previously known reports show that change in the expression of the gene or the transcript thereof can serve as a marker for liver cancer.

The 199th target gene is the hsa-miR-6813-5p gene, a congener thereof, a transcript thereof, or a variant or a derivative thereof. None of the previously known reports show that change in the expression of the gene or the transcript thereof can serve as a marker for liver cancer.

The 200th target gene is the hsa-miR-665 gene, a congener thereof, a transcript thereof, or a variant or a derivative thereof. None of the previously known reports show that change in the expression of the gene or the transcript thereof can serve as a marker for liver cancer.

The 201st target gene is the hsa-miR-486-3p gene, a congener thereof, a transcript thereof, or a variant or a derivative thereof. The previously known report shows that change in the expression of the gene or the transcript thereof can serve as a marker for liver cancer (Patent Literatures 2 and 3).

The 202nd target gene is the hsa-miR-4466 gene, a congener thereof, a transcript thereof, or a variant or a derivative thereof. None of the previously known reports show that change in the expression of the gene or the transcript thereof can serve as a marker for liver cancer.

The 203rd target gene is the hsa-miR-30c-1-3p gene, a congener thereof, a transcript thereof, or a variant or a derivative thereof. The previously known report shows that change in the expression of the gene or the transcript thereof can serve as a marker for liver cancer (Patent Literatures 3 and 5).

The 204th target gene is the hsa-miR-3621 gene, a congener thereof, a transcript thereof, or a variant or a derivative thereof. None of the previously known reports show that change in the expression of the gene or the transcript thereof can serve as a marker for liver cancer.

The 205th target gene is the hsa-miR-6743-5p gene, a congener thereof, a transcript thereof, or a variant or a derivative thereof. None of the previously known reports show that change in the expression of the gene or the transcript thereof can serve as a marker for liver cancer.

The 206th target gene is the hsa-miR-4298 gene, a congener thereof, a transcript thereof, or a variant or a derivative thereof. None of the previously known reports show that change in the expression of the gene or the transcript thereof can serve as a marker for liver cancer.

The 207th target gene is the hsa-miR-4741 gene, a congener thereof, a transcript thereof, or a variant or a derivative thereof. None of the previously known reports show that change in the expression of the gene or the transcript thereof can serve as a marker for liver cancer.

The 208th target gene is the hsa-miR-3619-3p gene, a congener thereof, a transcript thereof, or a variant or a derivative thereof. None of the previously known reports show that change in the expression of the gene or the transcript thereof can serve as a marker for liver cancer.

The 209th target gene is the hsa-miR-6824-5p gene, a congener thereof, a transcript thereof, or a variant or a derivative thereof. None of the previously known reports show that change in the expression of the gene or the transcript thereof can serve as a marker for liver cancer.

The 210th target gene is the hsa-miR-5698 gene, a congener thereof, a transcript thereof, or a variant or a derivative thereof. None of the previously known reports show that change in the expression of the gene or the transcript thereof can serve as a marker for liver cancer.

The 211th target gene is the hsa-miR-371a-5p gene, a congener thereof, a transcript thereof, or a variant or a derivative thereof. None of the previously known reports show that change in the expression of the gene or the transcript thereof can serve as a marker for liver cancer.

The 212th target gene is the hsa-miR-4488 gene, a congener thereof, a transcript thereof, or a variant or a derivative thereof. None of the previously known reports show that change in the expression of the gene or the transcript thereof can serve as a marker for liver cancer.

The 213th target gene is the hsa-miR-1233-5p gene, a congener thereof, a transcript thereof, or a variant or a derivative thereof. None of the previously known reports show that change in the expression of the gene or the transcript thereof can serve as a marker for liver cancer.

The 214th target gene is the hsa-miR-4723-5p gene, a congener thereof, a transcript thereof, or a variant or a derivative thereof. None of the previously known reports show that change in the expression of the gene or the transcript thereof can serve as a marker for liver cancer.

The 215th target gene is the hsa-miR-24-3p gene, a congener thereof, a transcript thereof, or a variant or a derivative thereof. The previously known report shows that change in the expression of the gene or the transcript thereof can serve as a marker for liver cancer (Patent Literature 2).

The 216th target gene is the hsa-miR-1238-5p gene, a congener thereof, a transcript thereof, or a variant or a derivative thereof. None of the previously known reports show that change in the expression of the gene or the transcript thereof can serve as a marker for liver cancer.

The 217th target gene is the hsa-miR-4442 gene, a congener thereof, a transcript thereof, or a variant or a derivative thereof. None of the previously known reports show that change in the expression of the gene or the transcript thereof can serve as a marker for liver cancer.

The 218th target gene is the hsa-miR-3928-3p gene, a congener thereof, a transcript thereof, or a variant or a derivative thereof. None of the previously known reports show that change in the expression of the gene or the transcript thereof can serve as a marker for liver cancer.

The 219th target gene is the hsa-miR-6716-5p gene, a congener thereof, a transcript thereof, or a variant or a derivative thereof. None of the previously known reports show that change in the expression of the gene or the transcript thereof can serve as a marker for liver cancer.

The 220th target gene is the hsa-miR-6089 gene, a congener thereof, a transcript thereof, or a variant or a derivative thereof. None of the previously known reports show that change in the expression of the gene or the transcript thereof can serve as a marker for liver cancer.

The 221st target gene is the hsa-miR-6124 gene, a congener thereof, a transcript thereof, or a variant or a derivative thereof. None of the previously known reports show that change in the expression of the gene or the transcript thereof can serve as a marker for liver cancer.

The 222nd target gene is the hsa-miR-6778-5p gene, a congener thereof, a transcript thereof, or a variant or a derivative thereof. None of the previously known reports show that change in the expression of the gene or the transcript thereof can serve as a marker for liver cancer.

The 223rd target gene is the hsa-miR-557 gene, a congener thereof, a transcript thereof, or a variant or a derivative thereof. The previously known report shows that change in the expression of the gene or the transcript thereof can serve as a marker for liver cancer (Patent Literature 2).

The 224th target gene is the hsa-miR-6090 gene, a congener thereof, a transcript thereof, or a variant or a derivative thereof. None of the previously known reports show that change in the expression of the gene or the transcript thereof can serve as a marker for liver cancer.

The 225th target gene is the hsa-miR-6757-5p gene, a congener thereof, a transcript thereof, or a variant or a derivative thereof. None of the previously known reports show that change in the expression of the gene or the transcript thereof can serve as a marker for liver cancer.

The 226th target gene is the hsa-miR-4448 gene, a congener thereof, a transcript thereof, or a variant or a derivative thereof. None of the previously known reports show that change in the expression of the gene or the transcript thereof can serve as a marker for liver cancer.

The 227th target gene is the hsa-miR-671-5p gene, a congener thereof, a transcript thereof, or a variant or a derivative thereof. None of the previously known reports show that change in the expression of the gene or the transcript thereof can serve as a marker for liver cancer.

The 228th target gene is the hsa-miR-3178 gene, a congener thereof, a transcript thereof, or a variant or a derivative thereof. None of the previously known reports show that change in the expression of the gene or the transcript thereof can serve as a marker for liver cancer.

The 229th target gene is the hsa-miR-4725-3p gene, a congener thereof, a transcript thereof, or a variant or a derivative thereof. None of the previously known reports show that change in the expression of the gene or the transcript thereof can serve as a marker for liver cancer.

The 230th target gene is the hsa-miR-940 gene, a congener thereof, a transcript thereof, or a variant or a derivative thereof. None of the previously known reports show that change in the expression of the gene or the transcript thereof can serve as a marker for liver cancer.

The 231st target gene is the hsa-miR-6789-5p gene, a congener thereof, a transcript thereof, or a variant or a derivative thereof. None of the previously known reports show that change in the expression of the gene or the transcript thereof can serve as a marker for liver cancer.

The 232nd target gene is the hsa-miR-4484 gene, a congener thereof, a transcript thereof, or a variant or a derivative thereof. None of the previously known reports show that change in the expression of the gene or the transcript thereof can serve as a marker for liver cancer.

The 233rd target gene is the hsa-miR-4634 gene, a congener thereof, a transcript thereof, or a variant or a derivative thereof. None of the previously known reports show that change in the expression of the gene or the transcript thereof can serve as a marker for liver cancer.

The 234th target gene is the hsa-miR-4745-5p gene, a congener thereof, a transcript thereof, or a variant or a derivative thereof. None of the previously known reports show that change in the expression of the gene or the transcript thereof can serve as a marker for liver cancer.

The 235th target gene is the hsa-miR-4730 gene, a congener thereof, a transcript thereof, or a variant or a derivative thereof. None of the previously known reports show that change in the expression of the gene or the transcript thereof can serve as a marker for liver cancer.

The 236th target gene is the hsa-miR-6803-5p gene, a congener thereof, a transcript thereof, or a variant or a derivative thereof. None of the previously known reports show that change in the expression of the gene or the transcript thereof can serve as a marker for liver cancer.

The 237th target gene is the hsa-miR-6798-5p gene, a congener thereof, a transcript thereof, or a variant or a derivative thereof. None of the previously known reports show that change in the expression of the gene or the transcript thereof can serve as a marker for liver cancer.

The 238th target gene is the hsa-miR-3648 gene, a congener thereof, a transcript thereof, or a variant or a derivative thereof. None of the previously known reports show that change in the expression of the gene or the transcript thereof can serve as a marker for liver cancer.

The 239th target gene is the hsa-miR-4783-3p gene, a congener thereof, a transcript thereof, or a variant or a derivative thereof. None of the previously known reports show that change in the expression of the gene or the transcript thereof can serve as a marker for liver cancer.

The 240th target gene is the hsa-miR-6836-3p gene, a congener thereof, a transcript thereof, or a variant or a derivative thereof. None of the previously known reports show that change in the expression of the gene or the transcript thereof can serve as a marker for liver cancer.

2. Nucleic Acid Probe or Primer for Detection of Liver Cancer

In the present invention, a nucleic acid capable of specifically binding to any of the target nucleic acids as the liver cancer markers described above can be used as a nucleic acid, for example, a nucleic acid probe or a primer, for the detection or diagnosis of liver cancer.

In the present invention, the nucleic acid probe or the primer that can be used for detecting liver cancer or for diagnosing liver cancer enables qualitative and/or quantitative measurement of the presence, expression level, or abundance of a target nucleic acid as the liver cancer marker described above, for example, human-derived hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR-671-5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p, or hsa-miR-6836-3p, or a combination thereof, or a congener thereof, a transcript thereof, or a variant or derivative thereof, and, optionally in combination therewith, hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, or hsa-miR-663a, or a combination thereof, a congener thereof, a transcript thereof, or a variant or derivative thereof; and optionally in combination therewith, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557, and hsa-miR-6090, or a combination thereof, a congener thereof, a transcript thereof, or a variant or derivative thereof.

The expression level of each target nucleic acid described above is increased or decreased (hereinafter, referred to as "increased/decreased") depending on the type of the target nucleic acid in a subject having liver cancer as compared with a healthy subject. Hence, the nucleic acid of the present invention can be effectively used for measuring the expression level of the target nucleic acid described above in a body fluid derived from a subject (e.g., a human) suspected of having liver cancer and a body fluid derived from a healthy subject and comparing them to detect liver cancer.

The nucleic acid probe or the primer that can be used in the present invention is a nucleic acid probe capable of specifically binding to a polynucleotide consisting of a nucleotide sequence represented by at least one of SEQ ID NOs: 1 to 167 and 714 to 729, or a primer for amplifying a polynucleotide consisting of a nucleotide sequence represented by at least one of SEQ ID NOs: 1 to 167 and 714 to 729.

The nucleic acid probe or the primer that can be further used in the present invention may comprise a nucleic acid probe capable of specifically binding to a polynucleotide consisting of a nucleotide sequence represented by at least one of SEQ ID NOs: 168 to 183, or a primer for amplifying a polynucleotide consisting of a nucleotide sequence represented by at least one of SEQ ID NOs: 168 to 183.

The nucleic acid probe or the primer that can be further used in the present invention may comprise a nucleic acid probe capable of specifically binding to a polynucleotide consisting of a nucleotide sequence represented by at least one of SEQ ID NOs: 184 to 224, or a primer for amplifying a polynucleotide consisting of a nucleotide sequence represented by at least one of SEQ ID NOs: 184 to 224.

Specifically, these nucleic acid probes or primers comprise a combination of one or more polynucleotides selected from a group of polynucleotides comprising nucleotide sequences represented by any of SEQ ID NOs: 1 to 765 or nucleotide sequences derived from the nucleotide sequences by the replacement of u with t, and a group of complementary polynucleotides thereof, a group of polynucleotides respectively hybridizing under stringent conditions (mentioned later) to DNAs consisting of nucleotide sequences complementary to these nucleotide sequences, and a group of complementary polynucleotides thereof, and a group of polynucleotides comprising 15 or more, preferably 17 or more consecutive nucleotides in the nucleotide sequences of these polynucleotide groups. These polynucleotides can be used as nucleic acid probes and primers for detecting the liver cancer markers as target nucleic acids.

More specifically, examples of the nucleic acid probe or the primer that can be used in the present invention include one or more polynucleotide(s) selected from the group consisting of the following polynucleotides (a) to (e):
- (a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
- (b) a polynucleotide comprising a nucleotide sequence represented by any of SEQ ID NOs: 1 to 167 and 714 to 729,
- (c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
- (d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and
- (e) a polynucleotide hybridizing under stringent conditions to any of the polynucleotides (a) to (d).

In addition to at least one or more polynucleotide(s) selected from the group consisting of the polynucleotides (a) to (e), the nucleic acid probe or the primer that can be further used in the present invention may comprise a polynucleotide selected from the group consisting of the following polynucleotides (f) to (j):
- (f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
- (g) a polynucleotide comprising a nucleotide sequence represented by any of SEQ ID NOs: 168 to 183,
- (h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
- (i) a polynucleotide comprising a nucleotide sequence complementary to a nucleotide sequence represented by any of SEQ ID NOs: 168 to 183 or a nucleotide sequence derived from the nucleotide sequence by the replacement of u with t, and
- (j) a polynucleotide hybridizing under stringent conditions to any of the polynucleotides (f) to (i).

In addition to at least one or more polynucleotide(s) selected from the group consisting of the polynucleotides (a) to (j), the nucleic acid probe or the primer that can be further used in the present invention may comprise a polynucleotide selected from the group consisting of the following polynucleotides (k) to (o):
- (k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides,
- (l) a polynucleotide comprising a nucleotide sequence represented by any of SEQ ID NOs: 184 to 224,
- (m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides,
- (n) a polynucleotide comprising a nucleotide sequence complementary to a nucleotide sequence represented by any of SEQ ID NOs: 184 to 224 or a nucleotide sequence derived from the nucleotide sequence by the replacement of u with t, and
- (o) a polynucleotide hybridizing under stringent conditions to any of the polynucleotides (k) to (n).

For these polynucleotides, the "fragment thereof comprising 15 or more consecutive nucleotides" can comprise the number of nucleotides in the range from, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide, though the fragment is not limited thereto.

These polynucleotides or fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR-671-5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p, hsa-miR-6836-3p, hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, hsa-miR-663a, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090 represented by SEQ ID NOs: 1 to 224 and 714 to 729 are known in the art, and their obtainment methods are also known as mentioned above. Therefore, each polynucleotide that can be used as a nucleic acid probe or a primer in the present invention can be prepared by cloning the gene.

Such a nucleic acid probe or a primer can be chemically synthesized using an automated DNA synthesizer. In general, a phosphoramidite method is used in this synthesis, and single-stranded DNA up to approximately 100 nucleotides can be automatically synthesized by this method. The automated DNA synthesizer is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probe and the primer for detecting the polynucleotide consisting of a nucleotide sequence represented by any of SEQ ID NOs: 1 to 224 and 714 to 729 do not exist as miRNAs or precursors thereof in vivo. For example, the nucleotide sequences represented by SEQ ID NO: 1 and SEQ ID NO: 131 are produced from the precursor represented by SEQ ID NO: 225. This precursor has a hairpin-like structure as shown in FIG. 1, and the nucleotide sequences represented by SEQ ID NO: 1 and SEQ ID NO: 131 have mismatch sequences with each other. Therefore, a nucleotide sequence completely complementary to the nucleotide sequence represented by SEQ ID NO: 1 or SEQ ID NO: 131 is not naturally produced in vivo. Likewise, the nucleic acid probe and the primer for detecting the nucleotide sequence represented by any of SEQ ID NOs: 1 to 224 and 714 to 729 each have an artificial nucleotide sequence that does not exist in vivo.

3. Kit or Device for Detection of Liver Cancer

The present invention also provides a kit or a device for the detection of liver cancer, comprising one or more polynucleotide(s) (which may include a variant, a fragment, or a derivative thereof; hereinafter, also referred to as a polynucleotide for detection) that can be used as a nucleic acid probe or a primer in the present invention for measuring a target nucleic acid as a liver cancer marker.

The target nucleic acid as a liver cancer marker according to the present invention is preferably selected from the following group 1:

miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p.

An additional target nucleic acid that may be optionally used in the measurement is preferably selected from the following group 2: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a.

An additional target nucleic acid that can be optionally further used in the measurement is preferably selected from the following group 3: miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090.

The kit or the device of the present invention comprises a nucleic acid capable of specifically binding to any of the target nucleic acids as the liver cancer markers described above, preferably one or more polynucleotide(s) selected from the nucleic acid probes or the primers described in Section 2 above, specifically, the polynucleotides described in Section 2 above, or variant(s) thereof.

Specifically, the kit or the device of the present invention may comprise at least one or more polynucleotide(s) comprising (or consisting of) a nucleotide sequence represented by any of SEQ ID NOs: 1 to 167 and 714 to 729 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention may further comprise one or more polynucleotide(s) comprising (or consisting of) a nucleotide sequence represented by any of SEQ ID NOs: 168 to 183 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention may further comprise one or more polynucleotide(s) comprising (or consisting of) a nucleotide sequence represented by any of SEQ ID NOs: 184 to 224 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that may be contained in the kit or the device of the present invention is, for example, one or more, preferably two or more polynucleotides selected from the group consisting of the following polynucleotides (1) to (3):

(1) a polynucleotide comprising 15 or more consecutive nucleotides in a nucleotide sequence derived from a nucleotide sequence represented by any of SEQ ID NOs: 1 to 167 and 714 to 729 by the replacement of u with t, or a complementary sequence thereof.

(2) a polynucleotide comprising 15 or more consecutive nucleotides in a nucleotide sequence derived from a nucleotide sequence represented by any of SEQ ID NOs: 168 to 183 by the replacement of u with t, or a complementary sequence thereof and (3) a polynucleotide comprising 15 or more consecutive nucleotides in a nucleotide sequence derived from a nucleotide sequence represented by any of SEQ ID NOs: 184 to 224 by the replacement of u with t, or a complementary sequence thereof.

In a preferred embodiment, the polynucleotide is a polynucleotide consisting of a nucleotide sequence represented by any of SEQ ID NOs: 1 to 167 and 714 to 729 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 168 to 183 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 184 to 224 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment may be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide.

Specific examples of the aforementioned polynucleotide combination constituting the kit or the device of the present invention can include any combination of the polynucleotides consisting of nucleotide sequences represented by SEQ ID NOs shown in Table 1 (SEQ ID NOs: 1 to 224 and 714 to 729 corresponding to the miRNA markers in Table 1) or complementary sequences thereof. However, these are given merely for illustrative purposes, and all of various other possible combinations are included in the present invention.

The aforementioned combination constituting the kit or the device for discriminating a liver cancer patient from a healthy subject according to the present invention is desirably, for example, a combination of two or more of the aforementioned polynucleotides consisting of nucleotide sequences represented by SEQ ID NOs shown in Table 1. Usually, a combination of two of these polynucleotides can produce adequate performance.

The combination of two polynucleotides consisting of the nucleotide sequences or the complementary sequences thereof for specifically discriminating a liver cancer patient from a healthy subject is preferably a combination comprising at least one or more of newly found polynucleotides consisting of the nucleotide sequences represented by SEQ ID NOs: 1 to 167 and 714 to 729, among the combinations of two selected from the polynucleotides consisting of the nucleotide sequences represented by SEQ ID NOs: 1 to 224 and 714 to 729.

The combination of polynucleotides with cancer type specificity capable of discriminating a liver cancer patient not only from a healthy subject but also from other cancer patients is preferably, for example, a combination of a plurality of polynucleotides comprising at least one polynucleotide selected from the group consisting of polynucleotides consisting of the nucleotide sequences represented by SEQ ID NOs: 1, 2, 3, 5, 7, 9, 12, 17, 20, 22, 27, 28, 29, 38, 39, 44, 46, 48, 51, 54, 61, 76, 89, 93, 101, 109, 116, 123, 132, 134, 136, 148, 150, 151, 155, 157, 164, 166, 167, 172, 180, 186, 188, 189, 197, 198, 214, 216, 714, 715, 716, 717, 718, 719, 720, 721, 722, 723, 724, 725, 726, 727, 728 and 729 or complementary sequences thereof (hereinafter, this group is referred to as "cancer type-specific polynucleotide group 1"), with any of the polynucleotides of the other SEQ ID NOs.

The combination of polynucleotides with cancer type specificity capable of discriminating a liver cancer patient not only from a healthy subject but also from other cancer patients is more preferably a combination of a plurality of polynucleotides selected from cancer type-specific polynucleotide group 1.

The combination of polynucleotides with cancer type specificity capable of discriminating a liver cancer patient not only from a healthy subject but also from other cancer patients is more preferably a combination comprising at least one or more polynucleotide(s) selected from the group consisting of polynucleotides consisting of the nucleotide sequences represented by SEQ ID NOs: 1, 3, 7, 9, 22, 38, 44, 134, 148, 155, 157, 164, 167, 172, 214, 714, 715, 716 and 717 or complementary sequences thereof (hereinafter, this group is referred to as "cancer type-specific polynucleotide group 2") included in the cancer type-specific polynucleotide group 1, among the combinations of a plurality of polynucleotides selected from the cancer type-specific polynucleotide group 1.

The number of the polynucleotides with cancer type specificity in the combination described above can be 1, 2, 3, 4, 5, 6, 7, 8, 9, 10 or more in the combination and is more preferably 4 or more in the combination. Usually, the combination of 4 of the polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of three polynucleotides selected from the cancer type-specific polynucleotide group 1 or complementary sequences thereof are listed below.
  (1) a combination of SEQ ID NOs: 1, 7, 9, and 148 (markers: hsa-miR-1343-3p, hsa-miR-6131, hsa-miR-7641, and hsa-miR-642a-3p);
  (2) a combination of SEQ ID NOs: 1, 9, 155, and 172 (markers: hsa-miR-1343-3p, hsa-miR-7641, hsa-miR-3131, and hsa-miR-614);
  (3) a combination of SEQ ID NOs: 1, 9, 148, and 155 (markers: hsa-miR-1343-3p, hsa-miR-7641, hsa-miR-642a-3p, and hsa-miR-3131);
  (4) a combination of SEQ ID NOs: 1, 155, 172, and 715 (markers: hsa-miR-1343-3p, hsa-miR-3131, hsa-miR-614, and hsa-miR-4448); and
  (5) a combination of SEQ ID NOs: 1, 155, 164, and 715 (markers: hsa-miR-1343-3p, hsa-miR-3131, hsa-miR-3162-5p, and hsa-miR-4448).

Non-limiting examples of the combination of the polynucleotide consisting of the nucleotide sequence represented by SEQ ID NO: 3 or a complementary sequence thereof with polynucleotides consisting of nucleotide sequences represented by SEQ ID NOs of three polynucleotides selected from the cancer type-specific polynucleotide group 1 or complementary sequences thereof are further listed below.
  (1) a combination of SEQ ID NOs: 3, 7, 9, and 148 (markers: hsa-miR-6515-3p, hsa-miR-6131, hsa-miR-7641, and hsa-miR-642a-3p);
  (2) a combination of SEQ ID NOs: 3, 22, 27, and 46 (markers: hsa-miR-6515-3p, hsa-miR-663b, hsa-miR-6729-5p, and hsa-miR-1908-5p);
  (3) a combination of SEQ ID NOs: 1, 3, 29, and 155 (markers: hsa-miR-1343-3p, hsa-miR-6515-3p, hsa-miR-4706, and hsa-miR-3131);
  (4) a combination of SEQ ID NOs: 1, 3, 151, and 155 (markers: hsa-miR-1343-3p, hsa-miR-6515-3p, hsa-miR-5195-3p, and hsa-miR-3131); and
  (5) a combination of SEQ ID NOs: 3, 7, 148, and 715 (markers: hsa-miR-6515-3p, hsa-miR-6131, hsa-miR-642a-3p, and hsa-miR-4448).

Non-limiting examples of the combination of the polynucleotide consisting of the nucleotide sequence represented by SEQ ID NO: 7 or a complementary sequence thereof with polynucleotides consisting of nucleotide sequences represented by SEQ ID NOs of three polynucleotides selected from the cancer type-specific polynucleotide group 1 or complementary sequences thereof are further listed below.
  (1) a combination of SEQ ID NOs: 7, 28, 148, and 717 (markers: hsa-miR-6131, hsa-miR-8069, hsa-miR-642a-3p, and hsa-miR-3178);
  (2) a combination of SEQ ID NOs: 7, 9, 148, and 186 (markers: hsa-miR-6131, hsa-miR-7641, hsa-miR-642a-3p, and hsa-miR-6085);
  (3) a combination of SEQ ID NOs: 7, 148, 172, and 715 (markers: hsa-miR-6131, hsa-miR-642a-3p, hsa-miR-614, and hsa-miR-4448);
  (4) a combination of SEQ ID NOs: 7, 9, 148, and 723 (markers: hsa-miR-6131, hsa-miR-7641, hsa-miR-642a-3p, and hsa-miR-4745-5p); and
  (5) a combination of SEQ ID NOs: 7, 9, 28, and 148 (markers: hsa-miR-6131, hsa-miR-7641, hsa-miR-8069, and hsa-miR-642a-3p).

Non-limiting examples of the combination of the polynucleotide consisting of the nucleotide sequence represented by SEQ ID NO: 9 or a complementary sequence thereof with polynucleotides consisting of nucleotide sequences represented by SEQ ID NOs of three polynucleotides selected from the cancer type-specific polynucleotide group 1 or complementary sequences thereof are further listed below.
  (1) a combination of SEQ ID NOs: 7, 9, 148, and 157 (markers: hsa-miR-6131, hsa-miR-7641, hsa-miR-642a-3p, and hsa-miR-4463);
  (2) a combination of SEQ ID NOs: 7, 9, 148, and 722 (markers: hsa-miR-6131, hsa-miR-7641, hsa-miR-642a-3p, and hsa-miR-4634);
  (3) a combination of SEQ ID NOs: 7, 9, 27, and 148 (markers: hsa-miR-6131, hsa-miR-7641, hsa-miR-6729-5p, and hsa-miR-642a-3p);

(4) a combination of SEQ ID NOs: 7, 9, 148, and 725 (markers: hsa-miR-6131, hsa-miR-7641, hsa-miR-642a-3p, and hsa-miR-6803-5p); and
(5) a combination of SEQ ID NOs: 7, 9, 148, and 729 (markers: hsa-miR-6131, hsa-miR-7641, hsa-miR-642a-3p, and hsa-miR-6836-3p).

Non-limiting examples of the combination of the polynucleotide consisting of the nucleotide sequence represented by SEQ ID NO: 22 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 22, and 148 (markers: hsa-miR-6131, hsa-miR-7641, hsa-miR-663b, and hsa-miR-642a-3p);
(2) a combination of SEQ ID NOs: 7, 22, 28, and 148 (markers: hsa-miR-6131, hsa-miR-663b, hsa-miR-8069, and hsa-miR-642a-3p);
(3) a combination of SEQ ID NOs: 7, 22, 148, and 189 (markers: hsa-miR-6131, hsa-miR-663b, hsa-miR-642a-3p, and hsa-miR-328-5p);
(4) a combination of SEQ ID NOs: 2, 7, 22, and 148 (markers: hsa-miR-6726-5p, hsa-miR-6131, hsa-miR-663b, and hsa-miR-642a-3p); and
(5) a combination of SEQ ID NOs: 7, 22, 148, and 720 (markers: hsa-miR-6131, hsa-miR-663b, hsa-miR-642a-3p, and hsa-miR-6789-5p).

Non-limiting examples of the combination of the polynucleotide consisting of the nucleotide sequence represented by SEQ ID NO: 38 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 38, and 148 (markers: hsa-miR-6131, hsa-miR-7641, hsa-miR-3622a-5p, and hsa-miR-642a-3p);
(2) a combination of SEQ ID NOs: 7, 38, 51, and 148 (markers: hsa-miR-6131, hsa-miR-3622a-5p, hsa-miR-6781-5p, and hsa-miR-642a-3p);
(3) a combination of SEQ ID NOs: 7, 38, 148, and 718 (markers: hsa-miR-6131, hsa-miR-3622a-5p, hsa-miR-642a-3p, and hsa-miR-4725-3p);
(4) a combination of SEQ ID NOs: 7, 38, 148, and 216 (markers: hsa-miR-6131, hsa-miR-3622a-5p, hsa-miR-642a-3p, and hsa-miR-1238-5p); and
(5) a combination of SEQ ID NOs: 7, 38, 148, and 728 (markers: hsa-miR-6131, hsa-miR-3622a-5p, hsa-miR-642a-3p, and hsa-miR-4783-3p).

Non-limiting examples of the combination of the polynucleotide consisting of the nucleotide sequence represented by SEQ ID NO: 44 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 44, and 148 (markers: hsa-miR-6131, hsa-miR-7641, hsa-miR-4665-5p, and hsa-miR-642a-3p);
(2) a combination of SEQ ID NOs: 7, 44, 123, and 148 (markers: hsa-miR-6131, hsa-miR-4665-5p, hsa-miR-4739, and hsa-miR-642a-3p);
(3) a combination of SEQ ID NOs: 7, 38, 44, and 148 (markers: hsa-miR-6131, hsa-miR-3622a-5p, hsa-miR-4665-5p, and hsa-miR-642a-3p);
(4) a combination of SEQ ID NOs: 7, 44, 148, and 723 (markers: hsa-miR-6131, hsa-miR-4665-5p, hsa-miR-642a-3p, and hsa-miR-4745-5p); and
(5) a combination of SEQ ID NOs: 7, 44, 48, and 148 (markers: hsa-miR-6131, hsa-miR-4665-5p, hsa-miR-6765-5p, and hsa-miR-642a-3p).

Non-limiting examples of the combination of the polynucleotide consisting of the nucleotide sequence represented by SEQ ID NO: 134 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 134, and 148 (markers: hsa-miR-6131, hsa-miR-7641, hsa-miR-4492, and hsa-miR-642a-3p);
(2) a combination of SEQ ID NOs: 7, 134, 148, and 724 (markers: hsa-miR-6131, hsa-miR-4492, hsa-miR-642a-3p, and hsa-miR-4730);
(3) a combination of SEQ ID NOs: 7, 22, 134, and 148 (markers: hsa-miR-6131, hsa-miR-663b, hsa-miR-4492, and hsa-miR-642a-3p);
(4) a combination of SEQ ID NOs: 7, 134, 148, and 189 (markers: hsa-miR-6131, hsa-miR-4492, hsa-miR-642a-3p, and hsa-miR-328-5p); and
(5) a combination of SEQ ID NOs: 7, 134, 148, and 714 (markers: hsa-miR-6131, hsa-miR-4492, hsa-miR-642a-3p, and hsa-miR-6757-5p).

Non-limiting examples of the combination of the polynucleotide consisting of the nucleotide sequence represented by SEQ ID NO: 148 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 726 (markers: hsa-miR-6131, hsa-miR-7641, hsa-miR-642a-3p, and hsa-miR-6798-5p);
(2) a combination of SEQ ID NOs: 7, 9, 148, and 151 (markers: hsa-miR-6131, hsa-miR-7641, hsa-miR-642a-3p, and hsa-miR-5195-3p);
(3) a combination of SEQ ID NOs: 7, 9, 109, and 148 (markers: hsa-miR-6131, hsa-miR-7641, hsa-miR-6826-5p, and hsa-miR-642a-3p);
(4) a combination of SEQ ID NOs: 5, 7, 9, and 148 (markers: hsa-miR-4257, hsa-miR-6131, hsa-miR-7641, and hsa-miR-642a-3p); and
(5) a combination of SEQ ID NOs: 7, 9, 76, and 148 (markers: hsa-miR-6131, hsa-miR-7641, hsa-miR-3917, and hsa-miR-642a-3p).

Non-limiting examples of the combination of the polynucleotide consisting of the nucleotide sequence represented by SEQ ID NO: 155 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 155 (markers: hsa-miR-6131, hsa-miR-7641, hsa-miR-642a-3p, and hsa-miR-3131);

(2) a combination of SEQ ID NOs: 7, 38, 148, and 155 (markers: hsa-miR-6131, hsa-miR-3622a-5p, hsa-miR-642a-3p, and hsa-miR-3131);
(3) a combination of SEQ ID NOs: 1, 9, 155, and 167 (markers: hsa-miR-1343-3p, hsa-miR-7641, hsa-miR-3131, and hsa-miR-6724-5p);
(4) a combination of SEQ ID NOs: 1, 3, 155, and 715 (markers: hsa-miR-1343-3p, hsa-miR-6515-3p, hsa-miR-3131, and hsa-miR-4448); and
(5) a combination of SEQ ID NOs: 1, 3, 38, and 155 (markers: hsa-miR-1343-3p, hsa-miR-6515-3p, hsa-miR-3622a-5p, and hsa-miR-3131).

Non-limiting examples of the combination of the polynucleotide consisting of the nucleotide sequence represented by SEQ ID NO: 157 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 48, 157, and 714 (markers: hsa-miR-6131, hsa-miR-6765-5p, hsa-miR-4463, and hsa-miR-6757-5p);
(2) a combination of SEQ ID NOs: 7, 38, 148, and 157 (markers: hsa-miR-6131, hsa-miR-3622a-5p, hsa-miR-642a-3p, and hsa-miR-4463);
(3) a combination of SEQ ID NOs: 1, 44, 155, and 157 (markers: hsa-miR-1343-3p, hsa-miR-4665-5p, hsa-miR-3131, and hsa-miR-4463);
(4) a combination of SEQ ID NOs: 7, 76, 157, and 714 (markers: hsa-miR-6131, hsa-miR-3917, hsa-miR-4463, and hsa-miR-6757-5p); and
(5) a combination of SEQ ID NOs: 7, 148, 157, and 189 (markers: hsa-miR-6131, hsa-miR-642a-3p, hsa-miR-4463, and hsa-miR-328-5p).

Non-limiting examples of the combination of the polynucleotide consisting of the nucleotide sequence represented by SEQ ID NO: 164 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 164 (markers: hsa-miR-6131, hsa-miR-7641, hsa-miR-642a-3p, and hsa-miR-3162-5p);
(2) a combination of SEQ ID NOs: 7, 76, 164, and 714 (markers: hsa-miR-6131, hsa-miR-3917, hsa-miR-3162-5p, and hsa-miR-6757-5p);
(3) a combination of SEQ ID NOs: 7, 38, 164, and 714 (markers: hsa-miR-6131, hsa-miR-3622a-5p, hsa-miR-3162-5p, and hsa-miR-6757-5p);
(4) a combination of SEQ ID NOs: 7, 38, 148, and 164 (markers: hsa-miR-6131, hsa-miR-3622a-5p, hsa-miR-642a-3p, and hsa-miR-3162-5p); and
(5) a combination of SEQ ID NOs: 1, 7, 164, and 714 (markers: hsa-miR-1343-3p, hsa-miR-6131, hsa-miR-3162-5p, and hsa-miR-6757-5p).

Non-limiting examples of the combination of the polynucleotide consisting of the nucleotide sequence represented by SEQ ID NO: 167 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 167 (markers: hsa-miR-6131, hsa-miR-7641, hsa-miR-642a-3p, and hsa-miR-6724-5p);
(2) a combination of SEQ ID NOs: 1, 7, 167, and 714 (markers: hsa-miR-1343-3p, hsa-miR-6131, hsa-miR-6724-5p, and hsa-miR-6757-5p);
(3) a combination of SEQ ID NOs: 7, 151, 167, and 714 (markers: hsa-miR-6131, hsa-miR-5195-3p, hsa-miR-6724-5p, and hsa-miR-6757-5p);
(4) a combination of SEQ ID NOs: 7, 148, 167, and 189 (markers: hsa-miR-6131, hsa-miR-642a-3p, hsa-miR-6724-5p, and hsa-miR-328-5p); and
(5) a combination of SEQ ID NOs: 7, 28, 167, and 714 (markers: hsa-miR-6131, hsa-miR-8069, hsa-miR-6724-5p, and hsa-miR-6757-5p).

Non-limiting examples of the combination of the polynucleotide consisting of the nucleotide sequence represented by SEQ ID NO: 172 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 172 (markers: hsa-miR-6131, hsa-miR-7641, hsa-miR-642a-3p, and hsa-miR-614);
(2) a combination of SEQ ID NOs: 7, 150, 172, and 714 (markers: hsa-miR-6131, hsa-miR-4728-5p, hsa-miR-614, and hsa-miR-6757-5p);
(3) a combination of SEQ ID NOs: 7, 172, 714, and 715 (markers: hsa-miR-6131, hsa-miR-614, hsa-miR-6757-5p, and hsa-miR-4448);
(4) a combination of SEQ ID NOs: 7, 38, 155, and 172 (markers: hsa-miR-6131, hsa-miR-3622a-5p, hsa-miR-3131, and hsa-miR-614); and
(5) a combination of SEQ ID NOs: 1, 2, 155, and 172 (markers: hsa-miR-1343-3p, hsa-miR-6726-5p, hsa-miR-3131, and hsa-miR-614).

Non-limiting examples of the combination of the polynucleotide consisting of the nucleotide sequence represented by SEQ ID NO: 214 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 214 (markers: hsa-miR-6131, hsa-miR-7641, hsa-miR-642a-3p, and hsa-miR-4723-5p);
(2) a combination of SEQ ID NOs: 7, 148, 189, and 214 (markers: hsa-miR-6131, hsa-miR-642a-3p, hsa-miR-328-5p, and hsa-miR-4723-5p);
(3) a combination of SEQ ID NOs: 2, 7, 148, and 214 (markers: hsa-miR-6726-5p, hsa-miR-6131, hsa-miR-642a-3p, and hsa-miR-4723-5p);
(4) a combination of SEQ ID NOs: 1, 7, 214, and 714 (markers: hsa-miR-1343-3p, hsa-miR-6131, hsa-miR-4723-5p, and hsa-miR-6757-5p); and
(5) a combination of SEQ ID NOs: 7, 39, 148, and 214 (markers: hsa-miR-6131, hsa-miR-615-5p, hsa-miR-642a-3p, and hsa-miR-4723-5p).

Non-limiting examples of the combination of the polynucleotide consisting of the nucleotide sequence represented by SEQ ID NO: 714 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 714 (markers: hsa-miR-6131, hsa-miR-7641, hsa-miR-642a-3p, and hsa-miR-6757-5p);
(2) a combination of SEQ ID NOs: 7, 54, 148, and 714 (markers: hsa-miR-6131, hsa-miR-6784-5p, hsa-miR-642a-3p, and hsa-miR-6757-5p);
(3) a combination of SEQ ID NOs: 7, 148, 151, and 714 (markers: hsa-miR-6131, hsa-miR-642a-3p, hsa-miR-5195-3p, and hsa-miR-6757-5p);
(4) a combination of SEQ ID NOs: 7, 38, 148, and 714 (markers: hsa-miR-6131, hsa-miR-3622a-5p, hsa-miR-642a-3p, and hsa-miR-6757-5p); and
(5) a combination of SEQ ID NOs: 7, 28, 148, and 714 (markers: hsa-miR-6131, hsa-miR-8069, hsa-miR-642a-3p, and hsa-miR-6757-5p).

Non-limiting examples of the combination of the polynucleotide consisting of the nucleotide sequence represented by SEQ ID NO: 715 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 2, 7, 148, and 715 (markers: hsa-miR-6726-5p, hsa-miR-6131, hsa-miR-642a-3p, and hsa-miR-4448);
(2) a combination of SEQ ID NOs: 7, 9, 148, and 715 (markers: hsa-miR-6131, hsa-miR-7641, hsa-miR-642a-3p, and hsa-miR-4448);
(3) a combination of SEQ ID NOs: 7, 17, 148, and 715 (markers: hsa-miR-6131, hsa-miR-204-3p, hsa-miR-642a-3p, and hsa-miR-4448);
(4) a combination of SEQ ID NOs: 7, 38, 148, and 715 (markers: hsa-miR-6131, hsa-miR-3622a-5p, hsa-miR-642a-3p, and hsa-miR-4448); and
(5) a combination of SEQ ID NOs: 7, 148, 715, and 725 (markers: hsa-miR-6131, hsa-miR-642a-3p, hsa-miR-6803-5p, and hsa-miR-4448).

Non-limiting examples of the combination of the polynucleotide consisting of the nucleotide sequence represented by SEQ ID NO: 716 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 716 (markers: hsa-miR-6131, hsa-miR-7641, hsa-miR-642a-3p, and hsa-miR-671-5p);
(2) a combination of SEQ ID NOs: 7, 148, 714, and 716 (markers: hsa-miR-6131, hsa-miR-642a-3p, 6757-5p, and hsa-miR-671-5p);
(3) a combination of SEQ ID NOs: 2, 7, 148, and 716 (markers: hsa-miR-6726-5p, hsa-miR-6131, hsa-miR-642a-3p, and hsa-miR-671-5p);
(4) a combination of SEQ ID NOs: 7, 38, 148, and 716 (markers: hsa-miR-6131, hsa-miR-3622a-5p, hsa-miR-642a-3p, and hsa-miR-671-5p); and
(5) a combination of SEQ ID NOs: 7, 148, 715, and 716 (markers: hsa-miR-6131, hsa-miR-642a-3p, hsa-miR-4448, and hsa-miR-671-5p).

Non-limiting examples of the combination of the polynucleotide consisting of the nucleotide sequence represented by SEQ ID NO: 717 or a complementary sequence thereof with polynucleotides consisting of nucleotide sequences represented by SEQ ID NOs of three polynucleotides selected from the cancer type-specific polynucleotide group 1 or complementary sequences thereof are further listed below.
(1) a combination of SEQ ID NOs: 7, 9, 148, and 717 (markers: hsa-miR-6131, hsa-miR-7641, hsa-miR-642a-3p, and hsa-miR-3178);
(2) a combination of SEQ ID NOs: 7, 38, 148, and 717 (markers: hsa-miR-6131, hsa-miR-3622a-5p, hsa-miR-642a-3p, and hsa-miR-3178);
(3) a combination of SEQ ID NOs: 7, 27, 148, and 717 (markers: hsa-miR-6131, hsa-miR-6729-5p, hsa-miR-642a-3p, and hsa-miR-3178);
(4) a combination of SEQ ID NOs: 7, 44, 148, and 717 (markers: hsa-miR-6131, hsa-miR-4665-5p, hsa-miR-642a-3p, and hsa-miR-3178); and
(5) a combination of SEQ ID NOs: 7, 148, 715, and 717 (markers: hsa-miR-6131, hsa-miR-642a-3p, hsa-miR-4448, and hsa-miR-3178).

The kit or the device of the present invention may also comprise a polynucleotide that is already known or that will be found in the future, to enable detection of liver cancer, in addition to the polynucleotide(s) (which can include variant(s), fragment(s), and derivative(s)) according to the present invention described above.

The kit of the present invention may also comprise an antibody for measuring a marker for liver cancer examination known in the art, such as AFP, CEA, CA19-9 and PIVKA-II, in addition to the polynucleotide(s) according to the present invention as described above.

These polynucleotides contained in the kit of the present invention may be packaged in different containers either individually or in any combination.

The kit of the present invention may comprise a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the polynucleotides of at least one or more, preferably at least two or more, more preferably at least three or more, most preferably at least five or more to all of the liver cancer marker miRNAs, respectively, of the group 1 described above. The kit or the device of the present invention may optionally further comprise nucleic acids capable of specifically binding to the polynucleotides of at least one or more, preferably at least two or more, more preferably at least three or more, most preferably at least five or more to all of the liver cancer marker miRNAs, respectively, of the group 2 described above. The kit or the device of the present invention may optionally further comprise nucleic acids capable of specifically binding to the polynucleotides of at least one or more, preferably at least two or more, more preferably at least three or more, most preferably at least five or more to all of the liver cancer marker miRNAs, respectively, of the group 3 described above.

The kit or the device of the present invention can be used for detecting liver cancer as described in Section 4 below.

4. Method for Detecting Liver Cancer

The present invention further provides a method for detecting liver cancer, comprising using the kit or the device of the present invention (comprising the above-mentioned nucleic acid(s) that can be used in the present invention) described in Section 3 above to measure expression level(s) of one or more liver cancer-derived gene(s) being an expression level of liver cancer-derived gene(s) selected from the following group: miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-3p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p; optionally an expression level of liver cancer-derived gene(s) selected from the following group: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a; and optionally an expression level of liver cancer-derived gene(s) selected from miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR 3p, miR-1238-5p, miR-4442, miR-3928-3p, miR-6716-5p, miR-6089, miR-6124, miR-6778-5p, miR-557 and miR-6090 in a sample in vitro, further comparing, for example, the expression level(s) of the aforementioned gene(s) in the sample (e.g., blood, serum, or plasma) collected from a subject suspected of having liver cancer with a control expression level in the sample collected from a healthy subject (including a non-liver cancer patient), and evaluating the subject as having liver cancer when the expression level(s) of the target nucleic acid(s) is statistically significantly different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the liver cancer-derived gene from the sample such as blood, serum, or plasma according to the present invention is particularly preferably prepared by the addition of a reagent for RNA extraction in 3D-Gene® RNA extraction reagent from liquid sample kit (Toray Industries, Inc.). A general acidic phenol method (acid guanidinium-phenol-chloroform (AGPC)) may be used, or Trizol® (Life Technologies Corp.) may be used. The liver cancer-derived gene may be prepared by the addition of a reagent for RNA extraction containing acidic phenol, such as Trizol® (Life Technologies Corp.) or Isogen (Nippon Gene Co., Ltd.). Alternatively, a kit such as miRNeasy® Mini Kit (Qiagen N. V.) can be used, though the method is not limited thereto.

The present invention also provides use of the kit or the device of the present invention for detecting in vitro an expression product of a liver cancer-derived miRNA gene in a sample derived from a subject.

In the method of the present invention, the kit or device described above comprising a single polynucleotide or any possible combination of the polynucleotides that can be used in the present invention as described above is used.

In the detection or (genetic) diagnosis of liver cancer according to the present invention, each polynucleotide contained in the kit or the device of the present invention can be used as a probe or a primer. In the case of using the polynucleotide as a primer, TaqMan® MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine of the subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of liver cancer or the detection of the presence or absence of liver cancer. Specifically, the detection of liver cancer using the kit or the device can be performed by detecting in vitro an expression level of a gene using the nucleic acid probe or the primer contained in the kit or the device in a sample such as blood, serum, plasma, or urine from a subject suspected of having liver cancer. The subject suspected of having liver cancer can be evaluated as having liver cancer when the expression level of a target miRNA marker measured using polynucleotide(s) (including variant(s), fragment(s), and derivative(s) thereof) consisting of a nucleotide sequence represented by at least one or more of SEQ ID NOs: 1 to 167 and 714 to 729 or a complementary sequence thereof, optionally a nucleotide sequence represented by one or more of SEQ ID NOs: 168 to 183 or a complementary sequence thereof, and optionally a nucleotide sequence represented by one or more of SEQ ID NOs: 184 to 224 or a complementary sequence thereof in the sample such as blood, serum, plasma, or urine of the subject is statistically significantly different compared with the expression level thereof in the sample such as blood, serum, or plasma, or urine of a healthy subject.

The method of the present invention can be combined with a diagnostic imaging method such as ultrasonography, CT scanning, MRI scanning, or angiography examination. The method of the present invention is capable of specifically detecting liver cancer and can substantially discriminate liver cancer from the other cancers.

The method for detecting the absence of an expression product of a liver cancer-derived gene or the presence of the expression product of a liver cancer-derived gene in a sample using the kit or the device of the present invention comprises collecting a body fluid such as blood, serum, plasma, or urine of a subject, and measuring the expression level of the target gene contained therein using one or more polynucleotide(s) (including variant(s), fragment(s), or derivative(s)) selected from the polynucleotide group of the present invention, to evaluate the presence or absence of liver cancer or to detect liver cancer. Using the method for detecting liver cancer according to the present invention, for example, the presence or absence of amelioration of the disease or the degree of amelioration thereof in a liver cancer patient when a therapeutic drug is administered to the patient for amelioration of the disease can be also evaluated or diagnosed.

The method of the present invention may comprise, for example, the following steps (a), (b), and (c):
(a) a step of contacting in vitro a sample derived from a subject with a polynucleotide in the kit or the device of the present invention;
(b) a step of measuring an expression level of the target nucleic acid in the sample using the polynucleotide as a nucleic acid probe or a primer; and
(c) a step of evaluating the presence or absence of liver cancer (cells) in the subject on the basis of a measurement result obtained in the step (b).

Specifically, the present invention provides a method for detecting liver cancer, comprising measuring an expression level of a target nucleic acid in a sample of a subject using nucleic acid(s) capable of specifically binding to at least one or more (preferably at least two or more) polynucleotide(s) selected from the group consisting of miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-5p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p, and evaluating in vitro whether or not the subject has liver cancer using the measured expression level and a control expression level of a healthy subject measured in the same way as above.

The term "evaluation" used herein is evaluation support based on results of in vitro examination, not physician's judgment.

As described above, in a preferred embodiment of the method of the present invention, specifically, miR-1343-3p is hsa-miR-1343-3p, miR-6726-5p is hsa-miR-6726-5p, miR-6515-3p is hsa-miR-6515-3p, miR-4651 is hsa-miR-4651, miR-4257 is hsa-miR-4257, miR-3188 is hsa-miR- 3188, miR-6131 is hsa-miR-6131, miR-6766-3p is hsa-miR-6766-3p, miR-7641 is hsa-miR-7641, miR-1249 is hsa-miR-1249, miR-3679-3p is hsa-miR-3679-3p, miR-6787-5p is hsa-miR-6787-5p, miR-4454 is hsa-miR-4454, miR-3135b is hsa-miR-3135b, miR-6765-3p is hsa-miR-6765-3p, miR-7975 is hsa-miR-7975, miR-204-3p is hsa-miR-204-3p, miR-7977 is hsa-miR-7977, miR-7110-5p is hsa-miR-7110-5p, miR-6717-5p is hsa-miR-6717-5p, miR-6870-5p is hsa-miR-6870-5p, miR-663b is hsa-miR-663b, miR-6875-5p is hsa-miR-6875-5p, miR-8072 is hsa-miR-8072, miR-6816-5p is hsa-miR-6816-5p, miR-4281 is hsa-miR-4281, miR-6729-5p is hsa-miR-6729-5p, miR-8069 is hsa-miR-8069, miR-4706 is hsa-miR-4706, miR-7108-5p is hsa-miR-7108-5p, miR-4433b-3p is hsa-miR-4433b-3p, miR-6893-5p is hsa-miR-6893-5p, miR-6857-5p is hsa-miR-6857-5p, miR-1227-5p is hsa-miR-1227-5p, miR-6741-5p is hsa-miR-6741-5p, miR-451a is hsa-miR-451a, miR-8063 is hsa-miR-8063, miR-3622a-5p is hsa-miR-3622a-5p, miR-615-5p is hsa-miR-615-5p, miR-128-1-5p is hsa-miR-128-1-5p, miR-6825-5p is hsa-miR-6825-5p, miR-1260b is hsa-miR-1260b, miR-4433-3p is hsa-miR-4433-3p, miR-4665-5p is hsa-miR-4665-5p, miR-7845-5p is hsa-miR-7845-5p, miR-1908-5p is hsa-miR-1908-5p, miR-6840-3p is hsa-miR-6840-3p, miR-6765-5p is hsa-miR-6765-5p, miR-296-5p is hsa-miR-296-5p, miR-3675-3p is hsa-miR-3675-3p, miR-6781-5p is hsa-miR-6781-5p, miR-423-5p is hsa-miR-423-5p, miR-3663-3p is hsa-miR-3663-3p, miR-6784-5p is hsa-miR-6784-5p, miR-6749-5p is hsa-miR-6749-5p, miR-1231 is hsa-miR-1231, miR-4746-3p is hsa-miR-4746-3p, miR-6780b-5p is hsa-miR-6780b-5p, miR-4758-5p is hsa-miR-4758-5p, miR-3679-5p is hsa-miR-3679-5p, miR-3184-5p is hsa-miR-3184-5p, miR-6125 is hsa-miR-6125, miR-6721-5p is hsa-miR-6721-5p, miR-6791-5p is hsa-miR-6791-5p, miR-3185 is hsa-miR-3185, miR-1260a is hsa-miR-1260a, miR-3197 is hsa-miR-3197, miR-6845-5p is hsa-miR-6845-5p, miR-6887-5p is hsa-miR-6887-5p, miR-6738-5p is hsa-miR-6738-5p, miR-6872-3p is hsa-miR-6872-3p, miR-4497 is hsa-miR-4497, miR-1229-5p is hsa-miR-1229-5p, miR-6820-5p is hsa-miR-6820-5p, miR-6777-5p is hsa-miR-6777-5p, miR-3917 is hsa-miR-3917, miR-5787 is hsa-miR-5787, miR-4286 is hsa-miR-4286, miR-6877-5p is hsa-miR-6877-5p, miR-1225-3p is hsa-miR-1225-3p, miR-6088 is hsa-miR-6088, miR-6800-5p is hsa-miR-6800-5p, miR-1246 is hsa-miR-1246, miR-4467 is hsa-miR-4467, miR-4419b is hsa-miR-4419b, miR-1914-3p is hsa-miR-1914-3p, miR-4632-5p is hsa-miR-4632-5p, miR-1915-5p is hsa-miR-1915-5p, miR-3940-5p is hsa-miR-3940-5p, miR-1185-2-3p is hsa-miR-1185-2-3p, miR-6746-5p is hsa-miR-6746-5p, miR-5001-5p is hsa-miR-5001-5p, miR-1228-5p is hsa-miR-1228-5p, miR-5572 is hsa-miR-5572, miR-4327 is hsa-miR-4327, miR-4638-5p is hsa-miR-4638-5p, miR-6799-5p is hsa-miR-6799-5p, miR-6861-5p is hsa-miR-6861-5p, miR-6727-5p is hsa-miR-6727-5p, miR-4513 is hsa-miR-4513, miR-6805-3p is hsa-miR-6805-3p, miR-6808-5p is hsa-miR-6808-5p, miR-4449 is hsa-miR-4449, miR-1199-5p is hsa-miR-1199-5p, miR-1275 is hsa-miR-1275, miR-4792 is hsa-miR-4792, miR-4443 is hsa-miR-4443, miR-6891-5p is hsa-miR-6891-5p, miR-6826-5p is hsa-miR-6826-5p, miR-6807-5p is hsa-miR-6807-5p, miR-7150 is hsa-miR-7150, miR-4534 is hsa-miR-4534, miR-4476 is hsa-miR-4476, miR-4649-5p is hsa-miR-4649-5p, miR-4525 is hsa-miR-4525, miR-1915-3p is hsa-miR-1915-3p, miR-4516 is hsa-miR-4516, miR-4417 is hsa-miR-4417, miR-642b-3p is hsa-miR-642b-3p, miR-3141 is hsa-miR-3141, miR-5100 is hsa-miR-5100, miR-6848-5p is hsa-miR-6848-5p, miR-4739 is hsa-miR-4739, miR-4459 is hsa-miR-4459, miR-1237-5p is hsa-miR-1237-5p, miR-296-3p is hsa-miR-296-3p, miR-4665-3p is hsa-miR-4665-3p, miR-6786-5p is hsa-miR-6786-5p, miR-4258 is hsa-miR-4258, miR-6510-5p is hsa-miR-6510-5p, miR-1343-5p is hsa-miR-1343-5p, miR-1247-3p is hsa-miR-1247-3p, miR-6805-5p is hsa-miR-6805-5p, miR-4492 is hsa-miR-4492, miR-1469 is hsa-miR-1469, miR-1268b is hsa-miR-1268b, miR-6858-5p is hsa-miR-6858-5p, miR-3937 is hsa-miR-3937, miR-939-5p is hsa-miR-939-5p, miR-3656 is hsa-miR-3656, miR-744-5p is hsa-miR-744-5p, miR-4687-3p is hsa-miR-4687-3p, miR-4763-3p is hsa-miR-4763-3p, miR-3620-5p is hsa-miR-3620-5p, miR-3195 is hsa-miR-3195, miR-6842-5p is hsa-miR-6842-5p, miR-4707-5p is hsa-miR-4707-5p, miR-642a-3p is hsa-miR-642a-3p, miR-7113-3p is hsa-miR-7113-3p, miR-4728-5p is hsa-miR-4728-5p, miR-5195-3p is hsa-miR-5195-3p, miR-1185-1-3p is hsa-miR-1185-1-3p, miR-6774-5p is hsa-miR-6774-5p, miR-8059 is hsa-miR-8059, miR-3131 is hsa-miR-3131, miR-7847-3p is hsa-miR-7847-3p, miR-4463 is hsa-miR-4463, miR-128-2-5p is hsa-miR-128-2-5p, miR-4508 is hsa-miR-4508, miR-6806-5p is hsa-miR-6806-5p, miR-7111-5p is hsa-miR-7111-5p, miR-6782-5p is hsa-miR-6782-5p, miR-4734 is hsa-miR-4734, miR-3162-5p is hsa-miR-3162-5p, miR-887-3p is hsa-miR-887-3p, miR-6752-5p is hsa-miR-6752-5p, miR-6724-5p is hsa-miR-6724-5p, miR-6757-5p is hsa-miR-6757-5p, miR-4448 is hsa-miR-4448, miR-671-5p is hsa-miR-671-5p, miR-3178 is hsa-miR-3178, miR-4725-3p is hsa-miR-4725-3p, miR-940 is hsa-miR-940, miR-6789-5p is hsa-miR-6789-5p, miR-4484 is hsa-miR-4484, miR-4634 is hsa-miR-4634, miR-4745-5p is hsa-miR-4745-5p, miR-4730 is hsa-miR-4730, miR-6803-5p is hsa-miR-6803-5p, miR-6798-5p is hsa-miR-6798-5p, miR-3648 is hsa-miR-3648, miR-4783-3p is hsa-miR-4783-3p, and miR-6836-3p is hsa-miR-6836-3p.

In a preferred embodiment of the method of the present invention, specifically, the nucleic acid (specifically, probe or primer) is selected from the group consisting of the following polynucleotides (a) to (e):

(a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 167 and 714 to 729, (c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and (e) a polynucleotide hybridizing under stringent conditions to any of the polynucleotides (a) to (d).

In the method of the present invention, nucleic acid(s) capable of specifically binding to at least one or more polynucleotide(s) selected from the followings: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a may be further used.

In a preferred embodiment, as for such an additional nucleic acid, specifically, miR-23b-3p is hsa-miR-23b-3p, miR-23a-3p is hsa-miR-23a-3p, miR-625-3p is hsa-miR-625-3p, miR-1228-3p is hsa-miR-1228-3p, miR-614 is hsa-miR-614, miR-1913 is hsa-miR-1913, miR-92a-2-5p is hsa-miR-92a-2-5p, miR-187-5p is hsa-miR-187-5p, miR-16-5p is hsa-miR-16-5p, miR-92b-3p is hsa-miR-92b-3p, miR-150-3p is hsa-miR-150-3p, miR-564 is hsa-miR-564, miR-125a-3p is hsa-miR-125a-3p, miR-92b-5p is hsa-miR-92b-5p, miR-92a-3p is hsa-miR-92a-3p, and miR-663a is hsa-miR-663a.

In a preferred embodiment, such a nucleic acid is specifically selected from the group consisting of the following polynucleotides (f) to (j):
 (f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
 (g) a polynucleotide comprising a nucleotide sequence represented by any of SEQ ID NOs: 168 to 183,
 (h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
 (i) a polynucleotide comprising a nucleotide sequence complementary to a nucleotide sequence represented by any of SEQ ID NOs: 168 to 183 or a nucleotide sequence derived from the nucleotide sequence by the replacement of u with t, and
 (j) a polynucleotide hybridizing under stringent conditions to any of the polynucleotides (f) to (i).

In the method of the present invention, a nucleic acid capable of specifically binding to at least one or more polynucleotide(s) selected from the group consisting of miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090 may be further used.

In a preferred embodiment, as for such an additional nucleic acid, specifically, miR-4688 is hsa-miR-4688, miR-4648 is hsa-miR-4648, miR-6085 is hsa-miR-6085, miR-6126 is hsa-miR-6126, miR-6880-5p is hsa-miR-6880-5p, miR-328-5p is hsa-miR-328-5p, miR-6768-5p is hsa-miR-6768-5p, miR-3180 is hsa-miR-3180, miR-6087 is hsa-miR-6087, miR-1273g-3p is hsa-miR-1273g-3p, miR-1225-5p is hsa-miR-1225-5p, miR-3196 is hsa-miR-3196, miR-4695-5p is hsa-miR-4695-5p, miR-6732-5p is hsa-miR-6732-5p, miR-638 is hsa-miR-638, miR-6813-5p is hsa-miR-6813-5p, miR-665 is hsa-miR-665, miR-486-3p is hsa-miR-486-3p, miR-4466 is hsa-miR-4466, miR-30c-1-3p is hsa-miR-30c-1-3p, miR-3621 is hsa-miR-3621, miR-6743-5p is hsa-miR-6743-5p, miR-4298 is hsa-miR-4298, miR-4741 is hsa-miR-4741, miR-3619-3p is hsa-miR-3619-3p, miR-6824-5p is hsa-miR-6824-5p, miR-5698 is hsa-miR-5698, miR-371a-5p is hsa-miR-371a-5p, miR-4488 is hsa-miR-4488, miR-1233-5p is hsa-miR-1233-5p, miR-4723-5p is hsa-miR-4723-5p, miR-24-3p is hsa-miR-24-3p, miR-1238-5p is hsa-miR-1238-5p, miR-4442 is hsa-miR-4442, miR-3928-3p is hsa-miR-3928-3p, miR-6716-5p is hsa-miR-6716-5p, miR-6089 is hsa-miR-6089, miR-6124 is hsa-miR-6124, miR-6778-5p is hsa-miR-6778-5p, miR-557 is hsa-miR-557, and miR-6090 is hsa-miR-6090.

In a preferred embodiment, such a nucleic acid is specifically a polynucleotide selected from the group consisting of the following polynucleotides (k) to (o):
 (k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides,
 (l) a polynucleotide comprising a nucleotide sequence represented by any of SEQ ID NOs: 184 to 224,
 (m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides,
 (n) a polynucleotide comprising a nucleotide sequence complementary to a nucleotide sequence represented by any of SEQ ID NOs: 184 to 224 or a nucleotide sequence derived from the nucleotide sequence by the replacement of u with t, and
 (o) a polynucleotide hybridizing under stringent conditions to any of the polynucleotides (k) to (n).

Examples of the sample used in the method of the present invention can include samples prepared from a living tissue (preferably a liver tissue) or a body fluid such as blood, serum, plasma, or urine of the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse and a rat without any limitation, and is preferably a human.

The steps of the method of the present invention can be changed according to the type of the sample to be assayed.

In the case of using RNA as an analyte, the detection of liver cancer (cells) may comprise, for example, the following steps (a), (b), and (c):
 (a) a step of binding RNA prepared from the sample of a subject or a complementary polynucleotide (cDNA) transcribed therefrom to a polynucleotide in the kit or the device of the present invention;
 (b) a step of measuring the sample-derived RNA or the cDNA synthesized from the RNA, bound with the polynucleotide by hybridization using the polynucleotide as a nucleic acid probe or by quantitative RT-PCR using the polynucleotide as a primer; and
 (c) a step of evaluating the presence or absence of liver cancer (or liver cancer-derived gene expression) on the basis of the measurement results of the step (b).

For example, various hybridization methods can be used for detecting, examining, evaluating, or diagnosing liver cancer (or liver cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which comprises labeling the nucleic acid probe (a complementary strand) with a radioisotope ($^{32}$P, $^{33}$P, $^{35}$S, etc.), a fluorescent material, or the like, hybridizing the labeled product with the living tissue-derived RNA from the subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNA from the living tissue-derived RNA of the subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention are attached to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of them. 3D-Gene® Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probes using an image detector (examples thereof can include Typhoon 9410 (GE Healthcare Japan Corp.) and 3D-Gene® scanner (Toray Industries, Inc.)).

The "stringent conditions" used herein are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent washing conditions. Examples of the hybridization conditions include, but not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3 to 10×SSC and 0.1 to 1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include treatment for approximately 15 seconds to 1 minute at 5 to 10° C. plus a Tm value calculated from the sequence of the primer, using a PCR buffer with composition such as 10 mM Tris-HCL (pH 8.3), 50 mM KCL, and 1 to 2 mM MgCl$_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan® MicroRNA Assays (Life Technologies Corp.); LNA®-based MicroRNA PCR (Exiqon); or Ncode® miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a liver cancer patient and a sample derived from a healthy subject as supervising samples, and determining or evaluating the presence and/or absence of the liver cancer-derived gene in the sample.

Specifically, the present invention further provides the method comprising: a first step of measuring in vitro an expression level of a target gene (target nucleic acids) in multiple samples known to determine or evaluate the presence or absence of the liver cancer-derived gene in the samples, using the polynucleotide, the kit, or the device (e.g., chip) for detection of the present invention, or a combination thereof; a second step of constructing a discriminant with the measurement values of the expression level of the target gene obtained in the first step as supervising samples; a third step of measuring in vitro an expression level of the target gene in a sample derived from a subject in the same way as in the first step; and a fourth step of substituting the measurement value of the expression level of the target gene obtained in the third step into the discriminant obtained in the second step, and determining or evaluating the presence or absence of the liver cancer-derived gene in the sample on the basis of the results obtained from the discriminant, wherein the target gene can be detected using the polynucleotide or using a polynucleotide for detection contained in the kit or the device (e.g., chip). In this context, the discriminant can be prepared by use of Fisher's linear discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this formula, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be substituted as explanatory variables into the discriminant to determine clusters on the basis of the signs of the discriminant scores.

The Fisher's linear discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer., 2002). In the Fisher's linear discriminant analysis, direction w of projection is determined so as to maximize Formula 2. In this formula, μ represents an average input, ng represents the number of data associated with class g, and μg represents an average input of the data associated with class g. The numerator and the denominator are interclass variance and intraclass variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)} \qquad \text{Formula 2}$$

$$\text{subject to } \mu = \sum_{i=1}^{n} \frac{x_i}{n}, \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining an associated cluster, based on a closer Mahalanobis' distance from each cluster. In this Formula 3, μ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1} (x - \mu)\}^{\frac{1}{2}} \qquad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be substituted as explanatory variables into the discriminant to determine classes. In this respect, the result of the discriminant analysis may be classes, may be a probability of data to be classified into correct classes, or may be the distance from the hyperplane. In SVM, a method of nonlinearly converting a feature vector to a high dimension and performing linear discriminant analysis in the space is known as a method for tackling nonlinear problems. A formula in which an inner product of two factors in a nonlinearly mapped space is expressed only by inputs in their original spaces is called kernel. Examples of the kernel can include a linear kernel, a RBF (radial basis function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a liver cancer patient group and a healthy subject group. For example, liver tissue examination can be used for confirming each subject either as a liver cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \qquad \text{Formula 4}$$

$$\text{subject to } y^T a = 0, 0 \le a_i \le C, i = 1, \ldots, l,$$

Formula 5 is a finally obtained discriminant, and a group to which the data point is associated can be determined on the basis of the sign of a value obtained according to the discriminant. In this formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right) \qquad \text{Formula 5}$$

For example, a RBF kernel defined by Formula 6 can be used as the kernel function. In this formula, x represents a support vector, and $\gamma$ represents a kernel parameter for adjusting the complexity of the hyperplane.

$$K(x_i, x_j) = \exp(-r\|x_i - x_j\|^2), r < 0 \qquad \text{Formula 6}$$

In addition, an approach such as neural network, k-nearest neighbor algorithms, decision trees, or logistic regression analysis can be selected as a method for determining or evaluating the presence and/or absence of expression of a liver cancer-derived target gene in a sample derived from a subject, or for evaluating the expression level thereof by comparison with a control derived from a healthy subject.

The method of the present invention can comprise, for example, the following steps (a), (b), and (c):

(a) measuring an expression level of a target gene in tissues containing liver cancer-derived genes derived from liver cancer patients and/or samples that are already known to contain no liver cancer-derived gene derived from healthy subjects, using the polynucleotide, the kit, or the device (e.g., DNA chip) for detection according to the present invention;

(b) preparing the discriminants of Formulae 1 to 3, 5, and 6 described above from the measurement values of the expression level measured in the step (a); and (c) measuring an expression level of the target gene in a sample derived from a subject using the polynucleotide, the kit, or the device (e.g., DNA chip) for detection according to the present invention, substituting the obtained measurement value into the discriminants prepared in the step (b), and determining or evaluating the presence and/or absence of the liver cancer-derived target gene in the sample, or evaluating the expression level thereof by comparison with a healthy subject-derived control, on the basis of the obtained results. In this context, in the discriminants of Formulae 1 to 3, 5, and 6, x represents an explanatory variable and includes a value obtained by measuring a polynucleotide selected from the polynucleotides described above in the Section 2, or a fragment thereof, etc. Specifically, the explanatory variable for discriminating a liver cancer patient from a healthy subject according to the present invention is a gene expression level selected from, for example, the following expression levels (1) to (3):

(1) a gene expression level in the serum of a pancreatic cancer patient or a healthy subject measured by any of DNA comprising 15 or more consecutive nucleotides in a nucleotide sequence represented by any of SEQ ID NOs: 1 to 167 and 714 to 729 or a complementary sequence thereof, (2) a gene expression level in the serum of a pancreatic cancer patient or a healthy subject measured by any of DNA comprising 15 or more consecutive nucleotides in a nucleotide sequence represented by any of SEQ ID NOs: 168 to 183 or a complementary sequence thereof, and (3) a gene expression level in the serum of a liver cancer patient or a healthy subject measured by any DNA comprising 15 or more consecutive nucleotides in a nucleotide sequence represented by any of SEQ ID NOs: 184 to 224 or a complementary sequence thereof.

As described above, for the method for determining or evaluating the presence and/or absence of a liver cancer-derived gene in a sample derived from a subject, the preparation of a discriminant requires a discriminant prepared in a training cohort. For enhancing the discriminant accuracy of the discriminant, it is necessary for the discriminant to use genes that show clear difference between two groups in the training cohort when preparing the discriminant.

Each gene that is used for an explanatory variable in a discriminant is preferably determined as follows. First, comprehensive gene expression levels of a liver cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a liver cancer patient group and gene expression levels of a healthy subject group may be calculated to select a gene that is used for an explanatory variable in a discriminant. Alternatively, ROC curves may be prepared using gene expression levels of a liver cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). A gene expression level of another independent liver cancer patient or healthy subject is substituted as an explanatory variable into this discriminant to calculate discrimination results of the group to which this independent liver cancer patient or healthy subject belongs. Specifically, the found gene set for diagnosis and the discriminant constructed using the gene set for diagnosis can be evaluated in an independent sample cohort to find a more universal gene set for diagnosis capable of detecting liver cancer and a more universal method for discriminating liver cancer.

Split-sample method is preferably used for evaluating the discriminant performance (generality) of the discriminant. Specifically, a data set is divided into a training cohort and a validation cohort, and gene selection by a statistical test and discriminant preparation are performed using the training cohort. Accuracy, sensitivity, and specificity are calculated using results of discriminating a validation cohort according to the discriminant and a true group to which the validation cohort associates, to evaluate the discriminant performance. On the other hand, instead of dividing a data set, the gene selection by a statistical test and discriminant preparation may be performed using all of samples, and accuracy, sensitivity, and specificity can be calculated by the discriminant analysis using a newly prepared samples cohort for evaluation of the discriminant performance.

The present invention provides a polynucleotide for detection or for disease diagnosis useful in the diagnosis and treatment of liver cancer, a method for detecting liver cancer using the polynucleotide, and a kit and a device for the detection of liver cancer, comprising the polynucleotide. Particularly, in order to select a gene for diagnosis and prepare a discriminant so as to exhibit accuracy beyond a liver cancer diagnosis method using an existing tumor marker CEA, a gene set for diagnosis and a discriminant for the method of the present invention, that exhibit accuracy beyond AFP, CEA, CA19-9 and/or PIVKA-II, can be constructed, for example, by comparing expressed genes in serum derived from a patient confirmed to be negative using AFP, CEA, CA19-9, and/or PIVKA-II but finally found to have liver cancer by detailed examination such as computed tomography using a contrast medium, with genes expressed in serum derived from a patient having no liver cancer.

For example, the gene set for diagnosis is set to any combination selected from one or two or more of the polynucleotides based on a nucleotide sequence represented by any of SEQ ID NOs: 1 to 167 and 714 to 729 or a complementary sequence thereof as described above, optionally one or two or more of the polynucleotides based on a nucleotide sequence represented by any of SEQ ID NOs: 168 to 183 or a complementary sequence thereof, and optionally one or two or more of the polynucleotides based on a nucleotide sequence represented by any of SEQ ID NOs: 184 to 224 or a complementary sequence thereof. Further, a discriminant is constructed using expression levels of the gene set for diagnosis in samples derived from class I liver cancer patients as a result of tissue diagnosis and samples derived from class II healthy subjects as a result of tissue diagnosis. As a result, the presence or absence of liver cancer-derived genes in an unknown sample can be determined with 100% accuracy at the maximum by measuring expression levels of the gene set for diagnosis in an unknown sample.

EXAMPLES

Hereinafter, the present invention is described further specifically with reference to Examples below. However, the scope of the present invention is not intended to be limited by these Examples.

Reference Example 1

<Collection of Samples from Liver Cancer Patients and Healthy Subjects>

Sera were collected using VENOJECT II vacuum blood collecting tube VP-AS109K60 (Terumo Corp.) from 100 healthy subjects and 34 liver cancer patients (15 cases with stage I, 9 cases with stage II, 5 cases with stage IIIA, 2 cases with stage IIIB, 1 case with stage IIIC, and 2 cases with stage IV) confirmed to have no primary cancer other than liver cancer after acquisition of informed consent, and used as a training cohort. Likewise, sera were collected using VENOJECT II vacuum blood collecting tube VP-AS109K60 (Terumo Corp.) from 50 healthy subjects and 16 liver cancer patients (9 cases with stage I, 5 cases with stage II, and 2 cases with stage IIIA) confirmed to have no primary cancer other than liver cancer after acquisition of informed consent, and used as a validation cohort.

<Extraction of Total RNA>

Total RNA was obtained from 300 μL of the serum sample obtained from each of 200 persons in total of 150 healthy subjects and 50 liver cancer patients included in the training cohort and the validation cohort, using a reagent for RNA extraction in 3D-Gene® RNA extraction reagent from liquid sample kit (Toray Industries, Inc.) according to the protocol provided by the manufacturer.

<Measurement of Gene Expression Level> miRNAs in the total RNA obtained from the serum sample of each of 200 persons in total of 150 healthy subjects and 50 liver cancer patients included in the training cohort and the validation cohort were fluorescently labeled using 3D-Gene® miRNA Labeling kit (Toray Industries, Inc.) according to the protocol (ver 2.20) provided by the manufacturer. The oligo DNA chip used was 3D-Gene® Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene® scanner (Toray Industries, Inc.) to obtain images. Fluorescence intensity was digitized using 3D-Gene® Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 150 liver cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Cancers Other than Liver Cancer>

Sera were collected using VENOJECT II vacuum blood collecting tube VP-AS109K60 (Terumo Corp.) from each of 72 pancreatic cancer patients, 61 bile duct cancer patients, 38 stomach cancer patients, 25 esophageal cancer patients, 35 colorectal cancer patients, and 16 benign pancreaticobiliary disease patients confirmed to have no cancer in other organs after acquisition of informed consent, and used as a training cohort together with the samples of 35 liver cancer patients and 99 healthy subjects of Reference Example 1. Likewise, sera were collected using VENOJECT II vacuum blood collecting tube VP-AS109K60 (Terumo Corp.) from each of 28 pancreatic cancer patients, 37 bile duct cancer patients, 12 stomach cancer patients, 25 esophageal cancer patients, 15 colorectal cancer patients, and 5 benign pancreaticobiliary disease patients confirmed to have no cancer in other organs after acquisition of informed consent, and used as a validation cohort together with the samples of 17 liver cancer patients confirmed to have no cancer in organs except for liver cancer and 51 healthy subjects of Reference Example 1. Subsequent operations were conducted in the same way as in Reference Example 1.

Example 1

<Selection of Gene Marker Using Samples in the Training Cohort, and Method for Evaluating Liver Cancer Discriminant Performance of the Single Gene Marker Using Samples in the Validation Cohort>

In this Example, a gene marker for discriminating a liver cancer patient from a healthy subject was selected from the training cohort, and studied in samples of the validation cohort independent of the training cohort, for a method for evaluating liver cancer discriminant performance of each selected gene marker alone.

Specifically, first, the miRNA expression levels in the training cohort and the validation cohort obtained in the above-mentioned Reference Examples were combined and normalized by quantile normalization.

Next, genes for diagnosis were selected in the training cohort. Here, in order to acquire diagnostic markers with higher reliability, only genes having the gene expression level of $2^6$ or higher in 50% or more of the samples in either of the liver cancer patient group in the training cohort or the healthy subject group of the training cohort were selected. In order to further acquire statistically significant genes for discriminating a liver cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant and described in Table 2.

In this way, hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR- 744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, and hsa-miR-663a genes represented by SEQ ID NOs: 1 to 183 were found as liver cancer markers relative to the healthy subjects.

Among them, genes newly found as markers for examining the presence or absence of liver cancer are polynucleotides consisting of the nucleotide sequences represented by SEQ ID NOs: 1 to 167.

A discriminant for determining the presence or absence of liver cancer was further prepared by Fisher's linear discriminant analysis with the expression levels of these genes as an indicator. Specifically, any newly found polynucleotide consisting of a nucleotide sequence represented by any of SEQ ID NOs: 1 to 183 in the training cohort was input to Formula 2 to construct a discriminant. Calculated accuracy, sensitivity, and specificity are shown in Table 3. In this respect, a discriminant coefficient and a constant term are shown in Table 4.

Figure 2:
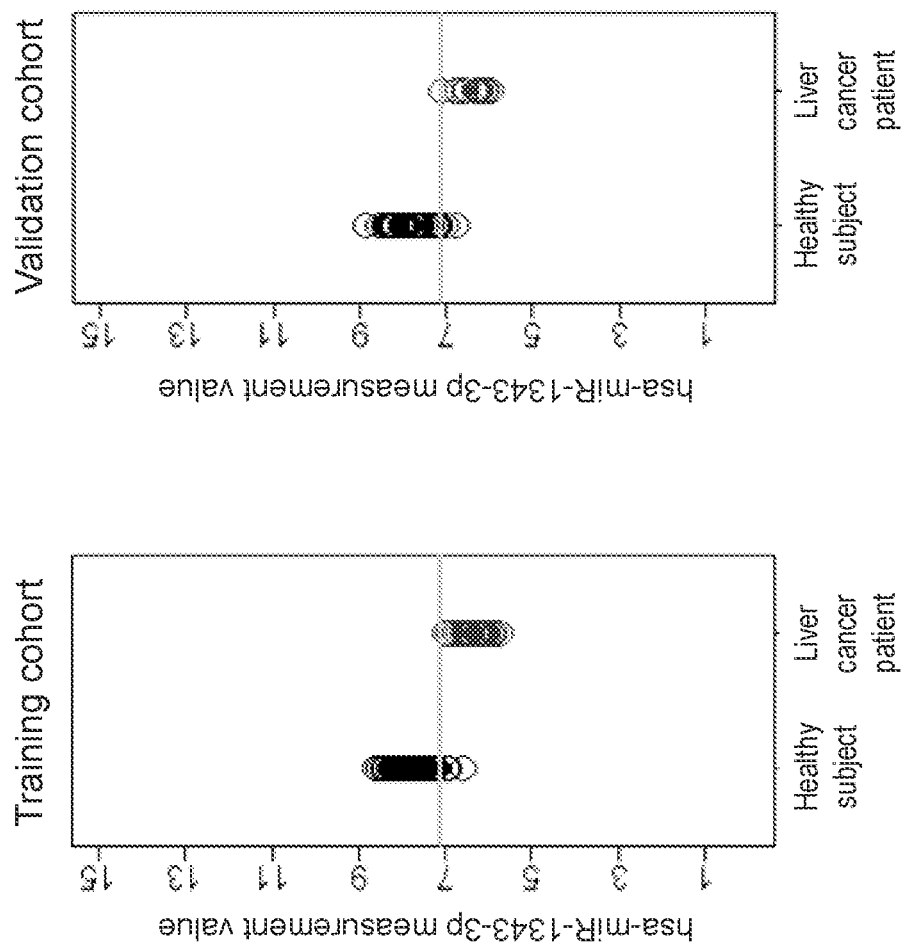
FIG. 2 Left diagram: the measurement values of hsa-miR-1343-3p (SEQ ID NO: 1) in healthy subjects (100 persons) and liver cancer patients (34 persons) selected as a training cohort were each plotted on the ordinate. The horizontal line in the diagram depicts a threshold (7.09) that was optimized by Fisher's linear discriminant analysis and discriminated between the two groups. Right diagram: the measurement values of hsa-miR-1343-3p (SEQ ID NO: 1) in healthy subjects (50 persons) and liver cancer patients (16 persons) selected as a validation cohort were each plotted on the ordinate. The horizontal line in the diagram depicts the threshold (7.09) that was set in the training cohort and discriminated between the two groups.

Accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (100 persons) and the liver cancer patients (34 persons) in the training cohort. As a result, the gene expression level measurement values were found to be significantly lower in the liver cancer patient group than in the healthy subject group (see the left diagram of FIG. 2). These results were also reproducible for the healthy subjects (50 persons) and the liver cancer patients (16 persons) in the validation cohort (see the right diagram of FIG. 2). Likewise, the results obtained about the other polynucleotides shown in SEQ ID NOs: 2 to 183 showed that the gene expression level measurement values were significantly lower (−) or higher (+) in the liver cancer patient group than in the healthy subject group (Table 2). These results were able to be validated in the validation cohort. For example, as for this nucleotide sequence represented by SEQ ID NO: 1, the number of samples that were correctly identified in the detection of liver cancer was calculated using the threshold (7.09) that was set in the training cohort and discriminated between the two groups. As a result, 15 true positives, 49 true negatives, 1 false positive, and 1 false negatives were obtained in the validation cohort. From these values, 97% accuracy, 94% sensitivity, and 98% specificity were obtained as the detection performance. In this way, the detection performance was calculated as to all of the polynucleotides shown in SEQ ID NOs: 1 to 183, and described in Table 3.

Likewise, 72 polynucleotides consisting of the nucleotide sequences represented by SEQ ID NOs: 1, 2, 3, 4, 5, 6, 7, 8, 9, 10, 11, 12, 13, 14, 15, 16, 17, 19, 21, 22, 23, 24, 25, 27, 28, 29, 30, 31, 32, 33, 34, 35, 37, 39, 40, 41, 43, 44, 45, 46, 47, 48, 50, 51, 54, 55, 56, 57, 58, 60, 61, 62, 63, 64, 65, 68, 73, 80, 86, 88, 91, 93, 94, 99, 114, 117, 170, 171, 172, 173, 174 and 175 exhibited sensitivity of 93.8%, 93.8%, 93.8%, 87.5%, 75%, 87.5%, 62.5%, 81.2%, 93.8%, 93.8%, 75%, 93.8%, 62.5%, 93.8%, 56.2%, 56.2%, 56.2%, 93.8%, 68.8%, 87.5%, 93.8%, 81.2%, 87.5%, 62.5%, 56.2%, 68.8%, 81.2%, 81.2%, 62.5%, 87.5%, 68.8%, 75%, 75%, 75%, 62.5%, 93.8%, 75%, 56.2%, 62.5%, 62.5%, 68.8%, 87.5%, 75%, 62.5%, 75%, 68.8%, 62.5%, 68.8%, 68.8%, 68.8%, 62.5%, 62.5%, 75%, 62.5%, 75%, 68.8%, 56.2%, 81.2%, 68.8%, 56.2%, 62.5%, 56.2%, 56.2%, 68.8%, 56.2%, 62.5%, 87.5%, 87.5%, 75%, 68.8%, 62.5% and 81.2% respectively, in the validation cohort (Table 3). As seen from Comparative Example mentioned later, AFP, which had the highest sensitivity among four existing markers, had sensitivity of 53.3% in the validation cohort (Table 5), demonstrating that, for example, the 72 polynucleotides consisting of the nucleotide sequences represented by SEQ ID NOs: 1, 2, 3, 4, 5, 6, 7, 8, 9, 10, 11, 12, 13, 14, 15, 16, 17, 19, 21, 22, 23, 24, 25, 27, 28, 29, 30, 31, 32, 33, 34, 35, 37, 39, 40, 41, 43, 44, 45, 46, 47, 48, 50, 51, 54, 55, 56, 57, 58, 60, 61, 62, 63, 64, 65, 68, 73, 80, 86, 88, 91, 93, 94, 99, 114, 117, 170, 171, 172, 173, 174 and 175 can discriminate, each alone, liver cancer in the validation cohort with sensitivity beyond AFP.

Also, for example, 7 polynucleotides consisting of the nucleotide sequences represented by SEQ ID NOs: 1, 6, 15, 31, 46, 50, and 58 were able to correctly determine all of the nine stage 1 liver cancer samples contained in the validation cohort to have liver cancer. Thus, these polynucleotides can detect even early liver cancer and contribute to the early diagnosis of liver cancer.

Example 2

<Method for Evaluating Liver Cancer Discriminant Performance by Combination of Multiple Gene Markers Using Samples in the Validation Cohort>

In this Example, a method for evaluating liver cancer discriminant performance by a combination of the gene markers selected in Example 1 was studied. Specifically, Fisher's linear discriminant analysis was conducted as to 16,533 combinations of two expression level measurement values comprising at least one or more of the expression level measurement values of the newly found polynucleotides consisting of the nucleotide sequences represented by SEQ ID NOs: 1 to 167 among the polynucleotides consisting of the nucleotide sequences represented by SEQ ID NOs: 1 to 183 selected in Example 1, to construct a discriminant for determining the presence or absence of liver cancer. Next, accuracy, sensitivity, and specificity in the validation cohort were calculated using the discriminant thus prepared, and the discriminant performance of the selected polynucleotides was validated using the independent samples.

Figure 3:
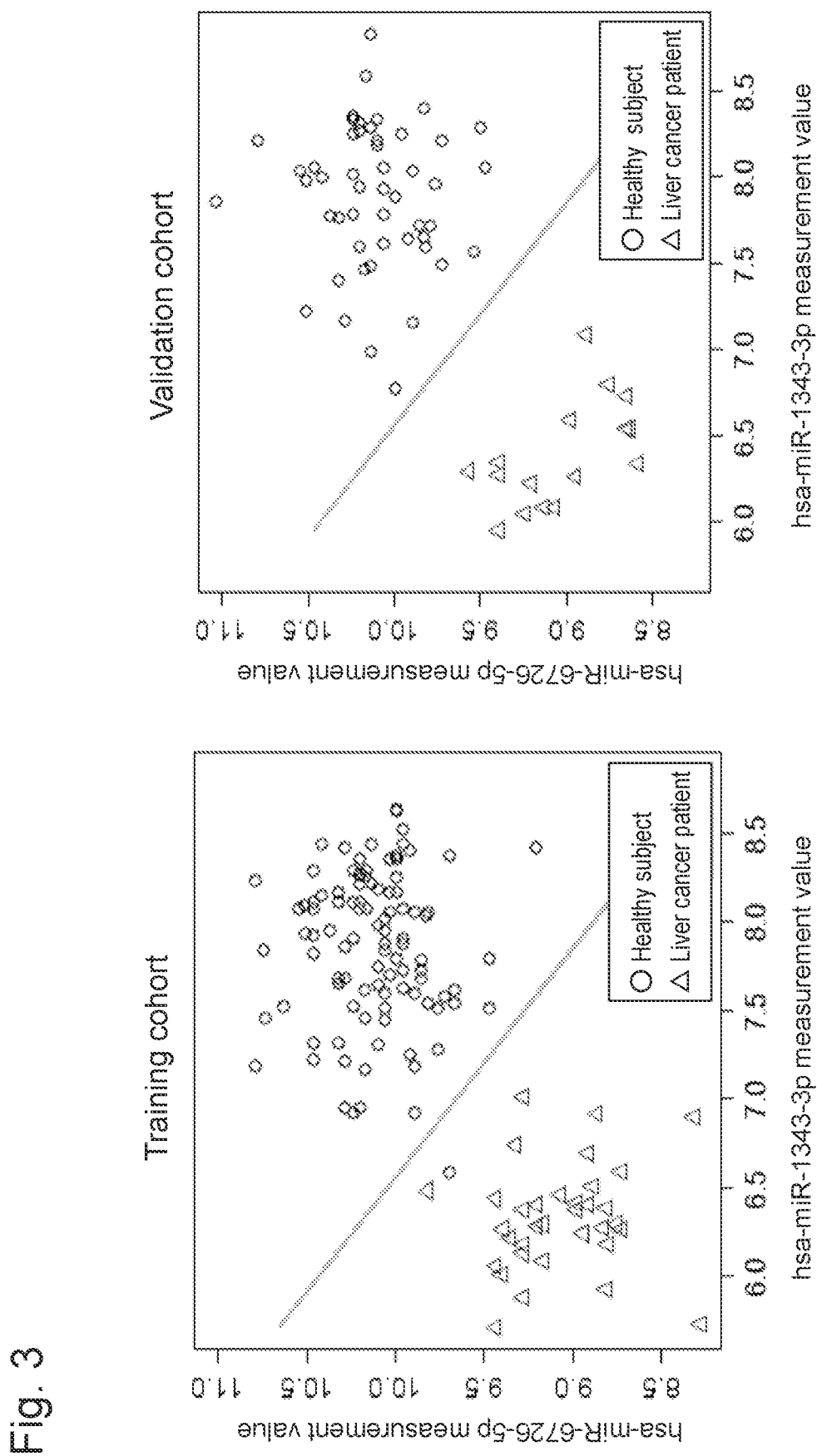
FIG. 3 Left diagram: the measurement values of hsa-miR-1343-3p (SEQ ID NO: 1) in healthy subjects (100 persons, circles) and liver cancer patients (34 persons, triangles) selected as a training cohort were each plotted on the abscissa against their measurement values of hsa-miR-6726-5p (SEQ ID NO: 2) on the ordinate. The line in the diagram depicts a discriminant function (0=0.77x+y−15.07) that was optimized by Fisher's linear discriminant analysis and discriminated between the two groups. Right diagram: the measurement values of hsa-miR-1343-3p (SEQ ID NO: 1) in healthy subjects (50 persons, circles) and liver cancer patients (16 persons, triangles) selected as a validation cohort were each plotted on the abscissa against their measurement values of hsa-miR-6726-5p (SEQ ID NO: 2) on the ordinate. The line in the diagram depicts the threshold (0=0.77x+y−15.07) that was set in the training cohorts and discriminated between the two groups.

For example, the expression level measurement values of polynucleotides consisting of the nucleotide sequences represented by SEQ ID NO: 1 and SEQ ID NO: 2 were compared between the healthy subjects (100 persons) and the liver cancer patients (34 persons) in the training cohort. As a result, a scatter diagram that significantly separated the expression level measurement values of the liver cancer patient group from those of the healthy subject group was obtained (see the left diagram of FIG. 3). These results were also reproducible for the healthy subjects (50 persons) and the liver cancer patients (16 persons) in the validation cohort (see the right diagram of FIG. 3). Likewise, a scatter diagram that significantly separated the expression level measurement values of the liver cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 167 among the polynucleotides consisting of the nucleotide sequences represented by SEQ ID NOs: 1 to 183. These results were able to be validated in the validation cohort. For example, as for these nucleotide sequences represented by SEQ ID NO: 1 and SEQ ID NO: 2, the number of correctly or incorrectly identified samples in the detection of liver cancer was calculated using the function (0=0.77x+y−15.07) that was set in the training cohort and discriminated between the two groups. As a result, 16 true positives, 50 true negatives, 0 false positives, and 0 false negatives were obtained. From these values, 100% accuracy, 100% sensitivity, and 100% specificity were obtained as the detection performance. In this way, the detection performance was calculated for all combinations of two expression level measurement values comprising at least one more of the expression level measurement values of any of the newly found polynucleotides consisting of the nucleotide sequences represented by SEQ ID NOs: 1 to 167 among the polynucleotides consisting of the nucleotide sequences represented by SEQ ID NOs: 1 to 183. Among them, 182 combinations comprising the expression level measurement value of the polynucleotide consisting of the nucleotide sequence represented by SEQ ID NO: 1 and the detection performance thereof were described in Table 6 as an example. For example, all of combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 100%, 100%, 100%, 94%, and 94%, respectively, in the validation cohort. Likewise, the sensitivity was also calculated as to the combinations of two polynucleotides consisting of the nucleotide sequences represented by SEQ ID NO: 1 and any of SEQ ID NOs: 6 to 251. As a result, all of these combinations exhibited sensitivity of 88% or higher (Table 6), which was beyond the sensitivity (53.3%) of the existing liver cancer marker AFP (Table 5). Thus, a combination of two of the polynucleotides consisting of the nucleotide sequences represented by SEQ ID NOs: 1 to 183 also produced excellent liver cancer detection sensitivity.

In addition, markers for the detection of liver cancer with more excellent sensitivity are obtained by combining the expression level measurement values of 3, 4, 5, 6, 7, 8, 9, 10 or more of the polynucleotides consisting of the nucleotide sequences represented by SEQ ID NOs: 1 to 183. For example, the newly found polynucleotides consisting of the nucleotide sequences represented by SEQ ID NOs: 1 to 167 among the polynucleotides consisting of the nucleotide sequences represented by SEQ ID NOs: 1 to 183 selected in Example 1 were measured to obtain their expression levels of the healthy subject group and the liver cancer group in the validation cohort. All of the polynucleotides were ranked in the descending order of their P values based on the Student's t-test which indicate statistical significance of difference between groups (i.e., one having the lowest P value was ranked in the first place), and liver cancer detection sensitivity was evaluated for each of combinations of one or more polynucleotides to which the polynucleotides were added one by one from the top to the bottom according to the rank. In short, the order in terms of SEQ ID NOs in which the polynucleotides were combined in this evaluation is in reverse in terms of SEQ ID NO: 167 to SEQ ID NOs: 166, 165, ... shown in Table 2 in order. As a result, the sensitivity in the validation cohort was 12.5% for 1 polynucleotide (SEQ ID NO: 167), 43.8% for 2 polynucleotides (SEQ ID NOs: 166 and 167), 68.8% for 4 polynucleotides (SEQ ID NOs: 164 to 167), 87.5% for 6 polynucleotides (SEQ ID NOs: 162 to 167), 93.8% for 10 polynucleotides (SEQ ID NOs: 158 to 167), 100% for 20 polynucleotides (SEQ ID NOs: 148 to 167), 100% for 30 polynucleotides (SEQ ID NOs: 138 to 167), 100% for 50 polynucleotides (SEQ ID NOs: 118 to 167), 100% for 80 polynucleotides (SEQ ID NOs: 88 to 167), 100% for 110 polynucleotides (SEQ ID NOs: 58 to 167), 100% for 150 polynucleotides (SEQ ID NOs: 18 to 167), and 100% for 167 polynucleotides (SEQ ID NOs: 1 to 167).

These results demonstrated that a combination of a plurality of polynucleotides can produce higher liver cancer discriminant performance than that of each polynucleotide alone or a combination of a fewer number of polynucleotides. In this context, the combinations of a plurality of polynucleotides are not limited to the combinations of the polynucleotides added in the order of statistically significant difference as described above, and any combination of a plurality of polynucleotides can be used in the detection of liver cancer.

From these results, it can be concluded that all of the polynucleotides consisting of the nucleotide sequences represented by SEQ ID NOs: 1 to 183 serve as excellent markers for the detection of liver cancer.

TABLE 2

| SEQ ID NO: | Gene name | P value after Bonferroni correction | Expression level in liver cancer patient relative to healthy subject |
|---|---|---|---|
| 1 | hsa-miR-1343-3p | 6.65.E−37 | − |
| 2 | hsa-miR-6726-5p | 2.01.E−34 | − |
| 3 | hsa-miR-6515-3p | 4.26.E−28 | + |
| 4 | hsa-miR-4651 | 1.83.E−27 | − |
| 5 | hsa-miR-4257 | 5.63.E−27 | − |
| 6 | hsa-miR-3188 | 1.06.E−25 | + |
| 7 | hsa-miR-6131 | 4.08.E−25 | − |
| 8 | hsa-miR-6766-3p | 1.86.E−24 | + |
| 9 | hsa-miR-7641 | 5.24.E−24 | − |
| 10 | hsa-miR-1249 | 1.67.E−23 | + |
| 11 | hsa-miR-3679-3p | 3.33.E−23 | + |
| 12 | hsa-miR-6787-5p | 5.69.E−23 | − |
| 13 | hsa-miR-4454 | 6.89.E−23 | − |
| 14 | hsa-miR-3135b | 3.83.E−21 | − |
| 15 | hsa-miR-6765-3p | 2.37.E−20 | − |
| 16 | hsa-miR-7975 | 1.57.E−19 | − |
| 17 | hsa-miR-204-3p | 2.58.E−19 | − |
| 18 | hsa-miR-7977 | 5.17.E−18 | − |
| 19 | hsa-miR-7110-5p | 1.34.E−16 | + |
| 20 | hsa-miR-6717-5p | 1.77.E−16 | − |
| 21 | hsa-miR-6870-5p | 1.86.E−16 | + |
| 22 | hsa-miR-663b | 1.91.E−16 | − |
| 23 | hsa-miR-6875-5p | 1.98.E−16 | + |
| 24 | hsa-miR-8072 | 2.20.E−16 | + |
| 25 | hsa-miR-6816-5p | 4.02.E−16 | + |
| 26 | hsa-miR-4281 | 1.18.E−15 | − |
| 27 | hsa-miR-6729-5p | 1.90.E−15 | + |
| 28 | hsa-miR-8069 | 4.12.E−15 | + |
| 29 | hsa-miR-4706 | 9.80.E−15 | − |
| 30 | hsa-miR-7108-5p | 1.34.E−14 | + |
| 31 | hsa-miR-4433b-3p | 1.44.E−14 | + |
| 32 | hsa-miR-6893-5p | 2.25.E−14 | − |
| 33 | hsa-miR-6857-5p | 3.37.E−14 | + |
| 34 | hsa-miR-1227-5p | 5.86.E−14 | + |
| 35 | hsa-miR-6741-5p | 1.52.E−13 | − |
| 36 | hsa-miR-451a | 1.99.E−13 | − |
| 37 | hsa-miR-8063 | 2.08.E−13 | − |
| 38 | hsa-miR-3622a-5p | 2.29.E−13 | − |
| 39 | hsa-miR-615-5p | 2.47.E−13 | − |

TABLE 2-continued

| SEQ ID NO: | Gene name | P value after Bonferroni correction | Expression level in liver cancer patient relative to healthy subject |
|---|---|---|---|
| 40 | hsa-miR-128-1-5p | 6.21.E−13 | + |
| 41 | hsa-miR-6825-5p | 1.19.E−12 | + |
| 42 | hsa-miR-1260b | 2.03.E−12 | − |
| 43 | hsa-miR-4433-3p | 2.67.E−12 | + |
| 44 | hsa-miR-4665-5p | 3.11.E−12 | − |
| 45 | hsa-miR-7845-5p | 3.97.E−12 | + |
| 46 | hsa-miR-1908-5p | 4.05.E−12 | + |
| 47 | hsa-miR-6840-3p | 5.71.E−12 | − |
| 48 | hsa-miR-6765-5p | 5.84.E−12 | + |
| 49 | hsa-miR-296-5p | 6.23.E−12 | + |
| 50 | hsa-miR-3675-3p | 1.58.E−11 | + |
| 51 | hsa-miR-6781-5p | 5.32.E−11 | + |
| 52 | hsa-miR-423-5p | 5.46.E−11 | − |
| 53 | hsa-miR-3663-3p | 5.53.E−11 | − |
| 54 | hsa-miR-6784-5p | 5.78.E−11 | + |
| 55 | hsa-miR-6749-5p | 7.92.E−11 | − |
| 56 | hsa-miR-1231 | 1.43.E−10 | + |
| 57 | hsa-miR-4746-3p | 1.47.E−10 | + |
| 58 | hsa-miR-6780b-5p | 1.80.E−10 | + |
| 59 | hsa-miR-4758-5p | 1.80.E−10 | − |
| 60 | hsa-miR-3679-5p | 2.45.E−10 | + |
| 61 | hsa-miR-3184-5p | 3.79.E−10 | + |
| 62 | hsa-miR-6125 | 4.04.E−10 | + |
| 63 | hsa-miR-6721-5p | 9.40.E−10 | + |
| 64 | hsa-miR-6791-5p | 1.05.E−09 | + |
| 65 | hsa-miR-3185 | 1.24.E−09 | + |
| 66 | hsa-miR-1260a | 1.37.E−09 | − |
| 67 | hsa-miR-3197 | 1.86.E−09 | + |
| 68 | hsa-miR-6845-5p | 2.23.E−09 | + |
| 69 | hsa-miR-6887-5p | 2.95.E−09 | − |
| 70 | hsa-miR-6738-5p | 5.06.E−09 | − |
| 71 | hsa-miR-6872-3p | 5.23.E−09 | − |
| 72 | hsa-miR-4497 | 5.30.E−09 | − |
| 73 | hsa-miR-1229-5p | 6.30.E−09 | + |
| 74 | hsa-miR-6820-5p | 6.66.E−09 | − |
| 75 | hsa-miR-6777-5p | 7.32.E−09 | − |
| 76 | hsa-miR-3917 | 7.71.E−09 | − |
| 77 | hsa-miR-5787 | 7.78.E−09 | + |
| 78 | hsa-miR-4286 | 1.22.E−08 | − |
| 79 | hsa-miR-6877-5p | 1.34.E−08 | − |
| 80 | hsa-miR-1225-3p | 1.56.E−08 | + |
| 81 | hsa-miR-6088 | 1.57.E−08 | − |
| 82 | hsa-miR-6800-5p | 1.94.E−08 | + |
| 83 | hsa-miR-1246 | 3.37.E−08 | − |
| 84 | hsa-miR-4467 | 4.44.E−08 | + |
| 85 | hsa-miR-4419b | 5.34.E−08 | − |
| 86 | hsa-miR-1914-3p | 6.12.E−08 | − |
| 87 | hsa-miR-4632-5p | 7.12.E−08 | + |
| 88 | hsa-miR-1915-5p | 7.21.E−08 | − |
| 89 | hsa-miR-3940-5p | 7.68.E−08 | + |
| 90 | hsa-miR-1185-2-3p | 8.95.E−08 | + |
| 91 | hsa-miR-6746-5p | 1.20.E−07 | − |
| 92 | hsa-miR-5001-5p | 1.89.E−07 | − |
| 93 | hsa-miR-1228-5p | 2.11.E−07 | + |
| 94 | hsa-miR-5572 | 2.20.E−07 | + |
| 95 | hsa-miR-4327 | 2.34.E−07 | + |
| 96 | hsa-miR-4638-5p | 2.46.E−07 | − |
| 97 | hsa-miR-6799-5p | 3.24.E−07 | + |
| 98 | hsa-miR-6861-5p | 5.31.E−07 | − |
| 99 | hsa-miR-6727-5p | 5.46.E−07 | − |
| 100 | hsa-miR-4513 | 7.37.E−07 | − |
| 101 | hsa-miR-6805-5p | 1.20.E−06 | + |
| 102 | hsa-miR-6808-5p | 1.48.E−06 | + |
| 103 | hsa-miR-4449 | 1.92.E−06 | + |
| 104 | hsa-miR-1199-5p | 1.96.E−06 | − |
| 105 | hsa-miR-1275 | 2.60.E−06 | + |
| 106 | hsa-miR-4792 | 3.93.E−06 | + |
| 107 | hsa-miR-4443 | 4.56.E−06 | + |
| 108 | hsa-miR-6891-5p | 4.68.E−06 | + |
| 109 | hsa-miR-6826-5p | 5.09.E−06 | − |
| 110 | hsa-miR-6807-5p | 5.61.E−06 | + |
| ill | hsa-miR-7150 | 5.87.E−06 | + |
| 112 | hsa-miR-4534 | 6.23.E−06 | + |
| 113 | hsa-miR-4476 | 6.58.E−06 | − |
| 114 | hsa-miR-4649-5p | 6.78.E−06 | − |
| 115 | hsa-miR-4525 | 6.95.E−06 | − |
| 116 | hsa-miR-1915-3p | 7.86.E−06 | + |
| 117 | hsa-miR-4516 | 9.89.E−06 | − |
| 118 | hsa-miR-4417 | 1.02.E−05 | + |
| 119 | hsa-miR-642b-3p | 1.44.E−05 | − |
| 120 | hsa-miR-3141 | 1.52.E−05 | + |
| 121 | hsa-miR-5100 | 1.70.E−05 | − |
| 122 | hsa-miR-6848-5p | 2.10.E−05 | + |
| 123 | hsa-miR-4739 | 2.86.E−05 | + |
| 124 | hsa-miR-4459 | 3.57.E−05 | + |
| 125 | hsa-miR-1237-5p | 3.74.E−05 | + |
| 126 | hsa-miR-296-3p | 4.27.E−05 | − |
| 127 | hsa-miR-4665-3p | 4.37.E−05 | + |
| 128 | hsa-miR-6786-5p | 6.36.E−05 | + |
| 129 | hsa-miR-4258 | 7.87.E−05 | − |
| 130 | hsa-miR-6510-5p | 8.68.E−05 | + |
| 131 | hsa-miR-1343-5p | 8.90.E−05 | + |
| 132 | hsa-miR-1247-3p | 1.33.E−04 | + |
| 133 | hsa-miR-6805-5p | 1.34.E−04 | + |
| 134 | hsa-miR-4492 | 1.62.E−04 | + |
| 135 | hsa-miR-1469 | 1.93.E−04 | + |
| 136 | hsa-miR-1268b | 2.29.E−04 | + |
| 137 | hsa-miR-6858-5p | 2.37.E−04 | + |
| 138 | hsa-miR-3937 | 3.14.E−04 | + |
| 139 | hsa-miR-939-5p | 3.53.E−04 | + |
| 140 | hsa-miR-3656 | 3.91.E−04 | + |
| 141 | hsa-miR-744-5p | 4.32.E−04 | + |
| 142 | hsa-miR-4687-3p | 4.42.E−04 | + |
| 143 | hsa-miR-4763-3p | 4.53.E−04 | + |
| 144 | hsa-miR-3620-5p | 5.43.E−04 | + |
| 145 | hsa-miR-3195 | 6.21.E−04 | + |
| 146 | hsa-miR-6842-5p | 6.44.E−04 | + |
| 147 | hsa-miR-4707-5p | 7.50.E−04 | + |
| 148 | hsa-miR-642a-3p | 8.01.E−04 | + |
| 149 | hsa-miR-7113-3p | 8.81.E−04 | + |
| 150 | hsa-miR-4728-5p | 1.13.E−03 | − |
| 151 | hsa-miR-5195-3p | 1.39.E−03 | − |
| 152 | hsa-miR-1185-1-3p | 1.99.E−03 | + |
| 153 | hsa-miR-6774-5p | 2.01.E−03 | + |
| 154 | hsa-miR-8059 | 2.34.E−03 | − |
| 155 | hsa-miR-3131 | 2.51.E−03 | − |
| 156 | hsa-miR-7847-3p | 2.78.E−03 | − |
| 157 | hsa-miR-4463 | 3.86.E−03 | + |
| 158 | hsa-miR-128-2-5p | 4.01.E−03 | − |
| 159 | hsa-miR-4508 | 4.42.E−03 | + |
| 160 | hsa-miR-6806-5p | 4.85.E−03 | − |
| 161 | hsa-miR-7111-5p | 5.18.E−03 | + |
| 162 | hsa-miR-6782-5p | 5.20.E−03 | + |
| 163 | hsa-miR-4734 | 6.28.E−03 | + |
| 164 | hsa-miR-3162-5p | 8.46.E−03 | + |
| 165 | hsa-miR-887-3p | 8.47.E−03 | + |
| 166 | hsa-miR-6752-5p | 8.98.E−03 | + |
| 167 | hsa-miR-6724-5p | 9.90.E−03 | + |
| 168 | hsa-miR-23b-3p | 4.55.E−23 | − |
| 169 | hsa-miR-23a-3p | 4.37.E−21 | − |
| 170 | hsa-miR-625-3p | 8.87.E−20 | + |
| 171 | hsa-miR-1228-3p | 1.35.E−19 | + |
| 172 | hsa-miR-614 | 2.37.E−18 | − |
| 173 | hsa-miR-1913 | 5.84.E−18 | + |
| 174 | hsa-miR-92a-2-5p | 9.35.E−16 | + |
| 175 | hsa-miR-187-5p | 1.18.E−15 | − |
| 176 | hsa-miR-16-5p | 2.32.E−14 | − |
| 177 | hsa-miR-92b-3p | 2.82.E−12 | − |
| 178 | hsa-miR-150-3p | 8.73.E−11 | + |
| 179 | hsa-miR-564 | 1.08.E−09 | − |
| 180 | hsa-miR-125a-3p | 1.64.E−07 | − |
| 181 | hsa-miR-92b-5p | 5.34.E−07 | + |
| 182 | hsa-miR-92a-3p | 6.00.E−06 | − |
| 183 | hsa-miR-663a | 7.49.E−04 | + |

TABLE 3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1 | 95.5 | 97.1 | 95 | 97 | 93.8 | 98 |
| 2 | 97 | 97.1 | 97 | 95.5 | 93.8 | 96 |
| 3 | 91.8 | 82.4 | 95 | 90.9 | 93.8 | 90 |
| 4 | 96.3 | 91.2 | 98 | 95.5 | 87.5 | 98 |
| 5 | 96.3 | 88.2 | 99 | 92.4 | 75 | 98 |
| 6 | 94.8 | 88.2 | 97 | 95.5 | 87.5 | 98 |
| 7 | 92.5 | 73.5 | 99 | 90.9 | 62.5 | 100 |
| 8 | 94.8 | 88.2 | 97 | 92.4 | 81.2 | 96 |
| 9 | 91.8 | 82.4 | 95 | 95.5 | 93.8 | 96 |
| 10 | 94.7 | 94.1 | 94.9 | 92.4 | 93.8 | 92 |
| 11 | 94 | 91.2 | 95 | 86.4 | 75 | 90 |
| 12 | 91.8 | 76.5 | 97 | 93.9 | 93.8 | 94 |
| 13 | 91.8 | 70.6 | 99 | 89.4 | 62.5 | 98 |
| 14 | 97 | 91.2 | 99 | 97 | 93.8 | 98 |
| 15 | 91.8 | 73.5 | 98 | 87.9 | 56.2 | 98 |
| 16 | 90.3 | 64.7 | 99 | 87.9 | 56.2 | 98 |
| 17 | 90.3 | 67.6 | 98 | 81.8 | 56.2 | 90 |
| 18 | 88.1 | 58.8 | 98 | 84.8 | 43.8 | 98 |
| 19 | 88.1 | 76.5 | 92 | 90.9 | 93.8 | 90 |
| 20 | 92.5 | 73.5 | 99 | 86.4 | 50 | 98 |
| 21 | 92.5 | 79.4 | 97 | 92.4 | 68.8 | 100 |
| 22 | 88.8 | 58.8 | 99 | 97 | 87.5 | 100 |
| 23 | 91 | 73.5 | 97 | 90.9 | 93.8 | 90 |
| 24 | 91.8 | 79.4 | 96 | 84.8 | 81.2 | 86 |
| 25 | 89.6 | 82.4 | 92 | 93.9 | 87.5 | 96 |
| 26 | 88.8 | 76.5 | 93 | 84.8 | 50 | 96 |
| 27 | 91.8 | 73.5 | 98 | 89.4 | 62.5 | 98 |
| 28 | 83.6 | 50 | 95 | 86.4 | 56.2 | 96 |
| 29 | 88.8 | 73.5 | 94 | 87.9 | 68.8 | 94 |
| 30 | 85.8 | 64.7 | 93 | 86.4 | 81.2 | 88 |
| 31 | 88.8 | 76.5 | 93 | 83.3 | 81.2 | 84 |
| 32 | 89.6 | 61.8 | 99 | 89.4 | 62.5 | 98 |
| 33 | 89.6 | 79.4 | 93 | 92.4 | 87.5 | 94 |
| 34 | 86.6 | 64.7 | 94 | 84.8 | 68.8 | 90 |
| 35 | 88.1 | 64.7 | 96 | 87.9 | 75 | 92 |
| 36 | 86.6 | 50 | 99 | 80.3 | 31.2 | 96 |
| 37 | 84.3 | 64.7 | 91 | 89.4 | 75 | 94 |
| 38 | 85.8 | 50 | 98 | 86.4 | 43.8 | 100 |
| 39 | 87.3 | 52.9 | 99 | 92.4 | 75 | 98 |
| 40 | 85.1 | 64.7 | 92 | 78.8 | 62.5 | 84 |
| 41 | 94 | 85.3 | 97 | 93.9 | 93.8 | 94 |
| 42 | 85.8 | 52.9 | 97 | 84.8 | 50 | 96 |
| 43 | 82.1 | 64.7 | 88 | 86.4 | 75 | 90 |
| 44 | 82.1 | 50 | 93 | 80.3 | 56.2 | 88 |
| 45 | 88.1 | 70.6 | 94 | 84.8 | 62.5 | 92 |
| 46 | 82.8 | 52.9 | 93 | 86.4 | 62.5 | 94 |
| 47 | 86.6 | 55.9 | 97 | 89.4 | 68.8 | 96 |
| 48 | 88.1 | 67.6 | 95 | 92.4 | 87.5 | 94 |
| 49 | 82.8 | 50 | 94 | 72.7 | 25 | 88 |
| 50 | 94 | 85.3 | 97 | 89.4 | 75 | 94 |
| 51 | 84.3 | 55.9 | 94 | 83.3 | 62.5 | 90 |
| 52 | 83.6 | 41.2 | 98 | 86.4 | 43.8 | 100 |
| 53 | 85.8 | 52.9 | 97 | 84.8 | 43.8 | 98 |
| 54 | 91 | 79.4 | 95 | 87.9 | 75 | 92 |
| 55 | 86.6 | 58.8 | 96 | 90.9 | 68.8 | 98 |
| 56 | 83.6 | 55.9 | 93 | 84.8 | 62.5 | 92 |
| 57 | 86.6 | 67.6 | 93 | 89.4 | 68.8 | 96 |
| 58 | 85.1 | 55.9 | 95 | 92.4 | 68.8 | 100 |
| 59 | 85.1 | 47.1 | 98 | 81.8 | 31.2 | 98 |
| 60 | 82.1 | 50 | 93 | 89.4 | 68.8 | 96 |
| 61 | 86.6 | 67.6 | 93 | 86.4 | 62.5 | 94 |
| 62 | 85.8 | 61.8 | 94 | 87.9 | 62.5 | 96 |
| 63 | 82.1 | 58.8 | 90 | 84.8 | 75 | 88 |
| 64 | 83.6 | 61.8 | 91 | 89.4 | 62.5 | 98 |
| 65 | 85.1 | 64.7 | 92 | 89.4 | 75 | 94 |
| 66 | 85.8 | 52.9 | 97 | 78.8 | 31.2 | 94 |
| 67 | 84.3 | 58.8 | 93 | 83.3 | 50 | 94 |
| 68 | 84.3 | 47.1 | 97 | 90.9 | 68.8 | 98 |
| 69 | 80.6 | 26.5 | 99 | 80.3 | 18.8 | 100 |
| 70 | 86.6 | 55.9 | 97 | 83.3 | 50 | 94 |
| 71 | 83.6 | 38.2 | 99 | 84.8 | 37.5 | 100 |
| 72 | 79.1 | 41.2 | 92 | 74.2 | 31.2 | 88 |
| 73 | 85.1 | 55.9 | 95 | 86.4 | 56.2 | 96 |
| 74 | 85.8 | 47.1 | 99 | 81.8 | 31.2 | 98 |
| 75 | 82.1 | 32.4 | 99 | 83.3 | 31.2 | 100 |
| 76 | 82.1 | 32.4 | 99 | 81.8 | 37.5 | 96 |
| 77 | 81.3 | 32.4 | 98 | 87.9 | 50 | 100 |
| 78 | 82.1 | 38.2 | 97 | 78.8 | 25 | 96 |
| 79 | 79.1 | 41.2 | 92 | 78.8 | 37.5 | 92 |
| 80 | 88.8 | 64.7 | 97 | 95.5 | 81.2 | 100 |
| 81 | 79.1 | 47.1 | 90 | 80.3 | 43.8 | 92 |
| 82 | 84.3 | 52.9 | 95 | 81.8 | 50 | 92 |
| 83 | 82.1 | 41.2 | 96 | 78.8 | 31.2 | 94 |
| 84 | 76.1 | 41.2 | 88 | 84.8 | 50 | 96 |
| 85 | 79.9 | 32.4 | 96 | 78.8 | 18.8 | 98 |
| 86 | 83.6 | 55.9 | 93 | 83.3 | 68.8 | 88 |
| 87 | 86.6 | 50 | 99 | 80.3 | 18.8 | 100 |
| 88 | 82.1 | 41.2 | 96 | 86.4 | 56.2 | 96 |
| 89 | 82.1 | 38.2 | 97 | 80.3 | 37.5 | 94 |
| 90 | 83.6 | 50 | 95 | 80.3 | 43.8 | 92 |
| 91 | 78.4 | 44.1 | 90 | 84.8 | 62.5 | 92 |
| 92 | 88.1 | 64.7 | 96 | 81.8 | 37.5 | 96 |
| 93 | 82.8 | 50 | 94 | 84.8 | 56.2 | 94 |
| 94 | 88.1 | 67.6 | 95 | 84.8 | 56.2 | 94 |
| 95 | 82.8 | 50 | 94 | 77.3 | 31.2 | 92 |
| 96 | 82.1 | 35.3 | 98 | 80.3 | 18.8 | 100 |
| 97 | 84.3 | 50 | 96 | 77.3 | 18.8 | 96 |
| 98 | 79.1 | 41.2 | 92 | 78.8 | 37.5 | 92 |
| 99 | 83.6 | 55.9 | 93 | 90.9 | 68.8 | 98 |
| 100 | 76.1 | 14.7 | 97 | 81.8 | 31.2 | 98 |
| 101 | 78.4 | 44.1 | 90 | 78.8 | 31.2 | 94 |
| 102 | 79.9 | 32.4 | 96 | 77.3 | 31.2 | 92 |
| 103 | 81.3 | 41.2 | 95 | 75.8 | 12.5 | 96 |
| 104 | 82.1 | 44.1 | 95 | 84.8 | 50 | 96 |
| 105 | 77.6 | 32.4 | 93 | 77.3 | 25 | 94 |
| 106 | 84.3 | 50 | 96 | 86.4 | 50 | 98 |
| 107 | 85.1 | 50 | 97 | 86.4 | 50 | 98 |
| 108 | 82.1 | 47.1 | 94 | 87.9 | 50 | 100 |
| 109 | 79.9 | 26.5 | 98 | 77.3 | 6.2 | 100 |
| 110 | 79.1 | 35.3 | 94 | 78.8 | 31.2 | 94 |
| 111 | 84.3 | 44.1 | 98 | 83.3 | 31.2 | 100 |
| 112 | 80.6 | 35.3 | 96 | 75.8 | 12.5 | 96 |
| 113 | 78.4 | 20.6 | 98 | 81.8 | 25 | 100 |
| 114 | 83.6 | 47.1 | 96 | 86.4 | 56.2 | 96 |
| 115 | 79.1 | 38.2 | 93 | 80.3 | 25 | 98 |
| 116 | 82.1 | 44.1 | 95 | 78.8 | 31.2 | 94 |
| 117 | 84.3 | 50 | 96 | 87.9 | 62.5 | 96 |
| 118 | 82.8 | 41.2 | 97 | 83.3 | 43.8 | 96 |
| 119 | 82.8 | 41.2 | 97 | 83.3 | 31.2 | 100 |
| 120 | 79.1 | 23.5 | 98 | 75.8 | 18.8 | 94 |
| 121 | 82 | 39.4 | 96 | 74.2 | 12.5 | 94 |
| 122 | 77.6 | 32.4 | 93 | 74.2 | 31.2 | 88 |
| 123 | 82.1 | 38.2 | 97 | 80.3 | 31.2 | 96 |
| 124 | 80.6 | 32.4 | 97 | 83.3 | 37.5 | 98 |
| 125 | 76.9 | 20.6 | 96 | 78.8 | 18.8 | 98 |
| 126 | 77.6 | 20.6 | 97 | 78.8 | 25 | 96 |
| 127 | 82.8 | 35.3 | 99 | 83.3 | 37.5 | 98 |
| 128 | 79.9 | 32.4 | 96 | 71.2 | 37.5 | 82 |
| 129 | 82.8 | 38.2 | 98 | 81.8 | 31.2 | 98 |
| 130 | 82.1 | 32.4 | 99 | 83.3 | 31.2 | 100 |
| 131 | 83.6 | 44.1 | 97 | 83.3 | 37.5 | 98 |
| 132 | 85.8 | 44.1 | 100 | 84.8 | 43.8 | 98 |
| 133 | 78.4 | 26.5 | 96 | 81.8 | 43.8 | 94 |
| 134 | 79.9 | 35.3 | 95 | 77.3 | 31.2 | 92 |
| 135 | 84.3 | 14.7 | 100 | 72.7 | 0 | 96 |
| 136 | 69.4 | 8.8 | 90 | 68.2 | 6.2 | 88 |
| 137 | 77.6 | 14.7 | 99 | 72.7 | 0 | 96 |
| 138 | 77.6 | 29.4 | 94 | 78.8 | 25 | 96 |
| 139 | 82.1 | 32.4 | 99 | 80.3 | 31.2 | 96 |
| 140 | 75.4 | 20.6 | 94 | 77.3 | 12.5 | 98 |
| 141 | 76.9 | 20.6 | 96 | 83.3 | 31.2 | 100 |
| 142 | 74.6 | 20.6 | 93 | 81.8 | 31.2 | 98 |
| 143 | 77.6 | 23.5 | 96 | 80.3 | 25 | 98 |
| 144 | 78.4 | 29.4 | 95 | 77.3 | 31.2 | 92 |
| 145 | 76.9 | 23.5 | 95 | 74.2 | 12.5 | 94 |
| 146 | 81.3 | 29.4 | 99 | 86.4 | 50 | 98 |
| 147 | 73.1 | 8.8 | 95 | 72.7 | 0 | 96 |
| 148 | 79.9 | 26.5 | 98 | 77.3 | 12.5 | 98 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 149 | 78.4 | 17.6 | 99 | 75.8 | 12.5 | 96 |
| 150 | 74.6 | 23.5 | 92 | 74.2 | 18.8 | 92 |
| 151 | 73.9 | 8.8 | 96 | 75.8 | 6.2 | 98 |
| 152 | 79.9 | 29.4 | 97 | 74.2 | 12.5 | 94 |
| 153 | 73.9 | 11.8 | 95 | 72.7 | 0 | 96 |
| 154 | 75.4 | 14.7 | 96 | 75.8 | 12.5 | 96 |
| 155 | 79.1 | 23.5 | 98 | 77.3 | 12.5 | 98 |
| 156 | 75.4 | 5.9 | 99 | 77.3 | 6.2 | 100 |
| 157 | 76.1 | 20.6 | 95 | 77.3 | 18.8 | 96 |
| 158 | 80.6 | 29.4 | 98 | 78.8 | 12.5 | 100 |
| 159 | 73.9 | 11.8 | 95 | 75.8 | 31.2 | 90 |
| 160 | 76.1 | 5.9 | 100 | 75.8 | 0 | 100 |
| 161 | 79.1 | 23.5 | 98 | 78.8 | 12.5 | 100 |
| 162 | 79.1 | 17.6 | 100 | 77.3 | 18.8 | 96 |
| 163 | 72.4 | 8.8 | 94 | 78.8 | 31.2 | 94 |
| 164 | 75.4 | 14.7 | 96 | 72.7 | 6.2 | 94 |
| 165 | 70.9 | 2.9 | 94 | 68.2 | 0 | 90 |
| 166 | 76.1 | 14.7 | 97 | 72.7 | 6.2 | 94 |
| 167 | 76.9 | 23.5 | 95 | 74.2 | 12.5 | 94 |
| 168 | 88.8 | 64.7 | 97 | 81.8 | 43.8 | 94 |
| 169 | 87.3 | 58.8 | 97 | 80.3 | 37.5 | 94 |
| 170 | 91 | 76.5 | 96 | 90.9 | 87.5 | 92 |
| 171 | 91.8 | 85.3 | 94 | 89.4 | 87.5 | 90 |
| 172 | 87.3 | 79.4 | 90 | 89.4 | 75 | 94 |
| 173 | 88.8 | 79.4 | 92 | 87.7 | 68.8 | 93.9 |
| 174 | 89.6 | 76.5 | 94 | 84.8 | 62.5 | 92 |
| 175 | 90.3 | 70.6 | 97 | 93.9 | 81.2 | 98 |
| 176 | 85.8 | 55.9 | 96 | 83.3 | 43.8 | 96 |
| 177 | 86.6 | 52.9 | 98 | 83.3 | 37.5 | 98 |
| 178 | 83.6 | 38.2 | 99 | 81.8 | 50 | 92 |
| 179 | 82.8 | 41.2 | 97 | 84.8 | 43.8 | 98 |
| 180 | 84.3 | 41.2 | 99 | 87.9 | 50 | 100 |
| 181 | 82.1 | 32.4 | 99 | 75.8 | 0 | 100 |
| 182 | 82.1 | 32.4 | 99 | 78.8 | 18.8 | 98 |
| 183 | 76.9 | 14.7 | 98 | 77.3 | 6.2 | 100 |

TABLE 4

| SEQ ID NO: | Discriminant coefficient | Constant term |
|---|---|---|
| 1 | 2.471 | 17.511 |
| 2 | 3.389 | 32.503 |
| 3 | 4.221 | 29.467 |
| 4 | 5.669 | 61.422 |
| 5 | 2.340 | 14.902 |
| 6 | 3.403 | 21.347 |
| 7 | 1.666 | 16.714 |
| 8 | 3.780 | 23.286 |
| 9 | 1.162 | 7.705 |
| 10 | 3.871 | 23.895 |
| 11 | 3.327 | 20.777 |
| 12 | 3.912 | 32.887 |
| 13 | 1.850 | 20.690 |
| 14 | 2.777 | 21.161 |
| 15 | 1.469 | 12.157 |
| 16 | 1.640 | 15.602 |
| 17 | 1.594 | 20.057 |
| 18 | 1.741 | 16.417 |
| 19 | 1.740 | 14.012 |
| 20 | 2.167 | 12.838 |
| 21 | 3.215 | 24.454 |
| 22 | 2.867 | 24.605 |
| 23 | 3.272 | 30.031 |
| 24 | 5.400 | 67.222 |
| 25 | 4.398 | 44.949 |
| 26 | 4.110 | 47.240 |
| 27 | 8.336 | 105.482 |
| 28 | 6.984 | 90.484 |
| 29 | 3.912 | 29.950 |
| 30 | 4.452 | 41.269 |
| 31 | 3.737 | 30.649 |
| 32 | 1.541 | 12.525 |
| 33 | 1.731 | 9.319 |
| 34 | 6.775 | 65.355 |
| 35 | 4.246 | 28.999 |
| 36 | 0.707 | 5.520 |
| 37 | 2.475 | 20.255 |
| 38 | 1.782 | 9.870 |
| 39 | 1.749 | 10.960 |
| 40 | 2.724 | 20.676 |
| 41 | 1.635 | 11.008 |
| 42 | 2.017 | 16.782 |
| 43 | 3.750 | 27.935 |
| 44 | 3.268 | 30.852 |
| 45 | 3.074 | 20.807 |
| 46 | 4.135 | 48.094 |
| 47 | 2.722 | 23.696 |
| 48 | 4.645 | 49.638 |
| 49 | 4.364 | 34.762 |
| 50 | 2.395 | 13.357 |
| 51 | 5.700 | 60.009 |
| 52 | 1.785 | 12.550 |
| 53 | 3.691 | 44.502 |
| 54 | 3.410 | 43.229 |
| 55 | 4.359 | 43.584 |
| 56 | 3.783 | 25.006 |
| 57 | 2.734 | 18.058 |
| 58 | 2.978 | 26.851 |
| 59 | 6.061 | 51.915 |
| 60 | 2.729 | 18.883 |
| 61 | 2.150 | 17.585 |
| 62 | 5.256 | 63.263 |
| 63 | 3.936 | 30.117 |
| 64 | 4.508 | 41.792 |
| 65 | 2.386 | 16.961 |
| 66 | 1.810 | 12.154 |
| 67 | 2.969 | 28.301 |
| 68 | 3.512 | 34.056 |
| 69 | 1.951 | 12.101 |
| 70 | 3.135 | 22.180 |
| 71 | 1.606 | 9.267 |
| 72 | 2.696 | 34.139 |
| 73 | 4.474 | 34.903 |
| 74 | 2.012 | 14.274 |
| 75 | 1.959 | 12.395 |
| 76 | 2.215 | 12.602 |
| 77 | 5.057 | 66.741 |
| 78 | 1.620 | 11.678 |
| 79 | 4.288 | 30.633 |
| 80 | 2.430 | 13.696 |
| 81 | 3.351 | 33.938 |
| 82 | 3.921 | 34.024 |
| 83 | 1.278 | 9.389 |
| 84 | 2.183 | 21.651 |
| 85 | 1.944 | 11.599 |
| 86 | 4.824 | 36.279 |
| 87 | 3.858 | 31.074 |
| 88 | 1.277 | 7.779 |
| 89 | 4.555 | 56.233 |
| 90 | 1.520 | 8.345 |
| 91 | 3.667 | 23.791 |
| 92 | 3.455 | 26.548 |
| 93 | 3.821 | 45.609 |
| 94 | 1.784 | 12.053 |
| 95 | 4.842 | 42.664 |
| 96 | 1.392 | 8.122 |
| 97 | 3.251 | 27.595 |
| 98 | 4.026 | 29.199 |
| 99 | 5.471 | 69.803 |
| 100 | 2.281 | 13.200 |
| 101 | 2.499 | 18.849 |
| 102 | 5.118 | 35.429 |
| 103 | 3.691 | 24.076 |
| 104 | 2.471 | 16.246 |
| 105 | 2.973 | 21.963 |
| 106 | 1.588 | 10.669 |
| 107 | 2.017 | 13.094 |

TABLE 4-continued

| SEQ ID NO: | Discriminant coefficient | Constant term |
|---|---|---|
| 108 | 4.206 | 32.002 |
| 109 | 1.659 | 9.895 |
| 110 | 2.739 | 16.192 |
| 111 | 3.174 | 24.976 |
| 112 | 2.780 | 19.682 |
| 113 | 1.225 | 8.488 |
| 114 | 2.404 | 24.762 |
| 115 | 2.895 | 19.963 |
| 116 | 4.205 | 46.806 |
| 117 | 4.490 | 59.177 |
| 118 | 5.016 | 41.382 |
| 119 | 2.142 | 20.182 |
| 120 | 4.030 | 28.787 |
| 121 | 2.093 | 21.502 |
| 122 | 4.832 | 36.040 |
| 123 | 3.672 | 42.382 |
| 124 | 3.305 | 27.456 |
| 125 | 4.919 | 62.904 |
| 126 | 1.924 | 11.325 |
| 127 | 2.696 | 15.869 |
| 128 | 7.275 | 92.098 |
| 129 | 1.903 | 17.010 |
| 130 | 1.935 | 12.644 |
| 131 | 3.379 | 35.351 |
| 132 | 2.384 | 15.077 |
| 133 | 6.549 | 74.981 |
| 134 | 5.238 | 55.302 |
| 135 | 2.785 | 28.718 |
| 136 | 3.118 | 31.040 |
| 137 | 3.097 | 23.331 |
| 138 | 4.424 | 38.383 |
| 139 | 1.611 | 12.320 |
| 140 | 4.840 | 56.003 |
| 141 | 2.484 | 17.251 |
| 142 | 3.851 | 37.749 |
| 143 | 3.720 | 31.374 |
| 144 | 3.991 | 31.836 |
| 145 | 4.065 | 33.772 |
| 146 | 2.441 | 14.617 |
| 147 | 3.795 | 27.973 |
| 148 | 2.362 | 18.895 |
| 149 | 2.354 | 13.716 |
| 150 | 5.065 | 35.714 |
| 151 | 2.922 | 20.137 |
| 152 | 1.539 | 9.313 |
| 153 | 4.631 | 31.436 |
| 154 | 3.326 | 25.477 |
| 155 | 2.223 | 15.649 |
| 156 | 2.416 | 15.308 |
| 157 | 4.655 | 51.632 |
| 158 | 2.552 | 27.736 |
| 159 | 6.563 | 85.503 |
| 160 | 2.281 | 14.772 |
| 161 | 5.241 | 39.899 |
| 162 | 2.291 | 14.195 |
| 163 | 6.256 | 74.602 |
| 164 | 2.920 | 22.423 |
| 165 | 2.285 | 16.474 |
| 166 | 3.720 | 42.108 |
| 167 | 4.806 | 47.920 |
| 168 | 1.156 | 5.990 |
| 169 | 1.212 | 6.218 |
| 170 | 3.292 | 19.092 |
| 171 | 4.244 | 27.332 |
| 172 | 1.867 | 12.024 |
| 173 | 3.494 | 22.197 |
| 174 | 2.062 | 19.948 |
| 175 | 1.942 | 18.936 |
| 176 | 0.886 | 4.794 |
| 177 | 1.182 | 6.543 |
| 178 | 1.678 | 10.850 |
| 179 | 1.358 | 7.646 |
| 180 | 1.032 | 6.311 |
| 181 | 2.498 | 20.322 |
| 182 | 1.203 | 7.922 |
| 183 | 2.779 | 28.552 |

TABLE 5-1

Training cohort

| Sample name | Cancer stage | AFP (ng/mL) | CEA (ng/mL) | CA19-9 (U/mL) | PIVKA-II (mAU/mL) |
|---|---|---|---|---|---|
| HC03 | I | 13.2 | 3.1 | — | 99 |
| HC04 | I | 37210 | 1 | — | 13550 |
| HC05 | IV | 3 | — | — | 18 |
| HC06 | I | 26.1 | 5.7 | — | 136 |
| HC07 | III | 3.2 | 3.4 | — | 2452 |
| HC09 | II | 34.7 | 5 | 26.2 | 1932 |
| HC10 | I | 74 | 2.6 | — | 10 |
| HC12 | I | 3.4 | — | — | 39 |
| HC13 | III | — | 0.6 | 5.1 | — |
| HC15 | II | — | 1.9 | 0.1 | — |
| HC17 | II | 2.3 | — | — | 556 |
| HC18 | IV | 36145 | — | — | 167 |
| HC19 | I | 8.5 | 3.7 | — | 13 |
| HC20 | I | 4.6 | 3.2 | 6.4 | 344 |
| HC23 | III | 151.3 | 1.9 | — | 29521 |
| HC24 | III | 103299 | 1.9 | — | 55837 |
| HC25 | I | 179.7 | 12.1 | — | 220 |
| HC26 | I | 25.3 | 1.4 | — | 36 |
| HC27 | I | 8.5 | 4.7 | — | 28 |
| HC29 | I | 29.2 | — | — | 979 |
| HC30 | III B | 77.4 | — | — | 176940 |
| HC31 | II | 7 | — | — | 34 |
| HC32 | III | 2.2 | 1.8 | — | 40 |
| HC34 | II | 6.9 | — | — | 688 |
| HC36 | II | 25.3 | 1.9 | — | 3481 |
| HC38 | I | 5.4 | 4.8 | — | 92 |
| HC40 | IIIB | 5.7 | — | — | 95 |
| HC41 | II | 93.7 | 5.8 | 104.9 | 26 |
| HC42 | I | 1.9 | 6.5 | — | 25 |
| HC45 | II | 10.3 | — | — | 51 |
| HC47 | IIIC | 235.5 | — | — | 3601 |
| HC48 | I | 107.9 | — | — | 52 |
| HC49 | I | 4.5 | 4.3 | 26.7 | 22 |
| HC50 | II | 133338 | 2.9 | — | 829 |
| Sensitivity | | 56.3% | 18.2% | 16.7% | 65.6% |

TABLE 5-2

Validation cohort

| Sample name | Cancer stage | AFP (ng/mL) | CEA (ng/mL) | CA19-9 (U/mL) | PIVKA-II (mAU/mL) |
|---|---|---|---|---|---|
| HC01 | II | 10.8 | 2.8 | — | 678 |
| HC02 | I | 3.8 | 1.4 | 11.4 | 26 |
| HC08 | I | 13 | 3 | — | 245 |
| HC11 | I | 17.2 | 3.4 | — | 15 |
| HC14 | I | 1.8 | 5.7 | — | 18 |
| HC16 | I | 6 | — | — | 21 |
| HC21 | II | 5.3 | 5.3 | 14.8 | 22 |
| HC22 | I | 1.7 | — | — | 76 |
| HC28 | I | — | 4.4 | 11 | — |
| HC33 | III | 40 | 1.1 | — | 25 |
| HC35 | II | 4.2 | 5.2 | — | 20 |
| HC37 | III | 59992 | — | — | 14358 |
| HC39 | II | 555 | — | — | 194 |
| HC43 | I | 18 | — | — | 32 |
| HC44 | I | 7.5 | 1 | 32.7 | 462 |
| HC46 | II | 1075 | — | — | 46 |
| Sensitivity | | 53.3% | 30.0% | 0.0% | 46.7% |

The reference values of AFP, CEA, CA19-9, and PIVKA-II were 10 ng/mL, 5 ng/mL, 37 U/mL, and 40 mAU/mL, respectively. Each sample that exhibited a measurement value equal to or higher than the reference values was determined to be positive, and the sensitivity of each tumor marker was calculated.

TABLE 6

| SEQ ID NO: | Training cohort | | | Validation cohort | | | SEQ ID NO: | Training cohort | | | Validation cohort | | |
|---|---|---|---|---|---|---|---|---|---|---|---|---|---|
| | Accuracy (%) | Sensitivity (%) | Specificity (%) | Accuracy (%) | Sensitivity (%) | Specificity (%) | | Accuracy (%) | Sensitivity (%) | Specificity (%) | Accuracy (%) | Sensitivity (%) | Specificity (%) |
| 1_2 | 99.3 | 100 | 99 | 100 | 100 | 100 | 1_76 | 96.3 | 97.1 | 96 | 97 | 93.8 | 98 |
| 1_3 | 100 | 100 | 100 | 98.5 | 100 | 98 | 1_77 | 97.8 | 97.1 | 98 | 97 | 93.8 | 98 |
| 1_4 | 99.3 | 100 | 99 | 100 | 100 | 100 | 1_78 | 97 | 97.1 | 97 | 97 | 93.8 | 98 |
| 1_5 | 97.8 | 97.1 | 98 | 97 | 93.8 | 98 | 1_79 | 97 | 97.1 | 97 | 97 | 93.8 | 98 |
| 1_6 | 99.3 | 97.1 | 100 | 97 | 93.8 | 98 | 1_80 | 97 | 94.1 | 98 | 95.5 | 87.5 | 98 |
| 1_7 | 96.3 | 91.2 | 98 | 97 | 87.5 | 100 | 1_81 | 98.5 | 97.1 | 99 | 95.5 | 93.8 | 96 |
| 1_8 | 100 | 100 | 100 | 97 | 93.8 | 98 | 1_82 | 95.5 | 97.1 | 95 | 97 | 93.8 | 98 |
| 1_9 | 97.8 | 97.1 | 98 | 97 | 100 | 96 | 1_83 | 96.3 | 91.2 | 98 | 97 | 93.8 | 98 |
| 1_10 | 99.2 | 100 | 99 | 100 | 100 | 100 | 1_84 | 97.8 | 97.1 | 98 | 97 | 93.8 | 98 |
| 1_11 | 98.5 | 100 | 98 | 97 | 93.8 | 98 | 1_85 | 96.3 | 97.1 | 96 | 97 | 93.8 | 98 |
| 1_12 | 97.8 | 100 | 97 | 97 | 93.8 | 98 | 1_86 | 97 | 97.1 | 97 | 95.5 | 93.8 | 96 |
| 1_13 | 98.5 | 97.1 | 99 | 98.5 | 93.8 | 100 | 1_87 | 97 | 97.1 | 97 | 97 | 93.8 | 98 |
| 1_14 | 99.3 | 100 | 99 | 98.5 | 93.8 | 100 | 1_88 | 96.3 | 94.1 | 97 | 98.5 | 100 | 98 |
| 1_15 | 97.8 | 94.1 | 99 | 98.5 | 93.8 | 100 | 1_89 | 95.5 | 97.1 | 95 | 95.5 | 93.8 | 96 |
| 1_16 | 97.8 | 94.1 | 99 | 97 | 93.8 | 98 | 1_90 | 98.5 | 100 | 98 | 95.5 | 93.8 | 96 |
| 1_17 | 99.3 | 100 | 99 | 97 | 100 | 96 | 1_91 | 96.3 | 97.1 | 96 | 97 | 93.8 | 98 |
| 1_18 | 97.8 | 97.1 | 98 | 97 | 93.8 | 98 | 1_92 | 97 | 97.1 | 97 | 97 | 93.8 | 98 |
| 1_19 | 96.3 | 94.1 | 97 | 97 | 93.8 | 98 | 1_93 | 97 | 100 | 96 | 95.5 | 93.8 | 96 |
| 1_20 | 96.3 | 94.1 | 97 | 97 | 93.8 | 98 | 1_94 | 96.3 | 94.1 | 97 | 97 | 93.8 | 98 |
| 1_21 | 95.5 | 94.1 | 96 | 97 | 93.8 | 98 | 1_95 | 97 | 97.1 | 97 | 97 | 93.8 | 98 |
| 1_22 | 97 | 94.1 | 98 | 97 | 93.8 | 98 | 1_96 | 99.3 | 100 | 99 | 97 | 100 | 96 |
| 1_23 | 97.8 | 97.1 | 98 | 98.5 | 100 | 98 | 1_97 | 97 | 100 | 96 | 95.5 | 93.8 | 96 |
| 1_24 | 98.5 | 100 | 98 | 97 | 93.8 | 98 | 1_98 | 97 | 100 | 96 | 95.5 | 93.8 | 96 |
| 1_25 | 97.8 | 97.1 | 98 | 97 | 93.8 | 98 | 1_99 | 97 | 97.1 | 97 | 97 | 93.8 | 98 |
| 1_26 | 97 | 97.1 | 97 | 97 | 93.8 | 98 | 1_100 | 98.5 | 100 | 98 | 95.5 | 93.8 | 96 |
| 1_27 | 97.8 | 97.1 | 98 | 95.5 | 93.8 | 96 | 1_101 | 97.8 | 100 | 97 | 93.9 | 93.8 | 94 |
| 1_28 | 97.8 | 100 | 97 | 97 | 93.8 | 98 | 1_102 | 97.8 | 100 | 97 | 97 | 93.8 | 98 |
| 1_29 | 97.8 | 100 | 97 | 97 | 100 | 96 | 1_103 | 97 | 97.1 | 97 | 97 | 93.8 | 98 |
| 1_30 | 98.5 | 97.1 | 99 | 93.9 | 87.5 | 96 | 1_104 | 97.8 | 97.1 | 98 | 97 | 93.8 | 98 |
| 1_31 | 95.5 | 91.2 | 97 | 97 | 93.8 | 98 | 1_105 | 96.3 | 97.1 | 96 | 97 | 93.8 | 98 |
| 1_32 | 99.3 | 100 | 99 | 97 | 100 | 96 | 1_106 | 97 | 100 | 96 | 95.5 | 93.8 | 96 |
| 1_33 | 96.3 | 94.1 | 97 | 97 | 93.8 | 98 | 1_107 | 96.3 | 97.1 | 96 | 97 | 93.8 | 98 |
| 1_34 | 96.3 | 97.1 | 96 | 97 | 93.8 | 98 | 1_108 | 96.3 | 97.1 | 96 | 95.5 | 93.8 | 96 |
| 1_35 | 97.8 | 97.1 | 98 | 97 | 93.8 | 98 | 1_109 | 96.3 | 97.1 | 96 | 97 | 93.8 | 98 |
| 1_36 | 99.3 | 100 | 99 | 98.5 | 93.8 | 100 | 1_110 | 97 | 97.1 | 97 | 98.5 | 100 | 98 |
| 1_37 | 97 | 94.1 | 98 | 97 | 93.8 | 98 | 1_111 | 97.8 | 100 | 97 | 97 | 100 | 96 |
| 1_38 | 98.5 | 97.1 | 99 | 97 | 93.8 | 98 | 1_112 | 96.3 | 97.1 | 96 | 97 | 93.8 | 98 |
| 1_39 | 99.3 | 97.1 | 100 | 100 | 100 | 100 | 1_113 | 98.5 | 100 | 98 | 97 | 100 | 96 |
| 1_40 | 97 | 97.1 | 97 | 97 | 93.8 | 98 | 1_114 | 96.3 | 100 | 95 | 95.5 | 93.8 | 96 |
| 1_41 | 95.5 | 94.1 | 96 | 97 | 93.8 | 98 | 1_115 | 97.8 | 97.1 | 98 | 98.5 | 100 | 98 |
| 1_42 | 96.3 | 97.1 | 96 | 97 | 93.8 | 98 | 1_116 | 95.5 | 97.1 | 95 | 97 | 93.8 | 98 |
| 1_43 | 96.3 | 94.1 | 97 | 97 | 93.8 | 98 | 1_117 | 97 | 94.1 | 98 | 97 | 93.8 | 98 |
| 1_44 | 98.5 | 100 | 98 | 97 | 100 | 96 | 1_118 | 95.5 | 97.1 | 95 | 97 | 93.8 | 98 |
| 1_45 | 97.8 | 97.1 | 98 | 97 | 93.8 | 98 | 1_119 | 97 | 97.1 | 97 | 97 | 93.8 | 98 |
| 1_46 | 97 | 97.1 | 97 | 97 | 93.8 | 98 | 1_120 | 95.5 | 97.1 | 95 | 97 | 93.8 | 98 |
| 1_47 | 97 | 94.1 | 98 | 97 | 93.8 | 98 | 1_121 | 97 | 97 | 97 | 97 | 93.8 | 98 |
| 1_48 | 97.8 | 97.1 | 98 | 97 | 93.8 | 98 | 1_122 | 95.5 | 97.1 | 95 | 97 | 93.8 | 98 |
| 1_49 | 98.5 | 97.1 | 99 | 98.5 | 93.8 | 100 | 1_123 | 97 | 97.1 | 97 | 98.5 | 100 | 98 |
| 1_50 | 96.3 | 97.1 | 96 | 97 | 93.8 | 98 | 1_124 | 95.5 | 97.1 | 95 | 97 | 93.8 | 98 |
| 1_51 | 97 | 97.1 | 97 | 97 | 93.8 | 98 | 1_125 | 98.5 | 97.1 | 99 | 97 | 93.8 | 98 |
| 1_52 | 99.3 | 100 | 99 | 98.5 | 100 | 98 | 1_126 | 96.3 | 94.1 | 97 | 93.9 | 93.8 | 94 |
| 1_53 | 95.5 | 97.1 | 95 | 97 | 93.8 | 98 | 1_127 | 97 | 97.1 | 97 | 98.5 | 100 | 98 |
| 1_54 | 96.3 | 94.1 | 97 | 97 | 93.8 | 98 | 1_128 | 96.3 | 97.1 | 96 | 95.5 | 93.8 | 96 |
| 1_55 | 97.8 | 97.1 | 98 | 97 | 93.8 | 98 | 1_129 | 97 | 100 | 96 | 97 | 100 | 96 |
| 1_56 | 96.3 | 97.1 | 96 | 97 | 93.8 | 98 | 1_130 | 95.5 | 97.1 | 95 | 97 | 93.8 | 98 |
| 1_57 | 97 | 94.1 | 98 | 97 | 93.8 | 98 | 1_131 | 97 | 100 | 96 | 93.9 | 93.8 | 94 |
| 1_58 | 96.3 | 94.1 | 97 | 97 | 93.8 | 98 | 1_132 | 96.3 | 94.1 | 97 | 97 | 93.8 | 98 |
| 1_59 | 97 | 94.1 | 98 | 98.5 | 93.8 | 100 | 1_133 | 96.3 | 97.1 | 96 | 95.5 | 93.8 | 96 |
| 1_60 | 97 | 97.1 | 97 | 97 | 93.8 | 98 | 1_134 | 98.5 | 100 | 98 | 97 | 93.8 | 98 |
| 1_61 | 95.5 | 94.1 | 96 | 97 | 93.8 | 98 | 1_135 | 98.5 | 97.1 | 99 | 95.5 | 93.8 | 96 |
| 1_62 | 97 | 94.1 | 98 | 97 | 93.8 | 98 | 1_136 | 97 | 97.1 | 97 | 97 | 93.8 | 98 |
| 1_63 | 96.3 | 94.1 | 97 | 97 | 93.8 | 98 | 1_137 | 97 | 97.1 | 97 | 98.5 | 100 | 98 |
| 1_64 | 97.8 | 94.1 | 99 | 97 | 93.8 | 98 | 1_138 | 96.3 | 97.1 | 96 | 97 | 93.8 | 98 |
| 1_65 | 97.8 | 97.1 | 98 | 97 | 93.8 | 98 | 1_139 | 96.3 | 94.1 | 97 | 97 | 93.8 | 98 |
| 1_66 | 97.8 | 97.1 | 98 | 97 | 93.8 | 98 | 1_140 | 96.3 | 97.1 | 96 | 97 | 93.8 | 98 |
| 1_67 | 97 | 94.1 | 98 | 97 | 93.8 | 98 | 1_141 | 97.8 | 97.1 | 98 | 97 | 100 | 96 |
| 1_68 | 98.5 | 100 | 98 | 98.5 | 100 | 98 | 1_142 | 95.5 | 94.1 | 96 | 97 | 93.8 | 98 |
| 1_69 | 96.3 | 94.1 | 97 | 97 | 93.8 | 98 | 1_143 | 95.5 | 97.1 | 95 | 97 | 93.8 | 98 |
| 1_70 | 97.8 | 94.1 | 99 | 97 | 93.8 | 98 | 1_144 | 95.5 | 94.1 | 96 | 97 | 93.8 | 98 |
| 1_71 | 97.8 | 97.1 | 98 | 97 | 93.8 | 98 | 1_145 | 97 | 94.1 | 98 | 97 | 93.8 | 98 |
| 1_72 | 97.8 | 100 | 97 | 95.5 | 100 | 94 | 1_146 | 95.5 | 94.1 | 96 | 97 | 93.8 | 98 |
| 1_73 | 95.5 | 94.1 | 96 | 97 | 93.8 | 98 | 1_147 | 98.5 | 97.1 | 99 | 97 | 93.8 | 98 |
| 1_74 | 99.3 | 100 | 99 | 98.5 | 100 | 98 | 1_148 | 96.3 | 94.1 | 97 | 97 | 93.8 | 98 |
| 1_75 | 98.5 | 100 | 98 | 97 | 93.8 | 98 | 1_149 | 95.5 | 97.1 | 95 | 97 | 93.8 | 98 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1_150 | 95.5 | 97.1 | 95 | 97 | 93.8 | 98 |
| 1_151 | 97.8 | 97.1 | 98 | 95.5 | 93.8 | 96 |
| 1_152 | 96.3 | 97.1 | 96 | 97 | 93.8 | 98 |
| 1_153 | 97.8 | 100 | 97 | 97 | 93.8 | 98 |
| 1_154 | 97.8 | 97.1 | 98 | 95.5 | 93.8 | 96 |
| 1_155 | 98.5 | 97.1 | 99 | 97 | 93.8 | 98 |
| 1_156 | 96.3 | 97.1 | 96 | 97 | 93.8 | 98 |
| 1_157 | 97 | 97.1 | 97 | 95.5 | 93.8 | 96 |
| 1_158 | 96.3 | 100 | 95 | 97 | 100 | 96 |
| 1_159 | 95.5 | 97.1 | 95 | 97 | 93.8 | 98 |
| 1_160 | 97 | 97.1 | 97 | 97 | 93.8 | 98 |
| 1_161 | 96.3 | 94.1 | 97 | 97 | 93.8 | 98 |
| 1_162 | 96.3 | 97.1 | 96 | 97 | 93.8 | 98 |
| 1_163 | 95.5 | 97.1 | 95 | 97 | 100 | 96 |
| 1_164 | 95.5 | 97.1 | 95 | 97 | 93.8 | 98 |
| 1_165 | 96.3 | 94.1 | 97 | 97 | 93.8 | 98 |
| 1_166 | 97 | 97.1 | 97 | 97 | 93.8 | 98 |
| 1_167 | 96.3 | 97.1 | 96 | 97 | 93.8 | 98 |
| 1_168 | 97 | 94.1 | 98 | 98.5 | 93.8 | 100 |
| 1_169 | 98.5 | 97.1 | 99 | 97 | 93.8 | 98 |
| 1_170 | 100 | 100 | 100 | 97 | 93.8 | 98 |
| 1_171 | 99.3 | 100 | 99 | 98.5 | 100 | 98 |
| 1_172 | 96.3 | 97.1 | 96 | 97 | 93.8 | 98 |
| 1_173 | 98.5 | 100 | 98 | 98.5 | 100 | 98 |
| 1_174 | 95.5 | 94.1 | 96 | 97 | 93.8 | 98 |
| 1_175 | 97 | 97.1 | 97 | 97 | 93.8 | 98 |
| 1_176 | 98.5 | 100 | 98 | 98.5 | 93.8 | 100 |
| 1_177 | 97.8 | 97.1 | 98 | 97 | 93.8 | 98 |
| 1_178 | 99.3 | 100 | 99 | 97 | 100 | 96 |
| 1_179 | 98.5 | 100 | 98 | 98.5 | 100 | 98 |
| 1_180 | 99.3 | 100 | 99 | 97 | 100 | 96 |
| 1_181 | 97.8 | 97.1 | 98 | 97 | 93.8 | 98 |
| 1_182 | 97 | 97.1 | 97 | 97 | 93.8 | 98 |
| 1_183 | 99.3 | 100 | 99 | 100 | 100 | 100 |

Example 3

<Selection of Gene Marker Using all Samples and Method for Evaluating Liver Cancer Discriminant Performance of Acquired Gene Marker>

In this Example, the samples in the training cohort and the validation cohort used in Examples 1 and 2 were integrated, and selection of a gene marker and evaluation of its liver cancer discriminant performance were conducted using all of the samples.

Specifically, the miRNA expression levels in the serum of the 50 liver cancer patients and the 150 healthy subjects obtained in the above-mentioned Reference Examples were normalized by quantile normalization. In order to acquire diagnostic markers with higher reliability, only genes having a gene expression level of $2^6$ or higher in 50% or more of the samples in either of the liver cancer patient group or the healthy subject group were selected in the gene marker selection. In order to further acquire statistical significance for discriminating a liver cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant. The acquired genes are described in Table 7. In this way, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090 genes represented by SEQ ID NOs: 184 to 224 were found as liver cancer markers relative to the healthy subjects, in addition to the genes described in Table 2. As with the polynucleotides shown in SEQ ID NOs: 1 to 183, the results obtained about the polynucleotides shown in SEQ ID NOs: 184 to 224 also showed that the expression level measurement values were significantly lower (−) or higher (+) in the liver cancer patient group than in the healthy subject group (Table 7). These results were able to be validated in the validation cohort. Thus, the presence or absence of liver cancer in the newly obtained samples can be determined by the methods described in Examples 1 and 2 by using the gene expression level measurement values described in Table 7 either alone or in combination with the gene expression level measurement values described in Table 2.

TABLE 7

| SEQ ID NO: | Gene name | P value after Bonferroni correction | Expression level in liver cancer patient relative to healthy subject |
|---|---|---|---|
| 1 | hsa-miR-1343-3p | 7.76.E−56 | − |
| 2 | hsa-miR-6726-5p | 1.12.E−51 | − |
| 3 | hsa-miR-6515-3p | 4.93.E−36 | + |
| 4 | hsa-miR-4651 | 9.12.E−42 | − |
| 5 | hsa-miR-4257 | 2.81.E−42 | − |
| 6 | hsa-miR-3188 | 1.06.E−41 | + |
| 7 | hsa-miR-6131 | 1.97.E−37 | − |
| 8 | hsa-miR-6766-3p | 4.59.E−35 | + |
| 9 | hsa-miR-7641 | 2.35.E−36 | − |
| 10 | hsa-miR-1249 | 2.50.E−34 | + |
| 11 | hsa-miR-3679-3p | 5.67.E−31 | + |
| 12 | hsa-miR-6787-5p | 9.25.E−36 | − |
| 13 | hsa-miR-4454 | 1.38.E−34 | − |
| 14 | hsa-miR-3135b | 3.23.E−23 | − |
| 15 | hsa-miR-6765-3p | 8.15.E−32 | − |
| 16 | hsa-miR-7975 | 4.38.E−28 | − |
| 17 | hsa-miR-204-3p | 2.40.E−25 | − |
| 18 | hsa-miR-7977 | 6.65.E−27 | − |
| 19 | hsa-miR-7110-5p | 2.91.E−28 | + |
| 20 | hsa-miR-6717-5p | 4.18.E−23 | − |
| 21 | hsa-miR-6870-5p | 2.08.E−27 | + |
| 22 | hsa-miR-663b | 1.18.E−29 | − |
| 23 | hsa-miR-6875-5p | 1.80.E−24 | + |
| 24 | hsa-miR-8072 | 1.13.E−21 | + |
| 25 | hsa-miR-6816-5p | 9.86.E−26 | + |
| 26 | hsa-miR-4281 | 1.18.E−24 | − |
| 27 | hsa-miR-6729-5p | 1.39.E−22 | + |
| 28 | hsa-miR-8069 | 9.35.E−19 | + |
| 29 | hsa-miR-4706 | 1.28.E−23 | − |
| 30 | hsa-miR-7108-5p | 3.30.E−21 | + |
| 31 | hsa-miR-4433b-3p | 1.04.E−21 | + |
| 32 | hsa-miR-6893-5p | 7.87.E−23 | − |
| 33 | hsa-miR-6857-5p | 1.05.E−22 | + |
| 34 | hsa-miR-1227-5p | 5.00.E−23 | + |
| 35 | hsa-miR-6741-5p | 2.98.E−21 | − |
| 36 | hsa-miR-451a | 1.60.E−19 | − |
| 37 | hsa-miR-8063 | 1.20.E−22 | − |
| 38 | hsa-miR-3622a-5p | 8.16.E−21 | − |
| 39 | hsa-miR-615-5p | 1.17.E−21 | − |
| 40 | hsa-miR-128-1-5p | 8.49.E−17 | + |
| 41 | hsa-miR-6825-5p | 4.10.E−25 | + |
| 42 | hsa-miR-1260b | 4.23.E−20 | − |
| 43 | hsa-miR-4433-3p | 7.63.E−20 | + |
| 44 | hsa-miR-4665-5p | 1.92.E−15 | − |
| 45 | hsa-miR-7845-5p | 9.71.E−18 | + |

TABLE 7-continued

| SEQ ID NO: | Gene name | P value after Bonferroni correction | Expression level in liver cancer patient relative to healthy subject |
|---|---|---|---|
| 46 | hsa-miR-1908-5p | 6.59.E−21 | + |
| 47 | hsa-miR-6840-3p | 1.70.E−20 | − |
| 48 | hsa-miR-6765-5p | 3.32.E−15 | + |
| 49 | hsa-miR-296-5p | 5.14.E−14 | + |
| 51 | hsa-miR-6781-5p | 6.41.E−18 | + |
| 52 | hsa-miR-423-5p | 1.91.E−15 | − |
| 53 | hsa-miR-3663-3p | 1.67.E−16 | − |
| 54 | hsa-miR-6784-5p | 8.43.E−18 | + |
| 55 | hsa-miR-6749-5p | 2.59.E−20 | − |
| 56 | hsa-miR-1231 | 1.33.E−14 | + |
| 57 | hsa-miR-4746-3p | 3.47.E−19 | + |
| 58 | hsa-miR-6780b-5p | 2.82.E−21 | + |
| 59 | hsa-miR-4758-5p | 4.87.E−15 | − |
| 60 | hsa-miR-3679-5p | 1.59.E−19 | + |
| 61 | hsa-miR-3184-5p | 6.75.E−18 | + |
| 62 | hsa-miR-6125 | 8.43.E−17 | + |
| 63 | hsa-miR-6721-5p | 3.93.E−15 | + |
| 64 | hsa-miR-6791-5p | 1.78.E−17 | + |
| 65 | hsa-miR-3185 | 5.38.E−17 | + |
| 66 | hsa-miR-1260a | 7.87.E−15 | − |
| 67 | hsa-miR-3197 | 1.51.E−14 | + |
| 68 | hsa-miR-6845-5p | 2.09.E−16 | + |
| 69 | hsa-miR-6887-5p | 3.08.E−15 | − |
| 70 | hsa-miR-6738-5p | 1.83.E−16 | − |
| 71 | hsa-miR-6872-3p | 5.80.E−14 | − |
| 72 | hsa-miR-4497 | 2.63.E−10 | − |
| 73 | hsa-miR-1229-5p | 1.21.E−14 | + |
| 74 | hsa-miR-6820-5p | 5.60.E−13 | + |
| 75 | hsa-miR-6777-5p | 7.03.E−15 | − |
| 76 | hsa-miR-3917 | 7.63.E−13 | − |
| 77 | hsa-miR-5787 | 5.42.E−15 | + |
| 78 | hsa-miR-4286 | 1.57.E−12 | − |
| 79 | hsa-miR-6877-5p | 1.83.E−14 | − |
| 80 | hsa-miR-1225-3p | 4.77.E−11 | + |
| 81 | hsa-miR-6088 | 4.12.E−13 | − |
| 82 | hsa-miR-6800-5p | 1.01.E−13 | + |
| 83 | hsa-miR-1246 | 1.20.E−10 | − |
| 84 | hsa-miR-4467 | 2.24.E−15 | + |
| 85 | hsa-miR-4419b | 3.03.E−12 | − |
| 86 | hsa-miR-1914-3p | 3.27.E−13 | − |
| 87 | hsa-miR-4632-5p | 6.04.E−12 | + |
| 88 | hsa-miR-1915-5p | 7.61.E−15 | − |
| 89 | hsa-miR-3940-5p | 7.23.E−12 | + |
| 91 | hsa-miR-6746-5p | 5.54.E−13 | − |
| 92 | hsa-miR-5001-5p | 2.14.E−13 | − |
| 93 | hsa-miR-1228-5p | 7.95.E−13 | + |
| 94 | hsa-miR-5572 | 5.18.E−16 | + |
| 95 | hsa-miR-4327 | 2.61.E−09 | + |
| 96 | hsa-miR-4638-5p | 1.48.E−10 | − |
| 97 | hsa-miR-6799-5p | 1.10.E−10 | + |
| 98 | hsa-miR-6861-5p | 8.44.E−11 | − |
| 99 | hsa-miR-6727-5p | 2.38.E−13 | − |
| 100 | hsa-miR-4513 | 8.83.E−12 | − |
| 101 | hsa-miR-6805-3p | 1.08.E−12 | + |
| 102 | hsa-miR-6808-5p | 3.32.E−10 | + |
| 103 | hsa-miR-4449 | 4.13.E−09 | + |
| 104 | hsa-miR-1199-5p | 1.45.E−11 | − |
| 105 | hsa-miR-1275 | 2.47.E−08 | + |
| 106 | hsa-miR-4792 | 9.54.E−13 | + |
| 107 | hsa-miR-4443 | 4.44.E−10 | + |
| 108 | hsa-miR-6891-5p | 3.67.E−12 | + |
| 109 | hsa-miR-6826-5p | 5.10.E−11 | − |
| 110 | hsa-miR-6807-5p | 1.03.E−09 | + |
| 111 | hsa-miR-7150 | 1.05.E−09 | + |
| 112 | hsa-miR-4534 | 1.61.E−09 | + |
| 113 | hsa-miR-4476 | 6.66.E−08 | − |
| 114 | hsa-miR-4649-5p | 1.12.E−10 | − |
| 115 | hsa-miR-4525 | 4.68.E−12 | − |
| 116 | hsa-miR-1915-3p | 1.92.E−10 | + |
| 117 | hsa-miR-4516 | 1.95.E−10 | − |
| 118 | hsa-miR-4417 | 3.89.E−10 | + |
| 119 | hsa-miR-642b-3p | 3.82.E−10 | − |
| 120 | hsa-miR-3141 | 1.02.E−08 | + |
| 121 | hsa-miR-5100 | 4.74.E−08 | − |
| 122 | hsa-miR-6848-5p | 7.00.E−10 | + |
| 123 | hsa-miR-4739 | 1.94.E−08 | + |
| 124 | hsa-miR-4459 | 1.30.E−08 | + |
| 125 | hsa-miR-1237-5p | 1.04.E−08 | + |
| 126 | hsa-miR-296-3p | 9.28.E−08 | − |
| 127 | hsa-miR-4665-3p | 9.58.E−12 | + |
| 128 | hsa-miR-6786-5p | 7.26.E−06 | + |
| 129 | hsa-miR-4258 | 4.38.E−08 | − |
| 130 | hsa-miR-6510-5p | 4.93.E−11 | + |
| 131 | hsa-miR-1343-5p | 1.77.E−10 | + |
| 132 | hsa-miR-1247-3p | 3.69.E−11 | + |
| 133 | hsa-miR-6805-5p | 1.78.E−09 | + |
| 134 | hsa-miR-4492 | 1.28.E−07 | + |
| 135 | hsa-miR-1469 | 8.04.E−06 | + |
| 136 | hsa-miR-1268b | 7.93.E−07 | + |
| 137 | hsa-miR-6858-5p | 2.19.E−06 | + |
| 138 | hsa-miR-3937 | 5.07.E−06 | + |
| 139 | hsa-miR-939-5p | 3.71.E−10 | + |
| 140 | hsa-miR-3656 | 9.45.E−10 | + |
| 141 | hsa-miR-744-5p | 6.81.E−08 | + |
| 142 | hsa-miR-4687-3p | 1.70.E−07 | + |
| 143 | hsa-miR-4763-3p | 1.79.E−06 | + |
| 144 | hsa-miR-3620-5p | 2.74.E−06 | + |
| 145 | hsa-miR-3195 | 1.35.E−04 | + |
| 146 | hsa-miR-6842-5p | 9.98.E−12 | + |
| 147 | hsa-miR-4707-5p | 7.25.E−06 | + |
| 148 | hsa-miR-642a-3p | 1.31.E−06 | + |
| 149 | hsa-miR-7113-3p | 2.95.E−07 | + |
| 150 | hsa-miR-4728-5p | 3.51.E−06 | − |
| 151 | hsa-miR-5195-3p | 9.06.E−07 | + |
| 152 | hsa-miR-1185--3p | 3.35.E−05 | + |
| 153 | hsa-miR-6774-5p | 5.14.E−04 | + |
| 154 | hsa-miR-8059 | 1.37.E−05 | − |
| 155 | hsa-miR-3131 | 6.97.E−08 | − |
| 156 | hsa-miR-7847-3p | 6.35.E−06 | − |
| 157 | hsa-miR-4463 | 1.04.E−07 | + |
| 158 | hsa-miR-128-2-5p | 3.84.E−06 | − |
| 159 | hsa-miR-4508 | 3.57.E−05 | + |
| 160 | hsa-miR-6806-5p | 2.04.E−06 | − |
| 161 | hsa-miR-7111-5p | 6.31.E−05 | + |
| 162 | hsa-miR-6782-5p | 2.11.E−07 | + |
| 163 | hsa-miR-4734 | 1.79.E−05 | + |
| 164 | hsa-miR-3162-5p | 7.73.E−04 | + |
| 165 | hsa-miR-887-3p | 7.67.E−05 | + |
| 166 | hsa-miR-6752-5p | 7.74.E−05 | + |
| 167 | hsa-miR-6724-5p | 4.17.E−05 | + |
| 168 | hsa-miR-23b-3p | 1.17.E−30 | − |
| 169 | hsa-miR-23a-3p | 5.61.E−28 | − |
| 170 | hsa-miR-625-3p | 1.19.E−16 | + |
| 171 | hsa-miR-1228-3p | 7.80.E−28 | + |
| 172 | hsa-miR-614 | 7.24.E−27 | + |
| 173 | hsa-miR-1913 | 1.52.E−26 | + |
| 174 | hsa-miR-92a-2-5p | 5.94.E−24 | + |
| 175 | hsa-miR-187-5p | 1.72.E−26 | − |
| 176 | hsa-miR-16-5p | 4.14.E−20 | − |
| 177 | hsa-miR-92b-3p | 1.09.E−17 | − |
| 178 | hsa-miR-150-3p | 1.47.E−13 | − |
| 179 | hsa-miR-564 | 2.36.E−15 | − |
| 180 | hsa-miR-125a-3p | 7.07.E−12 | − |
| 181 | hsa-miR-92b-5p | 8.01.E−10 | + |
| 182 | hsa-miR-92a-3p | 3.99.E−09 | − |
| 183 | hsa-miR-663a | 1.34.E−06 | + |
| 184 | hsa-miR-4688 | 4.97.E−07 | − |
| 185 | hsa-miR-4648 | 2.21.E−05 | + |
| 186 | hsa-miR-6085 | 2.31.E−05 | + |
| 187 | hsa-miR-6126 | 2.31.E−05 | + |
| 188 | hsa-miR-6880-5p | 2.44.E−05 | + |
| 189 | hsa-miR-328-5p | 2.90.E−05 | + |
| 190 | hsa-miR-6768-5p | 4.36.E−05 | + |
| 191 | hsa-miR-3180 | 6.14.E−05 | + |
| 192 | hsa-miR-6087 | 8.15.E−05 | − |
| 193 | hsa-miR-1273g-3p | 1.23.E−04 | − |
| 194 | hsa-miR-1225-5p | 1.23.E−04 | + |
| 195 | hsa-miR-3196 | 1.32.E−04 | + |
| 196 | hsa-miR-4695-5p | 1.47.E−04 | + |
| 197 | hsa-miR-6732-5p | 2.45.E−04 | + |

TABLE 7-continued

| SEQ ID NO: | Gene name | P value after Bonferroni correction | Expression level in liver cancer patient relative to healthy subject |
|---|---|---|---|
| 198 | hsa-miR-638 | 2.98.E−04 | − |
| 199 | hsa-miR-6813-5p | 3.27.E−04 | + |
| 200 | hsa-miR-665 | 3.46.E−04 | + |
| 201 | hsa-miR-486-3p | 4.04.E−04 | − |
| 202 | hsa-miR-4466 | 4.22.E−04 | − |
| 203 | hsa-miR-30c-1-3p | 5.71.E−04 | + |
| 204 | hsa-miR-3621 | 8.32.E−04 | − |
| 205 | hsa-miR-6743-5p | 8.89.E−04 | + |
| 206 | hsa-miR-4298 | 1.05.E−03 | − |
| 207 | hsa-miR-4741 | 1.07.E−03 | + |
| 208 | hsa-miR-3619-3p | 1.11.E−03 | + |
| 209 | hsa-miR-6824-5p | 1.17.E−03 | + |
| 210 | hsa-miR-5698 | 1.30.E−03 | − |
| 211 | hsa-miR-371a-5p | 1.51.E−03 | − |
| 212 | hsa-miR-4488 | 1.85.E−03 | − |
| 213 | hsa-miR-1233-5p | 1.90.E−03 | − |
| 214 | hsa-miR-4723-5p | 2.05.E−03 | + |
| 215 | hsa-miR-24-3p | 2.09.E−03 | − |
| 216 | hsa-miR-1238-5p | 2.18.E−03 | + |
| 217 | hsa-miR-4442 | 2.48.E−03 | − |
| 218 | hsa-miR-3928-3p | 2.71.E−03 | + |
| 219 | hsa-miR-6716-5p | 2.96.E−03 | + |
| 220 | hsa-miR-6089 | 3.43.E−03 | + |
| 221 | hsa-miR-6124 | 3.68.E−03 | + |
| 222 | hsa-miR-6778-5p | 4.10.E−03 | − |
| 223 | hsa-miR-557 | 6.88.E−03 | + |
| 224 | hsa-miR-6090 | 9.92.E−03 | + |

Example 4

<Method for Evaluating Liver Cancer-Specific Discriminant Performance by Combination of Multiple Gene Markers Using Samples in the Validation Cohort>

In this Example, novel additional gene markers for diagnosis were selected by comparing gene expression levels of miRNAs in sera of liver cancer patients with those of a control group consisting of healthy subjects, pancreatic cancer patients, bile duct cancer patients, stomach cancer patients, esophageal cancer patients, colorectal cancer patients, and benign pancreaticobiliary disease patients, in the same way as the method described in Example 1, and targeting the training cohort as the sample group described in Reference Example 2. One or two or more markers selected from the group consisting of the polynucleotides consisting of the nucleotide sequences represented by SEQ ID NOs: 714 to 729 thus selected and the gene markers selected in Example 1 were used to evaluate liver cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 4 expression level measurement values comprising at least one or more of the expression level measurement values of the polynucleotides consisting of the nucleotide sequences represented by SEQ ID NOs: 1 to 167 and 714 to 729, to construct a discriminant for determining the presence or absence of liver cancer. Next, accuracy, sensitivity, and specificity in the validation cohort were calculated using the discriminant thus prepared, with the liver cancer patient group as a positive sample group and, on the other hand, the healthy subject group, the pancreatic cancer patient group, the bile duct cancer patient group, the stomach cancer patient group, the esophageal cancer patient group, the colorectal cancer patient group, and the benign pancreaticobiliary disease patient group as negative sample groups. The discriminant performance of the selected polynucleotides was validated using independent samples.

Most of polynucleotides consisting of the nucleotide sequences represented by these SEQ ID NOs (SEQ ID NOs: 1 to 224 and 714 to 729 corresponding to the miRNA markers of Table 1) or complementary sequences thereof mentioned above were able to provide relatively high accuracy, sensitivity, and specificity in the determination of the presence or absence of liver cancer, and furthermore, were able to specifically discriminate liver cancer from other cancers. For example, among the combinations of a plurality of polynucleotides selected from the group consisting of polynucleotides consisting of the nucleotide sequences represented by SEQ ID NOs: 1, 2, 3, 5, 7, 9, 12, 17, 20, 22, 27, 28, 29, 38, 39, 44, 46, 48, 51, 54, 61, 76, 89, 93, 101, 109, 116, 123, 132, 134, 136, 148, 150, 151, 155, 157, 164, 166, 167, 172, 180, 186, 188, 189, 197, 198, 214, 216, 714, 715, 716, 717, 718, 719, 720, 721, 722, 723, 724, 725, 726, 727, 728 and 729 or complementary sequences thereof (the cancer type-specific polynucleotide group 1) as polynucleotides capable of specifically binding to target markers, combinations comprising at least one or more polynucleotide(s) selected from the group consisting of polynucleotides consisting of the nucleotide sequences represented by SEQ ID NOs: 1, 3, 7, 9, 22, 38, 44, 134, 148, 155, 157, 164, 167, 172, 214, 714, 715, 716, and 717 or complementary sequences thereof (the cancer type-specific polynucleotide group 2) were able to specifically discriminate liver cancer from other cancers with high accuracy.

The number of the polynucleotides with cancer type specificity in the combination mentioned above can be 1, 2, 3, 4, 5, 6, 7, 8, 9, 10 or more for the combination. The combinations of 4 or more polynucleotides were able to exhibit discriminant accuracy of 90% or higher.

Specifically, the discriminant accuracy of the measurement using the polynucleotide consisting of the nucleotide sequence represented by SEQ ID NO: 1 or a complementary sequence thereof is shown in Table 8-1. In Table 8-1, "SEQ ID NO" represents one polynucleotide or a combination of a plurality of polynucleotides used with the number of SEQ ID NO: (the same holds true for Tables 8-2 to 8-19). The measurement using, alone (one), the polynucleotide consisting of the nucleotide sequence represented by SEQ ID NO: 1 or a complementary sequence thereof exhibited accuracy of 71.2% in the training cohort and accuracy of 73.2% in the validation cohort. Also, for example, the measurement using the combinations of two polynucleotides comprising at least one polynucleotide consisting of the nucleotide sequence represented by SEQ ID NO: 1 or a complementary sequence thereof exhibited the highest accuracy of 88.1% in the training cohort and accuracy of 90% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited the highest accuracy of 90.2% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited the highest accuracy of 92.3% in the training cohort and accuracy of 93.2% in the validation cohort.

The discriminant accuracy of the measurement using the polynucleotide consisting of the nucleotide sequence represented by SEQ ID NO: 3 or a complementary sequence thereof is shown in Table 8-2. The measurement using, alone (one), the polynucleotide consisting of the nucleotide sequence represented by SEQ ID NO: 3 or a complementary sequence thereof exhibited accuracy of 78.7% in the training cohort and accuracy of 73.2% in the validation cohort. Also, for example, the measurement using the combinations of two polynucleotides comprising at least one polynucleotide consisting of the nucleotide sequence represented by SEQ ID NO: 3 or a complementary sequence thereof exhibited the highest accuracy of 88.7% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 3 or a complementary sequence thereof exhibited the highest accuracy of 91.8% in the training cohort and accuracy of 87.9% in the validation cohort. Furthermore, for example, the measurement using the combinations of four polynucleotides comprising at least one polynucleotide consisting of the nucleotide sequence represented by SEQ ID NO: 3 or a complementary sequence thereof exhibited the highest accuracy of 92.9% in the training cohort and accuracy of 93.2% in the validation cohort.

The discriminant accuracy of the measurement using the polynucleotide consisting of the nucleotide sequence represented by SEQ ID NO: 7 or a complementary sequence thereof is shown in Table 8-3. The measurement using, alone (one), the polynucleotide consisting of the nucleotide sequence represented by SEQ ID NO: 7 or a complementary sequence thereof exhibited accuracy of 85.5% in the training cohort and accuracy of 84.7% in the validation cohort. Also, for example, the measurement using the combinations of two polynucleotides comprising at least one polynucleotide consisting of the nucleotide sequence represented by SEQ ID NO: 7 or a complementary sequence thereof exhibited the highest accuracy of 91.5% in the training cohort and accuracy of 90.5% in the validation cohort. Furthermore, for example, the measurement using the combinations of three polynucleotides comprising at least one polynucleotide consisting of the nucleotide sequence represented by SEQ ID NO: 7 or a complementary sequence thereof exhibited the highest accuracy of 93.7% in the training cohort and accuracy of 92.1% in the validation cohort. Furthermore, for example, the measurement using the combinations of four polynucleotides comprising at least one polynucleotide consisting of the nucleotide sequence represented by SEQ ID NO: 7 or a complementary sequence thereof exhibited the highest accuracy of 94.4% in the training cohort and accuracy of 92.6% in the validation cohort.

The discriminant accuracy of the measurement using the polynucleotide consisting of the nucleotide sequence represented by SEQ ID NO: 9 or a complementary sequence thereof is shown in Table 8-4. The measurement using, alone (one), the polynucleotide consisting of the nucleotide sequence represented by SEQ ID NO: 9 or a complementary sequence thereof exhibited accuracy of 59.7% in the training cohort and accuracy of 59.5% in the validation cohort. Also, for example, the measurement using the combinations of two polynucleotides comprising at least one polynucleotide consisting of the nucleotide sequence represented by SEQ ID NO: 9 or a complementary sequence thereof exhibited the highest accuracy of 86% in the training cohort and accuracy of 81.1% in the validation cohort. Furthermore, for example, the measurement using the combinations of three polynucleotides comprising at least one polynucleotide consisting of the nucleotide sequence represented by SEQ ID NO: 9 or a complementary sequence thereof exhibited the highest accuracy of 91.8% in the training cohort and accuracy of 84.7% in the validation cohort. Furthermore, for example, the measurement using the combinations of four polynucleotides comprising at least one polynucleotide consisting of the nucleotide sequence represented by SEQ ID NO: 9 or a complementary sequence thereof exhibited the highest accuracy of 94.7% in the training cohort and accuracy of 92.1% in the validation cohort.

The discriminant accuracy of the measurement using the polynucleotide consisting of the nucleotide sequence represented by SEQ ID NO: 22 or a complementary sequence thereof is shown in Table 8-5. The measurement using, alone (one), the polynucleotide consisting of the nucleotide sequence represented by SEQ ID NO: 22 or a complementary sequence thereof exhibited accuracy of 76.5% in the training cohort and accuracy of 78.9% in the validation cohort. Also, for example, the measurement using the combinations of two polynucleotides comprising at least one polynucleotide consisting of the nucleotide sequence represented by SEQ ID NO: 22 or a complementary sequence thereof exhibited the highest accuracy of 85.8% in the training cohort and accuracy of 84.7% in the validation cohort. Furthermore, for example, the measurement using the combinations of three polynucleotides comprising at least one polynucleotide consisting of the nucleotide sequence represented by SEQ ID NO: 22 or a complementary sequence thereof exhibited the highest accuracy of 91.3% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 22 or a complementary sequence thereof exhibited the highest accuracy of 93.7% in the training cohort and accuracy of 93.7% in the validation cohort.

The discriminant accuracy of the measurement using the polynucleotide consisting of the nucleotide sequence represented by SEQ ID NO: 38 or a complementary sequence thereof is shown in Table 8-6. The measurement using, alone (one), the polynucleotide consisting of the nucleotide sequence represented by SEQ ID NO: 38 or a complementary sequence thereof exhibited accuracy of 65.5% in the training cohort and accuracy of 65.8% in the validation cohort. Also, for example, the measurement using the combinations of two polynucleotides comprising at least one polynucleotide consisting of the nucleotide sequence represented by SEQ ID NO: 38 or a complementary sequence thereof exhibited the highest accuracy of 86.3% in the training cohort and accuracy of 84.2% in the validation cohort. Furthermore, for example, the measurement using the combinations of three polynucleotides comprising at least one polynucleotide consisting of the nucleotide sequence represented by SEQ ID NO: 38 or a complementary sequence thereof exhibited the highest accuracy of 92.3% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 38 or a complementary sequence thereof exhibited the highest accuracy of 94.2% in the training cohort and accuracy of 92.1% in the validation cohort.

The discriminant accuracy of the measurement using the polynucleotide consisting of the nucleotide sequence represented by SEQ ID NO: 44 or a complementary sequence thereof is shown in Table 8-7. The measurement using, alone (one), the polynucleotide consisting of the nucleotide sequence represented by SEQ ID NO: 44 or a complementary sequence thereof exhibited accuracy of 62.6% in the training cohort and accuracy of 62.1% in the validation cohort. Also, for example, the measurement using the combinations of two polynucleotides comprising at least one polynucleotide consisting of the nucleotide sequence represented by SEQ ID NO: 44 or a complementary sequence thereof exhibited the highest accuracy of 90.5% in the training cohort and accuracy of 86.3% in the validation cohort. Furthermore, for example, the measurement using the combinations of three polynucleotides comprising at least one polynucleotide consisting of the nucleotide sequence represented by SEQ ID NO: 44 or a complementary sequence thereof exhibited the highest accuracy of 92.9% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 44 or a complementary sequence thereof exhibited the highest accuracy of 93.7% in the training cohort and accuracy of 91.6% in the validation cohort.

The discriminant accuracy of the measurement using the polynucleotide consisting of the nucleotide sequence represented by SEQ ID NO: 134 or a complementary sequence thereof is shown in Table 8-8. The measurement using, alone (one), the polynucleotide consisting of the nucleotide sequence represented by SEQ ID NO: 134 or a complementary sequence thereof exhibited accuracy of 53.4% in the training cohort and accuracy of 58.9% in the validation cohort. Also, for example, the measurement using the combinations of two polynucleotides comprising at least one polynucleotide consisting of the nucleotide sequence represented by SEQ ID NO: 134 or a complementary sequence thereof exhibited the highest accuracy of 87.3% in the training cohort and accuracy of 84.2% in the validation cohort. Furthermore, for example, the measurement using the combinations of three polynucleotides comprising at least one polynucleotide consisting of the nucleotide sequence represented by SEQ ID NO: 134 or a complementary sequence thereof exhibited the highest accuracy of 92.9% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 134 or a complementary sequence thereof exhibited the highest accuracy of 93.7% in the training cohort and accuracy of 92.1% in the validation cohort.

The discriminant accuracy of the measurement using the polynucleotide consisting of the nucleotide sequence represented by SEQ ID NO: 148 or a complementary sequence thereof is shown in Table 8-9. The measurement using, alone (one), the polynucleotide consisting of the nucleotide sequence represented by SEQ ID NO: 148 or a complementary sequence thereof exhibited accuracy of 73.6% in the training cohort and accuracy of 75.3% in the validation cohort. Also, for example, the measurement using the combinations of two polynucleotides comprising at least one polynucleotide consisting of the nucleotide sequence represented by SEQ ID NO: 148 or a complementary sequence thereof exhibited the highest accuracy of 86.3% in the training cohort and accuracy of 85.3% in the validation cohort. Furthermore, for example, the measurement using the combinations of three polynucleotides comprising at least one polynucleotide consisting of the nucleotide sequence represented by SEQ ID NO: 148 or a complementary sequence thereof exhibited the highest accuracy of 93.7% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 148 or a complementary sequence thereof exhibited the highest accuracy of 93.7% in the training cohort and accuracy of 92.1% in the validation cohort.

The discriminant accuracy of the measurement using the polynucleotide consisting of the nucleotide sequence represented by SEQ ID NO: 155 or a complementary sequence thereof is shown in Table 8-10. The measurement using, alone (one), the polynucleotide consisting of the nucleotide sequence represented by SEQ ID NO: 155 or a complementary sequence thereof exhibited accuracy of 60.8% in the training cohort and accuracy of 58.9% in the validation cohort. Also, for example, the measurement using the combinations of two polynucleotides comprising at least one polynucleotide consisting of the nucleotide sequence represented by SEQ ID NO: 155 or a complementary sequence thereof exhibited the highest accuracy of 86.5% in the training cohort and accuracy of 85.8% in the validation cohort. Furthermore, for example, the measurement using the combinations of three polynucleotides comprising at least one polynucleotide consisting of the nucleotide sequence represented by SEQ ID NO: 155 or a complementary sequence thereof exhibited the highest accuracy of 90.5% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 155 or a complementary sequence thereof exhibited the highest accuracy of 93.4% in the training cohort and accuracy of 91.6% in the validation cohort.

The discriminant accuracy of the measurement using the polynucleotide consisting of the nucleotide sequence represented by SEQ ID NO: 157 or a complementary sequence thereof is shown in Table 8-11. The measurement using, alone (one), the polynucleotide consisting of the nucleotide sequence represented by SEQ ID NO: 157 or a complementary sequence thereof exhibited accuracy of 70.3% in the training cohort and accuracy of 68.9% in the validation cohort. Also, for example, the measurement using the combinations of two polynucleotides comprising at least one polynucleotide consisting of the nucleotide sequence represented by SEQ ID NO: 157 or a complementary sequence thereof exhibited the highest accuracy of 86.5% in the training cohort and accuracy of 83.2% in the validation cohort. Furthermore, for example, the measurement using the combinations of three polynucleotides comprising at least one polynucleotide consisting of the nucleotide sequence represented by SEQ ID NO: 157 or a complementary sequence thereof exhibited the highest accuracy of 91% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 157 or a complementary sequence thereof exhibited the highest accuracy of 93.9% in the training cohort and accuracy of 92.6% in the validation cohort.

The discriminant accuracy of the measurement using the polynucleotide consisting of the nucleotide sequence represented by SEQ ID NO: 164 or a complementary sequence thereof is shown in Table 8-12. The measurement using, alone (one), the polynucleotide consisting of the nucleotide sequence represented by SEQ ID NO: 164 or a complementary sequence thereof exhibited accuracy of 72.4% in the training cohort and accuracy of 65.8% in the validation cohort. Also, for example, the measurement using the combinations of two polynucleotides comprising at least one polynucleotide consisting of the nucleotide sequence represented by SEQ ID NO: 164 or a complementary sequence thereof exhibited the highest accuracy of 87.6% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 164 or a complementary sequence thereof exhibited the highest accuracy of 91.5% in the training cohort and accuracy of 92.1% in the validation cohort. Furthermore, for example, the measurement using the combinations of four polynucleotides comprising at least one polynucleotide consisting of the nucleotide sequence represented by SEQ ID NO: 164 or a complementary sequence thereof exhibited the highest accuracy of 92.6% in the training cohort and accuracy of 90.5% in the validation cohort.

The discriminant accuracy of the measurement using the polynucleotide consisting of the nucleotide sequence represented by SEQ ID NO: 167 or a complementary sequence thereof is shown in Table 8-13. The measurement using, alone (one), the polynucleotide consisting of the nucleotide sequence represented by SEQ ID NO: 167 or a complementary sequence thereof exhibited accuracy of 62.1% in the training cohort and accuracy of 57.4% in the validation cohort. Also, for example, the measurement using the combinations of two polynucleotides comprising at least one polynucleotide consisting of the nucleotide sequence represented by SEQ ID NO: 167 or a complementary sequence thereof exhibited the highest accuracy of 89.2% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 167 or a complementary sequence thereof exhibited the highest accuracy of 92.1% in the training cohort and accuracy of 90% in the validation cohort. Furthermore, for example, the measurement using the combinations of four polynucleotides comprising at least one polynucleotide consisting of the nucleotide sequence represented by SEQ ID NO: 167 or a complementary sequence thereof exhibited the highest accuracy of 93.4% in the training cohort and accuracy of 91.1% in the validation cohort.

The discriminant accuracy of the measurement using the polynucleotide consisting of the nucleotide sequence represented by SEQ ID NO: 172 or a complementary sequence thereof is shown in Table 8-14. The measurement using, alone (one), the polynucleotide consisting of the nucleotide sequence represented by SEQ ID NO: 172 or a complementary sequence thereof exhibited accuracy of 76.8% in the training cohort and accuracy of 75.8% in the validation cohort. Also, for example, the measurement using the combinations of two polynucleotides comprising at least one polynucleotide consisting of the nucleotide sequence represented by SEQ ID NO: 172 or a complementary sequence thereof exhibited the highest accuracy of 86.3% in the training cohort and accuracy of 83.7% in the validation cohort. Furthermore, for example, the measurement using the combinations of three polynucleotides comprising at least one polynucleotide consisting of the nucleotide sequence represented by SEQ ID NO: 172 or a complementary sequence thereof exhibited the highest accuracy of 90.2% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 172 or a complementary sequence thereof exhibited the highest accuracy of 92.1% in the training cohort and accuracy of 93.2% in the validation cohort.

The discriminant accuracy of the measurement using the polynucleotide consisting of the nucleotide sequence represented by SEQ ID NO: 214 or a complementary sequence thereof is shown in Table 8-15. The measurement using, alone (one), the polynucleotide consisting of the nucleotide sequence represented by SEQ ID NO: 214 or a complementary sequence thereof exhibited accuracy of 69.5% in the training cohort and accuracy of 67.4% in the validation cohort. Also, for example, the measurement using the combinations of two polynucleotides comprising at least one polynucleotide consisting of the nucleotide sequence represented by SEQ ID NO: 214 or a complementary sequence thereof exhibited the highest accuracy of 89.2% in the training cohort and accuracy of 87.9% in the validation cohort. Furthermore, for example, the measurement using the combinations of three polynucleotides comprising at least one polynucleotide consisting of the nucleotide sequence represented by SEQ ID NO: 214 or a complementary sequence thereof exhibited the highest accuracy of 91.5% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 214 or a complementary sequence thereof exhibited the highest accuracy of 93.4% in the training cohort and accuracy of 92.6% in the validation cohort.

The discriminant accuracy of the measurement using the polynucleotide consisting of the nucleotide sequence represented by SEQ ID NO: 714 or a complementary sequence thereof is shown in Table 8-16. The measurement using, alone (one), the polynucleotide consisting of the nucleotide sequence represented by SEQ ID NO: 714 or a complementary sequence thereof exhibited accuracy of 44.7% in the training cohort and accuracy of 46.8% in the validation cohort. Also, for example, the measurement using the combinations of two polynucleotides comprising at least one polynucleotide consisting of the nucleotide sequence represented by SEQ ID NO: 714 or a complementary sequence thereof exhibited the highest accuracy of 90.2% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 714 or a complementary sequence thereof exhibited the highest accuracy of 92.1% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 714 or a complementary sequence thereof exhibited the highest accuracy of 94.4% in the training cohort and accuracy of 94.2% in the validation cohort.

The discriminant accuracy of the measurement using the polynucleotide consisting of the nucleotide sequence represented by SEQ ID NO: 715 or a complementary sequence thereof is shown in Table 8-17. The measurement using, alone (one), the polynucleotide consisting of the nucleotide sequence represented by SEQ ID NO: 715 or a complementary sequence thereof exhibited accuracy of 64.2% in the training cohort and accuracy of 65.8% in the validation cohort. Also, for example, the measurement using the combinations of two polynucleotides comprising at least one polynucleotide consisting of the nucleotide sequence represented by SEQ ID NO: 715 or a complementary sequence thereof exhibited the highest accuracy of 87.9% in the training cohort and accuracy of 86.8% in the validation cohort. Furthermore, for example, the measurement using the combinations of three polynucleotides comprising at least one polynucleotide consisting of the nucleotide sequence represented by SEQ ID NO: 715 or a complementary sequence thereof exhibited the highest accuracy of 91.8% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 715 or a complementary sequence thereof exhibited the highest accuracy of 93.9% in the training cohort and accuracy of 93.2% in the validation cohort.

The discriminant accuracy of the measurement using the polynucleotide consisting of the nucleotide sequence represented by SEQ ID NO: 716 or a complementary sequence thereof is shown in Table 8-18. The measurement using, alone (one), the polynucleotide consisting of the nucleotide sequence represented by SEQ ID NO: 716 or a complementary sequence thereof exhibited accuracy of 62.6% in the training cohort and accuracy of 58.9% in the validation cohort. Also, for example, the measurement using the combinations of two polynucleotides comprising at least one polynucleotide consisting of the nucleotide sequence represented by SEQ ID NO: 716 or a complementary sequence thereof exhibited the highest accuracy of 90.2% in the training cohort and accuracy of 86.3% in the validation cohort. Furthermore, for example, the measurement using the combinations of three polynucleotides comprising at least one polynucleotide consisting of the nucleotide sequence represented by SEQ ID NO: 716 or a complementary sequence thereof exhibited the highest accuracy of 91.3% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 716 or a complementary sequence thereof exhibited the highest accuracy of 93.7% in the training cohort and accuracy of 92.1% in the validation cohort.

The discriminant accuracy of the measurement using the polynucleotide consisting of the nucleotide sequence represented by SEQ ID NO: 717 or a complementary sequence thereof is shown in Table 8-19. The measurement using, alone (one), the polynucleotide consisting of the nucleotide sequence represented by SEQ ID NO: 717 or a complementary sequence thereof exhibited accuracy of 70.3% in the training cohort and accuracy of 66.3% in the validation cohort. Also, for example, the measurement using the combinations of two polynucleotides comprising at least one polynucleotide consisting of the nucleotide sequence represented by SEQ ID NO: 717 or a complementary sequence thereof exhibited the highest accuracy of 86.8% in the training cohort and accuracy of 84.7% in the validation cohort. Furthermore, for example, the measurement using the combinations of three polynucleotides comprising at least one polynucleotide consisting of the nucleotide sequence represented by SEQ ID NO: 717 or a complementary sequence thereof exhibited the highest accuracy of 92.3% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 717 or a complementary sequence thereof exhibited the highest accuracy of 93.1% in the training cohort and accuracy of 92.6% in the validation cohort.

Figure 4:
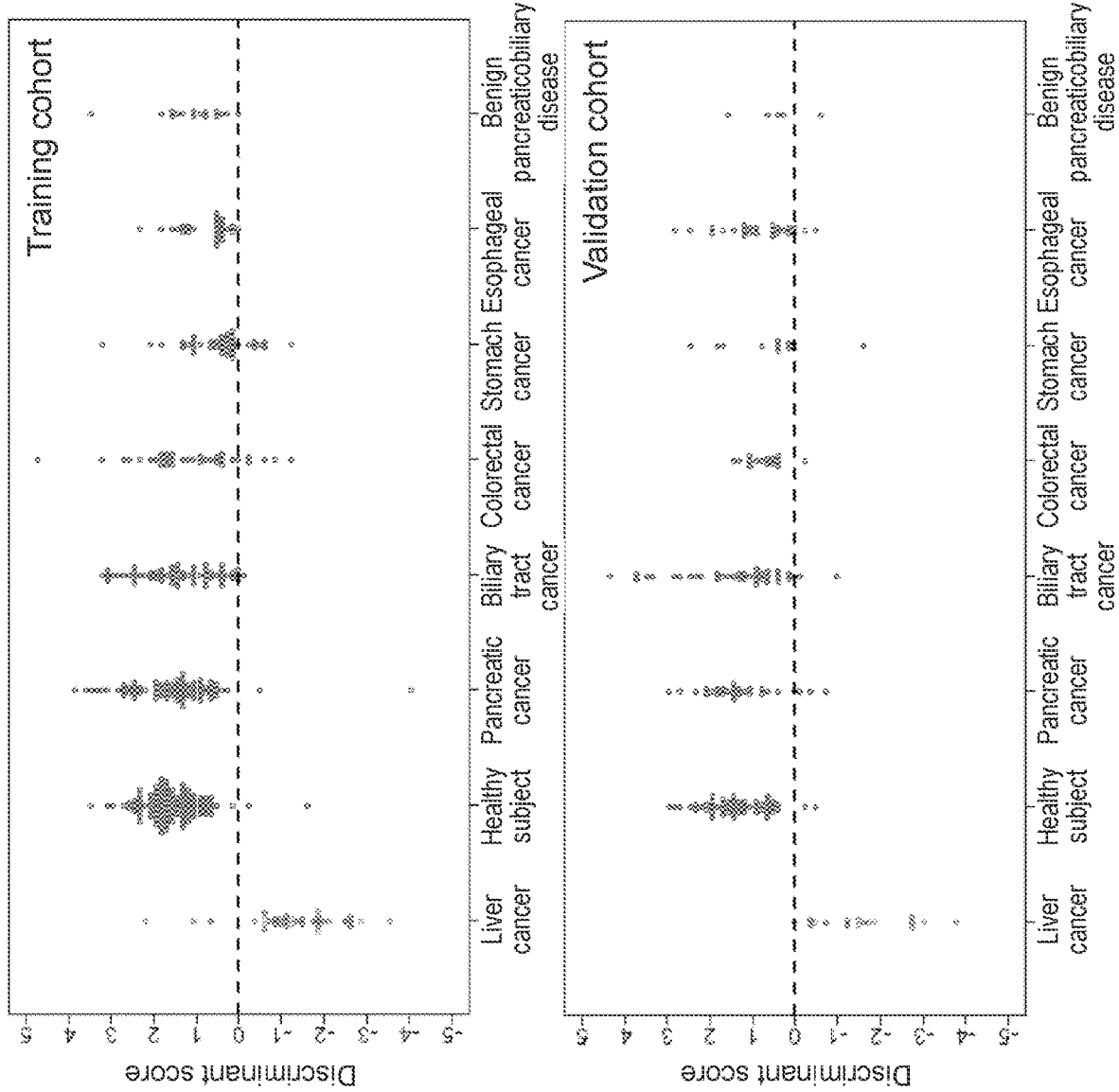
FIG. 4 Upper diagram: a discriminant (0.88×hsa-miR-6131−1.58×hsa-miR-642a-3p+0.39×hsa-miR-7641−0.33×hsa-miR-6729-5p+5.19) was prepared by use of Fisher's linear discriminant analysis from the measurement values of hsa-miR-6131 (SEQ ID NO: 7), hsa-miR-642a-3p (SEQ ID NO: 148), hsa-miR-7641 (SEQ ID NO: 9), and hsa-miR-6729-5p (SEQ ID NO: 27) in 35 liver cancer patients, 99 healthy subjects, 72 pancreatic cancer patients, 61 bile duct cancer patients, 35 colorectal cancer patients, 38 stomach cancer patients, 25 esophageal cancer patients, and 16 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared from the training cohorts as to the measurement values of hsa-miR-6131 (SEQ ID NO: 7), hsa-miR-642a-3p (SEQ ID NO: 148), hsa-miR-7641 (SEQ ID NO: 9), and hsa-miR-6729-5p (SEQ ID NO: 27) in 17 liver cancer patients, 51 healthy subjects, 28 pancreatic cancer patients, 37 bile duct cancer patients, 15 colorectal cancer patients, 12 stomach cancer patients, 25 esophageal cancer patients, and 5 benign pancreaticobiliary disease patients selected as a validation cohort were plotted on the ordinate against the sample groups on the abscissa. The dotted line in the diagram depicts the discriminant boundary that offered a discriminant score of 0 and discriminated between the two groups.

The expression level measurement values of the nucleotide sequences represented by SEQ ID NOs: 7, 9, 27, and 148 were compared among 35 liver cancer patients, 99 healthy subjects, 72 pancreatic cancer patients, 61 bile duct cancer patients, 38 stomach cancer patients, 25 esophageal cancer patients, 35 colorectal cancer patients, and 16 benign pancreaticobiliary disease patients in the training cohort. As a result, a scatter diagram that significantly separated the discriminant score of the liver cancer patient group from the discriminant scores of the other groups was obtained in the training cohort (see the upper diagram of FIG. 4). These results were also reproducible in the validation cohort (see the lower diagram of FIG. 4).

TABLE 8-1

| | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 1 | 71.2 | 94.3 | 68.9 | 73.2 | 100 | 70.5 |
| 1_155 | 88.1 | 91.4 | 87.8 | 90 | 88.2 | 90.2 |
| 1_7_155 | 90.2 | 88.6 | 90.4 | 90.5 | 88.2 | 90.8 |
| 1_7_9_148 | 92.3 | 91.4 | 92.4 | 93.2 | 100 | 92.5 |
| 1_9_155_172 | 91.3 | 94.3 | 91 | 91.6 | 94.1 | 91.3 |
| 1_9_148_155 | 90.2 | 91.4 | 90.1 | 90.5 | 100 | 89.6 |
| 1_155_172_715 | 91 | 91.4 | 91 | 93.2 | 100 | 92.5 |
| 1_155_164_715 | 90.8 | 94.3 | 90.4 | 93.7 | 100 | 93.1 |

TABLE 8-2

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 3 | 78.7 | 85.7 | 78 | 73.2 | 82.4 | 72.3 |
| 3_7 | 88.7 | 85.7 | 89 | 87.4 | 82.4 | 87.9 |
| 3_7_718 | 91.8 | 88.6 | 92.2 | 87.9 | 88.2 | 87.9 |
| 3_7_9_148 | 92.9 | 88.6 | 93.3 | 93.2 | 94.1 | 93.1 |
| 3_22_27_46 | 90.8 | 91.4 | 90.7 | 91.1 | 94.1 | 90.8 |
| 1_3_29_155 | 91 | 88.6 | 91.3 | 95.3 | 94.1 | 95.4 |
| 1_3_151_155 | 90.7 | 88.6 | 91 | 95.8 | 94.1 | 96 |
| 3_7_148_715 | 92.3 | 88.6 | 92.7 | 90 | 94.1 | 89.6 |

TABLE 8-3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 7 | 85.5 | 85.7 | 85.5 | 84.7 | 82.4 | 85 |
| 7_148 | 91.5 | 85.7 | 92.1 | 90.5 | 88.2 | 90.8 |
| 7_9_148 | 93.7 | 91.4 | 93.9 | 92.1 | 100 | 91.3 |
| 7_28_148_717 | 94.2 | 91.4 | 94.5 | 92.1 | 100 | 91.3 |
| 7_9_148_186 | 93.4 | 91.4 | 93.6 | 91.6 | 94.1 | 91.3 |
| 7_148_172_715 | 92.1 | 88.6 | 92.4 | 92.6 | 100 | 91.9 |
| 7_9_148_723 | 93.4 | 91.4 | 93.6 | 92.1 | 100 | 91.3 |
| 7_9_28_148 | 94.4 | 91.4 | 94.8 | 92.6 | 100 | 91.9 |

TABLE 8-4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 9 | 59.7 | 62.9 | 59.4 | 59.5 | 94.1 | 56.1 |
| 7_9 | 86 | 88.6 | 85.8 | 81.1 | 82.4 | 80.9 |
| 7_9_714 | 91.8 | 85.7 | 92.4 | 84.7 | 76.5 | 85.5 |
| 7_9_148_157 | 93.4 | 91.4 | 93.6 | 92.1 | 100 | 91.3 |
| 7_9_148_722 | 93.9 | 91.4 | 94.2 | 91.6 | 94.1 | 91.3 |
| 7_9_27_148 | 94.7 | 91.4 | 95 | 92.1 | 94.1 | 91.9 |
| 7_9_148_725 | 93.7 | 91.4 | 93.9 | 92.1 | 100 | 91.3 |
| 7_9_148_729 | 93.7 | 91.4 | 93.9 | 91.1 | 94.1 | 90.8 |

TABLE 8-5

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 22 | 76.5 | 77.1 | 76.5 | 78.9 | 76.5 | 79.2 |
| 3_22 | 85.8 | 88.6 | 85.5 | 84.7 | 88.2 | 84.4 |
| 7_22_148 | 91.3 | 88.6 | 91.5 | 91.6 | 88.2 | 91.9 |
| 7_9_22_148 | 93.7 | 91.4 | 93.9 | 93.7 | 100 | 93.1 |
| 7_22_28_148 | 93.7 | 91.4 | 93.9 | 92.6 | 94.1 | 92.5 |
| 7_22_148_189 | 91.8 | 85.7 | 92.4 | 92.1 | 88.2 | 92.5 |
| 2_7_22_148 | 92.1 | 91.4 | 92.1 | 92.6 | 100 | 91.9 |
| 7_22_148_720 | 92.3 | 82.9 | 93.3 | 93.2 | 88.2 | 93.6 |

TABLE 8-6

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 38 | 65.5 | 51.4 | 67 | 65.8 | 76.5 | 64.7 |
| 7_38 | 86.3 | 85.7 | 86.3 | 84.2 | 82.4 | 84.4 |
| 7_38_148 | 92.3 | 88.6 | 92.7 | 91.6 | 94.1 | 91.3 |
| 7_9_38_148 | 94.2 | 91.4 | 94.5 | 92.1 | 100 | 91.3 |
| 7_38_51_148 | 93.1 | 88.6 | 93.6 | 91.6 | 94.1 | 91.3 |
| 7_38_148_718 | 92.9 | 88.6 | 93.3 | 92.6 | 94.1 | 92.5 |
| 7_38_148_216 | 92.3 | 88.6 | 92.7 | 93.2 | 94.1 | 93.1 |
| 7_38_148_728 | 91.5 | 88.6 | 91.8 | 92.1 | 94.1 | 91.9 |

TABLE 8-7

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 44 | 62.6 | 62.9 | 62.6 | 62.1 | 94.1 | 59 |
| 7_44 | 90.5 | 85.7 | 91 | 86.3 | 88.2 | 86.1 |
| 7_44_148 | 92.9 | 91.4 | 93 | 91.1 | 100 | 90.2 |
| 7_9_44_148 | 93.7 | 91.4 | 93.9 | 91.6 | 100 | 90.8 |
| 7_44_123_148 | 93.4 | 91.4 | 93.6 | 91.1 | 100 | 90.2 |
| 7_38_44_148 | 92.9 | 91.4 | 93 | 91.1 | 100 | 90.2 |
| 7_44_148_723 | 93.1 | 91.4 | 93.3 | 91.1 | 100 | 90.2 |
| 7_44-48_148 | 93.7 | 91.4 | 93.9 | 92.1 | 100 | 91.3 |

TABLE 8-8

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 134 | 53.4 | 45.7 | 54.2 | 58.9 | 64.7 | 58.4 |
| 7_134 | 87.3 | 85.7 | 87.5 | 84.2 | 76.5 | 85 |
| 7_134_148 | 92.9 | 88.6 | 93.3 | 91.1 | 100 | 90.2 |
| 7_9_134_148 | 93.7 | 91.4 | 93.9 | 92.1 | 100 | 91.3 |
| 7_134_148_724 | 93.4 | 88.6 | 93.9 | 93.7 | 94.1 | 93.6 |
| 7_22_134_148 | 92.3 | 91.4 | 92.4 | 93.7 | 100 | 93.1 |
| 7_134_148_189 | 92.9 | 88.6 | 93.3 | 91.6 | 100 | 90.8 |
| 7_134_148_714 | 92.6 | 85.7 | 93.3 | 90 | 94.1 | 89.6 |

TABLE 8-9

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 148 | 73.6 | 85.7 | 72.4 | 75.3 | 82.4 | 74.6 |
| 48_148 | 86.3 | 88.6 | 86 | 85.3 | 88.2 | 85 |
| 7_28_148 | 93.7 | 85.7 | 94.5 | 91.6 | 94.1 | 91.3 |
| 7_9_148_726 | 93.7 | 91.4 | 93.9 | 92.1 | 100 | 91.3 |
| 7_9_148_151 | 93.6 | 91.4 | 93.9 | 93.7 | 94.1 | 93.6 |
| 7_9_109_148 | 93.7 | 91.4 | 93.9 | 92.1 | 100 | 91.3 |
| 5_7_9_148 | 92.9 | 91.4 | 93 | 93.2 | 100 | 92.5 |
| 7_9_76_148 | 93.4 | 91.4 | 93.6 | 91.6 | 100 | 90.8 |

TABLE 8-10

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 155 | 60.8 | 65.7 | 60.3 | 58.9 | 64.7 | 58.4 |
| 7_155 | 86.5 | 85.7 | 86.6 | 85.8 | 82.4 | 86.1 |
| 7_148_155 | 90.5 | 85.7 | 91 | 91.6 | 88.2 | 91.9 |
| 7_9_148_155 | 93.4 | 91.4 | 93.6 | 91.6 | 100 | 90.8 |
| 7_38_148_155 | 93.4 | 88.6 | 93.9 | 93.2 | 94.1 | 93.1 |
| 1_9_155_167 | 90 | 94.3 | 89.5 | 92.6 | 100 | 91.9 |
| 1_3_155_715 | 89.7 | 88.6 | 89.8 | 93.2 | 100 | 92.5 |
| 1_3_38_155 | 90 | 88.6 | 90.1 | 93.7 | 94.1 | 93.6 |

TABLE 8-11

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 157 | 70.3 | 71.4 | 70.1 | 68.9 | 94.1 | 66.5 |
| 7_157 | 86.5 | 85.7 | 86.6 | 83.2 | 82.4 | 83.2 |
| 7_148_157 | 91 | 88.6 | 91.3 | 91.6 | 94.1 | 91.3 |
| 7_48_157_714 | 93.9 | 88.6 | 94.5 | 92.6 | 94.1 | 92.5 |
| 7_38_148_157 | 92.3 | 88.6 | 92.7 | 92.6 | 94.1 | 92.5 |
| 1_44_155_157 | 89.4 | 94.3 | 89 | 90.5 | 100 | 89.6 |
| 7_76_157_714 | 92.9 | 82.9 | 93.9 | 90.5 | 94.1 | 90.2 |
| 7_148_157_189 | 91.8 | 88.6 | 92.1 | 92.1 | 94.1 | 91.9 |

TABLE 8-12

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 164 | 72.4 | 82.9 | 71.3 | 65.8 | 76.5 | 64.7 |
| 7_164 | 87.6 | 85.7 | 87.8 | 87.4 | 88.2 | 87.3 |
| 7_148_164 | 91.5 | 85.7 | 92.1 | 92.1 | 94.1 | 91.9 |
| 7_9_148_164 | 92.3 | 91.4 | 92.4 | 91.1 | 94.1 | 90.8 |
| 7_76_164_714 | 91.3 | 85.7 | 91.8 | 94.2 | 94.1 | 94.2 |
| 7_38_164_714 | 92.6 | 82.9 | 93.6 | 90.5 | 82.4 | 91.3 |
| 7_38_148_164 | 92.3 | 88.6 | 92.7 | 91.6 | 94.1 | 91.3 |
| 1_7_164_714 | 90.5 | 85.7 | 91 | 94.2 | 94.1 | 94.2 |

TABLE 8-13

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 167 | 62.1 | 68.6 | 61.4 | 57.4 | 70.6 | 56.1 |
| 7_167 | 89.2 | 85.7 | 89.5 | 87.4 | 82.4 | 87.9 |
| 7_148_167 | 92.1 | 85.7 | 92.7 | 90 | 88.2 | 90.2 |
| 7_9_148_167 | 93.1 | 91.4 | 93.3 | 92.6 | 100 | 91.9 |
| 1_7_167_714 | 92.6 | 85.7 | 93.3 | 94.7 | 100 | 94.2 |
| 7_151_167_714 | 92.9 | 85.7 | 93.6 | 92.1 | 88.2 | 92.5 |
| 7_148_167_189 | 92.9 | 85.7 | 93.6 | 92.6 | 88.2 | 93.1 |
| 7_28_167_714 | 93.4 | 85.7 | 94.2 | 91.1 | 88.2 | 91.3 |

TABLE 8-14

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 172 | 76.8 | 91.4 | 75.4 | 75.8 | 82.4 | 75.1 |
| 7_172 | 86.3 | 85.7 | 86.3 | 83.7 | 76.5 | 84.4 |
| 1_155_172 | 90.2 | 94.3 | 89.8 | 90.5 | 88.2 | 90.8 |
| 7_9_148_172 | 92.1 | 91.4 | 92.1 | 93.2 | 94.1 | 93.1 |
| 7_150_172_714 | 92.1 | 85.7 | 92.7 | 92.1 | 94.1 | 91.9 |
| 7_172_714_715 | 91.3 | 82.9 | 92.2 | 92.1 | 94.1 | 91.9 |
| 7_38_155_172 | 91.3 | 91.4 | 91.3 | 89.5 | 76.5 | 90.8 |
| 1_2_155_172 | 89.7 | 94.3 | 89.2 | 91.6 | 94.1 | 91.3 |

TABLE 8-15

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 214 | 69.5 | 77.1 | 68.7 | 67.4 | 64.7 | 67.6 |
| 7_214 | 89.2 | 85.7 | 89.5 | 87.9 | 82.4 | 88.4 |
| 7_148_214 | 91.5 | 85.7 | 92.1 | 90.5 | 88.2 | 90.8 |
| 7_9_148_214 | 93.4 | 91.4 | 93.6 | 92.6 | 100 | 91.9 |
| 7_148_189_214 | 92.6 | 85.7 | 93.3 | 92.1 | 88.2 | 92.5 |
| 2_7_148_214 | 92.1 | 91.4 | 92.1 | 93.7 | 100 | 93.1 |
| 1_7_214_714 | 91 | 88.6 | 91.3 | 94.7 | 94.1 | 94.8 |
| 7_39_148_214 | 92.1 | 88.6 | 92.4 | 90 | 88.2 | 90.2 |

TABLE 8-16

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 714 | 44.7 | 31.4 | 46.1 | 46.8 | 41.2 | 47.4 |
| 7_714 | 90.2 | 82.9 | 91 | 87.4 | 82.4 | 87.9 |
| 7_157_714 | 92.1 | 85.7 | 92.7 | 91.1 | 94.1 | 90.8 |
| 7_9_148_714 | 93.4 | 91.4 | 93.6 | 92.1 | 94.1 | 91.9 |
| 7_54_148_714 | 93.4 | 88.6 | 93.9 | 95.3 | 94.1 | 95.4 |
| 7_148_151_714 | 94.4 | 88.6 | 95 | 94.2 | 94.1 | 94.2 |
| 7_38_148_714 | 93.4 | 85.7 | 94.2 | 93.2 | 94.1 | 93.1 |
| 7_28_148_714 | 93.9 | 85.7 | 94.8 | 93.7 | 94.1 | 93.6 |

TABLE 8-17

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 715 | 64.2 | 71.4 | 63.5 | 65.8 | 76.5 | 64.7 |
| 7_715 | 87.9 | 85.7 | 88.1 | 86.8 | 94.1 | 86.1 |
| 7_148_715 | 91.8 | 88.6 | 92.1 | 91.1 | 100 | 90.2 |
| 2_7_148_715 | 93.1 | 91.4 | 93.3 | 91.6 | 100 | 90.8 |
| 7_9_148_715 | 93.9 | 91.4 | 94.2 | 93.2 | 100 | 92.5 |
| 7_17_148_715 | 93.7 | 91.4 | 93.9 | 91.1 | 100 | 90.2 |
| 7_38_148_715 | 92.6 | 88.6 | 93 | 91.1 | 100 | 90.2 |
| 7_148_715_725 | 92.3 | 88.6 | 92.7 | 91.6 | 100 | 90.8 |

TABLE 8-18

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 716 | 62.6 | 80 | 60.9 | 58.9 | 70.6 | 57.8 |
| 7_716 | 90.2 | 85.7 | 90.7 | 86.3 | 76.5 | 87.3 |
| 7_148_716 | 91.3 | 85.7 | 91.8 | 91.6 | 88.2 | 91.9 |
| 7_9_148_716 | 93.7 | 91.4 | 93.9 | 92.1 | 100 | 91.3 |
| 7_148_714_716 | 93.1 | 85.7 | 93.9 | 92.1 | 88.2 | 92.5 |
| 2_7_148_716 | 91.8 | 91.4 | 91.8 | 92.6 | 100 | 91.9 |
| 7_38_148_716 | 92.6 | 88.6 | 93 | 92.1 | 94.1 | 91.9 |
| 7_148_715_716 | 91.8 | 88.6 | 92.1 | 91.6 | 100 | 90.8 |

TABLE 8-19

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 717 | 70.3 | 85.7 | 68.7 | 66.3 | 82.4 | 64.7 |
| 7_717 | 86.8 | 85.7 | 86.9 | 84.7 | 82.4 | 85 |
| 7_148_717 | 92.3 | 85.7 | 93 | 90.5 | 88.2 | 90.8 |
| 7_9_148_717 | 93.1 | 91.4 | 93.3 | 92.6 | 100 | 91.9 |
| 7_38_148_717 | 92.3 | 88.6 | 92.7 | 91.6 | 94.1 | 91.3 |
| 7_27_148_717 | 93.1 | 85.7 | 93.9 | 91.6 | 88.2 | 91.9 |
| 7_44_148_717 | 93.1 | 91.4 | 93.3 | 92.1 | 100 | 91.3 |
| 7_148_715_717 | 92.6 | 88.6 | 93 | 91.1 | 100 | 90.2 |

Comparative Example 1

<Liver Cancer Discriminant Performance of Existing Tumor Marker in Blood>

The concentrations of the existing tumor markers AFP, CEA, CA19-9, and PIVKA-II for detecting liver cancer in blood were measured in the training cohort and the validation cohort obtained in Reference Example 1. When the concentrations of these tumor markers in blood are higher than the reference values described in Non-Patent Literature 5 (AFP: 10 ng/mL, CEA: 5 ng/mL, CA19-9: 37 U/mL, PIVKA-II: 40 mAU/mL), subjects are usually suspected of having cancer. Thus, whether or not the concentration of each tumor marker in blood exceeded its reference value was determined for each sample, and the results were assessed for the ability of these tumor markers to detect cancer in liver cancer patients. The sensitivity of each existing marker in the training cohort and the validation cohort was calculated. The results are shown in Table 5. The sensitivity of AFP, which had the highest sensitivity among the 4 existing tumor markers measured, was as low as 56.3% in the training cohort, and was as low as 53.3% in the validation cohort, demonstrating that neither of the markers are useful in the detection of liver cancer (Table 5).

On the other hand, as shown above in Tables 3 and 6 of Examples 1 and 2, it can be concluded that all of the polynucleotides consisting of the nucleotide sequences represented by SEQ ID NOs: 1 to 183 have combinations of 1 or 2 polynucleotides exhibiting sensitivity beyond the existing liver cancer markers and thus serve as excellent diagnosis markers.

As shown in these Examples and Comparative Example, the kit, etc., and the method of the present invention can detect liver cancer with higher sensitivity than the existing tumor markers and therefore permit early detection of liver cancer. As a result, surgical resection having high potentiality of radical cure can be applied, leading to drastic improvement in survival rate.

INDUSTRIAL APPLICABILITY

According to the present invention, liver cancer can be effectively detected by a simple and inexpensive method. This enables early detection, diagnosis and treatment of liver cancer. The method of the present invention can detect liver cancer with limited invasiveness using the blood of a patient and therefore allows liver cancer to be detected conveniently and rapidly.

All publications, patents, and patent applications cited herein are incorporated herein by reference in their entirety.

The invention claimed is:

1. A method for detecting liver cancer, comprising determining an expression level of hsa-miR-6724-5p in a sample of a subject using a kit comprising a nucleic acid(s), as a primer(s) for PCR, or as a probe(s) for Northern Blotting, Southern blotting, or in situ hybridization, capable of specifically binding to hsa-miR-6724-5p, wherein the determining comprises the following steps of:
  (a) contacting hsa-miR-6724-5p in the sample or complementary polynucleotide(s) thereof prepared from hsa-miR-6724-5p with the nucleic acid(s);
  (b) measuring an expression level of hsa-miR-6724-5p by quantitative RT-PCR using the nucleic acid(s) as the primer(s), or Northern blotting, Southern blotting, or in situ hybridization using the nucleic acids as the probe(s); and
  (c) comparing the expression level of hsa-miR-6724-5p measured in step (b) with a control expression level of hsa-miR-6724-5p in a control sample of a healthy subject measured in the same way as in step (b), wherein a higher expression level of hsa-miR-6724-5p in the sample of the subject as compared to the control expression level is detected and is indicative that the subject has liver cancer; and
  treating the subject for liver cancer or performing a diagnostic procedure on the liver of the subject, wherein the treatment comprises: surgical resection and/or liver transplantation; local therapy which involves injecting a drug through centesis or performing cauterization to kill cancer; or hepatic arterial embolization; optionally in combination with a drug therapy or radiotherapy, and wherein the diagnostic procedure comprises a palpation or imaging test;
  wherein the subject is human, and wherein the sample is blood, serum, or plasma.

2. A method for detecting liver cancer, comprising determining an expression level of hsa-miR-6724-5p in a sample of a subject using a device comprising a nucleic acid(s), as a probe(s), capable of specifically binding to hsa-miR-6724-5p, wherein the determining comprises the following steps of:
  (a) binding hsa-miR-6724-5p in the sample or cDNA thereof prepared from hsa-miR-6724-5p to the nucleic acid(s) to measure an expression level of hsa-miR-6724-5p by hybridization using the nucleic acid(s); and
  (b) comparing the expression level of hsa-miR-6724-5p measured in step (a) with a control expression level of hsa-miR-6724-5p in a control sample of a healthy subject measured in the same way as in step (a), wherein a higher expression level of hsa-miR-6724-5p in the sample of the subject as compared to the control expression level is detected and is indicative that the subject has liver cancer; and
  treating the subject for liver cancer or performing a diagnostic procedure on the liver of the subject, wherein the treatment comprises: surgical resection and/or liver transplantation; local therapy which involves injecting a drug through centesis or performing cauterization to kill cancer; or hepatic arterial embolization; optionally in combination with a drug therapy or radiotherapy, and wherein the diagnostic procedure comprises a palpation or imaging test;
  wherein the subject is human, and wherein the sample is blood, serum, or plasma.

3. The method according to claim 1, wherein step (c) further comprises preparing a discriminant based on a formula.

4. The method according to claim 3, wherein the discriminant is compared to a threshold.

5. The method according to claim 2, wherein step (b) further comprises preparing a discriminant based on a formula.

6. The method according to claim 5, wherein the discriminant is compared to a threshold.

* * * * *

SEQUENCE LISTING

```
Sequence total quantity: 765
SEQ ID NO: 1           moltype = RNA   length = 22
FEATURE                Location/Qualifiers
source                 1..22
                       mol_type = transcribed RNA
                       organism = Homo sapiens
SEQUENCE: 1
```

```
ctcctggggc cgcactctc gc                                              22

SEQ ID NO: 2           moltype = RNA   length = 21
FEATURE                Location/Qualifiers
source                 1..21
                       mol_type = transcribed RNA
                       organism = Homo sapiens
SEQUENCE: 2
cgggagctgg ggtctgcagg t                                              21

SEQ ID NO: 3           moltype = RNA   length = 20
FEATURE                Location/Qualifiers
source                 1..20
                       mol_type = transcribed RNA
                       organism = Homo sapiens
SEQUENCE: 3
tctcttcatc tacccccag                                                 20

SEQ ID NO: 4           moltype = RNA   length = 20
FEATURE                Location/Qualifiers
source                 1..20
                       mol_type = transcribed RNA
                       organism = Homo sapiens
SEQUENCE: 4
cggggtgggt gaggtcgggc                                                20

SEQ ID NO: 5           moltype = RNA   length = 18
FEATURE                Location/Qualifiers
source                 1..18
                       mol_type = transcribed RNA
                       organism = Homo sapiens
SEQUENCE: 5
ccagaggtgg ggactgag                                                  18

SEQ ID NO: 6           moltype = RNA   length = 23
FEATURE                Location/Qualifiers
source                 1..23
                       mol_type = transcribed RNA
                       organism = Homo sapiens
SEQUENCE: 6
agaggctttg tgcggatacg ggg                                            23

SEQ ID NO: 7           moltype = RNA   length = 19
FEATURE                Location/Qualifiers
source                 1..19
                       mol_type = transcribed RNA
                       organism = Homo sapiens
SEQUENCE: 7
ggctggtcag atgggagtg                                                 19

SEQ ID NO: 8           moltype = RNA   length = 22
FEATURE                Location/Qualifiers
source                 1..22
                       mol_type = transcribed RNA
                       organism = Homo sapiens
SEQUENCE: 8
tgattgtctt cccccaccct ca                                             22

SEQ ID NO: 9           moltype = RNA   length = 19
FEATURE                Location/Qualifiers
source                 1..19
                       mol_type = transcribed RNA
                       organism = Homo sapiens
SEQUENCE: 9
ttgatctcgg aagctaagc                                                 19

SEQ ID NO: 10          moltype = RNA   length = 22
FEATURE                Location/Qualifiers
source                 1..22
                       mol_type = transcribed RNA
                       organism = Homo sapiens
SEQUENCE: 10
acgcccttcc cccccttctt ca                                             22

SEQ ID NO: 11          moltype = RNA   length = 22
FEATURE                Location/Qualifiers
source                 1..22
                       mol_type = transcribed RNA
                       organism = Homo sapiens
```

```
SEQUENCE: 11
cttcccccca gtaatcttca tc                                                 22

SEQ ID NO: 12           moltype = RNA    length = 22
FEATURE                 Location/Qualifiers
source                  1..22
                        mol_type = transcribed RNA
                        organism = Homo sapiens
SEQUENCE: 12
tggcggggt agagctggct gc                                                  22

SEQ ID NO: 13           moltype = RNA    length = 20
FEATURE                 Location/Qualifiers
source                  1..20
                        mol_type = transcribed RNA
                        organism = Homo sapiens
SEQUENCE: 13
ggatccgagt cacggcacca                                                    20

SEQ ID NO: 14           moltype = RNA    length = 22
FEATURE                 Location/Qualifiers
source                  1..22
                        mol_type = transcribed RNA
                        organism = Homo sapiens
SEQUENCE: 14
ggctggagcg agtgcagtgg tg                                                 22

SEQ ID NO: 15           moltype = RNA    length = 21
FEATURE                 Location/Qualifiers
source                  1..21
                        mol_type = transcribed RNA
                        organism = Homo sapiens
SEQUENCE: 15
tcacctggct ggcccgccca g                                                  21

SEQ ID NO: 16           moltype = RNA    length = 18
FEATURE                 Location/Qualifiers
source                  1..18
                        mol_type = transcribed RNA
                        organism = Homo sapiens
SEQUENCE: 16
atcctagtca cggcacca                                                      18

SEQ ID NO: 17           moltype = RNA    length = 21
FEATURE                 Location/Qualifiers
source                  1..21
                        mol_type = transcribed RNA
                        organism = Homo sapiens
SEQUENCE: 17
gctgggaagg caaagggacg t                                                  21

SEQ ID NO: 18           moltype = RNA    length = 18
FEATURE                 Location/Qualifiers
source                  1..18
                        mol_type = transcribed RNA
                        organism = Homo sapiens
SEQUENCE: 18
ttcccagcca acgcacca                                                      18

SEQ ID NO: 19           moltype = RNA    length = 21
FEATURE                 Location/Qualifiers
source                  1..21
                        mol_type = transcribed RNA
                        organism = Homo sapiens
SEQUENCE: 19
tgggggtgtg gggagagaga g                                                  21

SEQ ID NO: 20           moltype = RNA    length = 22
FEATURE                 Location/Qualifiers
source                  1..22
                        mol_type = transcribed RNA
                        organism = Homo sapiens
SEQUENCE: 20
aggcgatgtg gggatgtaga ga                                                 22

SEQ ID NO: 21           moltype = RNA    length = 19
FEATURE                 Location/Qualifiers
source                  1..19
                        mol_type = transcribed RNA
```

```
                                     -continued organism = Homo sapiens
SEQUENCE: 21
tgggggagat ggggttga                                                    19

SEQ ID NO: 22           moltype = RNA  length = 22
FEATURE                 Location/Qualifiers
source                  1..22
                        mol_type = transcribed RNA
                        organism = Homo sapiens
SEQUENCE: 22
ggtggcccgg ccgtgcctga gg                                               22

SEQ ID NO: 23           moltype = RNA  length = 21
FEATURE                 Location/Qualifiers
source                  1..21
                        mol_type = transcribed RNA
                        organism = Homo sapiens
SEQUENCE: 23
tgagggaccc aggacaggag a                                                21

SEQ ID NO: 24           moltype = RNA  length = 20
FEATURE                 Location/Qualifiers
source                  1..20
                        mol_type = transcribed RNA
                        organism = Homo sapiens
SEQUENCE: 24
ggcggcgggg aggtaggcag                                                  20

SEQ ID NO: 25           moltype = RNA  length = 21
FEATURE                 Location/Qualifiers
source                  1..21
                        mol_type = transcribed RNA
                        organism = Homo sapiens
SEQUENCE: 25
tggggcgggg caggtccctg c                                                21

SEQ ID NO: 26           moltype = RNA  length = 18
FEATURE                 Location/Qualifiers
source                  1..18
                        mol_type = transcribed RNA
                        organism = Homo sapiens
SEQUENCE: 26
gggtcccggg gagggggg                                                    18

SEQ ID NO: 27           moltype = RNA  length = 22
FEATURE                 Location/Qualifiers
source                  1..22
                        mol_type = transcribed RNA
                        organism = Homo sapiens
SEQUENCE: 27
tgggcgaggg cggctgagcg gc                                               22

SEQ ID NO: 28           moltype = RNA  length = 23
FEATURE                 Location/Qualifiers
source                  1..23
                        mol_type = transcribed RNA
                        organism = Homo sapiens
SEQUENCE: 28
ggatggttgg gggcggtcgg cgt                                              23

SEQ ID NO: 29           moltype = RNA  length = 25
FEATURE                 Location/Qualifiers
source                  1..25
                        mol_type = transcribed RNA
                        organism = Homo sapiens
SEQUENCE: 29
agcggggagg aagtgggcgc tgctt                                            25

SEQ ID NO: 30           moltype = RNA  length = 21
FEATURE                 Location/Qualifiers
source                  1..21
                        mol_type = transcribed RNA
                        organism = Homo sapiens
SEQUENCE: 30
gtgtggccgg caggcgggtg g                                                21

SEQ ID NO: 31           moltype = RNA  length = 21
FEATURE                 Location/Qualifiers
source                  1..21
```

```
                        mol_type = transcribed RNA
                        organism = Homo sapiens
SEQUENCE: 31
caggagtggg gggtgggacg t                                             21

SEQ ID NO: 32           moltype = RNA  length = 21
FEATURE                 Location/Qualifiers
source                  1..21
                        mol_type = transcribed RNA
                        organism = Homo sapiens
SEQUENCE: 32
caggcaggtg tagggtggag c                                             21

SEQ ID NO: 33           moltype = RNA  length = 22
FEATURE                 Location/Qualifiers
source                  1..22
                        mol_type = transcribed RNA
                        organism = Homo sapiens
SEQUENCE: 33
ttggggattg ggtcaggcca gt                                            22

SEQ ID NO: 34           moltype = RNA  length = 17
FEATURE                 Location/Qualifiers
source                  1..17
                        mol_type = transcribed RNA
                        organism = Homo sapiens
SEQUENCE: 34
gtggggccag gcggtgg                                                  17

SEQ ID NO: 35           moltype = RNA  length = 22
FEATURE                 Location/Qualifiers
source                  1..22
                        mol_type = transcribed RNA
                        organism = Homo sapiens
SEQUENCE: 35
gtgggtgctg gtgggagccg tg                                            22

SEQ ID NO: 36           moltype = RNA  length = 22
FEATURE                 Location/Qualifiers
source                  1..22
                        mol_type = transcribed RNA
                        organism = Homo sapiens
SEQUENCE: 36
aaaccgttac cattactgag tt                                            22

SEQ ID NO: 37           moltype = RNA  length = 22
FEATURE                 Location/Qualifiers
source                  1..22
                        mol_type = transcribed RNA
                        organism = Homo sapiens
SEQUENCE: 37
tcaaaatcag gagtcggggc tt                                            22

SEQ ID NO: 38           moltype = RNA  length = 22
FEATURE                 Location/Qualifiers
source                  1..22
                        mol_type = transcribed RNA
                        organism = Homo sapiens
SEQUENCE: 38
caggcacggg agctcaggtg ag                                            22

SEQ ID NO: 39           moltype = RNA  length = 22
FEATURE                 Location/Qualifiers
source                  1..22
                        mol_type = transcribed RNA
                        organism = Homo sapiens
SEQUENCE: 39
gggggtcccc ggtgctcgga tc                                            22

SEQ ID NO: 40           moltype = RNA  length = 23
FEATURE                 Location/Qualifiers
source                  1..23
                        mol_type = transcribed RNA
                        organism = Homo sapiens
SEQUENCE: 40
cggggccgta gcactgtctg aga                                           23

SEQ ID NO: 41           moltype = RNA  length = 22
FEATURE                 Location/Qualifiers
```

```
source                      1..22
                            mol_type = transcribed RNA
                            organism = Homo sapiens
SEQUENCE: 41
tggggaggtg tggagtcagc at                                                    22

SEQ ID NO: 42               moltype = RNA   length = 19
FEATURE                     Location/Qualifiers
source                      1..19
                            mol_type = transcribed RNA
                            organism = Homo sapiens
SEQUENCE: 42
atcccaccac tgccaccat                                                        19

SEQ ID NO: 43               moltype = RNA   length = 21
FEATURE                     Location/Qualifiers
source                      1..21
                            mol_type = transcribed RNA
                            organism = Homo sapiens
SEQUENCE: 43
acaggagtgg gggtgggaca t                                                     21

SEQ ID NO: 44               moltype = RNA   length = 23
FEATURE                     Location/Qualifiers
source                      1..23
                            mol_type = transcribed RNA
                            organism = Homo sapiens
SEQUENCE: 44
ctggggacg cgtgagcgcg agc                                                    23

SEQ ID NO: 45               moltype = RNA   length = 21
FEATURE                     Location/Qualifiers
source                      1..21
                            mol_type = transcribed RNA
                            organism = Homo sapiens
SEQUENCE: 45
aagggacagg gagggtcgtg g                                                     21

SEQ ID NO: 46               moltype = RNA   length = 21
FEATURE                     Location/Qualifiers
source                      1..21
                            mol_type = transcribed RNA
                            organism = Homo sapiens
SEQUENCE: 46
cggcggggac ggcgattggt c                                                     21

SEQ ID NO: 47               moltype = RNA   length = 22
FEATURE                     Location/Qualifiers
source                      1..22
                            mol_type = transcribed RNA
                            organism = Homo sapiens
SEQUENCE: 47
gcccaggact ttgtgcgggg tg                                                    22

SEQ ID NO: 48               moltype = RNA   length = 25
FEATURE                     Location/Qualifiers
source                      1..25
                            mol_type = transcribed RNA
                            organism = Homo sapiens
SEQUENCE: 48
gtgaggcggg gccaggaggg tgtgt                                                 25

SEQ ID NO: 49               moltype = RNA   length = 21
FEATURE                     Location/Qualifiers
source                      1..21
                            mol_type = transcribed RNA
                            organism = Homo sapiens
SEQUENCE: 49
agggcccccc ctcaatcctg t                                                     21

SEQ ID NO: 50               moltype = RNA   length = 22
FEATURE                     Location/Qualifiers
source                      1..22
                            mol_type = transcribed RNA
                            organism = Homo sapiens
SEQUENCE: 50
catctctaag gaactccccc aa                                                    22

SEQ ID NO: 51               moltype = RNA   length = 21
```

```
FEATURE                 Location/Qualifiers
source                  1..21
                        mol_type = transcribed RNA
                        organism = Homo sapiens
SEQUENCE: 51
cgggccggag gtcaagggcg t                                              21

SEQ ID NO: 52           moltype = RNA   length = 23
FEATURE                 Location/Qualifiers
source                  1..23
                        mol_type = transcribed RNA
                        organism = Homo sapiens
SEQUENCE: 52
tgaggggcag agagcgagac ttt                                            23

SEQ ID NO: 53           moltype = RNA   length = 23
FEATURE                 Location/Qualifiers
source                  1..23
                        mol_type = transcribed RNA
                        organism = Homo sapiens
SEQUENCE: 53
tgagcaccac acaggccggg cgc                                            23

SEQ ID NO: 54           moltype = RNA   length = 20
FEATURE                 Location/Qualifiers
source                  1..20
                        mol_type = transcribed RNA
                        organism = Homo sapiens
SEQUENCE: 54
gccgggqctt tgggtgaggg                                                20

SEQ ID NO: 55           moltype = RNA   length = 22
FEATURE                 Location/Qualifiers
source                  1..22
                        mol_type = transcribed RNA
                        organism = Homo sapiens
SEQUENCE: 55
tcgggcctgg ggttggggga gc                                             22

SEQ ID NO: 56           moltype = RNA   length = 20
FEATURE                 Location/Qualifiers
source                  1..20
                        mol_type = transcribed RNA
                        organism = Homo sapiens
SEQUENCE: 56
gtgtctgggc ggacagctgc                                                20

SEQ ID NO: 57           moltype = RNA   length = 21
FEATURE                 Location/Qualifiers
source                  1..21
                        mol_type = transcribed RNA
                        organism = Homo sapiens
SEQUENCE: 57
agcggtgctc ctgcgggccg a                                              21

SEQ ID NO: 58           moltype = RNA   length = 23
FEATURE                 Location/Qualifiers
source                  1..23
                        mol_type = transcribed RNA
                        organism = Homo sapiens
SEQUENCE: 58
tggggaaggc ttgcaggga aga                                             23

SEQ ID NO: 59           moltype = RNA   length = 23
FEATURE                 Location/Qualifiers
source                  1..23
                        mol_type = transcribed RNA
                        organism = Homo sapiens
SEQUENCE: 59
gtgagtggga gccggtgggg ctg                                            23

SEQ ID NO: 60           moltype = RNA   length = 23
FEATURE                 Location/Qualifiers
source                  1..23
                        mol_type = transcribed RNA
                        organism = Homo sapiens
SEQUENCE: 60
tgaggatatg gcagggaagg gga                                            23
```

-continued

```
SEQ ID NO: 61              moltype = RNA  length = 24
FEATURE                    Location/Qualifiers
source                     1..24
                           mol_type = transcribed RNA
                           organism = Homo sapiens
SEQUENCE: 61
tgagggcct cagaccgagc tttt                                          24

SEQ ID NO: 62              moltype = RNA  length = 20
FEATURE                    Location/Qualifiers
source                     1..20
                           mol_type = transcribed RNA
                           organism = Homo sapiens
SEQUENCE: 62
gcggaaggcg gagcggcgga                                              20

SEQ ID NO: 63              moltype = RNA  length = 23
FEATURE                    Location/Qualifiers
source                     1..23
                           mol_type = transcribed RNA
                           organism = Homo sapiens
SEQUENCE: 63
tgggcagggg cttattgtag gag                                          23

SEQ ID NO: 64              moltype = RNA  length = 22
FEATURE                    Location/Qualifiers
source                     1..22
                           mol_type = transcribed RNA
                           organism = Homo sapiens
SEQUENCE: 64
cccctggggc tgggcaggcg ga                                           22

SEQ ID NO: 65              moltype = RNA  length = 23
FEATURE                    Location/Qualifiers
source                     1..23
                           mol_type = transcribed RNA
                           organism = Homo sapiens
SEQUENCE: 65
agaagaaggc ggtcggtctg cgg                                          23

SEQ ID NO: 66              moltype = RNA  length = 18
FEATURE                    Location/Qualifiers
source                     1..18
                           mol_type = transcribed RNA
                           organism = Homo sapiens
SEQUENCE: 66
atcccacctc tgccacca                                                18

SEQ ID NO: 67              moltype = RNA  length = 23
FEATURE                    Location/Qualifiers
source                     1..23
                           mol_type = transcribed RNA
                           organism = Homo sapiens
SEQUENCE: 67
ggaggcgcag gctcggaaag gcg                                          23

SEQ ID NO: 68              moltype = RNA  length = 19
FEATURE                    Location/Qualifiers
source                     1..19
                           mol_type = transcribed RNA
                           organism = Homo sapiens
SEQUENCE: 68
cggggccaga gcagagagc                                               19

SEQ ID NO: 69              moltype = RNA  length = 23
FEATURE                    Location/Qualifiers
source                     1..23
                           mol_type = transcribed RNA
                           organism = Homo sapiens
SEQUENCE: 69
tgggggaca gatggagagg aca                                           23

SEQ ID NO: 70              moltype = RNA  length = 23
FEATURE                    Location/Qualifiers
source                     1..23
                           mol_type = transcribed RNA
                           organism = Homo sapiens
SEQUENCE: 70
cgaggggtag aagagcacag ggg                                          23
```

```
SEQ ID NO: 71              moltype = RNA   length = 21
FEATURE                    Location/Qualifiers
source                     1..21
                           mol_type = transcribed RNA
                           organism = Homo sapiens
SEQUENCE: 71
cccatgcctc ctgccgcggt c                                                   21

SEQ ID NO: 72              moltype = RNA   length = 17
FEATURE                    Location/Qualifiers
source                     1..17
                           mol_type = transcribed RNA
                           organism = Homo sapiens
SEQUENCE: 72
ctccgggacg gctgggc                                                        17

SEQ ID NO: 73              moltype = RNA   length = 24
FEATURE                    Location/Qualifiers
source                     1..24
                           mol_type = transcribed RNA
                           organism = Homo sapiens
SEQUENCE: 73
gtgggtaggg tttgggggag agcg                                                24

SEQ ID NO: 74              moltype = RNA   length = 19
FEATURE                    Location/Qualifiers
source                     1..19
                           mol_type = transcribed RNA
                           organism = Homo sapiens
SEQUENCE: 74
tgcggcagag ctgggtca                                                       19

SEQ ID NO: 75              moltype = RNA   length = 23
FEATURE                    Location/Qualifiers
source                     1..23
                           mol_type = transcribed RNA
                           organism = Homo sapiens
SEQUENCE: 75
acggggagtc aggcagtggt gga                                                 23

SEQ ID NO: 76              moltype = RNA   length = 20
FEATURE                    Location/Qualifiers
source                     1..20
                           mol_type = transcribed RNA
                           organism = Homo sapiens
SEQUENCE: 76
gctcggactg agcaggtggg                                                     20

SEQ ID NO: 77              moltype = RNA   length = 20
FEATURE                    Location/Qualifiers
source                     1..20
                           mol_type = transcribed RNA
                           organism = Homo sapiens
SEQUENCE: 77
gggctggggc gcgggaggt                                                      20

SEQ ID NO: 78              moltype = RNA   length = 17
FEATURE                    Location/Qualifiers
source                     1..17
                           mol_type = transcribed RNA
                           organism = Homo sapiens
SEQUENCE: 78
accccactcc tggtacc                                                        17

SEQ ID NO: 79              moltype = RNA   length = 22
FEATURE                    Location/Qualifiers
source                     1..22
                           mol_type = transcribed RNA
                           organism = Homo sapiens
SEQUENCE: 79
agggccgaag ggtggaagct gc                                                  22

SEQ ID NO: 80              moltype = RNA   length = 22
FEATURE                    Location/Qualifiers
source                     1..22
                           mol_type = transcribed RNA
                           organism = Homo sapiens
SEQUENCE: 80
```

```
tgagcccctg tgccgccccc ag                                                22

SEQ ID NO: 81           moltype = RNA   length = 20
FEATURE                 Location/Qualifiers
source                  1..20
                        mol_type = transcribed RNA
                        organism = Homo sapiens
SEQUENCE: 81
agagatgaag cggggggggcg                                                  20

SEQ ID NO: 82           moltype = RNA   length = 21
FEATURE                 Location/Qualifiers
source                  1..21
                        mol_type = transcribed RNA
                        organism = Homo sapiens
SEQUENCE: 82
gtaggtgaca gtcaggggcg g                                                 21

SEQ ID NO: 83           moltype = RNA   length = 19
FEATURE                 Location/Qualifiers
source                  1..19
                        mol_type = transcribed RNA
                        organism = Homo sapiens
SEQUENCE: 83
aatggatttt tggagcagg                                                    19

SEQ ID NO: 84           moltype = RNA   length = 22
FEATURE                 Location/Qualifiers
source                  1..22
                        mol_type = transcribed RNA
                        organism = Homo sapiens
SEQUENCE: 84
tgcggcggt agttatgggc tt                                                 22

SEQ ID NO: 85           moltype = RNA   length = 18
FEATURE                 Location/Qualifiers
source                  1..18
                        mol_type = transcribed RNA
                        organism = Homo sapiens
SEQUENCE: 85
gaggctgaag gaagatgg                                                     18

SEQ ID NO: 86           moltype = RNA   length = 22
FEATURE                 Location/Qualifiers
source                  1..22
                        mol_type = transcribed RNA
                        organism = Homo sapiens
SEQUENCE: 86
ggaggggtcc cgcactggga gg                                                22

SEQ ID NO: 87           moltype = RNA   length = 23
FEATURE                 Location/Qualifiers
source                  1..23
                        mol_type = transcribed RNA
                        organism = Homo sapiens
SEQUENCE: 87
gagggcagcg tgggtgtggc gga                                               23

SEQ ID NO: 88           moltype = RNA   length = 22
FEATURE                 Location/Qualifiers
source                  1..22
                        mol_type = transcribed RNA
                        organism = Homo sapiens
SEQUENCE: 88
accttgcctt gctgcccggg cc                                                22

SEQ ID NO: 89           moltype = RNA   length = 20
FEATURE                 Location/Qualifiers
source                  1..20
                        mol_type = transcribed RNA
                        organism = Homo sapiens
SEQUENCE: 89
gtgggttggg gcgggctctg                                                   20

SEQ ID NO: 90           moltype = RNA   length = 22
FEATURE                 Location/Qualifiers
source                  1..22
                        mol_type = transcribed RNA
                        organism = Homo sapiens
```

```
SEQUENCE: 90
atatacaggg ggagactctc at                                            22

SEQ ID NO: 91            moltype = RNA   length = 22
FEATURE                  Location/Qualifiers
source                   1..22
                         mol_type = transcribed RNA
                         organism = Homo sapiens
SEQUENCE: 91
ccgggagaag gaggtggcct gg                                            22

SEQ ID NO: 92            moltype = RNA   length = 24
FEATURE                  Location/Qualifiers
source                   1..24
                         mol_type = transcribed RNA
                         organism = Homo sapiens
SEQUENCE: 92
agggctggac tcagcggcgg agct                                          24

SEQ ID NO: 93            moltype = RNA   length = 21
FEATURE                  Location/Qualifiers
source                   1..21
                         mol_type = transcribed RNA
                         organism = Homo sapiens
SEQUENCE: 93
gtgggcgggg gcaggtgtgt g                                             21

SEQ ID NO: 94            moltype = RNA   length = 21
FEATURE                  Location/Qualifiers
source                   1..21
                         mol_type = transcribed RNA
                         organism = Homo sapiens
SEQUENCE: 94
gttggggtgc agggtctgc t                                              21

SEQ ID NO: 95            moltype = RNA   length = 19
FEATURE                  Location/Qualifiers
source                   1..19
                         mol_type = transcribed RNA
                         organism = Homo sapiens
SEQUENCE: 95
ggcttgcatg ggggactgg                                                19

SEQ ID NO: 96            moltype = RNA   length = 21
FEATURE                  Location/Qualifiers
source                   1..21
                         mol_type = transcribed RNA
                         organism = Homo sapiens
SEQUENCE: 96
actcggctgc ggtggacaag t                                             21

SEQ ID NO: 97            moltype = RNA   length = 20
FEATURE                  Location/Qualifiers
source                   1..20
                         mol_type = transcribed RNA
                         organism = Homo sapiens
SEQUENCE: 97
ggggaggtgt gcagggctgg                                               20

SEQ ID NO: 98            moltype = RNA   length = 22
FEATURE                  Location/Qualifiers
source                   1..22
                         mol_type = transcribed RNA
                         organism = Homo sapiens
SEQUENCE: 98
actgggtagg tggggctcca gg                                            22

SEQ ID NO: 99            moltype = RNA   length = 23
FEATURE                  Location/Qualifiers
source                   1..23
                         mol_type = transcribed RNA
                         organism = Homo sapiens
SEQUENCE: 99
ctcggggcag gcggctggga gcg                                           23

SEQ ID NO: 100           moltype = RNA   length = 22
FEATURE                  Location/Qualifiers
source                   1..22
                         mol_type = transcribed RNA
```

```
                          organism = Homo sapiens
SEQUENCE: 100
agactgacgg ctggaggccc at                                           22

SEQ ID NO: 101            moltype = RNA   length = 23
FEATURE                   Location/Qualifiers
source                    1..23
                          mol_type = transcribed RNA
                          organism = Homo sapiens
SEQUENCE: 101
ttgctctgct ccccgcccc cag                                           23

SEQ ID NO: 102            moltype = RNA   length = 22
FEATURE                   Location/Qualifiers
source                    1..22
                          mol_type = transcribed RNA
                          organism = Homo sapiens
SEQUENCE: 102
caggcaggga ggtgggacca tg                                           22

SEQ ID NO: 103            moltype = RNA   length = 22
FEATURE                   Location/Qualifiers
source                    1..22
                          mol_type = transcribed RNA
                          organism = Homo sapiens
SEQUENCE: 103
cgtcccgggg ctgcgcgagg ca                                           22

SEQ ID NO: 104            moltype = RNA   length = 20
FEATURE                   Location/Qualifiers
source                    1..20
                          mol_type = transcribed RNA
                          organism = Homo sapiens
SEQUENCE: 104
cctgagcccg ggccgcgcag                                              20

SEQ ID NO: 105            moltype = RNA   length = 17
FEATURE                   Location/Qualifiers
source                    1..17
                          mol_type = transcribed RNA
                          organism = Homo sapiens
SEQUENCE: 105
gtgggggaga ggctgtc                                                 17

SEQ ID NO: 106            moltype = RNA   length = 18
FEATURE                   Location/Qualifiers
source                    1..18
                          mol_type = transcribed RNA
                          organism = Homo sapiens
SEQUENCE: 106
cggtgagcgc tcgctggc                                                18

SEQ ID NO: 107            moltype = RNA   length = 17
FEATURE                   Location/Qualifiers
source                    1..17
                          mol_type = transcribed RNA
                          organism = Homo sapiens
SEQUENCE: 107
ttggaggcgt gggtttt                                                 17

SEQ ID NO: 108            moltype = RNA   length = 19
FEATURE                   Location/Qualifiers
source                    1..19
                          mol_type = transcribed RNA
                          organism = Homo sapiens
SEQUENCE: 108
taaggagggg gatgagggg                                               19

SEQ ID NO: 109            moltype = RNA   length = 23
FEATURE                   Location/Qualifiers
source                    1..23
                          mol_type = transcribed RNA
                          organism = Homo sapiens
SEQUENCE: 109
tcaataggaa agaggtggga cct                                          23

SEQ ID NO: 110            moltype = RNA   length = 22
FEATURE                   Location/Qualifiers
source                    1..22
```

```
                              mol_type = transcribed RNA
                              organism = Homo sapiens
SEQUENCE: 110
gtgagccagt ggaatggaga gg                                            22

SEQ ID NO: 111        moltype = RNA   length = 18
FEATURE               Location/Qualifiers
source                1..18
                      mol_type = transcribed RNA
                      organism = Homo sapiens
SEQUENCE: 111
ctggcagggg gagaggta                                                 18

SEQ ID NO: 112        moltype = RNA   length = 17
FEATURE               Location/Qualifiers
source                1..17
                      mol_type = transcribed RNA
                      organism = Homo sapiens
SEQUENCE: 112
ggatggagga ggggtct                                                  17

SEQ ID NO: 113        moltype = RNA   length = 22
FEATURE               Location/Qualifiers
source                1..22
                      mol_type = transcribed RNA
                      organism = Homo sapiens
SEQUENCE: 113
caggaaggat ttagggacag gc                                            22

SEQ ID NO: 114        moltype = RNA   length = 24
FEATURE               Location/Qualifiers
source                1..24
                      mol_type = transcribed RNA
                      organism = Homo sapiens
SEQUENCE: 114
tgggcgaggg gtgggctctc agag                                          24

SEQ ID NO: 115        moltype = RNA   length = 21
FEATURE               Location/Qualifiers
source                1..21
                      mol_type = transcribed RNA
                      organism = Homo sapiens
SEQUENCE: 115
gggggatgt gcatgctggt t                                              21

SEQ ID NO: 116        moltype = RNA   length = 20
FEATURE               Location/Qualifiers
source                1..20
                      mol_type = transcribed RNA
                      organism = Homo sapiens
SEQUENCE: 116
ccccagggcg acgcggcggg                                               20

SEQ ID NO: 117        moltype = RNA   length = 17
FEATURE               Location/Qualifiers
source                1..17
                      mol_type = transcribed RNA
                      organism = Homo sapiens
SEQUENCE: 117
gggagaaggg tcggggc                                                  17

SEQ ID NO: 118        moltype = RNA   length = 18
FEATURE               Location/Qualifiers
source                1..18
                      mol_type = transcribed RNA
                      organism = Homo sapiens
SEQUENCE: 118
ggtgggcttc ccggaggg                                                 18

SEQ ID NO: 119        moltype = RNA   length = 22
FEATURE               Location/Qualifiers
source                1..22
                      mol_type = transcribed RNA
                      organism = Homo sapiens
SEQUENCE: 119
agacacattt ggagagggac cc                                            22

SEQ ID NO: 120        moltype = RNA   length = 19
FEATURE               Location/Qualifiers
```

```
source                  1..19
                        mol_type = transcribed RNA
                        organism = Homo sapiens
SEQUENCE: 120
gagggcgggt ggaggagga                                                 19

SEQ ID NO: 121          moltype = RNA   length = 22
FEATURE                 Location/Qualifiers
source                  1..22
                        mol_type = transcribed RNA
                        organism = Homo sapiens
SEQUENCE: 121
ttcagatccc agcggtgcct ct                                             22

SEQ ID NO: 122          moltype = RNA   length = 23
FEATURE                 Location/Qualifiers
source                  1..23
                        mol_type = transcribed RNA
                        organism = Homo sapiens
SEQUENCE: 122
tgggggctgg gatgggccat ggt                                            23

SEQ ID NO: 123          moltype = RNA   length = 25
FEATURE                 Location/Qualifiers
source                  1..25
                        mol_type = transcribed RNA
                        organism = Homo sapiens
SEQUENCE: 123
aagggaggag gagcggaggg gccct                                          25

SEQ ID NO: 124          moltype = RNA   length = 22
FEATURE                 Location/Qualifiers
source                  1..22
                        mol_type = transcribed RNA
                        organism = Homo sapiens
SEQUENCE: 124
ccaggaggcg gaggaggtgg ag                                             22

SEQ ID NO: 125          moltype = RNA   length = 21
FEATURE                 Location/Qualifiers
source                  1..21
                        mol_type = transcribed RNA
                        organism = Homo sapiens
SEQUENCE: 125
cgggggcggg gccgaagcgc g                                              21

SEQ ID NO: 126          moltype = RNA   length = 22
FEATURE                 Location/Qualifiers
source                  1..22
                        mol_type = transcribed RNA
                        organism = Homo sapiens
SEQUENCE: 126
gagggttggg tggaggctct cc                                             22

SEQ ID NO: 127          moltype = RNA   length = 26
FEATURE                 Location/Qualifiers
source                  1..26
                        mol_type = transcribed RNA
                        organism = Homo sapiens
SEQUENCE: 127
ctcggccgcg gcgcgtagcc cccgcc                                         26

SEQ ID NO: 128          moltype = RNA   length = 21
FEATURE                 Location/Qualifiers
source                  1..21
                        mol_type = transcribed RNA
                        organism = Homo sapiens
SEQUENCE: 128
gcggtggggc cggaggggcg t                                              21

SEQ ID NO: 129          moltype = RNA   length = 17
FEATURE                 Location/Qualifiers
source                  1..17
                        mol_type = transcribed RNA
                        organism = Homo sapiens
SEQUENCE: 129
ccccgccacc gccttgg                                                   17

SEQ ID NO: 130          moltype = RNA   length = 22
```

```
FEATURE                 Location/Qualifiers
source                  1..22
                        mol_type = transcribed RNA
                        organism = Homo sapiens
SEQUENCE: 130
cagcagggga gagagaggag tc                                          22

SEQ ID NO: 131          moltype = RNA   length = 22
FEATURE                 Location/Qualifiers
source                  1..22
                        mol_type = transcribed RNA
                        organism = Homo sapiens
SEQUENCE: 131
tggggagcgg cccccgggtg gg                                          22

SEQ ID NO: 132          moltype = RNA   length = 24
FEATURE                 Location/Qualifiers
source                  1..24
                        mol_type = transcribed RNA
                        organism = Homo sapiens
SEQUENCE: 132
ccccgggaac gtcgagactg gagc                                        24

SEQ ID NO: 133          moltype = RNA   length = 22
FEATURE                 Location/Qualifiers
source                  1..22
                        mol_type = transcribed RNA
                        organism = Homo sapiens
SEQUENCE: 133
tagggggcgg cttgtggagt gt                                          22

SEQ ID NO: 134          moltype = RNA   length = 17
FEATURE                 Location/Qualifiers
source                  1..17
                        mol_type = transcribed RNA
                        organism = Homo sapiens
SEQUENCE: 134
ggggctgggc gcgcgcc                                                17

SEQ ID NO: 135          moltype = RNA   length = 22
FEATURE                 Location/Qualifiers
source                  1..22
                        mol_type = transcribed RNA
                        organism = Homo sapiens
SEQUENCE: 135
ctcggcgcgg ggcgcgggct cc                                          22

SEQ ID NO: 136          moltype = RNA   length = 20
FEATURE                 Location/Qualifiers
source                  1..20
                        mol_type = transcribed RNA
                        organism = Homo sapiens
SEQUENCE: 136
cgggcgtggt ggtggggtg                                              20

SEQ ID NO: 137          moltype = RNA   length = 22
FEATURE                 Location/Qualifiers
source                  1..22
                        mol_type = transcribed RNA
                        organism = Homo sapiens
SEQUENCE: 137
gtgaggaggg gctggcaggg ac                                          22

SEQ ID NO: 138          moltype = RNA   length = 23
FEATURE                 Location/Qualifiers
source                  1..23
                        mol_type = transcribed RNA
                        organism = Homo sapiens
SEQUENCE: 138
acaggcggct gtagcaatgg ggg                                         23

SEQ ID NO: 139          moltype = RNA   length = 24
FEATURE                 Location/Qualifiers
source                  1..24
                        mol_type = transcribed RNA
                        organism = Homo sapiens
SEQUENCE: 139
tggggagctg aggctctggg ggtg                                        24
```

| | | |
|---|---|---|
| SEQ ID NO: 140<br>FEATURE<br>source<br><br>SEQUENCE: 140<br>ggcgggtgcg ggggtgg | moltype = RNA   length = 17<br>Location/Qualifiers<br>1..17<br>mol_type = transcribed RNA<br>organism = Homo sapiens<br><br> | <br><br><br><br><br>17 |
| SEQ ID NO: 141<br>FEATURE<br>source<br><br>SEQUENCE: 141<br>tgcggggcta gggctaacag ca | moltype = RNA   length = 22<br>Location/Qualifiers<br>1..22<br>mol_type = transcribed RNA<br>organism = Homo sapiens<br><br> | <br><br><br><br><br>22 |
| SEQ ID NO: 142<br>FEATURE<br>source<br><br>SEQUENCE: 142<br>tggctgttgg aggggcagg c | moltype = RNA   length = 21<br>Location/Qualifiers<br>1..21<br>mol_type = transcribed RNA<br>organism = Homo sapiens<br><br> | <br><br><br><br><br>21 |
| SEQ ID NO: 143<br>FEATURE<br>source<br><br>SEQUENCE: 143<br>aggcaggggc tggtgctggg cggg | moltype = RNA   length = 24<br>Location/Qualifiers<br>1..24<br>mol_type = transcribed RNA<br>organism = Homo sapiens<br><br> | <br><br><br><br><br>24 |
| SEQ ID NO: 144<br>FEATURE<br>source<br><br>SEQUENCE: 144<br>gtgggctggg ctgggctggg cc | moltype = RNA   length = 22<br>Location/Qualifiers<br>1..22<br>mol_type = transcribed RNA<br>organism = Homo sapiens<br><br> | <br><br><br><br><br>22 |
| SEQ ID NO: 145<br>FEATURE<br>source<br><br>SEQUENCE: 145<br>cgcgccgggc ccgggtt | moltype = RNA   length = 17<br>Location/Qualifiers<br>1..17<br>mol_type = transcribed RNA<br>organism = Homo sapiens<br><br> | <br><br><br><br><br>17 |
| SEQ ID NO: 146<br>FEATURE<br>source<br><br>SEQUENCE: 146<br>tggggggtggt ctctagccaa gg | moltype = RNA   length = 22<br>Location/Qualifiers<br>1..22<br>mol_type = transcribed RNA<br>organism = Homo sapiens<br><br> | <br><br><br><br><br>22 |
| SEQ ID NO: 147<br>FEATURE<br>source<br><br>SEQUENCE: 147<br>gccccggcgc gggcgggttc tgg | moltype = RNA   length = 23<br>Location/Qualifiers<br>1..23<br>mol_type = transcribed RNA<br>organism = Homo sapiens<br><br> | <br><br><br><br><br>23 |
| SEQ ID NO: 148<br>FEATURE<br>source<br><br>SEQUENCE: 148<br>agacacattt ggagagggaa cc | moltype = RNA   length = 22<br>Location/Qualifiers<br>1..22<br>mol_type = transcribed RNA<br>organism = Homo sapiens<br><br> | <br><br><br><br><br>22 |
| SEQ ID NO: 149<br>FEATURE<br>source<br><br>SEQUENCE: 149<br>cctccctgcc cgcctctctg cag | moltype = RNA   length = 23<br>Location/Qualifiers<br>1..23<br>mol_type = transcribed RNA<br>organism = Homo sapiens<br><br> | <br><br><br><br><br>23 |

```
SEQ ID NO: 150            moltype = RNA   length = 23
FEATURE                   Location/Qualifiers
source                    1..23
                          mol_type = transcribed RNA
                          organism = Homo sapiens
SEQUENCE: 150
tgggagggga gaggcagcaa gca                                                 23

SEQ ID NO: 151            moltype = RNA   length = 21
FEATURE                   Location/Qualifiers
source                    1..21
                          mol_type = transcribed RNA
                          organism = Homo sapiens
SEQUENCE: 151
atccagttct ctgagggggc t                                                   21

SEQ ID NO: 152            moltype = RNA   length = 22
FEATURE                   Location/Qualifiers
source                    1..22
                          mol_type = transcribed RNA
                          organism = Homo sapiens
SEQUENCE: 152
atatacaggg ggagactctt at                                                  22

SEQ ID NO: 153            moltype = RNA   length = 25
FEATURE                   Location/Qualifiers
source                    1..25
                          mol_type = transcribed RNA
                          organism = Homo sapiens
SEQUENCE: 153
acttgggcag gagggaccct gtatg                                               25

SEQ ID NO: 154            moltype = RNA   length = 22
FEATURE                   Location/Qualifiers
source                    1..22
                          mol_type = transcribed RNA
                          organism = Homo sapiens
SEQUENCE: 154
ggggaactgt agatgaaaag gc                                                  22

SEQ ID NO: 155            moltype = RNA   length = 23
FEATURE                   Location/Qualifiers
source                    1..23
                          mol_type = transcribed RNA
                          organism = Homo sapiens
SEQUENCE: 155
tcgaggactg gtggaagggc ctt                                                 23

SEQ ID NO: 156            moltype = RNA   length = 21
FEATURE                   Location/Qualifiers
source                    1..21
                          mol_type = transcribed RNA
                          organism = Homo sapiens
SEQUENCE: 156
cgtggaggac gaggaggagg c                                                   21

SEQ ID NO: 157            moltype = RNA   length = 17
FEATURE                   Location/Qualifiers
source                    1..17
                          mol_type = transcribed RNA
                          organism = Homo sapiens
SEQUENCE: 157
gagactgggg tggggcc                                                        17

SEQ ID NO: 158            moltype = RNA   length = 23
FEATURE                   Location/Qualifiers
source                    1..23
                          mol_type = transcribed RNA
                          organism = Homo sapiens
SEQUENCE: 158
ggggggccgat acactgtacg aga                                                23

SEQ ID NO: 159            moltype = RNA   length = 17
FEATURE                   Location/Qualifiers
source                    1..17
                          mol_type = transcribed RNA
                          organism = Homo sapiens
SEQUENCE: 159
```

```
gcggggctgg gcgcgcg                                                      17

SEQ ID NO: 161        moltype = RNA   length = 24
FEATURE               Location/Qualifiers
source                1..24
                      mol_type = transcribed RNA
                      organism = Homo sapiens
SEQUENCE: 160
tgtaggcatg aggcagggcc cagg                                              24

SEQ ID NO: 161        moltype = RNA   length = 22
FEATURE               Location/Qualifiers
source                1..22
                      mol_type = transcribed RNA
                      organism = Homo sapiens
SEQUENCE: 161
tgggggagga aggacaggcc at                                                22

SEQ ID NO: 162        moltype = RNA   length = 25
FEATURE               Location/Qualifiers
source                1..25
                      mol_type = transcribed RNA
                      organism = Homo sapiens
SEQUENCE: 162
tagggggtggg ggaattcagg ggtgt                                            25

SEQ ID NO: 163        moltype = RNA   length = 22
FEATURE               Location/Qualifiers
source                1..22
                      mol_type = transcribed RNA
                      organism = Homo sapiens
SEQUENCE: 163
gctgcgggct gcggtcaggg cg                                                22

SEQ ID NO: 164        moltype = RNA   length = 23
FEATURE               Location/Qualifiers
source                1..23
                      mol_type = transcribed RNA
                      organism = Homo sapiens
SEQUENCE: 164
ttagggagta gaagggtggg gag                                               23

SEQ ID NO: 165        moltype = RNA   length = 22
FEATURE               Location/Qualifiers
source                1..22
                      mol_type = transcribed RNA
                      organism = Homo sapiens
SEQUENCE: 165
gtgaacgggc gccatcccga gg                                                22

SEQ ID NO: 166        moltype = RNA   length = 22
FEATURE               Location/Qualifiers
source                1..22
                      mol_type = transcribed RNA
                      organism = Homo sapiens
SEQUENCE: 166
gggggggtgtg gagccagggg gc                                               22

SEQ ID NO: 167        moltype = RNA   length = 23
FEATURE               Location/Qualifiers
source                1..23
                      mol_type = transcribed RNA
                      organism = Homo sapiens
SEQUENCE: 167
ctgggcccgc ggcgggcgtg ggg                                               23

SEQ ID NO: 168        moltype = RNA   length = 21
FEATURE               Location/Qualifiers
source                1..21
                      mol_type = transcribed RNA
                      organism = Homo sapiens
SEQUENCE: 168
atcacattgc caggattac c                                                  21

SEQ ID NO: 169        moltype = RNA   length = 21
FEATURE               Location/Qualifiers
source                1..21
                      mol_type = transcribed RNA
                      organism = Homo sapiens
```

-continued

```
SEQUENCE: 169
atcacattgc cagggatttc c                                             21

SEQ ID NO: 170         moltype = RNA   length = 22
FEATURE                Location/Qualifiers
source                 1..22
                       mol_type = transcribed RNA
                       organism = Homo sapiens
SEQUENCE: 170
gactatagaa ctttccccct ca                                            22

SEQ ID NO: 171         moltype = RNA   length = 20
FEATURE                Location/Qualifiers
source                 1..20
                       mol_type = transcribed RNA
                       organism = Homo sapiens
SEQUENCE: 171
tcacacctgc ctcgcccccc                                               20

SEQ ID NO: 172         moltype = RNA   length = 23
FEATURE                Location/Qualifiers
source                 1..23
                       mol_type = transcribed RNA
                       organism = Homo sapiens
SEQUENCE: 172
gaacgcctgt tcttgccagg tgg                                           23

SEQ ID NO: 173         moltype = RNA   length = 22
FEATURE                Location/Qualifiers
source                 1..22
                       mol_type = transcribed RNA
                       organism = Homo sapiens
SEQUENCE: 173
tctgccccct ccgctgctgc ca                                            22

SEQ ID NO: 174         moltype = RNA   length = 22
FEATURE                Location/Qualifiers
source                 1..22
                       mol_type = transcribed RNA
                       organism = Homo sapiens
SEQUENCE: 174
gggtggggat ttgttgcatt ac                                            22

SEQ ID NO: 175         moltype = RNA   length = 22
FEATURE                Location/Qualifiers
source                 1..22
                       mol_type = transcribed RNA
                       organism = Homo sapiens
SEQUENCE: 175
ggctacaaca caggacccgg gc                                            22

SEQ ID NO: 176         moltype = RNA   length = 22
FEATURE                Location/Qualifiers
source                 1..22
                       mol_type = transcribed RNA
                       organism = Homo sapiens
SEQUENCE: 176
tagcagcacg taaatattgg cg                                            22

SEQ ID NO: 177         moltype = RNA   length = 22
FEATURE                Location/Qualifiers
source                 1..22
                       mol_type = transcribed RNA
                       organism = Homo sapiens
SEQUENCE: 177
tattgcactc gtcccggcct cc                                            22

SEQ ID NO: 178         moltype = RNA   length = 22
FEATURE                Location/Qualifiers
source                 1..22
                       mol_type = transcribed RNA
                       organism = Homo sapiens
SEQUENCE: 178
ctggtacagg cctgggggac ag                                            22

SEQ ID NO: 179         moltype = RNA   length = 19
FEATURE                Location/Qualifiers
source                 1..19
                       mol_type = transcribed RNA
```

```
                        organism = Homo sapiens
SEQUENCE: 179
aggcacggtg tcagcaggc                                                19

SEQ ID NO: 180          moltype = RNA   length = 22
FEATURE                 Location/Qualifiers
source                  1..22
                        mol_type = transcribed RNA
                        organism = Homo sapiens
SEQUENCE: 180
acaggtgagg ttcttgggag cc                                            22

SEQ ID NO: 181          moltype = RNA   length = 22
FEATURE                 Location/Qualifiers
source                  1..22
                        mol_type = transcribed RNA
                        organism = Homo sapiens
SEQUENCE: 181
agggacggga cgcggtgcag tg                                            22

SEQ ID NO: 182          moltype = RNA   length = 22
FEATURE                 Location/Qualifiers
source                  1..22
                        mol_type = transcribed RNA
                        organism = Homo sapiens
SEQUENCE: 182
tattgcactt gtcccggcct gt                                            22

SEQ ID NO: 183          moltype = RNA   length = 22
FEATURE                 Location/Qualifiers
source                  1..22
                        mol_type = transcribed RNA
                        organism = Homo sapiens
SEQUENCE: 183
aggcggggcg ccgcgggacc gc                                            22

SEQ ID NO: 184          moltype = RNA   length = 22
FEATURE                 Location/Qualifiers
source                  1..22
                        mol_type = transcribed RNA
                        organism = Homo sapiens
SEQUENCE: 184
tagggcagc agaggacctg gg                                             22

SEQ ID NO: 185          moltype = RNA   length = 20
FEATURE                 Location/Qualifiers
source                  1..20
                        mol_type = transcribed RNA
                        organism = Homo sapiens
SEQUENCE: 185
tgtgggactg caaatgggag                                               20

SEQ ID NO: 186          moltype = RNA   length = 19
FEATURE                 Location/Qualifiers
source                  1..19
                        mol_type = transcribed RNA
                        organism = Homo sapiens
SEQUENCE: 186
aaggggctgg gggagcaca                                                19

SEQ ID NO: 187          moltype = RNA   length = 18
FEATURE                 Location/Qualifiers
source                  1..18
                        mol_type = transcribed RNA
                        organism = Homo sapiens
SEQUENCE: 187
gtgaaggccc ggcggaga                                                 18

SEQ ID NO: 188          moltype = RNA   length = 22
FEATURE                 Location/Qualifiers
source                  1..22
                        mol_type = transcribed RNA
                        organism = Homo sapiens
SEQUENCE: 188
tggtggagga agagggcagc tc                                            22

SEQ ID NO: 189          moltype = RNA   length = 23
FEATURE                 Location/Qualifiers
source                  1..23
```

```
                        mol_type = transcribed RNA
                        organism = Homo sapiens
SEQUENCE: 189
gggggggcag gagggctca ggg                                                23

SEQ ID NO: 190          moltype = RNA   length = 23
FEATURE                 Location/Qualifiers
source                  1..23
                        mol_type = transcribed RNA
                        organism = Homo sapiens
SEQUENCE: 190
cacacaggaa aagcggggcc ctg                                               23

SEQ ID NO: 191          moltype = RNA   length = 19
FEATURE                 Location/Qualifiers
source                  1..19
                        mol_type = transcribed RNA
                        organism = Homo sapiens
SEQUENCE: 191
tggggcggag cttccggag                                                    19

SEQ ID NO: 192          moltype = RNA   length = 18
FEATURE                 Location/Qualifiers
source                  1..18
                        mol_type = transcribed RNA
                        organism = Homo sapiens
SEQUENCE: 192
tgaggcgggg gggcgagc                                                     18

SEQ ID NO: 193          moltype = RNA   length = 21
FEATURE                 Location/Qualifiers
source                  1..21
                        mol_type = transcribed RNA
                        organism = Homo sapiens
SEQUENCE: 193
accactgcac tccagcctga g                                                 21

SEQ ID NO: 194          moltype = RNA   length = 22
FEATURE                 Location/Qualifiers
source                  1..22
                        mol_type = transcribed RNA
                        organism = Homo sapiens
SEQUENCE: 194
gtgggtacgg cccagtgggg gg                                                22

SEQ ID NO: 195          moltype = RNA   length = 18
FEATURE                 Location/Qualifiers
source                  1..18
                        mol_type = transcribed RNA
                        organism = Homo sapiens
SEQUENCE: 195
cggggcggca ggggcctc                                                     18

SEQ ID NO: 196          moltype = RNA   length = 22
FEATURE                 Location/Qualifiers
source                  1..22
                        mol_type = transcribed RNA
                        organism = Homo sapiens
SEQUENCE: 196
caggaggcag tgggcgagca gg                                                22

SEQ ID NO: 197          moltype = RNA   length = 20
FEATURE                 Location/Qualifiers
source                  1..20
                        mol_type = transcribed RNA
                        organism = Homo sapiens
SEQUENCE: 197
taggggtgg caggctggcc                                                    20

SEQ ID NO: 198          moltype = RNA   length = 25
FEATURE                 Location/Qualifiers
source                  1..25
                        mol_type = transcribed RNA
                        organism = Homo sapiens
SEQUENCE: 198
agggatcgcg ggcgggtggc ggcct                                             25

SEQ ID NO: 199          moltype = RNA   length = 23
FEATURE                 Location/Qualifiers
```

```
source                  1..23
                        mol_type = transcribed RNA
                        organism = Homo sapiens
SEQUENCE: 199
cagggggctgg ggtttcaggt tct                                              23

SEQ ID NO: 200          moltype = RNA   length = 20
FEATURE                 Location/Qualifiers
source                  1..20
                        mol_type = transcribed RNA
                        organism = Homo sapiens
SEQUENCE: 200
accaggaggc tgaggcccct                                                   20

SEQ ID NO: 201          moltype = RNA   length = 21
FEATURE                 Location/Qualifiers
source                  1..21
                        mol_type = transcribed RNA
                        organism = Homo sapiens
SEQUENCE: 201
cggggcagct cagtacagga t                                                 21

SEQ ID NO: 202          moltype = RNA   length = 18
FEATURE                 Location/Qualifiers
source                  1..18
                        mol_type = transcribed RNA
                        organism = Homo sapiens
SEQUENCE: 202
gggtgcgggc cggcgggg                                                     18

SEQ ID NO: 203          moltype = RNA   length = 22
FEATURE                 Location/Qualifiers
source                  1..22
                        mol_type = transcribed RNA
                        organism = Homo sapiens
SEQUENCE: 203
ctgggagagg gttgtttact cc                                                22

SEQ ID NO: 204          moltype = RNA   length = 20
FEATURE                 Location/Qualifiers
source                  1..20
                        mol_type = transcribed RNA
                        organism = Homo sapiens
SEQUENCE: 204
cgcgggtcgg ggtctgcagg                                                   20

SEQ ID NO: 205          moltype = RNA   length = 22
FEATURE                 Location/Qualifiers
source                  1..22
                        mol_type = transcribed RNA
                        organism = Homo sapiens
SEQUENCE: 205
aaggggcagg gacgggtggc cc                                                22

SEQ ID NO: 206          moltype = RNA   length = 22
FEATURE                 Location/Qualifiers
source                  1..22
                        mol_type = transcribed RNA
                        organism = Homo sapiens
SEQUENCE: 206
ctgggacagg aggaggaggc ag                                                22

SEQ ID NO: 207          moltype = RNA   length = 23
FEATURE                 Location/Qualifiers
source                  1..23
                        mol_type = transcribed RNA
                        organism = Homo sapiens
SEQUENCE: 207
cgggctgtcc ggaggggtcg gct                                               23

SEQ ID NO: 208          moltype = RNA   length = 22
FEATURE                 Location/Qualifiers
source                  1..22
                        mol_type = transcribed RNA
                        organism = Homo sapiens
SEQUENCE: 208
gggaccatcc tgcctgctgt gg                                                22

SEQ ID NO: 209          moltype = RNA   length = 22
```

```
FEATURE              Location/Qualifiers
source               1..22
                     mol_type = transcribed RNA
                     organism = Homo sapiens
SEQUENCE: 209
gtaggggagg ttgggccagg ga                                          22

SEQ ID NO: 210       moltype = RNA   length = 22
FEATURE              Location/Qualifiers
source               1..22
                     mol_type = transcribed RNA
                     organism = Homo sapiens
SEQUENCE: 210
tgggggagtg cagtgattgt gg                                          22

SEQ ID NO: 211       moltype = RNA   length = 20
FEATURE              Location/Qualifiers
source               1..20
                     mol_type = transcribed RNA
                     organism = Homo sapiens
SEQUENCE: 211
actcaaactg tgggggcact                                             20

SEQ ID NO: 212       moltype = RNA   length = 18
FEATURE              Location/Qualifiers
source               1..18
                     mol_type = transcribed RNA
                     organism = Homo sapiens
SEQUENCE: 212
aggggggcggg ctccggcg                                              18

SEQ ID NO: 213       moltype = RNA   length = 22
FEATURE              Location/Qualifiers
source               1..22
                     mol_type = transcribed RNA
                     organism = Homo sapiens
SEQUENCE: 213
agtgggaggc cagggcacgg ca                                          22

SEQ ID NO: 214       moltype = RNA   length = 24
FEATURE              Location/Qualifiers
source               1..24
                     mol_type = transcribed RNA
                     organism = Homo sapiens
SEQUENCE: 214
tgggggagcc atgagataag agca                                        24

SEQ ID NO: 215       moltype = RNA   length = 22
FEATURE              Location/Qualifiers
source               1..22
                     mol_type = transcribed RNA
                     organism = Homo sapiens
SEQUENCE: 215
tggctcagtt cagcaggaac ag                                          22

SEQ ID NO: 216       moltype = RNA   length = 23
FEATURE              Location/Qualifiers
source               1..23
                     mol_type = transcribed RNA
                     organism = Homo sapiens
SEQUENCE: 216
gtgagtggga gccccagtgt gtg                                         23

SEQ ID NO: 217       moltype = RNA   length = 17
FEATURE              Location/Qualifiers
source               1..17
                     mol_type = transcribed RNA
                     organism = Homo sapiens
SEQUENCE: 217
gccggacaag agggagg                                                17

SEQ ID NO: 218       moltype = RNA   length = 22
FEATURE              Location/Qualifiers
source               1..22
                     mol_type = transcribed RNA
                     organism = Homo sapiens
SEQUENCE: 218
ggaggaacct tggagcttcg gc                                          22
```

```
SEQ ID NO: 219        moltype = RNA   length = 20
FEATURE               Location/Qualifiers
source                1..20
                      mol_type = transcribed RNA
                      organism = Homo sapiens
SEQUENCE: 219
tgggaatggg ggtaagggcc                                                    20

SEQ ID NO: 220        moltype = RNA   length = 24
FEATURE               Location/Qualifiers
source                1..24
                      mol_type = transcribed RNA
                      organism = Homo sapiens
SEQUENCE: 220
ggaggccggg gtgggcggg gcgg                                                24

SEQ ID NO: 221        moltype = RNA   length = 20
FEATURE               Location/Qualifiers
source                1..20
                      mol_type = transcribed RNA
                      organism = Homo sapiens
SEQUENCE: 221
gggaaaagga aggggagga                                                     20

SEQ ID NO: 222        moltype = RNA   length = 22
FEATURE               Location/Qualifiers
source                1..22
                      mol_type = transcribed RNA
                      organism = Homo sapiens
SEQUENCE: 222
agtgggagga caggaggcag gt                                                 22

SEQ ID NO: 223        moltype = RNA   length = 23
FEATURE               Location/Qualifiers
source                1..23
                      mol_type = transcribed RNA
                      organism = Homo sapiens
SEQUENCE: 223
gtttgcacgg gtgggccttg tct                                                23

SEQ ID NO: 224        moltype = RNA   length = 19
FEATURE               Location/Qualifiers
source                1..19
                      mol_type = transcribed RNA
                      organism = Homo sapiens
SEQUENCE: 224
ggggagcgag gggcggggc                                                     19

SEQ ID NO: 225        moltype = RNA   length = 84
FEATURE               Location/Qualifiers
source                1..84
                      mol_type = transcribed RNA
                      organism = Homo sapiens
SEQUENCE: 225
gctggcgtcg gtgctgggga gcggccccg ggtgggcctc tgctctggcc cctcctgggg         60
cccgcactct cgctctgggc ccgc                                               84

SEQ ID NO: 226        moltype = RNA   length = 61
FEATURE               Location/Qualifiers
source                1..61
                      mol_type = transcribed RNA
                      organism = Homo sapiens
SEQUENCE: 226
gggggcggga gctgggtct gcaggttcgc actgatgcct gctcgccctg tctcccgcta         60
g                                                                        61

SEQ ID NO: 227        moltype = RNA   length = 57
FEATURE               Location/Qualifiers
source                1..57
                      mol_type = transcribed RNA
                      organism = Homo sapiens
SEQUENCE: 227
cattggaggg tgtggaagac atctgggcca actctgatct cttcatctac cccccag           57

SEQ ID NO: 228        moltype = RNA   length = 73
FEATURE               Location/Qualifiers
source                1..73
                      mol_type = transcribed RNA
                      organism = Homo sapiens
```

```
SEQUENCE: 228
cggcgacggc ggggtgggtg aggtcgggcc ccaagactcg gggtttgccg ggcgcctcag    60
ttcaccgcgg ccg                                                       73

SEQ ID NO: 229          moltype = RNA   length = 86
FEATURE                 Location/Qualifiers
source                  1..86
                        mol_type = transcribed RNA
                        organism = Homo sapiens
SEQUENCE: 229
ggcttagaaa cagtccctag gtaggatttg gggaggagct aagaagcccc tacagggccc    60
agaggtgggg actgagcctt agttgg                                         86

SEQ ID NO: 230          moltype = RNA   length = 85
FEATURE                 Location/Qualifiers
source                  1..85
                        mol_type = transcribed RNA
                        organism = Homo sapiens
SEQUENCE: 230
ggcgcctcct gctctgctgt gccgccaggg cctcccctag cgcgccttct ggagaggctt    60
tgtgcggata cggggctgga ggcct                                          85

SEQ ID NO: 231          moltype = RNA   length = 109
FEATURE                 Location/Qualifiers
source                  1..109
                        mol_type = transcribed RNA
                        organism = Homo sapiens
SEQUENCE: 231
tcccgcattc cctctgcttt ggtcaggtgg tgccctcctt ccatgggtag agccagagat    60
ggtgggttct ggctggtcag atgggagtgg acagagaccc ggggtcctc              109

SEQ ID NO: 232          moltype = RNA   length = 72
FEATURE                 Location/Qualifiers
source                  1..72
                        mol_type = transcribed RNA
                        organism = Homo sapiens
SEQUENCE: 232
atgagcgggt gggagcagat cttattgaga gttccttctc ctgctcctga ttgtcttccc    60
ccaccctcac ag                                                        72

SEQ ID NO: 233          moltype = RNA   length = 61
FEATURE                 Location/Qualifiers
source                  1..61
                        mol_type = transcribed RNA
                        organism = Homo sapiens
SEQUENCE: 233
tctcgtttga tctcggaagc taagcagggt tgggcctggt tagtacttgg atgggaaact    60
t                                                                    61

SEQ ID NO: 234          moltype = RNA   length = 53
FEATURE                 Location/Qualifiers
source                  1..53
                        mol_type = transcribed RNA
                        organism = Homo sapiens
SEQUENCE: 234
gtttgatctc ggaagctaag cagggtcggg cctggttagt acttggatgg gag           53

SEQ ID NO: 235          moltype = RNA   length = 66
FEATURE                 Location/Qualifiers
source                  1..66
                        mol_type = transcribed RNA
                        organism = Homo sapiens
SEQUENCE: 235
gggaggaggg aggagatggg ccaagttccc tctggctgga acgcccttcc ccccttctt    60
cacctg                                                               66

SEQ ID NO: 236          moltype = RNA   length = 68
FEATURE                 Location/Qualifiers
source                  1..68
                        mol_type = transcribed RNA
                        organism = Homo sapiens
SEQUENCE: 236
cgtggtgagg atatggcagg gaaggggagt ttccctctat tcccttcccc ccagtaatct    60
tcatcatg                                                             68

SEQ ID NO: 237          moltype = RNA   length = 61
FEATURE                 Location/Qualifiers
source                  1..61
                        mol_type = transcribed RNA
```

```
                    organism = Homo sapiens
SEQUENCE: 237
tcggctggcg ggggtagagc tggctgcagg cccggcccct ctcagctgct gccctctcca    60
g                                                                   61

SEQ ID NO: 238          moltype = RNA   length = 55
FEATURE                 Location/Qualifiers
source                  1..55
                        mol_type = transcribed RNA
                        organism = Homo sapiens
SEQUENCE: 238
ccggatccga gtcacggcac caaatttcat gcgtgtccgt gtgaagagac cacca         55

SEQ ID NO: 239          moltype = RNA   length = 68
FEATURE                 Location/Qualifiers
source                  1..68
                        mol_type = transcribed RNA
                        organism = Homo sapiens
SEQUENCE: 239
tgcccaggct ggagcgagtg cagtggtgca gtcagtccta gctcactgca gcctcgaact    60
cctgggct                                                            68

SEQ ID NO: 240          moltype = RNA   length = 87
FEATURE                 Location/Qualifiers
source                  1..87
                        mol_type = transcribed RNA
                        organism = Homo sapiens
SEQUENCE: 240
gtgaggcggg gccaggaggg tgtgtggcgt gggtgctgcg gggccgtcag ggtgcctgcg    60
ggacgctcac ctggctggcc cgcccag                                       87

SEQ ID NO: 241          moltype = RNA   length = 68
FEATURE                 Location/Qualifiers
source                  1..68
                        mol_type = transcribed RNA
                        organism = Homo sapiens
SEQUENCE: 241
gtgcaaagag caggaggaca ggggatttat ctcccaaggg aggtcccctg atcctagtca    60
cggcacca                                                            68

SEQ ID NO: 242          moltype = RNA   length = 110
FEATURE                 Location/Qualifiers
source                  1..110
                        mol_type = transcribed RNA
                        organism = Homo sapiens
SEQUENCE: 242
ggctacagtc tttcttcatg tgactcgtgg acttcccttt gtcatcctat gcctgagaat    60
atatgaagga ggctgggaag gcaaagggac gttcaattgt catcactggc              110

SEQ ID NO: 243          moltype = RNA   length = 49
FEATURE                 Location/Qualifiers
source                  1..49
                        mol_type = transcribed RNA
                        organism = Homo sapiens
SEQUENCE: 243
ttcccagcca acgcaccaaa aatgatatgg gtctgttgtc tggagaaac                49

SEQ ID NO: 244          moltype = RNA   length = 86
FEATURE                 Location/Qualifiers
source                  1..86
                        mol_type = transcribed RNA
                        organism = Homo sapiens
SEQUENCE: 244
ggggctgggg gtgtggggag agagagtgca cagccagctc aggattaaa gctctttctc     60
tctctctctc tcccacttcc ctgcag                                        86

SEQ ID NO: 245          moltype = RNA   length = 73
FEATURE                 Location/Qualifiers
source                  1..73
                        mol_type = transcribed RNA
                        organism = Homo sapiens
SEQUENCE: 245
ctggtgtttg aggcgatgtg gggatgtaga gacaacttcc cagtctcatt tcctcatcct    60
gccaggccac cat                                                      73

SEQ ID NO: 246          moltype = RNA   length = 60
FEATURE                 Location/Qualifiers
source                  1..60
                        mol_type = transcribed RNA
```

```
                        organism = Homo sapiens
SEQUENCE: 246
caaggtgggg gagatggggg ttgaacttca tttctcatgc tcatccccat ctcctttcag    60

SEQ ID NO: 247          moltype = RNA   length = 115
FEATURE                 Location/Qualifiers
source                  1..115
                        mol_type = transcribed RNA
                        organism = Homo sapiens
SEQUENCE: 247
ggtgccgagg gccgtccggc atcctaggcg ggtcgctgcg gtacctccct cctgtctgtg    60
gcggtgggat cccgtggccg tgttttcctg gtggcccggc cgtgcctgag gtttc        115

SEQ ID NO: 248          moltype = RNA   length = 72
FEATURE                 Location/Qualifiers
source                  1..72
                        mol_type = transcribed RNA
                        organism = Homo sapiens
SEQUENCE: 248
gagtctgagg gacccaggac aggagaaggc ctatggtgat ttgcattctt cctgccctgg    60
ctccatcctc ag                                                       72

SEQ ID NO: 249          moltype = RNA   length = 80
FEATURE                 Location/Qualifiers
source                  1..80
                        mol_type = transcribed RNA
                        organism = Homo sapiens
SEQUENCE: 249
gcgtcaagat ggcggcgggg aggtaggcag agcaggacgc cgctgctgcc gccgccaccg    60
ccgcctccgc tccagtcgcc                                               80

SEQ ID NO: 250          moltype = RNA   length = 66
FEATURE                 Location/Qualifiers
source                  1..66
                        mol_type = transcribed RNA
                        organism = Homo sapiens
SEQUENCE: 250
ccgagtgggg cggggcaggt ccctgcaggg actgtgacac tgaaggacct gcaccttcgc    60
ccacag                                                              66

SEQ ID NO: 251          moltype = RNA   length = 62
FEATURE                 Location/Qualifiers
source                  1..62
                        mol_type = transcribed RNA
                        organism = Homo sapiens
SEQUENCE: 251
gctggggtc ccccgacagt gtggagctgg ggccgggtcc cggggagggg ggttctgggc     60
ag                                                                  62

SEQ ID NO: 252          moltype = RNA   length = 65
FEATURE                 Location/Qualifiers
source                  1..65
                        mol_type = transcribed RNA
                        organism = Homo sapiens
SEQUENCE: 252
gagggtgggc gagggcggct gagcggctcc atccccggc ctgctcatcc ccctcgccct     60
ctcag                                                               65

SEQ ID NO: 253          moltype = RNA   length = 86
FEATURE                 Location/Qualifiers
source                  1..86
                        mol_type = transcribed RNA
                        organism = Homo sapiens
SEQUENCE: 253
cgcctgagcg tgcagcagga catcttcctg acctggtaat aattaggtga gaaggatggt    60
tggggcggt cggcgtaact caggga                                         86

SEQ ID NO: 254          moltype = RNA   length = 82
FEATURE                 Location/Qualifiers
source                  1..82
                        mol_type = transcribed RNA
                        organism = Homo sapiens
SEQUENCE: 254
gctacgggga gcggggagga agtgggcgct gcttctgcgt tatctggaag gagcagccca    60
ctcctgtcct gggctctgtg gt                                            82

SEQ ID NO: 255          moltype = RNA   length = 87
FEATURE                 Location/Qualifiers
source                  1..87
```

```
                              mol_type = transcribed RNA
                              organism = Homo sapiens
SEQUENCE: 255
gtgtggccgg caggcgggtg ggcggggcg gccggtggga accccgcccc gccccgcgcc    60
cgcactcacc cgcccgtctc cccacag                                      87

SEQ ID NO: 256            moltype = RNA   length = 102
FEATURE                   Location/Qualifiers
source                    1..102
                          mol_type = transcribed RNA
                          organism = Homo sapiens
SEQUENCE: 256
tgtgttccct atcctcctta tgtcccaccc ccactcctgt ttgaatattt caccagaaac    60
aggagtgggg ggtgggacgt aaggaggatg ggggaaagaa ca                     102

SEQ ID NO: 257            moltype = RNA   length = 69
FEATURE                   Location/Qualifiers
source                    1..69
                          mol_type = transcribed RNA
                          organism = Homo sapiens
SEQUENCE: 257
ccgggcaggc aggtgtaggg tggagcccac tgtggctcct gactcagccc tgctgccttc    60
acctgccag                                                          69

SEQ ID NO: 258            moltype = RNA   length = 93
FEATURE                   Location/Qualifiers
source                    1..93
                          mol_type = transcribed RNA
                          organism = Homo sapiens
SEQUENCE: 258
gcttgttggg gattgggtca ggccagtgtt caagggcccc tcctctagta ctccctgttt    60
gtgttctgcc actgactgag cttctcccca cag                                93

SEQ ID NO: 259            moltype = RNA   length = 88
FEATURE                   Location/Qualifiers
source                    1..88
                          mol_type = transcribed RNA
                          organism = Homo sapiens
SEQUENCE: 259
gtggggccag gcggtggtgg gcactgctgg ggtgggcaca gcagccatgc agagcgggca    60
tttgaccccg tgccaccctt ttccccag                                      88

SEQ ID NO: 260            moltype = RNA   length = 63
FEATURE                   Location/Qualifiers
source                    1..63
                          mol_type = transcribed RNA
                          organism = Homo sapiens
SEQUENCE: 260
aatgggtggg tgctggtggg agccgtgccc tggccactca ttcggctctc tccctcaccc    60
tag                                                                63

SEQ ID NO: 261            moltype = RNA   length = 72
FEATURE                   Location/Qualifiers
source                    1..72
                          mol_type = transcribed RNA
                          organism = Homo sapiens
SEQUENCE: 261
cttgggaatg gcaaggaaac cgttaccatt actgagttta gtaatggtaa tggttctctt    60
gctataccca ga                                                      72

SEQ ID NO: 262            moltype = RNA   length = 81
FEATURE                   Location/Qualifiers
source                    1..81
                          mol_type = transcribed RNA
                          organism = Homo sapiens
SEQUENCE: 262
tagaggcagt ttcaacagat gtgtagactt ttgatatgag aaattggttt caaaatcagg    60
agtcggggct ttactgcttt t                                            81

SEQ ID NO: 263            moltype = RNA   length = 83
FEATURE                   Location/Qualifiers
source                    1..83
                          mol_type = transcribed RNA
                          organism = Homo sapiens
SEQUENCE: 263
aatagagggt gcacaggcac gggagctcag gtgaggcagg gagctgagct cacctgacct    60
cccatgcctg tgcaccctct att                                          83

SEQ ID NO: 264            moltype = RNA   length = 96
```

| FEATURE | Location/Qualifiers |
|---|---|
| source | 1..96 |
| | mol_type = transcribed RNA |
| | organism = Homo sapiens |

SEQUENCE: 264
ctcgggaggg gcgggagggg ggtccccggt gctcggatct cgagggtgct tattgttcgg    60
tccgagcctg ggtctccctc ttccccccaa cccccc                             96

| SEQ ID NO: 265 | moltype = RNA   length = 82 |
|---|---|
| FEATURE | Location/Qualifiers |
| source | 1..82 |
| | mol_type = transcribed RNA |
| | organism = Homo sapiens |

SEQUENCE: 265
tgagctgttg gattcggggc cgtagcactg tctgagaggt ttacatttct cacagtgaac    60
cggtctcttt ttcagctgct tc                                            82

| SEQ ID NO: 266 | moltype = RNA   length = 66 |
|---|---|
| FEATURE | Location/Qualifiers |
| source | 1..66 |
| | mol_type = transcribed RNA |
| | organism = Homo sapiens |

SEQUENCE: 266
gggcatgggg aggtgtggag tcagcatggg gctaggaggc cccgcgctga cccgccttct    60
ccgcag                                                              66

| SEQ ID NO: 267 | moltype = RNA   length = 89 |
|---|---|
| FEATURE | Location/Qualifiers |
| source | 1..89 |
| | mol_type = transcribed RNA |
| | organism = Homo sapiens |

SEQUENCE: 267
tctccgttta tcccaccact gccaccatta ttgctactgt tcagcaggtg ctgctggtgg    60
tgatggtgat agtctggtgg gggcggtgg                                     89

| SEQ ID NO: 268 | moltype = RNA   length = 81 |
|---|---|
| FEATURE | Location/Qualifiers |
| source | 1..81 |
| | mol_type = transcribed RNA |
| | organism = Homo sapiens |

SEQUENCE: 268
catcctcctt acgtcccacc ccccactcct gtttctggtg aaatattcaa acaggagtgg    60
gggtgggaca taaggaggat a                                             81

| SEQ ID NO: 269 | moltype = RNA   length = 79 |
|---|---|
| FEATURE | Location/Qualifiers |
| source | 1..79 |
| | mol_type = transcribed RNA |
| | organism = Homo sapiens |

SEQUENCE: 269
ctcgaggtgc tgggggacgc gtgagcgcga gccgcttcct cacggctcgg ccgcggcgcg    60
tagccccgc cacatcggg                                                 79

| SEQ ID NO: 270 | moltype = RNA   length = 99 |
|---|---|
| FEATURE | Location/Qualifiers |
| source | 1..99 |
| | mol_type = transcribed RNA |
| | organism = Homo sapiens |

SEQUENCE: 270
gcaagggaca gggagggtcg tggcgacact cgcgccagct cccgggacgg ctgggctcgg    60
gctggtcgcc gacctccgac cctccactag atgcctggc                          99

| SEQ ID NO: 271 | moltype = RNA   length = 80 |
|---|---|
| FEATURE | Location/Qualifiers |
| source | 1..80 |
| | mol_type = transcribed RNA |
| | organism = Homo sapiens |

SEQUENCE: 271
cgggaatgcc gcggcgggga cggcgattgg tccgtatgtg tggtgccacc ggccgccggc    60
tccgccccgg ccccgcccc                                                80

| SEQ ID NO: 272 | moltype = RNA   length = 71 |
|---|---|
| FEATURE | Location/Qualifiers |
| source | 1..71 |
| | mol_type = transcribed RNA |
| | organism = Homo sapiens |

SEQUENCE: 272
tgaccacccc cgggcaaaga cctgcagatc ccctgttaga cagggcccca ggactttgtg    60
cggggtgccc a                                                        71

```
SEQ ID NO: 273          moltype = RNA   length = 80
FEATURE                 Location/Qualifiers
source                  1..80
                        mol_type = transcribed RNA
                        organism = Homo sapiens
SEQUENCE: 273
aggaccctcc cagagggccc cccctcaatc ctgttgtgcc taattcagag ggttgggtgg   60
aggctctcct gaagggctct                                               80

SEQ ID NO: 274          moltype = RNA   length = 73
FEATURE                 Location/Qualifiers
source                  1..73
                        mol_type = transcribed RNA
                        organism = Homo sapiens
SEQUENCE: 274
ggatgataag ttatggggct tctgtagaga tttctatgag aacatctcta aggaactccc   60
ccaaactgaa ttc                                                      73

SEQ ID NO: 275          moltype = RNA   length = 64
FEATURE                 Location/Qualifiers
source                  1..64
                        mol_type = transcribed RNA
                        organism = Homo sapiens
SEQUENCE: 275
aaccccgggc cggaggtcaa gggcgtcgct tctccctaat gttgcctctt ttccacggcc   60
tcag                                                                64

SEQ ID NO: 276          moltype = RNA   length = 94
FEATURE                 Location/Qualifiers
source                  1..94
                        mol_type = transcribed RNA
                        organism = Homo sapiens
SEQUENCE: 276
ataaaggaag ttaggctgag gggcagagag cgagactttt ctattttcca aaagctcggt   60
ctgaggcccc tcagtcttgc ttcctaaccc gcgc                               94

SEQ ID NO: 277          moltype = RNA   length = 97
FEATURE                 Location/Qualifiers
source                  1..97
                        mol_type = transcribed RNA
                        organism = Homo sapiens
SEQUENCE: 277
cccgggacct tggtccaggc gctggtctgc gtggtgctcg ggtggataag tctgatctga   60
gcaccacaca ggccgggcgc cgggaccaag ggggctc                            97

SEQ ID NO: 278          moltype = RNA   length = 67
FEATURE                 Location/Qualifiers
source                  1..67
                        mol_type = transcribed RNA
                        organism = Homo sapiens
SEQUENCE: 278
tacaggccgg ggctttgggt gagggacccc cggagtctgt cacggtctca ccccaactct   60
gccccag                                                             67

SEQ ID NO: 279          moltype = RNA   length = 69
FEATURE                 Location/Qualifiers
source                  1..69
                        mol_type = transcribed RNA
                        organism = Homo sapiens
SEQUENCE: 279
ggccctcggg cctggggttg ggggagctct gtcctgtctc actcattgct cctccctgc   60
ctggcccag                                                           69

SEQ ID NO: 280          moltype = RNA   length = 92
FEATURE                 Location/Qualifiers
source                  1..92
                        mol_type = transcribed RNA
                        organism = Homo sapiens
SEQUENCE: 280
gtcagtgtct gggcggacag ctgcaggaaa gggaagacca aggcttgctg tctgtccagt   60
ctgccaccct accctgtctg ttcttgccac ag                                 92

SEQ ID NO: 281          moltype = RNA   length = 71
FEATURE                 Location/Qualifiers
source                  1..71
                        mol_type = transcribed RNA
                        organism = Homo sapiens
SEQUENCE: 281
```

```
gtgtctgtgc cggtcccagg agaacctgca gaggcatcgg gtcagcggtg ctcctgcggg    60
ccgacactca c                                                         71

SEQ ID NO: 282            moltype = RNA   length = 79
FEATURE                   Location/Qualifiers
source                    1..79
                          mol_type = transcribed RNA
                          organism = Homo sapiens
SEQUENCE: 282
cagcctgggg aaggcttggc agggaagaca catgagcagt gcctccactt cacgcctctc    60
ccttgtctcc tttccctag                                                 79

SEQ ID NO: 283            moltype = RNA   length = 71
FEATURE                   Location/Qualifiers
source                    1..71
                          mol_type = transcribed RNA
                          organism = Homo sapiens
SEQUENCE: 283
ggtgagtggg agccggtggg gctggagtaa gggcacgccc ggggctgccc cacctgctga    60
ccaccctccc c                                                         71

SEQ ID NO: 284            moltype = RNA   length = 75
FEATURE                   Location/Qualifiers
source                    1..75
                          mol_type = transcribed RNA
                          organism = Homo sapiens
SEQUENCE: 284
aagcaagact gaggggcctc agaccgagct tttggaaaat agaaaagtct cgctctctgc    60
ccctcagcct aactt                                                     75

SEQ ID NO: 285            moltype = RNA   length = 96
FEATURE                   Location/Qualifiers
source                    1..96
                          mol_type = transcribed RNA
                          organism = Homo sapiens
SEQUENCE: 285
gctctggggc gtgccgccgc cgtcgctgcc acctccccta ccgctagtgg aagaagatgg    60
cggaaggcgg agcggcggat ctggacaccc agcggt                              96

SEQ ID NO: 286            moltype = RNA   length = 87
FEATURE                   Location/Qualifiers
source                    1..87
                          mol_type = transcribed RNA
                          organism = Homo sapiens
SEQUENCE: 286
ccctcatctc tgggcagggg cttattgtag gagtctctga agagagctgt ggactgacct    60
gctttaaccc ttccccaggt tcccatt                                        87

SEQ ID NO: 287            moltype = RNA   length = 67
FEATURE                   Location/Qualifiers
source                    1..67
                          mol_type = transcribed RNA
                          organism = Homo sapiens
SEQUENCE: 287
ccagacccct ggggctgggc aggcggaaag aggtctgaac tgcctctgcc tccttggtct    60
ccggcag                                                              67

SEQ ID NO: 288            moltype = RNA   length = 68
FEATURE                   Location/Qualifiers
source                    1..68
                          mol_type = transcribed RNA
                          organism = Homo sapiens
SEQUENCE: 288
gaatggaaga agaaggcggt cggtctgcgg gagccaggcc gcagagccat ccgccttctg    60
tccatgtc                                                             68

SEQ ID NO: 289            moltype = RNA   length = 73
FEATURE                   Location/Qualifiers
source                    1..73
                          mol_type = transcribed RNA
                          organism = Homo sapiens
SEQUENCE: 289
acctttccag ctcatcccac ctctgccacc aaaacactca tcgcggggtc agagggagtg    60
ccaaaaaagg taa                                                       73

SEQ ID NO: 290            moltype = RNA   length = 73
FEATURE                   Location/Qualifiers
source                    1..73
                          mol_type = transcribed RNA
```

-continued

```
                              organism = Homo sapiens
SEQUENCE: 290
ggcgagggga ggcgcaggct cggaaaggcg cgcgaggctc caggctcctt cccgatccac    60
cgctctcctc gct                                                       73

SEQ ID NO: 291          moltype = RNA   length = 61
FEATURE                 Location/Qualifiers
source                  1..61
                        mol_type = transcribed RNA
                        organism = Homo sapiens
SEQUENCE: 291
aactgcgggg ccagagcaga gagcccttgc acaccaccag cctctcctcc ctgtgcccca    60
g                                                                    61

SEQ ID NO: 292          moltype = RNA   length = 65
FEATURE                 Location/Qualifiers
source                  1..65
                        mol_type = transcribed RNA
                        organism = Homo sapiens
SEQUENCE: 292
gagaatgggg ggacagatgg agaggacaca ggctggcact gaggtcccct ccactttcct    60
cctag                                                                65

SEQ ID NO: 293          moltype = RNA   length = 64
FEATURE                 Location/Qualifiers
source                  1..64
                        mol_type = transcribed RNA
                        organism = Homo sapiens
SEQUENCE: 293
gaaggcgagg ggtagaagag cacaggggtt ctgataaacc cttctgcctg cattctactc    60
ccag                                                                 64

SEQ ID NO: 294          moltype = RNA   length = 62
FEATURE                 Location/Qualifiers
source                  1..62
                        mol_type = transcribed RNA
                        organism = Homo sapiens
SEQUENCE: 294
gtgggtctcg catcaggagg caaggccagg acccgctgac ccatgcctcc tgccgcggtc    60
ag                                                                   62

SEQ ID NO: 295          moltype = RNA   length = 89
FEATURE                 Location/Qualifiers
source                  1..89
                        mol_type = transcribed RNA
                        organism = Homo sapiens
SEQUENCE: 295
acctccggga cggctgggcg ccggcggccg ggagatccgc gcttcctgaa tcccggccgg    60
cccgccggc gcccgtccgc ccgcgggtc                                       89

SEQ ID NO: 296          moltype = RNA   length = 69
FEATURE                 Location/Qualifiers
source                  1..69
                        mol_type = transcribed RNA
                        organism = Homo sapiens
SEQUENCE: 296
gtgggtaggg tttgggggag agcgtgggct ggggttcagg gacaccctct caccactgcc    60
ctcccacag                                                            69

SEQ ID NO: 297          moltype = RNA   length = 62
FEATURE                 Location/Qualifiers
source                  1..62
                        mol_type = transcribed RNA
                        organism = Homo sapiens
SEQUENCE: 297
ccttctgcgg cagagctggg gtcaccagcc ctcatgtact tgtgacttct ccctgccac     60
ag                                                                   62

SEQ ID NO: 298          moltype = RNA   length = 66
FEATURE                 Location/Qualifiers
source                  1..66
                        mol_type = transcribed RNA
                        organism = Homo sapiens
SEQUENCE: 298
tcaagacggg gagtcaggca gtggtggaga tggagagccc tgagcctcca ctctcctggc    60
ccccag                                                               66

SEQ ID NO: 299          moltype = RNA   length = 93
FEATURE                 Location/Qualifiers
```

| | |
|---|---|
| source | 1..93 |
| | mol_type = transcribed RNA |
| | organism = Homo sapiens |

SEQUENCE: 299
ggcgcttttg tgcgcgcccg ggtctgttgg tgctcagagt gtggtcaggc ggctcggact 60
gagcaggtgg gtgcggggct cggaggaggc ggc 93

| | |
|---|---|
| SEQ ID NO: 300 | moltype = RNA length = 55 |
| FEATURE | Location/Qualifiers |
| source | 1..55 |
| | mol_type = transcribed RNA |
| | organism = Homo sapiens |

SEQUENCE: 300
gggggctggg gcgcggggag gtgctaggtc ggcctcggct cccgcgccgc acccc 55

| | |
|---|---|
| SEQ ID NO: 301 | moltype = RNA length = 93 |
| FEATURE | Location/Qualifiers |
| source | 1..93 |
| | mol_type = transcribed RNA |
| | organism = Homo sapiens |

SEQUENCE: 301
tacttatggc accccactcc tggtaccata gtcataagtt aggagatgtt agagctgtga 60
gtaccatgac ttaagtgtgg tggcttaaac atg 93

| | |
|---|---|
| SEQ ID NO: 302 | moltype = RNA length = 64 |
| FEATURE | Location/Qualifiers |
| source | 1..64 |
| | mol_type = transcribed RNA |
| | organism = Homo sapiens |

SEQUENCE: 302
agttcagggc cgaagggtgg aagctgctgg tgctcatctc agcctctgcc cttggcctcc 60
ccag 64

| | |
|---|---|
| SEQ ID NO: 303 | moltype = RNA length = 90 |
| FEATURE | Location/Qualifiers |
| source | 1..90 |
| | mol_type = transcribed RNA |
| | organism = Homo sapiens |

SEQUENCE: 303
gtgggtacgg cccagtgggg gggagaggga cacgccctgg gctctgccca gggtgcagcc 60
ggactgactg agcccctgtg ccgcccccag 90

| | |
|---|---|
| SEQ ID NO: 304 | moltype = RNA length = 51 |
| FEATURE | Location/Qualifiers |
| source | 1..51 |
| | mol_type = transcribed RNA |
| | organism = Homo sapiens |

SEQUENCE: 304
agagatgaag cgggggggcg gggtcttgct ctattgccta cgctgatctc a 51

| | |
|---|---|
| SEQ ID NO: 305 | moltype = RNA length = 82 |
| FEATURE | Location/Qualifiers |
| source | 1..82 |
| | mol_type = transcribed RNA |
| | organism = Homo sapiens |

SEQUENCE: 305
acctgtaggt gacagtcagg ggcggggtgt ggtggggctg gggctggccc cctcctcaca 60
cctctcctgg catcgccccc ag 82

| | |
|---|---|
| SEQ ID NO: 306 | moltype = RNA length = 73 |
| FEATURE | Location/Qualifiers |
| source | 1..73 |
| | mol_type = transcribed RNA |
| | organism = Homo sapiens |

SEQUENCE: 306
tgtatccttg aatggatttt tggagcagga gtggacacct gacccaaagg aaatcaatcc 60
ataggctagc aat 73

| | |
|---|---|
| SEQ ID NO: 307 | moltype = RNA length = 63 |
| FEATURE | Location/Qualifiers |
| source | 1..63 |
| | mol_type = transcribed RNA |
| | organism = Homo sapiens |

SEQUENCE: 307
tggtggcggc ggtagttatg ggcttctctt tctcaccagc agcccctggg ccgccgcctc 60
cct 63

| | |
|---|---|
| SEQ ID NO: 308 | moltype = RNA length = 68 |
| FEATURE | Location/Qualifiers |

| | | |
|---|---|---|
| source | 1..68<br>mol_type = transcribed RNA<br>organism = Homo sapiens | |

SEQUENCE: 308
```
ctcaggctca gtggtgcatg cttatagtcc cagccactct ggaggctgaa ggaagatggc    60
ttgagcct                                                             68
```

| | | |
|---|---|---|
| SEQ ID NO: 309<br>FEATURE<br>source | moltype = RNA  length = 80<br>Location/Qualifiers<br>1..80<br>mol_type = transcribed RNA<br>organism = Homo sapiens | |

SEQUENCE: 309
```
cgtgtgagcc cgccctgtgc ccggcccact tctgcttcct cttagcgcag gaggggtccc    60
gcactgggag gggccctcac                                                80
```

| | | |
|---|---|---|
| SEQ ID NO: 310<br>FEATURE<br>source | moltype = RNA  length = 61<br>Location/Qualifiers<br>1..61<br>mol_type = transcribed RNA<br>organism = Homo sapiens | |

SEQUENCE: 310
```
gagggcagcg tgggtgtggc ggaggcaggc gtgaccgttt gccgccctct cgctgctcta    60
g                                                                    61
```

| | | |
|---|---|---|
| SEQ ID NO: 311<br>FEATURE<br>source | moltype = RNA  length = 80<br>Location/Qualifiers<br>1..80<br>mol_type = transcribed RNA<br>organism = Homo sapiens | |

SEQUENCE: 311
```
tgagaggccg caccttgcct tgctgcccgg gccgtgcacc cgtgggcccc agggcgacgc    60
ggcgggggcg gccctagcga                                                80
```

| | | |
|---|---|---|
| SEQ ID NO: 312<br>FEATURE<br>source | moltype = RNA  length = 102<br>Location/Qualifiers<br>1..102<br>mol_type = transcribed RNA<br>organism = Homo sapiens | |

SEQUENCE: 312
```
gcttatcgag gaaaagatcg aggtgggttg gggcgggctc tggggatttg gtctcacagc    60
ccggatccca gcccacttac cttggttact ctccttcctt ct                      102
```

| | | |
|---|---|---|
| SEQ ID NO: 313<br>FEATURE<br>source | moltype = RNA  length = 86<br>Location/Qualifiers<br>1..86<br>mol_type = transcribed RNA<br>organism = Homo sapiens | |

SEQUENCE: 313
```
tttggtactt aaagagagga taccctttgt atgttcactt gattaatggc gaatatacag    60
ggggagactc tcatttgcgt atcaaa                                         86
```

| | | |
|---|---|---|
| SEQ ID NO: 314<br>FEATURE<br>source | moltype = RNA  length = 63<br>Location/Qualifiers<br>1..63<br>mol_type = transcribed RNA<br>organism = Homo sapiens | |

SEQUENCE: 314
```
cttgcccggg agaaggaggt ggcctggaga gctgctgtct ccagccgccg cctgtctcca    60
cag                                                                  63
```

| | | |
|---|---|---|
| SEQ ID NO: 315<br>FEATURE<br>source | moltype = RNA  length = 100<br>Location/Qualifiers<br>1..100<br>mol_type = transcribed RNA<br>organism = Homo sapiens | |

SEQUENCE: 315
```
agctcagggc ggctgcgcag agggctggac tcagcggcgg agctggctgc tggcctcagt    60
tctgcctctg tccaggtcct tgtgacccgc ccgtctctcc                         100
```

| | | |
|---|---|---|
| SEQ ID NO: 316<br>FEATURE<br>source | moltype = RNA  length = 73<br>Location/Qualifiers<br>1..73<br>mol_type = transcribed RNA<br>organism = Homo sapiens | |

SEQUENCE: 316
```
gtgggcgggg gcaggtgtgt ggtgggtggt ggcctgcggt gagcagggcc ctcacacctg    60
cctcgccccc cag                                                       73
```

```
SEQ ID NO: 317         moltype = RNA    length = 137
FEATURE                Location/Qualifiers
source                 1..137
                       mol_type = transcribed RNA
                       organism = Homo sapiens
SEQUENCE: 317
agccagacaa gagggtcatg gggagtcact gtcaacccag agcaggcact gccoctgcga    60
ccagcctggg gcatcggttg gggtgcaggg gtctgctggt gatgctttcc atctctttgc   120
tttgtcctga ttgtagc                                                  137

SEQ ID NO: 318         moltype = RNA    length = 85
FEATURE                Location/Qualifiers
source                 1..85
                       mol_type = transcribed RNA
                       organism = Homo sapiens
SEQUENCE: 318
ggcctgggta ggcttgcatg ggggactggg aagagaccat gaacaggtta gtccagggag    60
ttctcatcaa gcctttactc agtag                                          85

SEQ ID NO: 319         moltype = RNA    length = 68
FEATURE                Location/Qualifiers
source                 1..68
                       mol_type = transcribed RNA
                       organism = Homo sapiens
SEQUENCE: 319
gactcggctg cggtggacaa gtccggctcc agaacctgga caccgctcag ccggccgcgg    60
caggggtc                                                             68

SEQ ID NO: 320         moltype = RNA    length = 69
FEATURE                Location/Qualifiers
source                 1..69
                       mol_type = transcribed RNA
                       organism = Homo sapiens
SEQUENCE: 320
gaggagggga ggtgtgcagg gctggggtca ctgactctgc ttcccctgcc ctgcatggtg    60
tccccacag                                                            69

SEQ ID NO: 321         moltype = RNA    length = 64
FEATURE                Location/Qualifiers
source                 1..64
                       mol_type = transcribed RNA
                       organism = Homo sapiens
SEQUENCE: 321
gaggcactgg gtaggtgggg ctccagggct cctgacacct ggacctctcc tccccaggcc    60
caca                                                                 64

SEQ ID NO: 322         moltype = RNA    length = 65
FEATURE                Location/Qualifiers
source                 1..65
                       mol_type = transcribed RNA
                       organism = Homo sapiens
SEQUENCE: 322
gggtgctcgg ggcaggcggc tgggagcggc cctcacattg atggctcctg ccacctcctc    60
cgcag                                                                65

SEQ ID NO: 323         moltype = RNA    length = 86
FEATURE                Location/Qualifiers
source                 1..86
                       mol_type = transcribed RNA
                       organism = Homo sapiens
SEQUENCE: 323
attctaggtg gggagactga cggctggagg cccataagct gtctaaaact tcggccccca    60
gatttctggt ctccccactt cagaac                                         86

SEQ ID NO: 324         moltype = RNA    length = 62
FEATURE                Location/Qualifiers
source                 1..62
                       mol_type = transcribed RNA
                       organism = Homo sapiens
SEQUENCE: 324
tggcctaggg ggcggcttgt ggagtgtatg ggctgagcct tgctctgctc ccccgccccc    60
ag                                                                   62

SEQ ID NO: 325         moltype = RNA    length = 59
FEATURE                Location/Qualifiers
source                 1..59
                       mol_type = transcribed RNA
                       organism = Homo sapiens
SEQUENCE: 325
```

-continued

```
ggggccaggc agggaggtgg gaccatgggg gccttgctgt gtgaccaccg ttcctgcag      59

SEQ ID NO: 326         moltype = RNA   length = 66
FEATURE                Location/Qualifiers
source                 1..66
                       mol_type = transcribed RNA
                       organism = Homo sapiens
SEQUENCE: 326
agcagccctc ggcggcccgg ggggcgggcg gcggtgcccg tcccggggct gcgcgaggca      60
caggcg                                                                66

SEQ ID NO: 327         moltype = RNA   length = 119
FEATURE                Location/Qualifiers
source                 1..119
                       mol_type = transcribed RNA
                       organism = Homo sapiens
SEQUENCE: 327
agcctgcgcc ggagccgggg cctgagcccg ggccgcgcag gccgtgaact cgtcgagctg      60
cgcgtgcggc cggtgctcaa cctgccgggt cctggccccg cgctcccgcg cgccctgga     119

SEQ ID NO: 328         moltype = RNA   length = 80
FEATURE                Location/Qualifiers
source                 1..80
                       mol_type = transcribed RNA
                       organism = Homo sapiens
SEQUENCE: 328
cctctgtgag aaagggtgtg ggggagaggc tgtcttgtgt ctgtaagtat gccaaactta      60
ttttccccaa ggcagaggga                                                 80

SEQ ID NO: 329         moltype = RNA   length = 74
FEATURE                Location/Qualifiers
source                 1..74
                       mol_type = transcribed RNA
                       organism = Homo sapiens
SEQUENCE: 329
gcagcccggt gagcgctcgc tggcctggca gtgcgtcgga agaacagggc gggtggggcc      60
gcgcacatct ctgc                                                       74

SEQ ID NO: 330         moltype = RNA   length = 53
FEATURE                Location/Qualifiers
source                 1..53
                       mol_type = transcribed RNA
                       organism = Homo sapiens
SEQUENCE: 330
ggtgggggtt ggaggcgtgg gttttagaac ctatcccttt ctagccctga gca             53

SEQ ID NO: 331         moltype = RNA   length = 93
FEATURE                Location/Qualifiers
source                 1..93
                       mol_type = transcribed RNA
                       organism = Homo sapiens
SEQUENCE: 331
gtaaggaggg ggatgagggg tcatatctct tctcagggaa agcaggagcc cttcagcagg      60
gtcagggccc ctcatcttcc cctcctttcc cag                                  93

SEQ ID NO: 332         moltype = RNA   length = 98
FEATURE                Location/Qualifiers
source                 1..98
                       mol_type = transcribed RNA
                       organism = Homo sapiens
SEQUENCE: 332
cttggtcaat aggaaagagg tgggacctcc tggcttttcc tctgcagcat ggctcggacc      60
tagtgcaatg tttaagctcc cctctctttc ctgttcag                             98

SEQ ID NO: 333         moltype = RNA   length = 92
FEATURE                Location/Qualifiers
source                 1..92
                       mol_type = transcribed RNA
                       organism = Homo sapiens
SEQUENCE: 333
gtgagccagt ggaatggaga ggctgtgggc aggggagat gtgaaggaaa gaactaggac       60
ccattcatcc actgcattcc tgcttggccc ag                                   92

SEQ ID NO: 334         moltype = RNA   length = 94
FEATURE                Location/Qualifiers
source                 1..94
                       mol_type = transcribed RNA
                       organism = Homo sapiens
SEQUENCE: 334
```

```
cacggtgtcc cctggtggaa cctggcaggg ggagaggtaa ggtctttcag cctctccaaa    60
gcccatggtc aggtactcag gtgggggagc cctg                                94

SEQ ID NO: 335          moltype = RNA   length = 60
FEATURE                 Location/Qualifiers
source                  1..60
                        mol_type = transcribed RNA
                        organism = Homo sapiens
SEQUENCE: 335
tgtgaatgac cccttccag agccaaaatc accagggatg gaggaggggt cttgggtact     60

SEQ ID NO: 336          moltype = RNA   length = 70
FEATURE                 Location/Qualifiers
source                  1..70
                        mol_type = transcribed RNA
                        organism = Homo sapiens
SEQUENCE: 336
aaaagcctgt ccctaagtcc ctcccagcct tccagagttg gtgccaggaa ggatttaggg    60
acaggctttg                                                           70

SEQ ID NO: 337          moltype = RNA   length = 64
FEATURE                 Location/Qualifiers
source                  1..64
                        mol_type = transcribed RNA
                        organism = Homo sapiens
SEQUENCE: 337
tctgggcgag gggtgggctc tcagaggggc tggcagtact gctctgaggc ctgcctctcc    60
ccag                                                                 64

SEQ ID NO: 338          moltype = RNA   length = 75
FEATURE                 Location/Qualifiers
source                  1..75
                        mol_type = transcribed RNA
                        organism = Homo sapiens
SEQUENCE: 338
gtcagagggg ggatgtgcat gctggttggg gtgggctgcc tgtggaccaa tcagcgtgca    60
cttccccacc ctgaa                                                     75

SEQ ID NO: 339          moltype = RNA   length = 86
FEATURE                 Location/Qualifiers
source                  1..86
                        mol_type = transcribed RNA
                        organism = Homo sapiens
SEQUENCE: 339
agggagaagg gtcggggcag ggagggcagg gcaggctctg gggtgggggg tctgtgagtc    60
agccacggct ctgcccacgt ctcccc                                         86

SEQ ID NO: 340          moltype = RNA   length = 73
FEATURE                 Location/Qualifiers
source                  1..73
                        mol_type = transcribed RNA
                        organism = Homo sapiens
SEQUENCE: 340
gaaaacaacc aggtgggctt cccggagggc ggaacaccca gccccagcat ccagggctca    60
cctaccacgt ttg                                                       73

SEQ ID NO: 341          moltype = RNA   length = 77
FEATURE                 Location/Qualifiers
source                  1..77
                        mol_type = transcribed RNA
                        organism = Homo sapiens
SEQUENCE: 341
gagttgggag gttccctctc caaatgtgtc ttgatccccc accccaagac acatttggag    60
agggaccctc ccaactc                                                   77

SEQ ID NO: 342          moltype = RNA   length = 61
FEATURE                 Location/Qualifiers
source                  1..61
                        mol_type = transcribed RNA
                        organism = Homo sapiens
SEQUENCE: 342
tcacccggtg agggcgggtg gaggaggagg gtccccacca tcagccttca ctgggacggg    60
a                                                                    61

SEQ ID NO: 343          moltype = RNA   length = 119
FEATURE                 Location/Qualifiers
source                  1..119
                        mol_type = transcribed RNA
                        organism = Homo sapiens
```

```
SEQUENCE: 343
ccatgaggag ctggcagtgg gatggcctgg gggtaggagc gtggcttctg gagctagacc    60
acatgggttc agatcccagc ggtgcctcta actggccaca ggaccttggg cagtcagct    119

SEQ ID NO: 344          moltype = RNA   length = 70
FEATURE                 Location/Qualifiers
source                  1..70
                        mol_type = transcribed RNA
                        organism = Homo sapiens
SEQUENCE: 344
gtccctgggg gctgggatgg gccatggtgt gctctgatcc ccctgtggtc tcttggcccc    60
caggaactcc                                                           70

SEQ ID NO: 345          moltype = RNA   length = 74
FEATURE                 Location/Qualifiers
source                  1..74
                        mol_type = transcribed RNA
                        organism = Homo sapiens
SEQUENCE: 345
gggaggaaga agggaggagg agcggagggg cccttgtctt cccagagcct ctcccttcct    60
cccctccccc tccc                                                      74

SEQ ID NO: 346          moltype = RNA   length = 66
FEATURE                 Location/Qualifiers
source                  1..66
                        mol_type = transcribed RNA
                        organism = Homo sapiens
SEQUENCE: 346
acccaggagg cggaggaggt ggaggttgca gtgagccaag atcgtggcac tgactccagc    60
ctgggg                                                               66

SEQ ID NO: 347          moltype = RNA   length = 102
FEATURE                 Location/Qualifiers
source                  1..102
                        mol_type = transcribed RNA
                        organism = Homo sapiens
SEQUENCE: 347
gtgggagggc ccaggcgcgg gcaggggtgg gggtggcaga gcgctgtccc ggggcgggg     60
ccgaagcgcg gcgaccgtaa ctccttctgc tccgtccccc ag                       102

SEQ ID NO: 348          moltype = RNA   length = 113
FEATURE                 Location/Qualifiers
source                  1..113
                        mol_type = transcribed RNA
                        organism = Homo sapiens
SEQUENCE: 348
gccgggtggg gcggggcggc ctcaggaggg gcccagctcc cctggatgtg ctgcggtggg    60
gccggagggg cgtcacgtgc acccaagtga cgccccttct gattctgcct cag           113

SEQ ID NO: 349          moltype = RNA   length = 91
FEATURE                 Location/Qualifiers
source                  1..91
                        mol_type = transcribed RNA
                        organism = Homo sapiens
SEQUENCE: 349
acgccccccg ccccgccacc gccttggagg ctgacctctt actttcggtc ggtcttcttc    60
cctgggcttg gtttgggggc ggggggagtgt c                                  91

SEQ ID NO: 350          moltype = RNA   length = 54
FEATURE                 Location/Qualifiers
source                  1..54
                        mol_type = transcribed RNA
                        organism = Homo sapiens
SEQUENCE: 350
agcagcaggg gagagagagg agtcctctag acaccgactc tgtctcctgc agat          54

SEQ ID NO: 351          moltype = RNA   length = 136
FEATURE                 Location/Qualifiers
source                  1..136
                        mol_type = transcribed RNA
                        organism = Homo sapiens
SEQUENCE: 351
ccgcttgcct cgcccagcgc agccccggcc gctgggcgca cccgtcccgt tcgtccccgg    60
acgttgctct ctaccccggg aacgtcgaga ctggagcgcg cgaactgagc caccttcgcg    120
gaccccgaga gcggcg                                                    136

SEQ ID NO: 352          moltype = RNA   length = 80
FEATURE                 Location/Qualifiers
source                  1..80
```

```
                        mol_type = transcribed RNA
                        organism = Homo sapiens
SEQUENCE: 352
ctgcagcgtg cttctccagg ccccgcgcgc ggacagacac acggacaagt cccgccaggg    60
gctgggcgcg cgccagccgg                                                80

SEQ ID NO: 353          moltype = RNA   length = 47
FEATURE                 Location/Qualifiers
source                  1..47
                        mol_type = transcribed RNA
                        organism = Homo sapiens
SEQUENCE: 353
ctcggcgcgg ggcgcgggct ccggggttggg gcgagccaac gccgggg                 47

SEQ ID NO: 354          moltype = RNA   length = 50
FEATURE                 Location/Qualifiers
source                  1..50
                        mol_type = transcribed RNA
                        organism = Homo sapiens
SEQUENCE: 354
acccgggcgt ggtggtgggg gtgggtgcct gtaattccag ctagttggga               50

SEQ ID NO: 355          moltype = RNA   length = 67
FEATURE                 Location/Qualifiers
source                  1..67
                        mol_type = transcribed RNA
                        organism = Homo sapiens
SEQUENCE: 355
gtgaggaggg gctggcaggg accccctccaa gttggggacg gcagccagcc cctgctcacc   60
cctcgcc                                                              67

SEQ ID NO: 356          moltype = RNA   length = 106
FEATURE                 Location/Qualifiers
source                  1..106
                        mol_type = transcribed RNA
                        organism = Homo sapiens
SEQUENCE: 356
agaagaatgc ccaaccagcc ctcagttgct acagttccct gttgtttcag ctcgacaaca    60
acaggcggct gtagcaatgg ggggctggat gggcatctca atgtgc                   106

SEQ ID NO: 357          moltype = RNA   length = 82
FEATURE                 Location/Qualifiers
source                  1..82
                        mol_type = transcribed RNA
                        organism = Homo sapiens
SEQUENCE: 357
tgtgggcagg gccctgggga gctgaggctc tgggggtggc cggggctgac cctgggcctc    60
tgctccccag tgtctgaccg cg                                             82

SEQ ID NO: 358          moltype = RNA   length = 69
FEATURE                 Location/Qualifiers
source                  1..69
                        mol_type = transcribed RNA
                        organism = Homo sapiens
SEQUENCE: 358
ctttcggcca gcgggacggc atccgaggtg ggctaggctc gggcccgtgg cgggtgcggg    60
ggtgggagg                                                            69

SEQ ID NO: 359          moltype = RNA   length = 98
FEATURE                 Location/Qualifiers
source                  1..98
                        mol_type = transcribed RNA
                        organism = Homo sapiens
SEQUENCE: 359
ttgggcaagg tgcggggcta gggctaacag cagtcttact gaaggtttcc tggaaaccac    60
gcacatgctg ttgccactaa cctcaacctt actcggtc                            98

SEQ ID NO: 360          moltype = RNA   length = 80
FEATURE                 Location/Qualifiers
source                  1..80
                        mol_type = transcribed RNA
                        organism = Homo sapiens
SEQUENCE: 360
acctgaggag ccagccctcc tcccgcaccc aaacttggag cacttgacct ttggctgttg    60
gaggggggcag gctcgcgggt                                               80

SEQ ID NO: 361          moltype = RNA   length = 92
FEATURE                 Location/Qualifiers
source                  1..92
```

```
                        mol_type = transcribed RNA
                        organism = Homo sapiens
SEQUENCE: 361
cctgtccctc ctgccctgcg cctgcccagc cctcctgctc tggtgactga ggaccgccag    60
gcaggggctg gtgctgggcg gggggcggcg gg                                  92

SEQ ID NO: 362          moltype = RNA   length = 79
FEATURE                 Location/Qualifiers
source                  1..79
                        mol_type = transcribed RNA
                        organism = Homo sapiens
SEQUENCE: 362
gtgaggtggg ggccagcagg gagtgggctg ggctgggctg ggccaaggta caaggcctca    60
ccctgcatcc cgcacccag                                                 79

SEQ ID NO: 363          moltype = RNA   length = 84
FEATURE                 Location/Qualifiers
source                  1..84
                        mol_type = transcribed RNA
                        organism = Homo sapiens
SEQUENCE: 363
ccgcagccgc cgcgccgggc ccgggttggc cgctgacccc cgcggggccc ccggcggccg    60
gggcggggc ggggctgcc ccgg                                             84

SEQ ID NO: 364          moltype = RNA   length = 65
FEATURE                 Location/Qualifiers
source                  1..65
                        mol_type = transcribed RNA
                        organism = Homo sapiens
SEQUENCE: 364
agccctgggg gtggtctcta gccaaggctc tggggtctca cccttggctg gtctctgctc    60
cgcag                                                                65

SEQ ID NO: 365          moltype = RNA   length = 80
FEATURE                 Location/Qualifiers
source                  1..80
                        mol_type = transcribed RNA
                        organism = Homo sapiens
SEQUENCE: 365
ggttccggag ccccggcgcg ggcgggttct ggggtgtaga cgctgctggc cagcccgccc    60
cagccgaggt tctcggcacc                                                80

SEQ ID NO: 366          moltype = RNA   length = 97
FEATURE                 Location/Qualifiers
source                  1..97
                        mol_type = transcribed RNA
                        organism = Homo sapiens
SEQUENCE: 366
atctgagttg ggagggtccc tctccaaatg tgtcttgggg tgggggatca agacacattt    60
ggagagggaa cctcccaact cggcctctgc catcatt                             97

SEQ ID NO: 367          moltype = RNA   length = 59
FEATURE                 Location/Qualifiers
source                  1..59
                        mol_type = transcribed RNA
                        organism = Homo sapiens
SEQUENCE: 367
ctccagggag acagtgtgtg aggcctcttg ccatggcctc cctgcccgcc tctctgcag     59

SEQ ID NO: 368          moltype = RNA   length = 67
FEATURE                 Location/Qualifiers
source                  1..67
                        mol_type = transcribed RNA
                        organism = Homo sapiens
SEQUENCE: 368
gtgggagggg agaggcagca agcacacagg gcctgggact agcatgctga cctccctcct    60
gccccag                                                              67

SEQ ID NO: 369          moltype = RNA   length = 115
FEATURE                 Location/Qualifiers
source                  1..115
                        mol_type = transcribed RNA
                        organism = Homo sapiens
SEQUENCE: 369
gagcaaaaac cagagaacaa catgggagcg ttcctaaccc ctaaggcaac tggatgggag    60
acctgaccca tccagttctc tgaggggct cttgtgtgtt ctacaaggtt gttca         115

SEQ ID NO: 370          moltype = RNA   length = 86
FEATURE                 Location/Qualifiers
```

```
source                  1..86
                        mol_type = transcribed RNA
                        organism = Homo sapiens
SEQUENCE: 370
tttggtactt gaagagagga taccctttgt atgttcactt gattaatggc gaatatacag    60
ggggagactc ttatttgcgt atcaaa                                         86

SEQ ID NO: 371          moltype = RNA  length = 70
FEATURE                 Location/Qualifiers
source                  1..70
                        mol_type = transcribed RNA
                        organism = Homo sapiens
SEQUENCE: 371
tgtgcacttg ggcaggaggg accctgtatg tctccccgca gcaccgtcat cgtgtccctc    60
ttgtccacag                                                           70

SEQ ID NO: 372          moltype = RNA  length = 81
FEATURE                 Location/Qualifiers
source                  1..81
                        mol_type = transcribed RNA
                        organism = Homo sapiens
SEQUENCE: 372
tacaggtgca ggggaactgt agatgaaaag gcttggcact tgagggaaag cctcagttca    60
ttctcatttt gctcacctgt t                                              81

SEQ ID NO: 373          moltype = RNA  length = 63
FEATURE                 Location/Qualifiers
source                  1..63
                        mol_type = transcribed RNA
                        organism = Homo sapiens
SEQUENCE: 373
gagtcgagga ctggtggaag ggcctttccc ctcagaccaa ggccctggcc ccagcttctt    60
ctc                                                                  63

SEQ ID NO: 374          moltype = RNA  length = 103
FEATURE                 Location/Qualifiers
source                  1..103
                        mol_type = transcribed RNA
                        organism = Homo sapiens
SEQUENCE: 374
gtgtcggctg tggcgtgact gtccctctgt gtcccccact aggcccactg ctcagtggag    60
cgtggaggac gaggaggagg ccgtccacga gcaatgccag cat                     103

SEQ ID NO: 375          moltype = RNA  length = 67
FEATURE                 Location/Qualifiers
source                  1..67
                        mol_type = transcribed RNA
                        organism = Homo sapiens
SEQUENCE: 375
aatagattat tggtcaccac ctccagtttc tgaatttgtg agactggggt ggggcctgag    60
aatttgc                                                              67

SEQ ID NO: 376          moltype = RNA  length = 84
FEATURE                 Location/Qualifiers
source                  1..84
                        mol_type = transcribed RNA
                        organism = Homo sapiens
SEQUENCE: 376
tgtgcagtgg gaaggggggc cgatacactg tacgagagtg agtagcaggt ctcacagtga    60
accggtctct ttccctactg tgtc                                           84

SEQ ID NO: 377          moltype = RNA  length = 70
FEATURE                 Location/Qualifiers
source                  1..70
                        mol_type = transcribed RNA
                        organism = Homo sapiens
SEQUENCE: 377
aggacccagc ggggctgggc gcgcggagca gcgctgggtg cagcgcctgc gccggcagct    60
gcaagggccg                                                           70

SEQ ID NO: 378          moltype = RNA  length = 64
FEATURE                 Location/Qualifiers
source                  1..64
                        mol_type = transcribed RNA
                        organism = Homo sapiens
SEQUENCE: 378
tgctctgtag gcatgaggca gggcccaggt tccatgtgat gctgaagctc tgacattcct    60
gcag                                                                 64
```

```
SEQ ID NO: 379           moltype = RNA   length = 72
FEATURE                  Location/Qualifiers
source                   1..72
                         mol_type = transcribed RNA
                         organism = Homo sapiens
SEQUENCE: 379
ctggggagg aaggacaggc catctgctat tcgtccacca acctgacttg atcctctctt    60
ccctcctccc ag                                                       72

SEQ ID NO: 380           moltype = RNA   length = 69
FEATURE                  Location/Qualifiers
source                   1..69
                         mol_type = transcribed RNA
                         organism = Homo sapiens
SEQUENCE: 380
tggggtaggg gtgggggaat tcagggtgt cgaactcatg gctgccacct ttgtgtcccc    60
atcctgcag                                                           69

SEQ ID NO: 381           moltype = RNA   length = 70
FEATURE                  Location/Qualifiers
source                   1..70
                         mol_type = transcribed RNA
                         organism = Homo sapiens
SEQUENCE: 381
ctcgggcccg accgcgccgg cccgcacctc ccggcccgga gctgcgggct gcggtcaggg    60
cgatcccggg                                                          70

SEQ ID NO: 382           moltype = RNA   length = 82
FEATURE                  Location/Qualifiers
source                   1..82
                         mol_type = transcribed RNA
                         organism = Homo sapiens
SEQUENCE: 382
ctgactttt tagggagtag aagggtgggg agcatgaaca atgtttctca ctccctaccc    60
ctccactccc caaaaaagtc ag                                            82

SEQ ID NO: 383           moltype = RNA   length = 79
FEATURE                  Location/Qualifiers
source                   1..79
                         mol_type = transcribed RNA
                         organism = Homo sapiens
SEQUENCE: 383
gtgcagatcc ttgggagccc tgttagactc tggattttac acttggagtg aacgggcgcc    60
atcccgaggc tttgcacag                                                 79

SEQ ID NO: 384           moltype = RNA   length = 71
FEATURE                  Location/Qualifiers
source                   1..71
                         mol_type = transcribed RNA
                         organism = Homo sapiens
SEQUENCE: 384
atggagggg gtgtggagcc agggggccca ggtctacagc ttctccccgc tccctgcccc    60
catactccca g                                                        71

SEQ ID NO: 385           moltype = RNA   length = 92
FEATURE                  Location/Qualifiers
source                   1..92
                         mol_type = transcribed RNA
                         organism = Homo sapiens
SEQUENCE: 385
cgctgcgctt ctgggcccgc ggcggcgtg gggctgcccg ggccggtcga ccagcgcgcc    60
gtagctcccg aggcccgagc cgcgacccgc gg                                 92

SEQ ID NO: 386           moltype = RNA   length = 97
FEATURE                  Location/Qualifiers
source                   1..97
                         mol_type = transcribed RNA
                         organism = Homo sapiens
SEQUENCE: 386
ctcaggtgct ctggctgctt gggttcctgg catgctgatt tgtgacttaa gattaaaatc    60
acattgccag ggattaccac gcaaccacga ccttggc                             97

SEQ ID NO: 387           moltype = RNA   length = 73
FEATURE                  Location/Qualifiers
source                   1..73
                         mol_type = transcribed RNA
                         organism = Homo sapiens
SEQUENCE: 387
ggccggctgg ggttcctggg gatgggattt gcttcctgtc acaaatcaca ttgccaggga    60
```

-continued

```
tttccaaccg acc                                                         73

SEQ ID NO: 388          moltype = RNA   length = 85
FEATURE                 Location/Qualifiers
source                  1..85
                        mol_type = transcribed RNA
                        organism = Homo sapiens
SEQUENCE: 388
agggtagagg gatgaggggg aaagttctat agtcctgtaa ttagatctca ggactataga      60
actttccccc tcatccctct gccct                                            85

SEQ ID NO: 389          moltype = RNA   length = 90
FEATURE                 Location/Qualifiers
source                  1..90
                        mol_type = transcribed RNA
                        organism = Homo sapiens
SEQUENCE: 389
tctaagaaac gcagtggtct ctgaagcctg caggggcagg ccagccctgc actgaacgcc      60
tgttcttgcc aggtggcaga aggttgctgc                                       90

SEQ ID NO: 390          moltype = RNA   length = 80
FEATURE                 Location/Qualifiers
source                  1..80
                        mol_type = transcribed RNA
                        organism = Homo sapiens
SEQUENCE: 390
acctctacct cccggcagag gaggctgcag aggctggctt tccaaaactc tgcccctcc       60
gctgctgcca agtggctggt                                                  80

SEQ ID NO: 391          moltype = RNA   length = 75
FEATURE                 Location/Qualifiers
source                  1..75
                        mol_type = transcribed RNA
                        organism = Homo sapiens
SEQUENCE: 391
tcatccctgg gtggggattt gttgcattac ttgtgttcta tataaagtat tgcacttgtc      60
ccggcctgtg gaaga                                                       75

SEQ ID NO: 392          moltype = RNA   length = 109
FEATURE                 Location/Qualifiers
source                  1..109
                        mol_type = transcribed RNA
                        organism = Homo sapiens
SEQUENCE: 392
ggtcgggctc accatgacac agtgtgagac ctcgggctac aacacaggac ccgggcgctg      60
ctctgacccc tcgtgtcttg tgttgcagcc ggagggacgc aggtccgca                 109

SEQ ID NO: 393          moltype = RNA   length = 89
FEATURE                 Location/Qualifiers
source                  1..89
                        mol_type = transcribed RNA
                        organism = Homo sapiens
SEQUENCE: 393
gtcagcagtg ccttagcagc acgtaaatat tggcgttaag attctaaaat tatctccagt      60
attaactgtg ctgctgaagt aaggttgac                                        89

SEQ ID NO: 394          moltype = RNA   length = 81
FEATURE                 Location/Qualifiers
source                  1..81
                        mol_type = transcribed RNA
                        organism = Homo sapiens
SEQUENCE: 394
gttccactct agcagcacgt aaatattggc gtagtgaaat atatattaaa caccaatatt      60
actgtgctgc tttagtgtga c                                                81

SEQ ID NO: 395          moltype = RNA   length = 96
FEATURE                 Location/Qualifiers
source                  1..96
                        mol_type = transcribed RNA
                        organism = Homo sapiens
SEQUENCE: 395
cgggccccgg gcgggcggga gggacgggac gcggtgcagt gttgtttttt cccccgccaa      60
tattgcactc gtcccggcct ccggcccccc cggccc                                96

SEQ ID NO: 396          moltype = RNA   length = 84
FEATURE                 Location/Qualifiers
source                  1..84
                        mol_type = transcribed RNA
                        organism = Homo sapiens
```

```
SEQUENCE: 396
ctccccatgg ccctgtctcc caacccttgt accagtgctg ggctcagacc ctggtacagg    60
cctggggac agggacctgg ggac                                            84

SEQ ID NO: 397          moltype = RNA  length = 94
FEATURE                 Location/Qualifiers
source                  1..94
                        mol_type = transcribed RNA
                        organism = Homo sapiens
SEQUENCE: 397
cgggcagcgg gtgccaggca cggtgtcagc aggcaacatg gccgagaggc cggggcctcc    60
gggcggcgcc gtgtccgcga ccgcgtaccc tgac                                94

SEQ ID NO: 398          moltype = RNA  length = 86
FEATURE                 Location/Qualifiers
source                  1..86
                        mol_type = transcribed RNA
                        organism = Homo sapiens
SEQUENCE: 398
tgccagtctc taggtccctg agaccctta acctgtgagg acatccaggg tcacaggtga    60
ggttcttggg agcctggcgt ctggcc                                         86

SEQ ID NO: 399          moltype = RNA  length = 78
FEATURE                 Location/Qualifiers
source                  1..78
                        mol_type = transcribed RNA
                        organism = Homo sapiens
SEQUENCE: 399
cttctctacac aggttgggat cggttgcaat gctgtgtttc tgtatggtat tgcacttgtc   60
ccggcctgtt gagtttgg                                                  78

SEQ ID NO: 400          moltype = RNA  length = 93
FEATURE                 Location/Qualifiers
source                  1..93
                        mol_type = transcribed RNA
                        organism = Homo sapiens
SEQUENCE: 400
ccttccggcg tcccaggcgg ggcgccgcgg gaccgccctc gtgtctgtgg cggtgggatc    60
ccgcggccgt gttttcctgg tggcccggcc atg                                 93

SEQ ID NO: 401          moltype = RNA  length = 83
FEATURE                 Location/Qualifiers
source                  1..83
                        mol_type = transcribed RNA
                        organism = Homo sapiens
SEQUENCE: 401
gtctactccc agggtgccaa gctgtttcgt gttccctccc taggggatcc caggtagggg    60
cagcagagga cctgggcctg gac                                            83

SEQ ID NO: 402          moltype = RNA  length = 72
FEATURE                 Location/Qualifiers
source                  1..72
                        mol_type = transcribed RNA
                        organism = Homo sapiens
SEQUENCE: 402
tgtgggactg caaatgggag ctcagcacct gcctgccacc cacgcagacc agcccctgct    60
ctgttcccac ag                                                        72

SEQ ID NO: 403          moltype = RNA  length = 110
FEATURE                 Location/Qualifiers
source                  1..110
                        mol_type = transcribed RNA
                        organism = Homo sapiens
SEQUENCE: 403
gtctaccagg tgtgggccca gctttacata gttcatgctg aggccgggat ttcatgcaga    60
aaactggttg caaaaggtgc tgaagggggct ggggagcac aagggagaag              110

SEQ ID NO: 404          moltype = RNA  length = 89
FEATURE                 Location/Qualifiers
source                  1..89
                        mol_type = transcribed RNA
                        organism = Homo sapiens
SEQUENCE: 404
agcctgtggg aaagagaaga gcagggcagg gtgaaggccc ggcggagaca ctctgcccac    60
cccacaccct gcctatgggc cacacagct                                      89

SEQ ID NO: 405          moltype = RNA  length = 62
FEATURE                 Location/Qualifiers
source                  1..62
```

```
                       mol_type = transcribed RNA
                       organism = Homo sapiens
SEQUENCE: 405
gagggtggtg gaggaagagg gcagctccca tgactgcctg accgccttct ctcctccccc   60
ag                                                                  62

SEQ ID NO: 406         moltype = RNA   length = 75
FEATURE                Location/Qualifiers
source                 1..75
                       mol_type = transcribed RNA
                       organism = Homo sapiens
SEQUENCE: 406
tggagtgggg gggcaggagg ggctcaggga gaaagtgcat acagcccctg gccctctctg   60
cccttccgtc ccctg                                                    75

SEQ ID NO: 407         moltype = RNA   length = 72
FEATURE                Location/Qualifiers
source                 1..72
                       mol_type = transcribed RNA
                       organism = Homo sapiens
SEQUENCE: 407
ccaggcacac aggaaaagcg gggccctggg ttcggctgct accccaaagg ccacattctc   60
ctgtgcacac ag                                                       72

SEQ ID NO: 408         moltype = RNA   length = 153
FEATURE                Location/Qualifiers
source                 1..153
                       mol_type = transcribed RNA
                       organism = Homo sapiens
SEQUENCE: 408
gctccgcccc acgtcgcatg cgccccggga acgcgtgggg cggagcttcc ggaggccccg   60
ctctgctgcc gaccctgtgg agcggagggt gaagcctccg gatgccagtc cctcatcgct  120
ggcctggtcg cgctgtggcg aaggggggcgg agc                              153

SEQ ID NO: 409         moltype = RNA   length = 153
FEATURE                Location/Qualifiers
source                 1..153
                       mol_type = transcribed RNA
                       organism = Homo sapiens
SEQUENCE: 409
gctccgcccc acgtcgcatg cgccccggga acgcgtgggg cggagcttcc ggaggccccg   60
ccctgctgcc gaccctgtgg agcggagggt gaagcctccg gatgccagtc cctcatcgct  120
ggcccggtcg cgctgtggcg aaggggggcgg agc                              153

SEQ ID NO: 410         moltype = RNA   length = 49
FEATURE                Location/Qualifiers
source                 1..49
                       mol_type = transcribed RNA
                       organism = Homo sapiens
SEQUENCE: 410
ggtgaggcgg gggggcgagc cctgaggggc tctcgcttct ggcgccaag              49

SEQ ID NO: 411         moltype = RNA   length = 100
FEATURE                Location/Qualifiers
source                 1..100
                       mol_type = transcribed RNA
                       organism = Homo sapiens
SEQUENCE: 411
gaggtgggag gattgcttga gtcagggtgg ttgaggctgc agtaagttgt gatcatacca   60
ctgcactcca gcctgagtga cagagcaaga ccttgtctca                        100

SEQ ID NO: 412         moltype = RNA   length = 64
FEATURE                Location/Qualifiers
source                 1..64
                       mol_type = transcribed RNA
                       organism = Homo sapiens
SEQUENCE: 412
gggtgggggc ggggcggcag gggcctcccc cagtgccagg ccccattctg cttctctccc   60
agct                                                                64

SEQ ID NO: 413         moltype = RNA   length = 74
FEATURE                Location/Qualifiers
source                 1..74
                       mol_type = transcribed RNA
                       organism = Homo sapiens
SEQUENCE: 413
cctgcaggag gcagtgggcg agcaggcggg gcagcccaat gccatgggcc tgatctcacc   60
gctgcctcct tccc                                                     74
```

```
SEQ ID NO: 414          moltype = RNA   length = 60
FEATURE                 Location/Qualifiers
source                  1..60
                        mol_type = transcribed RNA
                        organism = Homo sapiens
SEQUENCE: 414
aggcctaggg ggtggcaggc tggccatcag tgtgggctaa ccctgtcctc tccctcccag    60

SEQ ID NO: 415          moltype = RNA   length = 100
FEATURE                 Location/Qualifiers
source                  1..100
                        mol_type = transcribed RNA
                        organism = Homo sapiens
SEQUENCE: 415
gtgagcgggc gcggcaggga tcgcgggcgg gtggcggcct agggcgcgga gggcggaccg    60
ggaatggcgc gccgtgcgcc gccggcgtaa ctgcggcgct                         100

SEQ ID NO: 416          moltype = RNA   length = 56
FEATURE                 Location/Qualifiers
source                  1..56
                        mol_type = transcribed RNA
                        organism = Homo sapiens
SEQUENCE: 416
gtaggcaggg gctggggttt caggttctca gtcagaacct tggcccctct ccccag        56

SEQ ID NO: 417          moltype = RNA   length = 72
FEATURE                 Location/Qualifiers
source                  1..72
                        mol_type = transcribed RNA
                        organism = Homo sapiens
SEQUENCE: 417
tctcctcgag gggtctctgc ctctacccag gactctttca tgaccaggag gctgaggccc    60
ctcacaggcg gc                                                        72

SEQ ID NO: 418          moltype = RNA   length = 68
FEATURE                 Location/Qualifiers
source                  1..68
                        mol_type = transcribed RNA
                        organism = Homo sapiens
SEQUENCE: 418
gcatcctgta ctgagctgcc ccgaggccct tcatgctgcc cagctcgggg cagctcagta    60
caggatac                                                             68

SEQ ID NO: 419          moltype = RNA   length = 64
FEATURE                 Location/Qualifiers
source                  1..64
                        mol_type = transcribed RNA
                        organism = Homo sapiens
SEQUENCE: 419
tcctgtactg agctgccccg agctgggcag catgaagggc ctcggggcag ctcagtacag    60
gatg                                                                 64

SEQ ID NO: 420          moltype = RNA   length = 54
FEATURE                 Location/Qualifiers
source                  1..54
                        mol_type = transcribed RNA
                        organism = Homo sapiens
SEQUENCE: 420
acgcgggtgc gggccggcgg ggtagaagcc acccggcccg gcccggcccg gcga           54

SEQ ID NO: 421          moltype = RNA   length = 89
FEATURE                 Location/Qualifiers
source                  1..89
                        mol_type = transcribed RNA
                        organism = Homo sapiens
SEQUENCE: 421
accatgctgt agtgtgtgta aacatcctac actctcagct gtgagctcaa ggtggctggg    60
agagggttgt ttactccttc tgccatgga                                      89

SEQ ID NO: 422          moltype = RNA   length = 85
FEATURE                 Location/Qualifiers
source                  1..85
                        mol_type = transcribed RNA
                        organism = Homo sapiens
SEQUENCE: 422
gtgagctgct ggggacgcgg gtcgggtct gcagggcggt gcggcagccg ccacctgacg     60
ccgcgccttt gtctgtgtcc cacag                                          85

SEQ ID NO: 423          moltype = RNA   length = 71
```

```
FEATURE                 Location/Qualifiers
source                  1..71
                        mol_type = transcribed RNA
                        organism = Homo sapiens
SEQUENCE: 423
gggtaaaggg gcagggacgg gtggccccag gaagaagggc ctggtggagc cgctcttctc    60
cctgcccaca g                                                        71

SEQ ID NO: 424          moltype = RNA   length = 73
FEATURE                 Location/Qualifiers
source                  1..73
                        mol_type = transcribed RNA
                        organism = Homo sapiens
SEQUENCE: 424
ggggaggtac ctgggacagg aggaggaggc agccttgcct cagaaaccaa actgtcaaaa    60
gtgtaggttc cac                                                      73

SEQ ID NO: 425          moltype = RNA   length = 90
FEATURE                 Location/Qualifiers
source                  1..90
                        mol_type = transcribed RNA
                        organism = Homo sapiens
SEQUENCE: 425
cgggcgggc gggtccggcc gcctccgagc ccggccggca gccccggcc ttaaagcgcg      60
ggctgtccgg aggggtcggc tttcccaccg                                    90

SEQ ID NO: 426          moltype = RNA   length = 83
FEATURE                 Location/Qualifiers
source                  1..83
                        mol_type = transcribed RNA
                        organism = Homo sapiens
SEQUENCE: 426
acggcatctt tgcactcagc aggcaggctg gtgcagcccg tggtggggga ccatcctgcc    60
tgctgtgggg taaggacggc tgt                                           83

SEQ ID NO: 427          moltype = RNA   length = 63
FEATURE                 Location/Qualifiers
source                  1..63
                        mol_type = transcribed RNA
                        organism = Homo sapiens
SEQUENCE: 427
gaggtgtagg ggaggttggg ccagggatgc cttcactgtg tctctctggt cttgccaccc    60
cag                                                                 63

SEQ ID NO: 428          moltype = RNA   length = 72
FEATURE                 Location/Qualifiers
source                  1..72
                        mol_type = transcribed RNA
                        organism = Homo sapiens
SEQUENCE: 428
ctgtgcacct gggggagtgc agtgattgtg gaatgcaaag tcccacaatc actgtactcc    60
ccaggtgcac ag                                                       72

SEQ ID NO: 429          moltype = RNA   length = 67
FEATURE                 Location/Qualifiers
source                  1..67
                        mol_type = transcribed RNA
                        organism = Homo sapiens
SEQUENCE: 429
gtggcactca aactgtgggg gcactttctg ctctctggtg aaagtgccgc catcttttga    60
gtgttac                                                             67

SEQ ID NO: 430          moltype = RNA   length = 62
FEATURE                 Location/Qualifiers
source                  1..62
                        mol_type = transcribed RNA
                        organism = Homo sapiens
SEQUENCE: 430
ggtaggggc gggctccggc gctgggaccc cactagggtg gcgccttggc cccgcccgc      60
cc                                                                  62

SEQ ID NO: 431          moltype = RNA   length = 82
FEATURE                 Location/Qualifiers
source                  1..82
                        mol_type = transcribed RNA
                        organism = Homo sapiens
SEQUENCE: 431
gtgagtggga ggcagggca cggcagggggg agctgcaggg ctatgggagg ggccccagcg    60
tctgagccct gtcctcccgc ag                                            82
```

```
SEQ ID NO: 432         moltype = RNA   length = 82
FEATURE                Location/Qualifiers
source                 1..82
                       mol_type = transcribed RNA
                       organism = Homo sapiens
SEQUENCE: 432
gtgagtggga ggccagggca cggcaggggg agctgcaggg ctatgggagg ggccccagcg      60
tctgagccct gtcctcccgc ag                                              82

SEQ ID NO: 433         moltype = RNA   length = 81
FEATURE                Location/Qualifiers
source                 1..81
                       mol_type = transcribed RNA
                       organism = Homo sapiens
SEQUENCE: 433
agttggtggg ggagccatga gataagagca cctcctagag aatgttgaac taaaggtgcc      60
ctctctggct cctccccaaa g                                               81

SEQ ID NO: 434         moltype = RNA   length = 68
FEATURE                Location/Qualifiers
source                 1..68
                       mol_type = transcribed RNA
                       organism = Homo sapiens
SEQUENCE: 434
ctccggtgcc tactgagctg atatcagttc tcattttaca cactggctca gttcagcagg      60
aacaggag                                                              68

SEQ ID NO: 435         moltype = RNA   length = 73
FEATURE                Location/Qualifiers
source                 1..73
                       mol_type = transcribed RNA
                       organism = Homo sapiens
SEQUENCE: 435
ctctgcctcc cgtgcctact gagctgaaac acagttggtt tgtgtacact ggctcagttc      60
agcaggaaca ggg                                                        73

SEQ ID NO: 436         moltype = RNA   length = 83
FEATURE                Location/Qualifiers
source                 1..83
                       mol_type = transcribed RNA
                       organism = Homo sapiens
SEQUENCE: 436
gtgagtggga gccccagtgt gtggttgggg ccatggcggg tgggcagccc agcctctgag      60
ccttcctcgt ctgtctgccc cag                                             83

SEQ ID NO: 437         moltype = RNA   length = 67
FEATURE                Location/Qualifiers
source                 1..67
                       mol_type = transcribed RNA
                       organism = Homo sapiens
SEQUENCE: 437
gcgccctccc tctctccccg gtgtgcaaat gtgtgtgtgc ggtgttatgc cggacaagag      60
ggaggtg                                                               67

SEQ ID NO: 438         moltype = RNA   length = 58
FEATURE                Location/Qualifiers
source                 1..58
                       mol_type = transcribed RNA
                       organism = Homo sapiens
SEQUENCE: 438
gctgaagctc taaggttccg cctgcgggca ggaagcggag gaaccttgga gcttcggc       58

SEQ ID NO: 439         moltype = RNA   length = 80
FEATURE                Location/Qualifiers
source                 1..80
                       mol_type = transcribed RNA
                       organism = Homo sapiens
SEQUENCE: 439
gagaggccaa gaccttggga atgggggtaa gggccttctg agcccaggtc cgaactctcc      60
attcctctgc agagcgctct                                                 80

SEQ ID NO: 440         moltype = RNA   length = 64
FEATURE                Location/Qualifiers
source                 1..64
                       mol_type = transcribed RNA
                       organism = Homo sapiens
SEQUENCE: 440
ccccgggccc ggcgttccct cccctccgt gcgccagtgg aggccggggt ggggcgggc       60
```

```
gggg                                                              64

SEQ ID NO: 441          moltype = RNA    length = 64
FEATURE                 Location/Qualifiers
source                  1..64
                        mol_type = transcribed RNA
                        organism = Homo sapiens
SEQUENCE: 441
ccccgggccc ggcgttccct cccttccgt gcgccagtgg aggccggggt ggggcggggc   60
gggg                                                              64

SEQ ID NO: 442          moltype = RNA    length = 85
FEATURE                 Location/Qualifiers
source                  1..85
                        mol_type = transcribed RNA
                        organism = Homo sapiens
SEQUENCE: 442
ggggaggtag ggaaaaggaa gggggaggag aaggtgagac caatgtcctg ggtgccactc   60
ctgcccagtg cctcccttcc tcgtt                                       85

SEQ ID NO: 443          moltype = RNA    length = 73
FEATURE                 Location/Qualifiers
source                  1..73
                        mol_type = transcribed RNA
                        organism = Homo sapiens
SEQUENCE: 443
gttcaagtgg gaggacagga ggcaggtgtg gttggaggaa gcagcctgaa cctgcctccc   60
tgacattcca cag                                                    73

SEQ ID NO: 444          moltype = RNA    length = 98
FEATURE                 Location/Qualifiers
source                  1..98
                        mol_type = transcribed RNA
                        organism = Homo sapiens
SEQUENCE: 444
agaatgggca aatgaacagt aaatttggag gcctggggcc ctccctgctg ctggagaagt   60
gtttgcacgg gtgggccttg tctttgaaag gaggtgga                         98

SEQ ID NO: 445          moltype = RNA    length = 60
FEATURE                 Location/Qualifiers
source                  1..60
                        mol_type = transcribed RNA
                        organism = Homo sapiens
SEQUENCE: 445
cgctgggtcc gcgcgcctg ggccgggcga tgtccgcttg ggggagcgag gggcggggcg    60

SEQ ID NO: 446          moltype = RNA    length = 23
FEATURE                 Location/Qualifiers
source                  1..23
                        mol_type = transcribed RNA
                        organism = Homo sapiens
SEQUENCE: 446
ctcctggggc ccgcactctc gct                                         23

SEQ ID NO: 447          moltype = RNA    length = 18
FEATURE                 Location/Qualifiers
source                  1..18
                        mol_type = transcribed RNA
                        organism = Homo sapiens
SEQUENCE: 447
ctcctggggc ccgcactc                                               18

SEQ ID NO: 448          moltype = RNA    length = 21
FEATURE                 Location/Qualifiers
source                  1..21
                        mol_type = transcribed RNA
                        organism = Homo sapiens
SEQUENCE: 448
caactctgat ctcttcatct a                                           21

SEQ ID NO: 449          moltype = RNA    length = 20
FEATURE                 Location/Qualifiers
source                  1..20
                        mol_type = transcribed RNA
                        organism = Homo sapiens
SEQUENCE: 449
tctcttcatc tacccccag                                              20

SEQ ID NO: 450          moltype = RNA    length = 23
```

```
                          -continued
FEATURE                 Location/Qualifiers
source                  1..23
                        mol_type = transcribed RNA
                        organism = Homo sapiens
SEQUENCE: 450
ggtgggtgag gtcgggcccc aag                                          23

SEQ ID NO: 451          moltype = RNA   length = 20
FEATURE                 Location/Qualifiers
source                  1..20
                        mol_type = transcribed RNA
                        organism = Homo sapiens
SEQUENCE: 451
cggggtgggt gaggtcgggc                                              20

SEQ ID NO: 452          moltype = RNA   length = 26
FEATURE                 Location/Qualifiers
source                  1..26
                        mol_type = transcribed RNA
                        organism = Homo sapiens
SEQUENCE: 452
ccttctggag aggctttgtg cggata                                       26

SEQ ID NO: 453          moltype = RNA   length = 15
FEATURE                 Location/Qualifiers
source                  1..15
                        mol_type = transcribed RNA
                        organism = Homo sapiens
SEQUENCE: 453
ccttctggag aggct                                                   15

SEQ ID NO: 454          moltype = RNA   length = 20
FEATURE                 Location/Qualifiers
source                  1..20
                        mol_type = transcribed RNA
                        organism = Homo sapiens
SEQUENCE: 454
ggctggtcag atgggagtgg                                              20

SEQ ID NO: 455          moltype = RNA   length = 20
FEATURE                 Location/Qualifiers
source                  1..20
                        mol_type = transcribed RNA
                        organism = Homo sapiens
SEQUENCE: 455
ggctggtcag atgggagtgg                                              20

SEQ ID NO: 456          moltype = RNA   length = 26
FEATURE                 Location/Qualifiers
source                  1..26
                        mol_type = transcribed RNA
                        organism = Homo sapiens
SEQUENCE: 456
aggagggagg agatgggcca agttcc                                       26

SEQ ID NO: 457          moltype = RNA   length = 15
FEATURE                 Location/Qualifiers
source                  1..15
                        mol_type = transcribed RNA
                        organism = Homo sapiens
SEQUENCE: 457
gggaggaggg aggag                                                   15

SEQ ID NO: 458          moltype = RNA   length = 21
FEATURE                 Location/Qualifiers
source                  1..21
                        mol_type = transcribed RNA
                        organism = Homo sapiens
SEQUENCE: 458
cttcccccca gtaatcttca t                                            21

SEQ ID NO: 459          moltype = RNA   length = 21
FEATURE                 Location/Qualifiers
source                  1..21
                        mol_type = transcribed RNA
                        organism = Homo sapiens
SEQUENCE: 459
cttcccccca gtaatcttca t                                            21
```

```
SEQ ID NO: 460         moltype = RNA  length = 21
FEATURE                Location/Qualifiers
source                 1..21
                       mol_type = transcribed RNA
                       organism = Homo sapiens
SEQUENCE: 460
cggatccgag tcacggcacc a                                                  21

SEQ ID NO: 461         moltype = RNA  length = 15
FEATURE                Location/Qualifiers
source                 1..15
                       mol_type = transcribed RNA
                       organism = Homo sapiens
SEQUENCE: 461
ggatccgagt cacgg                                                         15

SEQ ID NO: 462         moltype = RNA  length = 21
FEATURE                Location/Qualifiers
source                 1..21
                       mol_type = transcribed RNA
                       organism = Homo sapiens
SEQUENCE: 462
cccaggctgg agcgagtgca g                                                  21

SEQ ID NO: 463         moltype = RNA  length = 15
FEATURE                Location/Qualifiers
source                 1..15
                       mol_type = transcribed RNA
                       organism = Homo sapiens
SEQUENCE: 463
agctcactgc agcct                                                         15

SEQ ID NO: 464         moltype = RNA  length = 17
FEATURE                Location/Qualifiers
source                 1..17
                       mol_type = transcribed RNA
                       organism = Homo sapiens
SEQUENCE: 464
tcctagtcac ggcacca                                                       17

SEQ ID NO: 465         moltype = RNA  length = 17
FEATURE                Location/Qualifiers
source                 1..17
                       mol_type = transcribed RNA
                       organism = Homo sapiens
SEQUENCE: 465
tcctagtcac ggcacca                                                       17

SEQ ID NO: 466         moltype = RNA  length = 24
FEATURE                Location/Qualifiers
source                 1..24
                       mol_type = transcribed RNA
                       organism = Homo sapiens
SEQUENCE: 466
gaggctggga aggcaaaggg acgt                                               24

SEQ ID NO: 467         moltype = RNA  length = 15
FEATURE                Location/Qualifiers
source                 1..15
                       mol_type = transcribed RNA
                       organism = Homo sapiens
SEQUENCE: 467
gaaggaggct gggaa                                                         15

SEQ ID NO: 468         moltype = RNA  length = 21
FEATURE                Location/Qualifiers
source                 1..21
                       mol_type = transcribed RNA
                       organism = Homo sapiens
SEQUENCE: 468
gaggcgatgt ggggatgtag a                                                  21

SEQ ID NO: 469         moltype = RNA  length = 20
FEATURE                Location/Qualifiers
source                 1..20
                       mol_type = transcribed RNA
                       organism = Homo sapiens
SEQUENCE: 469
cccagtctca tttcctcatc                                                    20
```

```
SEQ ID NO: 470          moltype = RNA   length = 23
FEATURE                 Location/Qualifiers
source                  1..23
                        mol_type = transcribed RNA
                        organism = Homo sapiens
SEQUENCE: 470
gcccggccg tgcctgaggt ttc                                                  23

SEQ ID NO: 471          moltype = RNA   length = 15
FEATURE                 Location/Qualifiers
source                  1..15
                        mol_type = transcribed RNA
                        organism = Homo sapiens
SEQUENCE: 471
ggcggtggga tcccg                                                          15

SEQ ID NO: 472          moltype = RNA   length = 16
FEATURE                 Location/Qualifiers
source                  1..16
                        mol_type = transcribed RNA
                        organism = Homo sapiens
SEQUENCE: 472
ctgggggtcc cccgac                                                         16

SEQ ID NO: 473          moltype = RNA   length = 15
FEATURE                 Location/Qualifiers
source                  1..15
                        mol_type = transcribed RNA
                        organism = Homo sapiens
SEQUENCE: 473
gtgtggagct ggggc                                                          15

SEQ ID NO: 474          moltype = RNA   length = 25
FEATURE                 Location/Qualifiers
source                  1..25
                        mol_type = transcribed RNA
                        organism = Homo sapiens
SEQUENCE: 474
agcggggagg aagtgggcgc tgctt                                               25

SEQ ID NO: 475          moltype = RNA   length = 21
FEATURE                 Location/Qualifiers
source                  1..21
                        mol_type = transcribed RNA
                        organism = Homo sapiens
SEQUENCE: 475
agcggggagg aagtgggcgc t                                                   21

SEQ ID NO: 476          moltype = RNA   length = 27
FEATURE                 Location/Qualifiers
source                  1..27
                        mol_type = transcribed RNA
                        organism = Homo sapiens
SEQUENCE: 476
aaaccgttac cattactgag tttagta                                             27

SEQ ID NO: 477          moltype = RNA   length = 15
FEATURE                 Location/Qualifiers
source                  1..15
                        mol_type = transcribed RNA
                        organism = Homo sapiens
SEQUENCE: 477
gaaaccgtta ccatt                                                          15

SEQ ID NO: 478          moltype = RNA   length = 22
FEATURE                 Location/Qualifiers
source                  1..22
                        mol_type = transcribed RNA
                        organism = Homo sapiens
SEQUENCE: 478
caggcacggg agctcaggtg ag                                                  22

SEQ ID NO: 479          moltype = RNA   length = 17
FEATURE                 Location/Qualifiers
source                  1..17
                        mol_type = transcribed RNA
                        organism = Homo sapiens
SEQUENCE: 479
```

-continued

```
caggcacggg agctcag                                              17

SEQ ID NO: 480         moltype = RNA   length = 23
FEATURE                Location/Qualifiers
source                 1..23
                       mol_type = transcribed RNA
                       organism = Homo sapiens
SEQUENCE: 480
gggggtcccc ggtgctcgga tct                                       23

SEQ ID NO: 481         moltype = RNA   length = 16
FEATURE                Location/Qualifiers
source                 1..16
                       mol_type = transcribed RNA
                       organism = Homo sapiens
SEQUENCE: 481
tcgggagggg cgggag                                               16

SEQ ID NO: 482         moltype = RNA   length = 23
FEATURE                Location/Qualifiers
source                 1..23
                       mol_type = transcribed RNA
                       organism = Homo sapiens
SEQUENCE: 482
cggggccgta gcactgtctg aga                                       23

SEQ ID NO: 483         moltype = RNA   length = 20
FEATURE                Location/Qualifiers
source                 1..20
                       mol_type = transcribed RNA
                       organism = Homo sapiens
SEQUENCE: 483
cggggccgta gcactgtctg                                           20

SEQ ID NO: 484         moltype = RNA   length = 20
FEATURE                Location/Qualifiers
source                 1..20
                       mol_type = transcribed RNA
                       organism = Homo sapiens
SEQUENCE: 484
atcccaccac tgccaccatt                                           20

SEQ ID NO: 485         moltype = RNA   length = 15
FEATURE                Location/Qualifiers
source                 1..15
                       mol_type = transcribed RNA
                       organism = Homo sapiens
SEQUENCE: 485
atcccaccac tgcca                                                15

SEQ ID NO: 486         moltype = RNA   length = 23
FEATURE                Location/Qualifiers
source                 1..23
                       mol_type = transcribed RNA
                       organism = Homo sapiens
SEQUENCE: 486
acaggagtgg gggtgggaca taa                                       23

SEQ ID NO: 487         moltype = RNA   length = 20
FEATURE                Location/Qualifiers
source                 1..20
                       mol_type = transcribed RNA
                       organism = Homo sapiens
SEQUENCE: 487
acaggagtgg gggtgggaca                                           20

SEQ ID NO: 488         moltype = RNA   length = 23
FEATURE                Location/Qualifiers
source                 1..23
                       mol_type = transcribed RNA
                       organism = Homo sapiens
SEQUENCE: 488
ctgggggacg cgtgagcgcg agc                                       23

SEQ ID NO: 489         moltype = RNA   length = 21
FEATURE                Location/Qualifiers
source                 1..21
                       mol_type = transcribed RNA
                       organism = Homo sapiens
```

```
SEQUENCE: 489
ctgggggacg cgtgagcgcg a                                                        21

SEQ ID NO: 490          moltype = RNA   length = 22
FEATURE                 Location/Qualifiers
source                  1..22
                        mol_type = transcribed RNA
                        organism = Homo sapiens
SEQUENCE: 490
cgcggcgggg acggcgattg gt                                                       22

SEQ ID NO: 491          moltype = RNA   length = 17
FEATURE                 Location/Qualifiers
source                  1..17
                        mol_type = transcribed RNA
                        organism = Homo sapiens
SEQUENCE: 491
cggcggggac ggcgatt                                                             17

SEQ ID NO: 492          moltype = RNA   length = 23
FEATURE                 Location/Qualifiers
source                  1..23
                        mol_type = transcribed RNA
                        organism = Homo sapiens
SEQUENCE: 492
gagggccccc cctcaatcct gtt                                                      23

SEQ ID NO: 493          moltype = RNA   length = 16
FEATURE                 Location/Qualifiers
source                  1..16
                        mol_type = transcribed RNA
                        organism = Homo sapiens
SEQUENCE: 493
agggcccccc ctcaat                                                              16

SEQ ID NO: 494          moltype = RNA   length = 30
FEATURE                 Location/Qualifiers
source                  1..30
                        mol_type = transcribed RNA
                        organism = Homo sapiens
SEQUENCE: 494
tgaggggcag agagcgagac ttttctattt                                               30

SEQ ID NO: 495          moltype = RNA   length = 15
FEATURE                 Location/Qualifiers
source                  1..15
                        mol_type = transcribed RNA
                        organism = Homo sapiens
SEQUENCE: 495
tgaggggcag agagc                                                               15

SEQ ID NO: 496          moltype = RNA   length = 24
FEATURE                 Location/Qualifiers
source                  1..24
                        mol_type = transcribed RNA
                        organism = Homo sapiens
SEQUENCE: 496
gtgagtggga gccggtgggg ctgg                                                     24

SEQ ID NO: 497          moltype = RNA   length = 15
FEATURE                 Location/Qualifiers
source                  1..15
                        mol_type = transcribed RNA
                        organism = Homo sapiens
SEQUENCE: 497
ggggctggag taagg                                                               15

SEQ ID NO: 498          moltype = RNA   length = 23
FEATURE                 Location/Qualifiers
source                  1..23
                        mol_type = transcribed RNA
                        organism = Homo sapiens
SEQUENCE: 498
tgaggatatg gcagggaagg gga                                                      23

SEQ ID NO: 499          moltype = RNA   length = 19
FEATURE                 Location/Qualifiers
source                  1..19
                        mol_type = transcribed RNA
```

```
                        organism = Homo sapiens
SEQUENCE: 499
tgaggatatg gcagggaag                                                19

SEQ ID NO: 500          moltype = RNA   length = 23
FEATURE                 Location/Qualifiers
source                  1..23
                        mol_type = transcribed RNA
                        organism = Homo sapiens
SEQUENCE: 500
ctagtggaag aagatggcgg aag                                           23

SEQ ID NO: 501          moltype = RNA   length = 15
FEATURE                 Location/Qualifiers
source                  1..15
                        mol_type = transcribed RNA
                        organism = Homo sapiens
SEQUENCE: 501
tagtggaaga agatg                                                    15

SEQ ID NO: 502          moltype = RNA   length = 25
FEATURE                 Location/Qualifiers
source                  1..25
                        mol_type = transcribed RNA
                        organism = Homo sapiens
SEQUENCE: 502
tgggcagggg cttattgtag gagtc                                         25

SEQ ID NO: 503          moltype = RNA   length = 19
FEATURE                 Location/Qualifiers
source                  1..19
                        mol_type = transcribed RNA
                        organism = Homo sapiens
SEQUENCE: 503
tgggcagggg cttattgta                                                19

SEQ ID NO: 504          moltype = RNA   length = 23
FEATURE                 Location/Qualifiers
source                  1..23
                        mol_type = transcribed RNA
                        organism = Homo sapiens
SEQUENCE: 504
agaagaaggc ggtcggtctg cgg                                           23

SEQ ID NO: 505          moltype = RNA   length = 21
FEATURE                 Location/Qualifiers
source                  1..21
                        mol_type = transcribed RNA
                        organism = Homo sapiens
SEQUENCE: 505
aagaaggcgg tcggtctgcg g                                             21

SEQ ID NO: 506          moltype = RNA   length = 20
FEATURE                 Location/Qualifiers
source                  1..20
                        mol_type = transcribed RNA
                        organism = Homo sapiens
SEQUENCE: 506
atcccacctc tgccaccaaa                                               20

SEQ ID NO: 507          moltype = RNA   length = 15
FEATURE                 Location/Qualifiers
source                  1..15
                        mol_type = transcribed RNA
                        organism = Homo sapiens
SEQUENCE: 507
atcccacctc tgcca                                                    15

SEQ ID NO: 508          moltype = RNA   length = 23
FEATURE                 Location/Qualifiers
source                  1..23
                        mol_type = transcribed RNA
                        organism = Homo sapiens
SEQUENCE: 508
ggaggcgcag gctcggaaag gcg                                           23

SEQ ID NO: 509          moltype = RNA   length = 15
FEATURE                 Location/Qualifiers
source                  1..15
```

```
                            mol_type = transcribed RNA
                            organism = Homo sapiens
SEQUENCE: 509
gcaggctcgg aaagg                                                    15

SEQ ID NO: 510              moltype = RNA  length = 17
FEATURE                     Location/Qualifiers
source                      1..17
                            mol_type = transcribed RNA
                            organism = Homo sapiens
SEQUENCE: 510
cctccgggac ggctggg                                                  17

SEQ ID NO: 511              moltype = RNA  length = 15
FEATURE                     Location/Qualifiers
source                      1..15
                            mol_type = transcribed RNA
                            organism = Homo sapiens
SEQUENCE: 511
ctccgggacg gctgg                                                    15

SEQ ID NO: 512              moltype = RNA  length = 29
FEATURE                     Location/Qualifiers
source                      1..29
                            mol_type = transcribed RNA
                            organism = Homo sapiens
SEQUENCE: 512
ggtcaggcgg ctcggactga gcaggtggg                                     29

SEQ ID NO: 513              moltype = RNA  length = 15
FEATURE                     Location/Qualifiers
source                      1..15
                            mol_type = transcribed RNA
                            organism = Homo sapiens
SEQUENCE: 513
agagtgtggt caggc                                                    15

SEQ ID NO: 514              moltype = RNA  length = 15
FEATURE                     Location/Qualifiers
source                      1..15
                            mol_type = transcribed RNA
                            organism = Homo sapiens
SEQUENCE: 514
ggcgcgggga ggtgc                                                    15

SEQ ID NO: 515              moltype = RNA  length = 15
FEATURE                     Location/Qualifiers
source                      1..15
                            mol_type = transcribed RNA
                            organism = Homo sapiens
SEQUENCE: 515
ggcgcgggga ggtgc                                                    15

SEQ ID NO: 516              moltype = RNA  length = 22
FEATURE                     Location/Qualifiers
source                      1..22
                            mol_type = transcribed RNA
                            organism = Homo sapiens
SEQUENCE: 516
accccactcc tggtaccata gt                                            22

SEQ ID NO: 517              moltype = RNA  length = 15
FEATURE                     Location/Qualifiers
source                      1..15
                            mol_type = transcribed RNA
                            organism = Homo sapiens
SEQUENCE: 517
accccactcc tggta                                                    15

SEQ ID NO: 518              moltype = RNA  length = 15
FEATURE                     Location/Qualifiers
source                      1..15
                            mol_type = transcribed RNA
                            organism = Homo sapiens
SEQUENCE: 518
tgaagcgggg gggcg                                                    15

SEQ ID NO: 519              moltype = RNA  length = 15
FEATURE                     Location/Qualifiers
```

```
source                      1..15
                            mol_type = transcribed RNA
                            organism = Homo sapiens
SEQUENCE: 519
tgaagcgggg gggcg                                                         15

SEQ ID NO: 520              moltype = RNA   length = 21
FEATURE                     Location/Qualifiers
source                      1..21
                            mol_type = transcribed RNA
                            organism = Homo sapiens
SEQUENCE: 520
gaatggattt ttggagcagg a                                                  21

SEQ ID NO: 521              moltype = RNA   length = 15
FEATURE                     Location/Qualifiers
source                      1..15
                            mol_type = transcribed RNA
                            organism = Homo sapiens
SEQUENCE: 521
gaatggattt ttgga                                                         15

SEQ ID NO: 522              moltype = RNA   length = 25
FEATURE                     Location/Qualifiers
source                      1..25
                            mol_type = transcribed RNA
                            organism = Homo sapiens
SEQUENCE: 522
tgcggcggt agttatgggc ttctc                                               25

SEQ ID NO: 523              moltype = RNA   length = 25
FEATURE                     Location/Qualifiers
source                      1..25
                            mol_type = transcribed RNA
                            organism = Homo sapiens
SEQUENCE: 523
tgcggcggt agttatgggc ttctc                                               25

SEQ ID NO: 524              moltype = RNA   length = 18
FEATURE                     Location/Qualifiers
source                      1..18
                            mol_type = transcribed RNA
                            organism = Homo sapiens
SEQUENCE: 524
gaggctgaag gaagatgg                                                      18

SEQ ID NO: 525              moltype = RNA   length = 15
FEATURE                     Location/Qualifiers
source                      1..15
                            mol_type = transcribed RNA
                            organism = Homo sapiens
SEQUENCE: 525
gaggctgaag gaaga                                                         15

SEQ ID NO: 526              moltype = RNA   length = 23
FEATURE                     Location/Qualifiers
source                      1..23
                            mol_type = transcribed RNA
                            organism = Homo sapiens
SEQUENCE: 526
aggaggggtc ccgcactggg agg                                                23

SEQ ID NO: 527              moltype = RNA   length = 15
FEATURE                     Location/Qualifiers
source                      1..15
                            mol_type = transcribed RNA
                            organism = Homo sapiens
SEQUENCE: 527
tgggaggggc cctca                                                         15

SEQ ID NO: 528              moltype = RNA   length = 21
FEATURE                     Location/Qualifiers
source                      1..21
                            mol_type = transcribed RNA
                            organism = Homo sapiens
SEQUENCE: 528
gagggcagcg tgggtgtggc g                                                  21

SEQ ID NO: 529              moltype = RNA   length = 21
```

```
FEATURE                 Location/Qualifiers
source                  1..21
                        mol_type = transcribed RNA
                        organism = Homo sapiens
SEQUENCE: 529
gagggcagcg tgggtgtggc g                                           21

SEQ ID NO: 530          moltype = RNA   length = 23
FEATURE                 Location/Qualifiers
source                  1..23
                        mol_type = transcribed RNA
                        organism = Homo sapiens
SEQUENCE: 530
caccttgcct tgctgcccgg gcc                                         23

SEQ ID NO: 531          moltype = RNA   length = 22
FEATURE                 Location/Qualifiers
source                  1..22
                        mol_type = transcribed RNA
                        organism = Homo sapiens
SEQUENCE: 531
caccttgcct tgctgcccgg gc                                          22

SEQ ID NO: 532          moltype = RNA   length = 19
FEATURE                 Location/Qualifiers
source                  1..19
                        mol_type = transcribed RNA
                        organism = Homo sapiens
SEQUENCE: 532
gtgggttggg gcgggctct                                              19

SEQ ID NO: 533          moltype = RNA   length = 19
FEATURE                 Location/Qualifiers
source                  1..19
                        mol_type = transcribed RNA
                        organism = Homo sapiens
SEQUENCE: 533
gtgggttggg gcgggctct                                              19

SEQ ID NO: 534          moltype = RNA   length = 24
FEATURE                 Location/Qualifiers
source                  1..24
                        mol_type = transcribed RNA
                        organism = Homo sapiens
SEQUENCE: 534
atatacaggg ggagactctc attt                                        24

SEQ ID NO: 535          moltype = RNA   length = 15
FEATURE                 Location/Qualifiers
source                  1..15
                        mol_type = transcribed RNA
                        organism = Homo sapiens
SEQUENCE: 535
atatacaggg ggaga                                                  15

SEQ ID NO: 536          moltype = RNA   length = 26
FEATURE                 Location/Qualifiers
source                  1..26
                        mol_type = transcribed RNA
                        organism = Homo sapiens
SEQUENCE: 536
agggctggac tcagcggcgg agctgg                                      26

SEQ ID NO: 537          moltype = RNA   length = 17
FEATURE                 Location/Qualifiers
source                  1..17
                        mol_type = transcribed RNA
                        organism = Homo sapiens
SEQUENCE: 537
gcggcggagc tggctgc                                                17

SEQ ID NO: 538          moltype = RNA   length = 22
FEATURE                 Location/Qualifiers
source                  1..22
                        mol_type = transcribed RNA
                        organism = Homo sapiens
SEQUENCE: 538
gtgggcgggg gcaggtgtgt gg                                          22
```

-continued

| | | |
|---|---|---|
| SEQ ID NO: 539<br>FEATURE<br>source | moltype = RNA   length = 15<br>Location/Qualifiers<br>1..15<br>mol_type = transcribed RNA<br>organism = Homo sapiens | |
| SEQUENCE: 539<br>cgggggcagg tgtgt | | 15 |
| SEQ ID NO: 540<br>FEATURE<br>source | moltype = RNA   length = 16<br>Location/Qualifiers<br>1..16<br>mol_type = transcribed RNA<br>organism = Homo sapiens | |
| SEQUENCE: 540<br>tgctggtgat gctttc | | 16 |
| SEQ ID NO: 541<br>FEATURE<br>source | moltype = RNA   length = 16<br>Location/Qualifiers<br>1..16<br>mol_type = transcribed RNA<br>organism = Homo sapiens | |
| SEQUENCE: 541<br>tgctggtgat gctttc | | 16 |
| SEQ ID NO: 542<br>FEATURE<br>source | moltype = RNA   length = 22<br>Location/Qualifiers<br>1..22<br>mol_type = transcribed RNA<br>organism = Homo sapiens | |
| SEQUENCE: 542<br>actcggctgc ggtggacaag tc | | 22 |
| SEQ ID NO: 543<br>FEATURE<br>source | moltype = RNA   length = 20<br>Location/Qualifiers<br>1..20<br>mol_type = transcribed RNA<br>organism = Homo sapiens | |
| SEQUENCE: 543<br>actcggctgc ggtggacaag | | 20 |
| SEQ ID NO: 544<br>FEATURE<br>source | moltype = RNA   length = 18<br>Location/Qualifiers<br>1..18<br>mol_type = transcribed RNA<br>organism = Homo sapiens | |
| SEQUENCE: 544<br>tctaggtggg gagactga | | 18 |
| SEQ ID NO: 545<br>FEATURE<br>source | moltype = RNA   length = 16<br>Location/Qualifiers<br>1..16<br>mol_type = transcribed RNA<br>organism = Homo sapiens | |
| SEQUENCE: 545<br>gtggggagac tgacgg | | 16 |
| SEQ ID NO: 546<br>FEATURE<br>source | moltype = RNA   length = 26<br>Location/Qualifiers<br>1..26<br>mol_type = transcribed RNA<br>organism = Homo sapiens | |
| SEQUENCE: 546<br>gtcccggggc tgcgcgaggc acaggc | | 26 |
| SEQ ID NO: 547<br>FEATURE<br>source | moltype = RNA   length = 15<br>Location/Qualifiers<br>1..15<br>mol_type = transcribed RNA<br>organism = Homo sapiens | |
| SEQUENCE: 547<br>ggcccggggg gcggg | | 15 |
| SEQ ID NO: 548<br>FEATURE<br>source | moltype = RNA   length = 23<br>Location/Qualifiers<br>1..23<br>mol_type = transcribed RNA<br>organism = Homo sapiens | |
| SEQUENCE: 548<br>gtgggggaga ggctgtcttg tgt | | 23 |

| | | |
|---|---|---|
| SEQ ID NO: 549 | moltype = RNA   length = 15 | |
| FEATURE | Location/Qualifiers | |
| source | 1..15 | |
| | mol_type = transcribed RNA | |
| | organism = Homo sapiens | |
| SEQUENCE: 549 | | |
| gtgtgggga gaggc | | 15 |
| | | |
| SEQ ID NO: 550 | moltype = RNA   length = 17 | |
| FEATURE | Location/Qualifiers | |
| source | 1..17 | |
| | mol_type = transcribed RNA | |
| | organism = Homo sapiens | |
| SEQUENCE: 550 | | |
| ggtgagcgct cgctggc | | 17 |
| | | |
| SEQ ID NO: 551 | moltype = RNA   length = 15 | |
| FEATURE | Location/Qualifiers | |
| source | 1..15 | |
| | mol_type = transcribed RNA | |
| | organism = Homo sapiens | |
| SEQUENCE: 551 | | |
| cggtgagcgc tcgct | | 15 |
| | | |
| SEQ ID NO: 552 | moltype = RNA   length = 21 | |
| FEATURE | Location/Qualifiers | |
| source | 1..21 | |
| | mol_type = transcribed RNA | |
| | organism = Homo sapiens | |
| SEQUENCE: 552 | | |
| gttggaggcg tgggttttag a | | 21 |
| | | |
| SEQ ID NO: 553 | moltype = RNA   length = 15 | |
| FEATURE | Location/Qualifiers | |
| source | 1..15 | |
| | mol_type = transcribed RNA | |
| | organism = Homo sapiens | |
| SEQUENCE: 553 | | |
| gttggaggcg tgggt | | 15 |
| | | |
| SEQ ID NO: 554 | moltype = RNA   length = 25 | |
| FEATURE | Location/Qualifiers | |
| source | 1..25 | |
| | mol_type = transcribed RNA | |
| | organism = Homo sapiens | |
| SEQUENCE: 554 | | |
| caggaaggat ttagggacag gcttt | | 25 |
| | | |
| SEQ ID NO: 555 | moltype = RNA   length = 19 | |
| FEATURE | Location/Qualifiers | |
| source | 1..19 | |
| | mol_type = transcribed RNA | |
| | organism = Homo sapiens | |
| SEQUENCE: 555 | | |
| caggaaggat ttagggaca | | 19 |
| | | |
| SEQ ID NO: 556 | moltype = RNA   length = 15 | |
| FEATURE | Location/Qualifiers | |
| source | 1..15 | |
| | mol_type = transcribed RNA | |
| | organism = Homo sapiens | |
| SEQUENCE: 556 | | |
| tctgggcgag gggtg | | 15 |
| | | |
| SEQ ID NO: 557 | moltype = RNA   length = 15 | |
| FEATURE | Location/Qualifiers | |
| source | 1..15 | |
| | mol_type = transcribed RNA | |
| | organism = Homo sapiens | |
| SEQUENCE: 557 | | |
| tctgggcgag gggtg | | 15 |
| | | |
| SEQ ID NO: 558 | moltype = RNA   length = 23 | |
| FEATURE | Location/Qualifiers | |
| source | 1..23 | |
| | mol_type = transcribed RNA | |
| | organism = Homo sapiens | |
| SEQUENCE: 558 | | |

|  |  |  |
|---|---|---|
| gggggggatgt gcatgctggt tgg | | 23 |
| SEQ ID NO: 559<br>FEATURE<br>source | moltype = RNA   length = 15<br>Location/Qualifiers<br>1..15<br>mol_type = transcribed RNA<br>organism = Homo sapiens | |
| SEQUENCE: 559<br>atcagcgtgc acttc | | 15 |
| SEQ ID NO: 560<br>FEATURE<br>source | moltype = RNA   length = 20<br>Location/Qualifiers<br>1..20<br>mol_type = transcribed RNA<br>organism = Homo sapiens | |
| SEQUENCE: 560<br>ccccagggcg acgcggcggg | | 20 |
| SEQ ID NO: 561<br>FEATURE<br>source | moltype = RNA   length = 15<br>Location/Qualifiers<br>1..15<br>mol_type = transcribed RNA<br>organism = Homo sapiens | |
| SEQUENCE: 561<br>cgcggcgggg gcggc | | 15 |
| SEQ ID NO: 562<br>FEATURE<br>source | moltype = RNA   length = 23<br>Location/Qualifiers<br>1..23<br>mol_type = transcribed RNA<br>organism = Homo sapiens | |
| SEQUENCE: 562<br>agggtcgggg cagggagggc agg | | 23 |
| SEQ ID NO: 563<br>FEATURE<br>source | moltype = RNA   length = 15<br>Location/Qualifiers<br>1..15<br>mol_type = transcribed RNA<br>organism = Homo sapiens | |
| SEQUENCE: 563<br>gggagaaggg tcggg | | 15 |
| SEQ ID NO: 564<br>FEATURE<br>source | moltype = RNA   length = 18<br>Location/Qualifiers<br>1..18<br>mol_type = transcribed RNA<br>organism = Homo sapiens | |
| SEQUENCE: 564<br>ggtgggcttc ccggaggg | | 18 |
| SEQ ID NO: 565<br>FEATURE<br>source | moltype = RNA   length = 15<br>Location/Qualifiers<br>1..15<br>mol_type = transcribed RNA<br>organism = Homo sapiens | |
| SEQUENCE: 565<br>ggtgggcttc ccgga | | 15 |
| SEQ ID NO: 566<br>FEATURE<br>source | moltype = RNA   length = 20<br>Location/Qualifiers<br>1..20<br>mol_type = transcribed RNA<br>organism = Homo sapiens | |
| SEQUENCE: 566<br>aagacacatt tggagaggga | | 20 |
| SEQ ID NO: 567<br>FEATURE<br>source | moltype = RNA   length = 16<br>Location/Qualifiers<br>1..16<br>mol_type = transcribed RNA<br>organism = Homo sapiens | |
| SEQUENCE: 567<br>agacacattt ggagag | | 16 |
| SEQ ID NO: 568<br>FEATURE<br>source | moltype = RNA   length = 19<br>Location/Qualifiers<br>1..19<br>mol_type = transcribed RNA<br>organism = Homo sapiens | |

```
SEQUENCE: 568
gagggcgggt ggaggagga                                                    19

SEQ ID NO: 569         moltype = RNA   length = 15
FEATURE                Location/Qualifiers
source                 1..15
                       mol_type = transcribed RNA
                       organism = Homo sapiens
SEQUENCE: 569
gcgggtggag gagga                                                        15

SEQ ID NO: 570         moltype = RNA   length = 17
FEATURE                Location/Qualifiers
source                 1..17
                       mol_type = transcribed RNA
                       organism = Homo sapiens
SEQUENCE: 570
gatcccagcg gtgcctc                                                      17

SEQ ID NO: 571         moltype = RNA   length = 15
FEATURE                Location/Qualifiers
source                 1..15
                       mol_type = transcribed RNA
                       organism = Homo sapiens
SEQUENCE: 571
gatcccagcg gtgcc                                                        15

SEQ ID NO: 572         moltype = RNA   length = 23
FEATURE                Location/Qualifiers
source                 1..23
                       mol_type = transcribed RNA
                       organism = Homo sapiens
SEQUENCE: 572
aagggaggag gagcggaggg gcc                                               23

SEQ ID NO: 573         moltype = RNA   length = 15
FEATURE                Location/Qualifiers
source                 1..15
                       mol_type = transcribed RNA
                       organism = Homo sapiens
SEQUENCE: 573
gggaggagga gcgga                                                        15

SEQ ID NO: 574         moltype = RNA   length = 23
FEATURE                Location/Qualifiers
source                 1..23
                       mol_type = transcribed RNA
                       organism = Homo sapiens
SEQUENCE: 574
ccaggaggcg gaggaggtgg agg                                               23

SEQ ID NO: 575         moltype = RNA   length = 15
FEATURE                Location/Qualifiers
source                 1..15
                       mol_type = transcribed RNA
                       organism = Homo sapiens
SEQUENCE: 575
acccaggagg cggag                                                        15

SEQ ID NO: 576         moltype = RNA   length = 15
FEATURE                Location/Qualifiers
source                 1..15
                       mol_type = transcribed RNA
                       organism = Homo sapiens
SEQUENCE: 576
tggcagagcg ctgtc                                                        15

SEQ ID NO: 577         moltype = RNA   length = 15
FEATURE                Location/Qualifiers
source                 1..15
                       mol_type = transcribed RNA
                       organism = Homo sapiens
SEQUENCE: 577
tggcagagcg ctgtc                                                        15

SEQ ID NO: 578         moltype = RNA   length = 22
FEATURE                Location/Qualifiers
source                 1..22
                       mol_type = transcribed RNA
```

```
                           organism = Homo sapiens
SEQUENCE: 578
gagggttggg tggaggctct cc                                             22

SEQ ID NO: 579          moltype = RNA   length = 15
FEATURE                 Location/Qualifiers
source                  1..15
                        mol_type = transcribed RNA
                        organism = Homo sapiens
SEQUENCE: 579
gagggttggg tggag                                                     15

SEQ ID NO: 580          moltype = RNA   length = 21
FEATURE                 Location/Qualifiers
source                  1..21
                        mol_type = transcribed RNA
                        organism = Homo sapiens
SEQUENCE: 580
cagcagggga gagagaggag t                                              21

SEQ ID NO: 581          moltype = RNA   length = 20
FEATURE                 Location/Qualifiers
source                  1..20
                        mol_type = transcribed RNA
                        organism = Homo sapiens
SEQUENCE: 581
cagcagggga gagagaggag                                                20

SEQ ID NO: 582          moltype = RNA   length = 22
FEATURE                 Location/Qualifiers
source                  1..22
                        mol_type = transcribed RNA
                        organism = Homo sapiens
SEQUENCE: 582
ccgggaacgt cgagactgga gc                                             22

SEQ ID NO: 583          moltype = RNA   length = 15
FEATURE                 Location/Qualifiers
source                  1..15
                        mol_type = transcribed RNA
                        organism = Homo sapiens
SEQUENCE: 583
cgggaacgtc gagac                                                     15

SEQ ID NO: 584          moltype = RNA   length = 17
FEATURE                 Location/Qualifiers
source                  1..17
                        mol_type = transcribed RNA
                        organism = Homo sapiens
SEQUENCE: 584
aggggctggg cgcgcgc                                                   17

SEQ ID NO: 585          moltype = RNA   length = 15
FEATURE                 Location/Qualifiers
source                  1..15
                        mol_type = transcribed RNA
                        organism = Homo sapiens
SEQUENCE: 585
cagggctgg gcgcg                                                      15

SEQ ID NO: 586          moltype = RNA   length = 24
FEATURE                 Location/Qualifiers
source                  1..24
                        mol_type = transcribed RNA
                        organism = Homo sapiens
SEQUENCE: 586
cgggcgtggt ggtggggtg ggtg                                            24

SEQ ID NO: 587          moltype = RNA   length = 15
FEATURE                 Location/Qualifiers
source                  1..15
                        mol_type = transcribed RNA
                        organism = Homo sapiens
SEQUENCE: 587
cgggcgtggt ggtgg                                                     15

SEQ ID NO: 588          moltype = RNA   length = 24
FEATURE                 Location/Qualifiers
source                  1..24
```

```
                              mol_type = transcribed RNA
                              organism = Homo sapiens
SEQUENCE: 588
tggggagctg aggctctggg ggtg                                         24

SEQ ID NO: 589               moltype = RNA   length = 15
FEATURE                      Location/Qualifiers
source                       1..15
                              mol_type = transcribed RNA
                              organism = Homo sapiens
SEQUENCE: 589
ggccctgggg agctg                                                   15

SEQ ID NO: 590               moltype = RNA   length = 19
FEATURE                      Location/Qualifiers
source                       1..19
                              mol_type = transcribed RNA
                              organism = Homo sapiens
SEQUENCE: 590
tggcgggtgc gggggtggg                                               19

SEQ ID NO: 591               moltype = RNA   length = 15
FEATURE                      Location/Qualifiers
source                       1..15
                              mol_type = transcribed RNA
                              organism = Homo sapiens
SEQUENCE: 591
tggcgggtgc ggggg                                                   15

SEQ ID NO: 592               moltype = RNA   length = 25
FEATURE                      Location/Qualifiers
source                       1..25
                              mol_type = transcribed RNA
                              organism = Homo sapiens
SEQUENCE: 592
tgcggggcta gggctaacag cagtc                                        25

SEQ ID NO: 593               moltype = RNA   length = 15
FEATURE                      Location/Qualifiers
source                       1..15
                              mol_type = transcribed RNA
                              organism = Homo sapiens
SEQUENCE: 593
tgcggggcta gggct                                                   15

SEQ ID NO: 594               moltype = RNA   length = 20
FEATURE                      Location/Qualifiers
source                       1..20
                              mol_type = transcribed RNA
                              organism = Homo sapiens
SEQUENCE: 594
tggctgttgg aggggggcagg                                             20

SEQ ID NO: 595               moltype = RNA   length = 15
FEATURE                      Location/Qualifiers
source                       1..15
                              mol_type = transcribed RNA
                              organism = Homo sapiens
SEQUENCE: 595
ggaggggggca ggctc                                                  15

SEQ ID NO: 596               moltype = RNA   length = 24
FEATURE                      Location/Qualifiers
source                       1..24
                              mol_type = transcribed RNA
                              organism = Homo sapiens
SEQUENCE: 596
aggcaggggc tggtgctggg cggg                                         24

SEQ ID NO: 597               moltype = RNA   length = 15
FEATURE                      Location/Qualifiers
source                       1..15
                              mol_type = transcribed RNA
                              organism = Homo sapiens
SEQUENCE: 597
gggcgggggg cggcg                                                   15

SEQ ID NO: 598               moltype = RNA   length = 23
FEATURE                      Location/Qualifiers
```

```
source                  1..23
                        mol_type = transcribed RNA
                        organism = Homo sapiens
SEQUENCE: 598
gtgggctggg ctgggctggg cca                                               23

SEQ ID NO: 599          moltype = RNA   length = 15
FEATURE                 Location/Qualifiers
source                  1..15
                        mol_type = transcribed RNA
                        organism = Homo sapiens
SEQUENCE: 599
gggctgggct gggct                                                        15

SEQ ID NO: 600          moltype = RNA   length = 17
FEATURE                 Location/Qualifiers
source                  1..17
                        mol_type = transcribed RNA
                        organism = Homo sapiens
SEQUENCE: 600
ggggcggggg cgggggc                                                      17

SEQ ID NO: 601          moltype = RNA   length = 15
FEATURE                 Location/Qualifiers
source                  1..15
                        mol_type = transcribed RNA
                        organism = Homo sapiens
SEQUENCE: 601
cgcgccgggc ccggg                                                        15

SEQ ID NO: 602          moltype = RNA   length = 23
FEATURE                 Location/Qualifiers
source                  1..23
                        mol_type = transcribed RNA
                        organism = Homo sapiens
SEQUENCE: 602
gccccggcgc gggcgggttc tgg                                               23

SEQ ID NO: 603          moltype = RNA   length = 16
FEATURE                 Location/Qualifiers
source                  1..16
                        mol_type = transcribed RNA
                        organism = Homo sapiens
SEQUENCE: 603
ggagccccgg cgcggg                                                       16

SEQ ID NO: 604          moltype = RNA   length = 24
FEATURE                 Location/Qualifiers
source                  1..24
                        mol_type = transcribed RNA
                        organism = Homo sapiens
SEQUENCE: 604
agacacattt ggagagggaa cctc                                              24

SEQ ID NO: 605          moltype = RNA   length = 16
FEATURE                 Location/Qualifiers
source                  1..16
                        mol_type = transcribed RNA
                        organism = Homo sapiens
SEQUENCE: 605
agacacattt ggagag                                                       16

SEQ ID NO: 606          moltype = RNA   length = 22
FEATURE                 Location/Qualifiers
source                  1..22
                        mol_type = transcribed RNA
                        organism = Homo sapiens
SEQUENCE: 606
tgggagggga gaggcagcaa gc                                                22

SEQ ID NO: 607          moltype = RNA   length = 22
FEATURE                 Location/Qualifiers
source                  1..22
                        mol_type = transcribed RNA
                        organism = Homo sapiens
SEQUENCE: 607
tgggagggga gaggcagcaa gc                                                22

SEQ ID NO: 608          moltype = RNA   length = 21
```

```
FEATURE              Location/Qualifiers
source               1..21
                     mol_type = transcribed RNA
                     organism = Homo sapiens
SEQUENCE: 608
atccagttct ctgaggggc t                                              21

SEQ ID NO: 609       moltype = RNA   length = 21
FEATURE              Location/Qualifiers
source               1..21
                     mol_type = transcribed RNA
                     organism = Homo sapiens
SEQUENCE: 609
atccagttct ctgaggggc t                                              21

SEQ ID NO: 610       moltype = RNA   length = 23
FEATURE              Location/Qualifiers
source               1..23
                     mol_type = transcribed RNA
                     organism = Homo sapiens
SEQUENCE: 610
aatatacagg gggagactct tat                                           23

SEQ ID NO: 611       moltype = RNA   length = 15
FEATURE              Location/Qualifiers
source               1..15
                     mol_type = transcribed RNA
                     organism = Homo sapiens
SEQUENCE: 611
atatacaggg ggaga                                                    15

SEQ ID NO: 612       moltype = RNA   length = 24
FEATURE              Location/Qualifiers
source               1..24
                     mol_type = transcribed RNA
                     organism = Homo sapiens
SEQUENCE: 612
tcgaggactg gtggaagggc cttt                                          24

SEQ ID NO: 613       moltype = RNA   length = 16
FEATURE              Location/Qualifiers
source               1..16
                     mol_type = transcribed RNA
                     organism = Homo sapiens
SEQUENCE: 613
tcgaggactg gtggaa                                                   16

SEQ ID NO: 614       moltype = RNA   length = 18
FEATURE              Location/Qualifiers
source               1..18
                     mol_type = transcribed RNA
                     organism = Homo sapiens
SEQUENCE: 614
gagactgggg tgggcct                                                  18

SEQ ID NO: 615       moltype = RNA   length = 16
FEATURE              Location/Qualifiers
source               1..16
                     mol_type = transcribed RNA
                     organism = Homo sapiens
SEQUENCE: 615
agactggggt ggggcc                                                   16

SEQ ID NO: 616       moltype = RNA   length = 23
FEATURE              Location/Qualifiers
source               1..23
                     mol_type = transcribed RNA
                     organism = Homo sapiens
SEQUENCE: 616
gggggccgat acactgtacg aga                                           23

SEQ ID NO: 617       moltype = RNA   length = 20
FEATURE              Location/Qualifiers
source               1..20
                     mol_type = transcribed RNA
                     organism = Homo sapiens
SEQUENCE: 617
gggggccgat acactgtacg                                               20
```

```
SEQ ID NO: 618         moltype = RNA    length = 18
FEATURE                Location/Qualifiers
source                 1..18
                       mol_type = transcribed RNA
                       organism = Homo sapiens
SEQUENCE: 618
cagcggggct gggcgcgc                                                       18

SEQ ID NO: 619         moltype = RNA    length = 15
FEATURE                Location/Qualifiers
source                 1..15
                       mol_type = transcribed RNA
                       organism = Homo sapiens
SEQUENCE: 619
cagcggggct gggcg                                                          15

SEQ ID NO: 620         moltype = RNA    length = 24
FEATURE                Location/Qualifiers
source                 1..24
                       mol_type = transcribed RNA
                       organism = Homo sapiens
SEQUENCE: 620
gctgcgggct gcggtcaggg cgat                                                24

SEQ ID NO: 621         moltype = RNA    length = 20
FEATURE                Location/Qualifiers
source                 1..20
                       mol_type = transcribed RNA
                       organism = Homo sapiens
SEQUENCE: 621
gctgcgggct gcggtcaggg                                                     20

SEQ ID NO: 622         moltype = RNA    length = 23
FEATURE                Location/Qualifiers
source                 1..23
                       mol_type = transcribed RNA
                       organism = Homo sapiens
SEQUENCE: 622
agggagtaga agggtgggga gca                                                 23

SEQ ID NO: 623         moltype = RNA    length = 16
FEATURE                Location/Qualifiers
source                 1..16
                       mol_type = transcribed RNA
                       organism = Homo sapiens
SEQUENCE: 623
tagggagtag aagggt                                                         16

SEQ ID NO: 624         moltype = RNA    length = 27
FEATURE                Location/Qualifiers
source                 1..27
                       mol_type = transcribed RNA
                       organism = Homo sapiens
SEQUENCE: 624
gtgaacgggc gccatcccga ggctttg                                             27

SEQ ID NO: 625         moltype = RNA    length = 16
FEATURE                Location/Qualifiers
source                 1..16
                       mol_type = transcribed RNA
                       organism = Homo sapiens
SEQUENCE: 625
gtgaacgggc gccatc                                                         16

SEQ ID NO: 626         moltype = RNA    length = 25
FEATURE                Location/Qualifiers
source                 1..25
                       mol_type = transcribed RNA
                       organism = Homo sapiens
SEQUENCE: 626
ttctgggccc gcggcgggcg tgggg                                               25

SEQ ID NO: 627         moltype = RNA    length = 15
FEATURE                Location/Qualifiers
source                 1..15
                       mol_type = transcribed RNA
                       organism = Homo sapiens
SEQUENCE: 627
cgcggcgggc gtggg                                                          15
```

```
SEQ ID NO: 628            moltype = RNA   length = 26
FEATURE                   Location/Qualifiers
source                    1..26
                          mol_type = transcribed RNA
                          organism = Homo sapiens
SEQUENCE: 628
aaaatcacat tgccagggat taccac                                          26

SEQ ID NO: 629            moltype = RNA   length = 15
FEATURE                   Location/Qualifiers
source                    1..15
                          mol_type = transcribed RNA
                          organism = Homo sapiens
SEQUENCE: 629
aatcacattg ccagg                                                      15

SEQ ID NO: 630            moltype = RNA   length = 27
FEATURE                   Location/Qualifiers
source                    1..27
                          mol_type = transcribed RNA
                          organism = Homo sapiens
SEQUENCE: 630
atcacattgc caggatttc caaccga                                          27

SEQ ID NO: 631            moltype = RNA   length = 15
FEATURE                   Location/Qualifiers
source                    1..15
                          mol_type = transcribed RNA
                          organism = Homo sapiens
SEQUENCE: 631
aatcacattg ccagg                                                      15

SEQ ID NO: 632            moltype = RNA   length = 26
FEATURE                   Location/Qualifiers
source                    1..26
                          mol_type = transcribed RNA
                          organism = Homo sapiens
SEQUENCE: 632
gactatagaa ctttccccct catccc                                          26

SEQ ID NO: 633            moltype = RNA   length = 15
FEATURE                   Location/Qualifiers
source                    1..15
                          mol_type = transcribed RNA
                          organism = Homo sapiens
SEQUENCE: 633
aactttcccc ctcat                                                      15

SEQ ID NO: 634            moltype = RNA   length = 22
FEATURE                   Location/Qualifiers
source                    1..22
                          mol_type = transcribed RNA
                          organism = Homo sapiens
SEQUENCE: 634
cctcacacct gcctcgcccc cc                                              22

SEQ ID NO: 635            moltype = RNA   length = 15
FEATURE                   Location/Qualifiers
source                    1..15
                          mol_type = transcribed RNA
                          organism = Homo sapiens
SEQUENCE: 635
tcacacctgc ctcgc                                                      15

SEQ ID NO: 636            moltype = RNA   length = 17
FEATURE                   Location/Qualifiers
source                    1..17
                          mol_type = transcribed RNA
                          organism = Homo sapiens
SEQUENCE: 636
tgcaggggca ggccagc                                                    17

SEQ ID NO: 637            moltype = RNA   length = 17
FEATURE                   Location/Qualifiers
source                    1..17
                          mol_type = transcribed RNA
                          organism = Homo sapiens
SEQUENCE: 637
```

```
tgcaggggca ggccagc                                                       17

SEQ ID NO: 638         moltype = RNA   length = 22
FEATURE                Location/Qualifiers
source                 1..22
                       mol_type = transcribed RNA
                       organism = Homo sapiens
SEQUENCE: 638
ccggcagagg aggctgcaga gg                                                 22

SEQ ID NO: 639         moltype = RNA   length = 19
FEATURE                Location/Qualifiers
source                 1..19
                       mol_type = transcribed RNA
                       organism = Homo sapiens
SEQUENCE: 639
ccggcagagg aggctgcag                                                     19

SEQ ID NO: 640         moltype = RNA   length = 25
FEATURE                Location/Qualifiers
source                 1..25
                       mol_type = transcribed RNA
                       organism = Homo sapiens
SEQUENCE: 640
gggtggggat tgttgcatt acttg                                               25

SEQ ID NO: 641         moltype = RNA   length = 20
FEATURE                Location/Qualifiers
source                 1..20
                       mol_type = transcribed RNA
                       organism = Homo sapiens
SEQUENCE: 641
gggtggggat tgttgcatt                                                     20

SEQ ID NO: 642         moltype = RNA   length = 23
FEATURE                Location/Qualifiers
source                 1..23
                       mol_type = transcribed RNA
                       organism = Homo sapiens
SEQUENCE: 642
ggctacaaca caggacccgg gcg                                                23

SEQ ID NO: 643         moltype = RNA   length = 21
FEATURE                Location/Qualifiers
source                 1..21
                       mol_type = transcribed RNA
                       organism = Homo sapiens
SEQUENCE: 643
ggctacaaca caggacccgg g                                                  21

SEQ ID NO: 644         moltype = RNA   length = 27
FEATURE                Location/Qualifiers
source                 1..27
                       mol_type = transcribed RNA
                       organism = Homo sapiens
SEQUENCE: 644
tagcagcacg taaatattgg cgttaag                                            27

SEQ ID NO: 645         moltype = RNA   length = 15
FEATURE                Location/Qualifiers
source                 1..15
                       mol_type = transcribed RNA
                       organism = Homo sapiens
SEQUENCE: 645
tagcagcacg taaat                                                         15

SEQ ID NO: 646         moltype = RNA   length = 24
FEATURE                Location/Qualifiers
source                 1..24
                       mol_type = transcribed RNA
                       organism = Homo sapiens
SEQUENCE: 646
aatattgcac tcgtcccggc ctcc                                               24

SEQ ID NO: 647         moltype = RNA   length = 15
FEATURE                Location/Qualifiers
source                 1..15
                       mol_type = transcribed RNA
                       organism = Homo sapiens
```

```
SEQUENCE: 647
tattgcactc gtccc                                                        15

SEQ ID NO: 648          moltype = RNA   length = 24
FEATURE                 Location/Qualifiers
source                  1..24
                        mol_type = transcribed RNA
                        organism = Homo sapiens
SEQUENCE: 648
ctggtacagg cctgggggac aggg                                              24

SEQ ID NO: 649          moltype = RNA   length = 18
FEATURE                 Location/Qualifiers
source                  1..18
                        mol_type = transcribed RNA
                        organism = Homo sapiens
SEQUENCE: 649
ctggtacagg cctggggg                                                     18

SEQ ID NO: 650          moltype = RNA   length = 18
FEATURE                 Location/Qualifiers
source                  1..18
                        mol_type = transcribed RNA
                        organism = Homo sapiens
SEQUENCE: 650
ctccgggcgg cgccgtgt                                                     18

SEQ ID NO: 651          moltype = RNA   length = 18
FEATURE                 Location/Qualifiers
source                  1..18
                        mol_type = transcribed RNA
                        organism = Homo sapiens
SEQUENCE: 651
ctccgggcgg cgccgtgt                                                     18

SEQ ID NO: 652          moltype = RNA   length = 23
FEATURE                 Location/Qualifiers
source                  1..23
                        mol_type = transcribed RNA
                        organism = Homo sapiens
SEQUENCE: 652
cacaggtgag gttcttggga gcc                                               23

SEQ ID NO: 653          moltype = RNA   length = 15
FEATURE                 Location/Qualifiers
source                  1..15
                        mol_type = transcribed RNA
                        organism = Homo sapiens
SEQUENCE: 653
acaggtgagg ttctt                                                        15

SEQ ID NO: 654          moltype = RNA   length = 26
FEATURE                 Location/Qualifiers
source                  1..26
                        mol_type = transcribed RNA
                        organism = Homo sapiens
SEQUENCE: 654
agggacggga cgcggtgcag tgttgt                                            26

SEQ ID NO: 655          moltype = RNA   length = 15
FEATURE                 Location/Qualifiers
source                  1..15
                        mol_type = transcribed RNA
                        organism = Homo sapiens
SEQUENCE: 655
ggcgggcggg aggga                                                        15

SEQ ID NO: 656          moltype = RNA   length = 28
FEATURE                 Location/Qualifiers
source                  1..28
                        mol_type = transcribed RNA
                        organism = Homo sapiens
SEQUENCE: 656
gtatggtatt gcacttgtcc cggcctgt                                          28

SEQ ID NO: 657          moltype = RNA   length = 15
FEATURE                 Location/Qualifiers
source                  1..15
                        mol_type = transcribed RNA
```

```
                                  organism = Homo sapiens
SEQUENCE: 657
tattgcactt gtccc                                                             15

SEQ ID NO: 658          moltype = RNA   length = 26
FEATURE                 Location/Qualifiers
source                  1..26
                        mol_type = transcribed RNA
                        organism = Homo sapiens
SEQUENCE: 658
cggtgggatc ccgcggccgt gttttc                                                 26

SEQ ID NO: 659          moltype = RNA   length = 15
FEATURE                 Location/Qualifiers
source                  1..15
                        mol_type = transcribed RNA
                        organism = Homo sapiens
SEQUENCE: 659
ggggcgccgc gggac                                                             15

SEQ ID NO: 660          moltype = RNA   length = 23
FEATURE                 Location/Qualifiers
source                  1..23
                        mol_type = transcribed RNA
                        organism = Homo sapiens
SEQUENCE: 660
taggggcagc agaggacctg ggc                                                    23

SEQ ID NO: 661          moltype = RNA   length = 20
FEATURE                 Location/Qualifiers
source                  1..20
                        mol_type = transcribed RNA
                        organism = Homo sapiens
SEQUENCE: 661
tagggcagc agaggacctg                                                         20

SEQ ID NO: 662          moltype = RNA   length = 22
FEATURE                 Location/Qualifiers
source                  1..22
                        mol_type = transcribed RNA
                        organism = Homo sapiens
SEQUENCE: 662
tgtgggactg caaatgggag ct                                                     22

SEQ ID NO: 663          moltype = RNA   length = 22
FEATURE                 Location/Qualifiers
source                  1..22
                        mol_type = transcribed RNA
                        organism = Homo sapiens
SEQUENCE: 663
tgtgggactg caaatgggag ct                                                     22

SEQ ID NO: 664          moltype = RNA   length = 16
FEATURE                 Location/Qualifiers
source                  1..16
                        mol_type = transcribed RNA
                        organism = Homo sapiens
SEQUENCE: 664
gtgaaggccc ggcgga                                                            16

SEQ ID NO: 665          moltype = RNA   length = 15
FEATURE                 Location/Qualifiers
source                  1..15
                        mol_type = transcribed RNA
                        organism = Homo sapiens
SEQUENCE: 665
gtgaaggccc ggcgg                                                             15

SEQ ID NO: 666          moltype = RNA   length = 22
FEATURE                 Location/Qualifiers
source                  1..22
                        mol_type = transcribed RNA
                        organism = Homo sapiens
SEQUENCE: 666
gggggggcagg aggggctcag gg                                                    22

SEQ ID NO: 667          moltype = RNA   length = 16
FEATURE                 Location/Qualifiers
source                  1..16
```

```
                              mol_type = transcribed RNA
                              organism = Homo sapiens
SEQUENCE: 667
gtgggggggc aggagg                                                           16

SEQ ID NO: 668           moltype = RNA   length = 23
FEATURE                  Location/Qualifiers
source                   1..23
                         mol_type = transcribed RNA
                         organism = Homo sapiens
SEQUENCE: 668
tggggcggag cttccggagg ccc                                                   23

SEQ ID NO: 669           moltype = RNA   length = 16
FEATURE                  Location/Qualifiers
source                   1..16
                         mol_type = transcribed RNA
                         organism = Homo sapiens
SEQUENCE: 669
atcgctggcc tggtcg                                                           16

SEQ ID NO: 670           moltype = RNA   length = 26
FEATURE                  Location/Qualifiers
source                   1..26
                         mol_type = transcribed RNA
                         organism = Homo sapiens
SEQUENCE: 670
gaggggctct cgcttctggc gccaag                                                26

SEQ ID NO: 671           moltype = RNA   length = 15
FEATURE                  Location/Qualifiers
source                   1..15
                         mol_type = transcribed RNA
                         organism = Homo sapiens
SEQUENCE: 671
ggtgaggcgg ggggg                                                            15

SEQ ID NO: 672           moltype = RNA   length = 21
FEATURE                  Location/Qualifiers
source                   1..21
                         mol_type = transcribed RNA
                         organism = Homo sapiens
SEQUENCE: 672
cagcctgagt gacagagcaa g                                                     21

SEQ ID NO: 673           moltype = RNA   length = 15
FEATURE                  Location/Qualifiers
source                   1..15
                         mol_type = transcribed RNA
                         organism = Homo sapiens
SEQUENCE: 673
actgcactcc agcct                                                            15

SEQ ID NO: 674           moltype = RNA   length = 17
FEATURE                  Location/Qualifiers
source                   1..17
                         mol_type = transcribed RNA
                         organism = Homo sapiens
SEQUENCE: 674
gcggggcggc aggggcc                                                          17

SEQ ID NO: 675           moltype = RNA   length = 15
FEATURE                  Location/Qualifiers
source                   1..15
                         mol_type = transcribed RNA
                         organism = Homo sapiens
SEQUENCE: 675
gggggcgggg cggca                                                            15

SEQ ID NO: 676           moltype = RNA   length = 21
FEATURE                  Location/Qualifiers
source                   1..21
                         mol_type = transcribed RNA
                         organism = Homo sapiens
SEQUENCE: 676
aggaggcagt gggcgagcag g                                                     21

SEQ ID NO: 677           moltype = RNA   length = 21
FEATURE                  Location/Qualifiers
```

```
source                 1..21
                       mol_type = transcribed RNA
                       organism = Homo sapiens
SEQUENCE: 677
aggaggcagt gggcgagcag g                                              21

SEQ ID NO: 678         moltype = RNA   length = 16
FEATURE                Location/Qualifiers
source                 1..16
                       mol_type = transcribed RNA
                       organism = Homo sapiens
SEQUENCE: 678
ggcgcggagg gcggac                                                    16

SEQ ID NO: 679         moltype = RNA   length = 15
FEATURE                Location/Qualifiers
source                 1..15
                       mol_type = transcribed RNA
                       organism = Homo sapiens
SEQUENCE: 679
ggcgcggagg gcgga                                                     15

SEQ ID NO: 680         moltype = RNA   length = 22
FEATURE                Location/Qualifiers
source                 1..22
                       mol_type = transcribed RNA
                       organism = Homo sapiens
SEQUENCE: 680
accaggaggc tgaggcccct ca                                             22

SEQ ID NO: 681         moltype = RNA   length = 15
FEATURE                Location/Qualifiers
source                 1..15
                       mol_type = transcribed RNA
                       organism = Homo sapiens
SEQUENCE: 681
accaggaggc tgagg                                                     15

SEQ ID NO: 682         moltype = RNA   length = 23
FEATURE                Location/Qualifiers
source                 1..23
                       mol_type = transcribed RNA
                       organism = Homo sapiens
SEQUENCE: 682
cggggcagct cagtacagga tac                                            23

SEQ ID NO: 683         moltype = RNA   length = 15
FEATURE                Location/Qualifiers
source                 1..15
                       mol_type = transcribed RNA
                       organism = Homo sapiens
SEQUENCE: 683
agctcagtac aggat                                                     15

SEQ ID NO: 684         moltype = RNA   length = 19
FEATURE                Location/Qualifiers
source                 1..19
                       mol_type = transcribed RNA
                       organism = Homo sapiens
SEQUENCE: 684
gggtgcgggc cggcggggt                                                 19

SEQ ID NO: 685         moltype = RNA   length = 15
FEATURE                Location/Qualifiers
source                 1..15
                       mol_type = transcribed RNA
                       organism = Homo sapiens
SEQUENCE: 685
tgcgggccgg cgggg                                                     15

SEQ ID NO: 686         moltype = RNA   length = 27
FEATURE                Location/Qualifiers
source                 1..27
                       mol_type = transcribed RNA
                       organism = Homo sapiens
SEQUENCE: 686
caaggtggct gggagagggt tgtttac                                        27

SEQ ID NO: 687         moltype = RNA   length = 15
```

```
FEATURE              Location/Qualifiers
source               1..15
                     mol_type = transcribed RNA
                     organism = Homo sapiens
SEQUENCE: 687
gtgagctcaa ggtgg                                                    15

SEQ ID NO: 688       moltype = RNA   length = 15
FEATURE              Location/Qualifiers
source               1..15
                     mol_type = transcribed RNA
                     organism = Homo sapiens
SEQUENCE: 688
aggaggagga ggcag                                                    15

SEQ ID NO: 689       moltype = RNA   length = 15
FEATURE              Location/Qualifiers
source               1..15
                     mol_type = transcribed RNA
                     organism = Homo sapiens
SEQUENCE: 689
aggaggagga ggcag                                                    15

SEQ ID NO: 690       moltype = RNA   length = 26
FEATURE              Location/Qualifiers
source               1..26
                     mol_type = transcribed RNA
                     organism = Homo sapiens
SEQUENCE: 690
gcgggctgtc cggaggggtc ggcttt                                        26

SEQ ID NO: 691       moltype = RNA   length = 16
FEATURE              Location/Qualifiers
source               1..16
                     mol_type = transcribed RNA
                     organism = Homo sapiens
SEQUENCE: 691
gctgtccgga ggggtc                                                   16

SEQ ID NO: 692       moltype = RNA   length = 24
FEATURE              Location/Qualifiers
source               1..24
                     mol_type = transcribed RNA
                     organism = Homo sapiens
SEQUENCE: 692
tgggggagtg cagtgattgt ggaa                                          24

SEQ ID NO: 693       moltype = RNA   length = 19
FEATURE              Location/Qualifiers
source               1..19
                     mol_type = transcribed RNA
                     organism = Homo sapiens
SEQUENCE: 693
tgggggagtg cagtgattg                                                19

SEQ ID NO: 694       moltype = RNA   length = 22
FEATURE              Location/Qualifiers
source               1..22
                     mol_type = transcribed RNA
                     organism = Homo sapiens
SEQUENCE: 694
actcaaactg tgggggcact tt                                            22

SEQ ID NO: 695       moltype = RNA   length = 19
FEATURE              Location/Qualifiers
source               1..19
                     mol_type = transcribed RNA
                     organism = Homo sapiens
SEQUENCE: 695
actcaaactg tgggggcac                                                19

SEQ ID NO: 696       moltype = RNA   length = 19
FEATURE              Location/Qualifiers
source               1..19
                     mol_type = transcribed RNA
                     organism = Homo sapiens
SEQUENCE: 696
aggggcggg ctccggcgc                                                 19
```

```
SEQ ID NO: 697           moltype = RNA   length = 15
FEATURE                  Location/Qualifiers
source                   1..15
                         mol_type = transcribed RNA
                         organism = Homo sapiens
SEQUENCE: 697
gtagggggcg ggctc                                                          15

SEQ ID NO: 698           moltype = RNA   length = 19
FEATURE                  Location/Qualifiers
source                   1..19
                         mol_type = transcribed RNA
                         organism = Homo sapiens
SEQUENCE: 698
agtgggaggc cagggcacg                                                      19

SEQ ID NO: 699           moltype = RNA   length = 15
FEATURE                  Location/Qualifiers
source                   1..15
                         mol_type = transcribed RNA
                         organism = Homo sapiens
SEQUENCE: 699
aggggagct gcagg                                                           15

SEQ ID NO: 700           moltype = RNA   length = 25
FEATURE                  Location/Qualifiers
source                   1..25
                         mol_type = transcribed RNA
                         organism = Homo sapiens
SEQUENCE: 700
gggggagcca tgagataaga gcacc                                               25

SEQ ID NO: 701           moltype = RNA   length = 20
FEATURE                  Location/Qualifiers
source                   1..20
                         mol_type = transcribed RNA
                         organism = Homo sapiens
SEQUENCE: 701
tgggggagcc atgagataag                                                     20

SEQ ID NO: 702           moltype = RNA   length = 24
FEATURE                  Location/Qualifiers
source                   1..24
                         mol_type = transcribed RNA
                         organism = Homo sapiens
SEQUENCE: 702
actggctcag ttcagcagga acag                                                24

SEQ ID NO: 703           moltype = RNA   length = 15
FEATURE                  Location/Qualifiers
source                   1..15
                         mol_type = transcribed RNA
                         organism = Homo sapiens
SEQUENCE: 703
tggctcagtt cagca                                                          15

SEQ ID NO: 704           moltype = RNA   length = 20
FEATURE                  Location/Qualifiers
source                   1..20
                         mol_type = transcribed RNA
                         organism = Homo sapiens
SEQUENCE: 704
ctccccggtg tgcaaatgtg                                                     20

SEQ ID NO: 705           moltype = RNA   length = 15
FEATURE                  Location/Qualifiers
source                   1..15
                         mol_type = transcribed RNA
                         organism = Homo sapiens
SEQUENCE: 705
gtgtgcggtg ttatg                                                          15

SEQ ID NO: 706           moltype = RNA   length = 22
FEATURE                  Location/Qualifiers
source                   1..22
                         mol_type = transcribed RNA
                         organism = Homo sapiens
SEQUENCE: 706
ggcaggaagc ggaggaacct tg                                                  22
```

```
SEQ ID NO: 707           moltype = RNA   length = 17
FEATURE                  Location/Qualifiers
source                   1..17
                         mol_type = transcribed RNA
                         organism = Homo sapiens
SEQUENCE: 707
ggaggaacct tggagct                                                        17

SEQ ID NO: 708           moltype = RNA   length = 21
FEATURE                  Location/Qualifiers
source                   1..21
                         mol_type = transcribed RNA
                         organism = Homo sapiens
SEQUENCE: 708
tgggaatggg ggtaagggcc t                                                   21

SEQ ID NO: 709           moltype = RNA   length = 15
FEATURE                  Location/Qualifiers
source                   1..15
                         mol_type = transcribed RNA
                         organism = Homo sapiens
SEQUENCE: 709
cttctgagcc caggt                                                          15

SEQ ID NO: 710           moltype = RNA   length = 16
FEATURE                  Location/Qualifiers
source                   1..16
                         mol_type = transcribed RNA
                         organism = Homo sapiens
SEQUENCE: 710
cgggcccggc gttccc                                                         16

SEQ ID NO: 711           moltype = RNA   length = 15
FEATURE                  Location/Qualifiers
source                   1..15
                         mol_type = transcribed RNA
                         organism = Homo sapiens
SEQUENCE: 711
ccgggcccgg cgttc                                                          15

SEQ ID NO: 712           moltype = RNA   length = 18
FEATURE                  Location/Qualifiers
source                   1..18
                         mol_type = transcribed RNA
                         organism = Homo sapiens
SEQUENCE: 712
aaaaggaagg gggaggag                                                       18

SEQ ID NO: 713           moltype = RNA   length = 16
FEATURE                  Location/Qualifiers
source                   1..16
                         mol_type = transcribed RNA
                         organism = Homo sapiens
SEQUENCE: 713
aaggaagggg gaggag                                                         16

SEQ ID NO: 714           moltype = RNA   length = 22
FEATURE                  Location/Qualifiers
source                   1..22
                         mol_type = transcribed RNA
                         organism = Homo sapiens
SEQUENCE: 714
tagggatggg aggccaggat ga                                                  22

SEQ ID NO: 715           moltype = RNA   length = 20
FEATURE                  Location/Qualifiers
source                   1..20
                         mol_type = transcribed RNA
                         organism = Homo sapiens
SEQUENCE: 715
ggctccttgg tctaggggta                                                     20

SEQ ID NO: 716           moltype = RNA   length = 23
FEATURE                  Location/Qualifiers
source                   1..23
                         mol_type = transcribed RNA
                         organism = Homo sapiens
SEQUENCE: 716
```

```
aggaagccct ggaggggctg gag                                              23

SEQ ID NO: 718          moltype = RNA   length = 17
FEATURE                 Location/Qualifiers
source                  1..17
                        mol_type = transcribed RNA
                        organism = Homo sapiens
SEQUENCE: 717
ggggcgcggc cggatcg                                                     17

SEQ ID NO: 718          moltype = RNA   length = 22
FEATURE                 Location/Qualifiers
source                  1..22
                        mol_type = transcribed RNA
                        organism = Homo sapiens
SEQUENCE: 718
tggggaaggc gtcagtgtcg gg                                               22

SEQ ID NO: 719          moltype = RNA   length = 21
FEATURE                 Location/Qualifiers
source                  1..21
                        mol_type = transcribed RNA
                        organism = Homo sapiens
SEQUENCE: 719
aaggcagggc ccccgctccc c                                                21

SEQ ID NO: 720          moltype = RNA   length = 24
FEATURE                 Location/Qualifiers
source                  1..24
                        mol_type = transcribed RNA
                        organism = Homo sapiens
SEQUENCE: 720
gtaggggcgt cccgggcgcg cggg                                             24

SEQ ID NO: 721          moltype = RNA   length = 20
FEATURE                 Location/Qualifiers
source                  1..20
                        mol_type = transcribed RNA
                        organism = Homo sapiens
SEQUENCE: 721
aaaaggcggg agaagcccca                                                  20

SEQ ID NO: 722          moltype = RNA   length = 19
FEATURE                 Location/Qualifiers
source                  1..19
                        mol_type = transcribed RNA
                        organism = Homo sapiens
SEQUENCE: 722
cggcgcgacc ggcccgggg                                                   19

SEQ ID NO: 723          moltype = RNA   length = 23
FEATURE                 Location/Qualifiers
source                  1..23
                        mol_type = transcribed RNA
                        organism = Homo sapiens
SEQUENCE: 723
tgagtggggc tcccgggacg gcg                                              23

SEQ ID NO: 724          moltype = RNA   length = 23
FEATURE                 Location/Qualifiers
source                  1..23
                        mol_type = transcribed RNA
                        organism = Homo sapiens
SEQUENCE: 724
ctggcggagc ccattccatg cca                                              23

SEQ ID NO: 725          moltype = RNA   length = 22
FEATURE                 Location/Qualifiers
source                  1..22
                        mol_type = transcribed RNA
                        organism = Homo sapiens
SEQUENCE: 725
ctgggggtgg ggggctgggc gt                                               22

SEQ ID NO: 726          moltype = RNA   length = 23
FEATURE                 Location/Qualifiers
source                  1..23
                        mol_type = transcribed RNA
                        organism = Homo sapiens
```

```
SEQUENCE: 726
ccaggggat gggcgagctt ggg                                             23

SEQ ID NO: 727          moltype = RNA   length = 21
FEATURE                 Location/Qualifiers
source                  1..21
                        mol_type = transcribed RNA
                        organism = Homo sapiens
SEQUENCE: 727
agccgcgggg atcgccgagg g                                              21

SEQ ID NO: 728          moltype = RNA   length = 23
FEATURE                 Location/Qualifiers
source                  1..23
                        mol_type = transcribed RNA
                        organism = Homo sapiens
SEQUENCE: 728
ccccggtgtt ggggcgcgtc tgc                                            23

SEQ ID NO: 729          moltype = RNA   length = 21
FEATURE                 Location/Qualifiers
source                  1..21
                        mol_type = transcribed RNA
                        organism = Homo sapiens
SEQUENCE: 729
atgcctcccc cggccccgca g                                              21

SEQ ID NO: 730          moltype = RNA   length = 69
FEATURE                 Location/Qualifiers
source                  1..69
                        mol_type = transcribed RNA
                        organism = Homo sapiens
SEQUENCE: 730
gggcttaggg atgggaggcc aggatgaaga ttaatcccta atccccaaca ctggccttgc    60
tatcccag                                                             69

SEQ ID NO: 731          moltype = RNA   length = 86
FEATURE                 Location/Qualifiers
source                  1..86
                        mol_type = transcribed RNA
                        organism = Homo sapiens
SEQUENCE: 731
aggagtgacc aaaagacaag agtgcgagcc ttctattatg cccagacagg gccaccagag    60
ggctccttgg tctagggta atgcca                                          86

SEQ ID NO: 732          moltype = RNA   length = 118
FEATURE                 Location/Qualifiers
source                  1..118
                        mol_type = transcribed RNA
                        organism = Homo sapiens
SEQUENCE: 732
gcaggtgaac tggcaggcca ggaagaggag gaagccctgg aggggctgga ggtgatggat    60
gttttcctcc ggttctcagg gctccacctc tttcgggccg tagagccagg gctggtgc     118

SEQ ID NO: 733          moltype = RNA   length = 84
FEATURE                 Location/Qualifiers
source                  1..84
                        mol_type = transcribed RNA
                        organism = Homo sapiens
SEQUENCE: 733
gaggctgggc ggggcgcggc cggatcggtc gagagcgtcc tggctgatga cggtctcccg    60
tgcccacgcc ccaaacgcag tctc                                           84

SEQ ID NO: 734          moltype = RNA   length = 90
FEATURE                 Location/Qualifiers
source                  1..90
                        mol_type = transcribed RNA
                        organism = Homo sapiens
SEQUENCE: 734
gtgtctctct ggagaccctg cagccttccc acccaccagg gagctttcca tgggctgtgg    60
ggaaggcgtc agtgtcgggt gagggaacac                                     90

SEQ ID NO: 735          moltype = RNA   length = 94
FEATURE                 Location/Qualifiers
source                  1..94
                        mol_type = transcribed RNA
                        organism = Homo sapiens
SEQUENCE: 735
gtgaggtgtg ggcccggccc caggagcggg gcctgggcag ccccgtgtgt tgaggaagga    60
```

```
aggcagggcc cccgctcccc gggcctgacc ccac                             94

SEQ ID NO: 736         moltype = RNA  length = 98
FEATURE                Location/Qualifiers
source                 1..98
                       mol_type = transcribed RNA
                       organism = Homo sapiens
SEQUENCE: 736
cgaggtaggg gcgtcccggg cgcgcgggcg ggtcccaggc tgggcccctc ggaggccggg  60
tgctcactgc cccgtcccgg cgccgtgtc tcctccag                          98

SEQ ID NO: 737         moltype = RNA  length = 83
FEATURE                Location/Qualifiers
source                 1..83
                       mol_type = transcribed RNA
                       organism = Homo sapiens
SEQUENCE: 737
gggtttcctc tgccttttt tccaatgaaa ataacgaaac ctgttatttc ccattgaggg   60
ggaaaaaggc gggagaagcc cca                                         83

SEQ ID NO: 738         moltype = RNA  length = 54
FEATURE                Location/Qualifiers
source                 1..54
                       mol_type = transcribed RNA
                       organism = Homo sapiens
SEQUENCE: 738
ggacaagggc ggcgcgaccg gcccggggct cttgggcggc cgcgtttccc ctcc        54

SEQ ID NO: 739         moltype = RNA  length = 62
FEATURE                Location/Qualifiers
source                 1..62
                       mol_type = transcribed RNA
                       organism = Homo sapiens
SEQUENCE: 739
gtgagtgggg ctcccgggac ggcgcccgcc ctggccctgg cccggcgacg tctcacggtc  60
cc                                                                62

SEQ ID NO: 740         moltype = RNA  length = 76
FEATURE                Location/Qualifiers
source                 1..76
                       mol_type = transcribed RNA
                       organism = Homo sapiens
SEQUENCE: 740
cgcaggcctc tggcggagcc cattccatgc cagatgctga gcgatggctg gtgtgtgctg  60
ctccacaggc ctggtg                                                 76

SEQ ID NO: 741         moltype = RNA  length = 65
FEATURE                Location/Qualifiers
source                 1..65
                       mol_type = transcribed RNA
                       organism = Homo sapiens
SEQUENCE: 741
ctcctctggg ggtgggggc tgggcgtggt ggacagcgat gcatccctcg ccttctcacc   60
ctcag                                                             65

SEQ ID NO: 742         moltype = RNA  length = 67
FEATURE                Location/Qualifiers
source                 1..67
                       mol_type = transcribed RNA
                       organism = Homo sapiens
SEQUENCE: 742
ggcagccagg gggatgggcg agcttgggcc cattcctttc cttaccctac ccccatccc   60
cctgtag                                                           67

SEQ ID NO: 743         moltype = RNA  length = 180
FEATURE                Location/Qualifiers
source                 1..180
                       mol_type = transcribed RNA
                       organism = Homo sapiens
SEQUENCE: 743
cgcgactgcg gcggcggtgg tgggggagc gcggggatc gccgagggcc ggtcggccgc    60
cccgggtgcc gcgcggtgcc gccggcggcg gtgaggcccc gcgcgtgtgt cccggctgcg 120
gtcggccgc ctcgaggggt ccccgtggcg tccccttccc cgccggccgc ctttctcgcg  180

SEQ ID NO: 744         moltype = RNA  length = 82
FEATURE                Location/Qualifiers
source                 1..82
                       mol_type = transcribed RNA
                       organism = Homo sapiens
```

```
SEQUENCE: 744
gggaaagcgg agggcgcgcc cagctcccgg gctgattgcg ctaacagtgg ccccggtgtt    60
ggggcgcgtc tgccgctgcc cc                                            82

SEQ ID NO: 745          moltype = RNA   length = 63
FEATURE                 Location/Qualifiers
source                  1..63
                        mol_type = transcribed RNA
                        organism = Homo sapiens
SEQUENCE: 745
ggctccgcag ggccctggcg caggcatcca gacagcgggc gaatgcctcc cccggccccg    60
cag                                                                 63

SEQ ID NO: 746          moltype = RNA   length = 20
FEATURE                 Location/Qualifiers
source                  1..20
                        mol_type = transcribed RNA
                        organism = Homo sapiens
SEQUENCE: 746
ggctccttgg tctaggggta                                               20

SEQ ID NO: 747          moltype = RNA   length = 15
FEATURE                 Location/Qualifiers
source                  1..15
                        mol_type = transcribed RNA
                        organism = Homo sapiens
SEQUENCE: 747
cttggtctag gggta                                                    15

SEQ ID NO: 748          moltype = RNA   length = 25
FEATURE                 Location/Qualifiers
source                  1..25
                        mol_type = transcribed RNA
                        organism = Homo sapiens
SEQUENCE: 748
aggaagccct ggaggggctg gaggt                                         25

SEQ ID NO: 749          moltype = RNA   length = 15
FEATURE                 Location/Qualifiers
source                  1..15
                        mol_type = transcribed RNA
                        organism = Homo sapiens
SEQUENCE: 749
aggaagagga ggaag                                                    15

SEQ ID NO: 750          moltype = RNA   length = 24
FEATURE                 Location/Qualifiers
source                  1..24
                        mol_type = transcribed RNA
                        organism = Homo sapiens
SEQUENCE: 750
gatcggtcga gagcgtcctg gctg                                          24

SEQ ID NO: 751          moltype = RNA   length = 15
FEATURE                 Location/Qualifiers
source                  1..15
                        mol_type = transcribed RNA
                        organism = Homo sapiens
SEQUENCE: 751
gctgggcggg gcgcg                                                    15

SEQ ID NO: 752          moltype = RNA   length = 23
FEATURE                 Location/Qualifiers
source                  1..23
                        mol_type = transcribed RNA
                        organism = Homo sapiens
SEQUENCE: 752
tggggaaggc gtcagtgtcg ggt                                           23

SEQ ID NO: 753          moltype = RNA   length = 16
FEATURE                 Location/Qualifiers
source                  1..16
                        mol_type = transcribed RNA
                        organism = Homo sapiens
SEQUENCE: 753
tggggaaggc gtcagt                                                   16

SEQ ID NO: 754          moltype = RNA   length = 23
FEATURE                 Location/Qualifiers
```

```
source                  1..23
                        mol_type = transcribed RNA
                        organism = Homo sapiens
SEQUENCE: 754
aggaaggaag gcagggcccc cgc                                              23

SEQ ID NO: 755          moltype = RNA   length = 15
FEATURE                 Location/Qualifiers
source                  1..15
                        mol_type = transcribed RNA
                        organism = Homo sapiens
SEQUENCE: 755
gggccccgc tcccc                                                        15

SEQ ID NO: 756          moltype = RNA   length = 20
FEATURE                 Location/Qualifiers
source                  1..20
                        mol_type = transcribed RNA
                        organism = Homo sapiens
SEQUENCE: 756
ggaaaaaggc gggagaagcc                                                  20

SEQ ID NO: 757          moltype = RNA   length = 15
FEATURE                 Location/Qualifiers
source                  1..15
                        mol_type = transcribed RNA
                        organism = Homo sapiens
SEQUENCE: 757
ggcgggagaa gcccc                                                       15

SEQ ID NO: 758          moltype = RNA   length = 20
FEATURE                 Location/Qualifiers
source                  1..20
                        mol_type = transcribed RNA
                        organism = Homo sapiens
SEQUENCE: 758
tgagtggggc tcccgggacg                                                  20

SEQ ID NO: 759          moltype = RNA   length = 20
FEATURE                 Location/Qualifiers
source                  1..20
                        mol_type = transcribed RNA
                        organism = Homo sapiens
SEQUENCE: 759
tgagtggggc tcccgggacg                                                  20

SEQ ID NO: 760          moltype = RNA   length = 22
FEATURE                 Location/Qualifiers
source                  1..22
                        mol_type = transcribed RNA
                        organism = Homo sapiens
SEQUENCE: 760
tggcggagcc cattccatgc ca                                               22

SEQ ID NO: 761          moltype = RNA   length = 21
FEATURE                 Location/Qualifiers
source                  1..21
                        mol_type = transcribed RNA
                        organism = Homo sapiens
SEQUENCE: 761
ctggcggagc ccattccatg c                                                21

SEQ ID NO: 762          moltype = RNA   length = 29
FEATURE                 Location/Qualifiers
source                  1..29
                        mol_type = transcribed RNA
                        organism = Homo sapiens
SEQUENCE: 762
gggagccgcg gggatcgccg agggccggt                                        29

SEQ ID NO: 763          moltype = RNA   length = 15
FEATURE                 Location/Qualifiers
source                  1..15
                        mol_type = transcribed RNA
                        organism = Homo sapiens
SEQUENCE: 763
ggcggcggtg gtggg                                                       15

SEQ ID NO: 764          moltype = RNA   length = 22
```

```
FEATURE             Location/Qualifiers
source              1..22
                    mol_type = transcribed RNA
                    organism = Homo sapiens
SEQUENCE: 764
ccccggtgtt ggggcgcgtc tg                                        22

SEQ ID NO: 765      moltype = RNA  length = 21
FEATURE             Location/Qualifiers
source              1..21
                    mol_type = transcribed RNA
                    organism = Homo sapiens
SEQUENCE: 765
cccggtgttg gggcgcgtct g                                         21
```